US009422292B2

(12) United States Patent
Albrecht et al.

(10) Patent No.: US 9,422,292 B2
(45) Date of Patent: Aug. 23, 2016

(54) BROMODOMAIN INHIBITORS AND USES THEREOF

(75) Inventors: Brian K. Albrecht, Cambridge, MA (US); Victor S. Gehling, Somerville, MA (US); Michael Charles Hewitt, Somerville, MA (US); Alexander M. Taylor, Cambridge, MA (US); Jean-Christophe Harmange, Andover, MA (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 179 days.

(21) Appl. No.: 14/114,983

(22) PCT Filed: May 4, 2012

(86) PCT No.: PCT/US2012/036569

§ 371 (c)(1), (2), (4) Date: Jan. 24, 2014

(87) PCT Pub. No.: WO2012/151512

PCT Pub. Date: Nov. 8, 2012

(65) Prior Publication Data

US 2014/0135316 A1 May 15, 2014

Related U.S. Application Data

(60) Provisional application No. 61/482,371, filed on May 4, 2011, provisional application No. 61/540,801, filed on Sep. 29, 2011.

(51) Int. Cl.

| | |
|---|---|
| ***A61K 31/551*** | (2006.01) |
| ***C07D 471/14*** | (2006.01) |
| ***C07D 487/04*** | (2006.01) |

(52) U.S. Cl.

CPC .................................... *C07D 487/04* (2013.01)

(58) Field of Classification Search

CPC ... A61K 31/551; C07D 471/14; C07D 487/04
USPC .......... 514/219, 220; 540/543, 555, 563, 564, 540/565, 566
See application file for complete search history.

(56) References Cited

U.S. PATENT DOCUMENTS

| | | | | |
|---|---|---|---|---|
| 3,523,939 A | | 8/1970 | Fryer et al. | |
| 3,681,343 A | | 8/1972 | Hester, Jr. | |
| 3,709,898 A | | 1/1973 | Hester, Jr. | |
| 3,763,144 A | | 10/1973 | Hellerback et al. | |
| 3,781,289 A | | 12/1973 | Hester, Jr. | |
| 3,850,942 A | * | 11/1974 | Hester, Jr. et al. .... | C07D 243/38 540/522 |
| 3,886,141 A | | 5/1975 | Chase | |
| 3,886,175 A | * | 5/1975 | Hester, Jr. ............ | C07D 487/04 504/219 |
| 3,887,575 A | * | 6/1975 | Hester, Jr. ............ | C07D 487/04 504/219 |
| 3,903,103 A | | 9/1975 | Hester, Jr. | |
| 3,966,736 A | | 6/1976 | Szmuszkovicz | |
| 4,110,337 A | * | 8/1978 | Szarvasi ............... | C07D 487/04 540/517 |
| 4,110,455 A | | 8/1978 | von Bebenburg et al. | |
| 4,155,904 A | | 5/1979 | Schlesinger | |
| 4,327,026 A | | 4/1982 | Branca et al. | |
| 4,374,773 A | | 2/1983 | Branca et al. | |
| 4,377,522 A | | 3/1983 | Branca et al. | |
| 4,455,307 A | | 6/1984 | Hester, Jr. | |
| 4,820,834 A | | 4/1989 | Evans et al. | |
| 4,959,361 A | | 9/1990 | Walser | |
| 4,992,437 A | | 2/1991 | Naka et al. | |
| 5,004,741 A | | 4/1991 | Evans et al. | |
| 5,175,159 A | | 12/1992 | Bock et al. | |
| 5,185,331 A | | 2/1993 | Freidinger et al. | |
| 5,185,442 A | | 2/1993 | Weber et al. | |
| 5,206,234 A | | 4/1993 | Bock et al. | |
| 5,382,579 A | | 1/1995 | Okano et al. | |
| 5,409,909 A | | 4/1995 | Okano et al. | |
| 5,428,004 A | | 6/1995 | Earley et al. | |
| 5,439,905 A | | 8/1995 | Naka et al. | |
| 5,550,126 A | | 8/1996 | Horwell et al. | |
| 5,593,988 A | | 1/1997 | Tahara et al. | |
| 5,681,833 A | | 10/1997 | Castro Pineiro et al. | |
| 5,683,998 A | | 11/1997 | Shibayama et al. | |
| 5,698,552 A | | 12/1997 | Weber et al. | |
| 5,712,274 A | | 1/1998 | Sueoka et al. | |
| 5,721,231 A | | 2/1998 | Moriwaki et al. | |

(Continued)

FOREIGN PATENT DOCUMENTS

| | | |
|---|---|---|
| CA | 2020806 A1 | 1/1991 |
| CA | 2032222 A1 | 6/1991 |

(Continued)

OTHER PUBLICATIONS

Gussio et al., All-Atom Models for the Non-Nucleoside Binding Site of HIV-1-Reverse Transcriptase Complexed with Inhibitors a 3D QSAR Approach, Journal of Medicinal Chemistry, vol. 39, No. 8, pp. 1645-1650, 1996.*
Kosychova et al., Synthesis of Substituted 5,6-Dihydro-4H-[1,2,4]Triazolo[4,3-a][1,5]Benzodiazepine, Chemistry of Heterocyclic Compounds, vol. 40, No. 6, pp. 811-815, 2004.*
Proctor, George R., et al., "Azabenzycycloheptones, Part 19, Formation of Some Heterocyclic Annulated Compounds from 1,2,3,4-tetrahydro-1-benzazepine derivatives," Journal of the Chemical Society, Perkin Transactions 1, Chemical Society, Letchworth, GB, Jan. 1, 1978, pp. 862-879.

(Continued)

*Primary Examiner* — Brenda Coleman
(74) *Attorney, Agent, or Firm* — McCarter & English, LLP; Steven G. Davis; Michael J. DeGrazia

(57) ABSTRACT

The present invention relates to compounds useful as inhibitors of bromodomain-containing proteins. The invention also provides pharmaceutically acceptable compositions comprising compounds of the present invention and methods of using said compositions in the treatment of various disorders.

17 Claims, No Drawings

(56) References Cited

U.S. PATENT DOCUMENTS

| | | | |
|---|---|---|---|
| 5,733,905 | A | 3/1998 | Albright et al. |
| 5,739,129 | A | 4/1998 | Aquino et al. |
| 5,753,647 | A | 5/1998 | Weber et al. |
| 5,753,649 | A | 5/1998 | Tahara et al. |
| 5,795,887 | A | 8/1998 | Aquino et al. |
| 5,840,895 | A | 11/1998 | Ohtsuka et al. |
| 5,843,941 | A | 12/1998 | Marsters, Jr. et al. |
| 5,869,483 | A | 2/1999 | Albright et al. |
| 5,929,069 | A | 7/1999 | Shudo |
| 6,121,256 | A | 9/2000 | Shudo |
| 6,433,167 | B1 | 8/2002 | Fujita et al. |
| 6,458,782 | B1 | 10/2002 | Kagechika et al. |
| 6,476,017 | B2 | 11/2002 | Shudo |
| 6,649,366 | B2 | 11/2003 | Chubinskaya et al. |
| 6,777,408 | B1 | 8/2004 | Liberatore et al. |
| 7,015,213 | B1 | 3/2006 | Bigg et al. |
| 7,160,880 | B1 | 1/2007 | Feldman et al. |
| 7,250,410 | B2 | 7/2007 | Bourguignon et al. |
| 7,435,730 | B2 | 10/2008 | Feldman et al. |
| 7,442,795 | B2 | 10/2008 | Bryans et al. |
| 7,473,689 | B2 | 1/2009 | Feldman et al. |
| 7,482,337 | B2 | 1/2009 | Himmelsbach et al. |
| 7,485,635 | B2 | 2/2009 | Feldman et al. |
| 7,528,127 | B2 | 5/2009 | Feldman et al. |
| 7,696,212 | B2 | 4/2010 | Himmelsbach et al. |
| 2001/0039272 | A1 | 11/2001 | Shudo |
| 2002/0052358 | A1 | 5/2002 | Chubinskaya et al. |
| 2004/0053919 | A1 | 3/2004 | Chubinskaya et al. |
| 2004/0138214 | A1 | 7/2004 | Himmelsbach et al. |
| 2004/0152888 | A1 | 8/2004 | Bourguignon et al. |
| 2006/0128695 | A1 | 6/2006 | Bourguignon et al. |
| 2007/0093475 | A1 | 4/2007 | Feldman et al. |
| 2007/0105844 | A1 | 5/2007 | Glick et al. |
| 2007/0135419 | A1 | 6/2007 | Feldman et al. |
| 2007/0135420 | A1 | 6/2007 | Feldman et al. |
| 2007/0135421 | A1 | 6/2007 | Feldman et al. |
| 2008/0306042 | A1* | 12/2008 | Cezanne .............. C07D 471/14 514/211.12 |
| 2009/0093457 | A1 | 4/2009 | Himmelsbach et al. |
| 2010/0041643 | A1 | 2/2010 | Adachi et al. |
| 2010/0144703 | A1 | 6/2010 | Himmelsbach et al. |
| 2010/0256123 | A1 | 10/2010 | Sakuma et al. |
| 2010/0286127 | A1 | 11/2010 | Miyoshi et al. |
| 2010/0331316 | A1 | 12/2010 | Paoletti et al. |
| 2011/0230460 | A1 | 9/2011 | Kempen et al. |
| 2011/0245236 | A1* | 10/2011 | Ali ....................... C07D 471/14 514/219 |

FOREIGN PATENT DOCUMENTS

| | | | |
|---|---|---|---|
| CA | 2032427 | A1 | 6/1991 |
| CA | 2050268 | A1 | 3/1992 |
| CA | 2056809 | A1 | 6/1992 |
| CA | 2059353 | A1 | 7/1992 |
| CA | 2062456 | A1 | 9/1992 |
| CA | 2071092 | A1 | 12/1992 |
| CA | 1327570 | C | 3/1994 |
| CA | 02258053 | A1 | 12/1997 |
| DE | 2640599 | A1 | 3/1978 |
| DE | 3936828 | A1 | 5/1990 |
| DE | 4006471 | A1 | 9/1990 |
| DE | 4027470 | A1 | 3/1992 |
| DE | 4107521 | A1 | 9/1992 |
| DE | 4128581 | A1 | 3/1993 |
| DE | 4219659 | A1 | 12/1993 |
| EP | 0169392 | A2 | 1/1986 |
| EP | 0315698 | A1 | 5/1989 |
| EP | 0328924 | A2 | 8/1989 |
| EP | 0342587 | A2 | 11/1989 |
| EP | 0348523 | A1 | 1/1990 |
| EP | 0367110 | A1 | 5/1990 |
| EP | 0407955 | A1 | 1/1991 |
| EP | 0480455 | A1 | 4/1992 |
| EP | 495473 | A1 | 7/1992 |
| EP | 0514125 | A1 | 11/1992 |
| EP | 0559891 | A1 | 9/1993 |
| EP | 0656361 | A4 | 1/1995 |
| EP | 636625 | A2 | 2/1995 |
| EP | 0661284 | A4 | 5/1995 |
| EP | 0692483 | A4 | 11/1995 |
| EP | 0989131 | A1 | 3/2000 |
| EP | 1297836 | A1 | 4/2003 |
| EP | 1887008 | A1 | 2/2008 |
| EP | 2239264 | A1 | 10/2010 |
| FR | 2154511 | A1 | 5/1973 |
| FR | 2220257 | A1 | 10/1974 |
| GB | 1409693 | A | 10/1975 |
| GB | 2259013 | A | 3/1993 |
| JP | 7179471 | | 7/1995 |
| JP | 11228576 | | 8/1999 |
| JP | 2959591 | B2 | 10/1999 |
| JP | 3223290 | B2 | 10/2001 |
| JP | 03264588 | B2 | 3/2002 |
| JP | 03264589 | B2 | 3/2002 |
| JP | 04226993 | B2 | 2/2009 |
| WO | 9303717 | A1 | 3/1993 |
| WO | 9307129 | A1 | 4/1993 |
| WO | 9312791 | A1 | 7/1993 |
| WO | 9313776 | A1 | 7/1993 |
| WO | 9319052 | A1 | 9/1993 |
| WO | 9406801 | A1 | 3/1994 |
| WO | 9426723 | A2 | 11/1994 |
| WO | 9514694 | A1 | 6/1995 |
| WO | 9528399 | A1 | 10/1995 |
| WO | 9711061 | A1 | 3/1997 |
| WO | 9747622 | A1 | 12/1997 |
| WO | 9811111 | A1 | 3/1998 |
| WO | 9828268 | A2 | 7/1998 |
| WO | 9858930 | A1 | 12/1998 |
| WO | 9929324 | A1 | 6/1999 |
| WO | 0006157 | A1 | 2/2000 |
| WO | 0012547 | A2 | 3/2000 |
| WO | 0054778 | A1 | 9/2000 |
| WO | 0069836 | A1 | 11/2000 |
| WO | 0147510 | A2 | 7/2001 |
| WO | 02098865 | A2 | 12/2002 |
| WO | 03/074525 | A1 | 9/2003 |
| WO | 2004041258 | A2 | 5/2004 |
| WO | 2004041820 | A1 | 5/2004 |
| WO | 2004/058769 | A2 | 7/2004 |
| WO | 2005/002590 | A1 | 1/2005 |
| WO | 2005099759 | A1 | 10/2005 |
| WO | 2006038560 | A1 | 4/2006 |
| WO | 2006129623 | A1 | 12/2006 |
| WO | 2007016087 | A2 | 2/2007 |
| WO | 2007050587 | A2 | 5/2007 |
| WO | 2007/079820 | A1 | 7/2007 |
| WO | 2008023847 | A1 | 2/2008 |
| WO | 2008109856 | A2 | 9/2008 |
| WO | 2009059191 | A1 | 5/2009 |
| WO | 2009081349 | A1 | 7/2009 |
| WO | 2009152589 | A1 | 12/2009 |
| WO | 2010008459 | A1 | 1/2010 |
| WO | 2010049466 | A1 | 5/2010 |
| WO | 2010121164 | A2 | 10/2010 |
| WO | 2010128685 | A1 | 11/2010 |
| WO | 2011037128 | A1 | 3/2011 |
| WO | 2011054553 | A1 | 5/2011 |
| WO | 2011054841 | A1 | 5/2011 |
| WO | 2011054843 | A1 | 5/2011 |
| WO | 2011054844 | A1 | 5/2011 |
| WO | 2011054845 | A1 | 5/2011 |
| WO | 2011054846 | A1 | 5/2011 |
| WO | 2011054848 | A1 | 5/2011 |
| WO | 2011054851 | A1 | 5/2011 |
| WO | 2011079315 | A1 | 6/2011 |
| WO | 2011/123678 | A2 | 10/2011 |
| WO | 2011143651 | A1 | 11/2011 |
| WO | 2011143657 | A1 | 11/2011 |
| WO | 2011143660 | A2 | 11/2011 |
| WO | 2011143669 | A2 | 11/2011 |
| WO | 2011/161031 | A1 | 12/2011 |
| WO | 2012/075383 | A2 | 6/2012 |

(56) References Cited

FOREIGN PATENT DOCUMENTS

| | | | |
|---|---|---|---|
| WO | 2013024104 | A1 | 2/2013 |
| WO | 2013030150 | A1 | 3/2013 |
| WO | 2013033268 | A2 | 3/2013 |
| WO | 2013033269 | A1 | 3/2013 |
| WO | 2013033270 | A2 | 3/2013 |
| WO | 2013033420 | A1 | 3/2013 |

OTHER PUBLICATIONS

Venkateswarlu, Peesapati, et al., "Synthesis and Biological Activity of Some New Heterocyclic Annelated Compounds from 2,3,4,5-tetrahydro-1-benzazepines," Indian Journal of Chemistry: IJC, Council of Scientific and Industrial Research, IN., vol. 35B, Dec. 1, 1996, pp. 1287-1293.

Grey, R., et al., "Structure-Based Design of 3-Aryl-6-Amino-Triazolo[4,3-b] Pyridazine Inhibitors of Pim-1 Kinase," Bioorg. Med, Chem, Lett., vol. 19, No. 11, Jun. 1, 2009, pp. 3019-3022.

Filippakopoulos, et al., "Selective Inhibition of BET Bromodomains," Nature, Dec. 30, 2010, vol. 468, pp. 1067-1073.

International Search Report and Written Opinion, dated Jul. 23, 2013, Int'l Appl'n No. PCT/US2013/044449, Int'l Filing Date Jun. 6, 2013.

International Search Report and Written Opinion, dated Feb. 21, 2013, Int'l Appl'n No. PCT/US2012/042825, Int'l Filing Date Jun. 15, 2012.

International Preliminary Report on Patentability, dated Nov. 5, 2013, Int'l Appl'n No. PCT/US2012/036569, Int'l Filing Date May 4, 2012.

International Search Report and Written Opinion, dated Jul. 23, 2013, Int'l Appl'n No. PCT/US2013/044444, Int'l Filing Date Jun. 6, 2013.

International Search Report and Written Opinion, dated Apr. 17, 2012, Int'l Appl'n No. PCT/US2011/063173, Int'l Filing Date Dec. 2, 2011.

International Preliminary Report on Patentability, mailed Jan. 3, 2014, International Application No. PCT/US2012/042825; International Filing Date: Jun. 15, 2012, 10 pages.

Terrett, N.K., et al., "Imidazoú2',3':6,5 3/4 Dipyridoú3,2-B:2',3'-E 3/4—1,4-Diazepines: Non-Nucleoside HIV-1 Reverse Transcriptase Inhibitors with Greater Enzyme Affinity than Nevirapine," Bioorganic & Medicinal Chemistry Letters, vol. 12, No. 2, Dec. 1, 1992, pp. 1745-1750, XP002912883.

Kosychova, et al., "Synthesis of new [1,2,4]triazolo[4,3-a][1,5]benzodiazepine derivatives," Lietuvos Mokslu Akademija. Chemija, vol. 22, No. 1, Jan. 1, 2011, pp. 60-64, XP055136653.

Kosychova, et al., "Synthesis of novel 5,6-dihydro-4H-[1,2,4] triazolo[4,3-a][1,5]benzodiazepines," Rigas Tehniskas Universitates Zinatniskie Raksti. Serija 1: Materialzinatne Un Lietiska Kimija, vol. 22, Jan. 1, 2010, pp. 94-99, XP009179817.

Di Bracco, M., et al., "1,5-Benzodiazepines. Part XII. Synthesis and Biological Evaluations of Tricyclic and Tetracyclic 1,5-benzodiazepine Derivatives as Nevirapine Analogues," European Journal of Medicinal Chemistry, vol. 36, No. 11-12, Dec. 1, 2001, pp. 935-949, XP027205317.

Jiban K. Chakrabarti, et al., "Chemistry of Adamantane. Part XI. 1,2-Disubstituted Adamantanes. Synthesis and Reactions of Adamantano[2,1-b ]- and protoadamantano-[4,5-b ][1,5]benzodiazepines," Journal of Heterocyclic Chemistry, vol. 15, No. 5, Aug. 1, 1978, pp. 705-710, XP055136791.

Szarvasi, E., et al., "(4H)Dihydro-5,6(s)-triazolo-(4,3-a)benzodiazepines-1,5 a activite analgesique et anti-inflammatoire," European Journal of Medicinal Chemistry, vol. 13, No. 2, Mar. 1, 1978, pp. 113-119, XP009179828.

* cited by examiner

BROMODOMAIN INHIBITORS AND USES THEREOF

RELATED APPLICATIONS

This application is a 35 U.S.C. §371 national stage filing of International Application No. PCT/US2012/036569, filed May 4, 2012, which claims the benefit of U.S. Provisional application No. 61/482,371, filed May 4, 2011 and U.S. Provisional application No. 61/540,842, filed Sep. 29, 2011. The entire contents of the above-referenced applications are incorporated herein by reference.

TECHNICAL FIELD OF THE INVENTION

The present invention relates to compounds useful as inhibitors of one or more bromodomain-containing proteins.

BACKGROUND OF THE INVENTION

Packaging the 3 billion nucleotides of the human genome into the nucleus of a cell requires tremendous compaction. To accomplish this feat, DNA in our chromosomes is wrapped around spools of proteins called histones to form dense repeating protein/DNA polymers known as chromatin: the defining template for gene regulation. Far from serving as mere packaging modules, chromatin templates form the basis of a newly appreciated and fundamentally important set of gene control mechanisms termed epigenetic regulation. By conferring a wide range of specific chemical modifications to histones and DNA, epigenetic regulators modulate the structure, function, and accessibility of our genome, thereby exerting a tremendous impact on gene expression. Hundreds of epigenetic effectors have recently been identified, many of which are chromatin-binding proteins or chromatin-modifying enzymes. Significantly, an increasing number of these proteins have been associated with a variety of disorders such as neurodegenerative disorders, metabolic diseases, inflammation, and cancer. Thus, highly selective therapeutic agents directed against this emerging class of gene regulatory proteins promise new approaches to the treatment of human diseases.

SUMMARY OF THE INVENTION

In one aspect, the invention provides a compound of formula I:

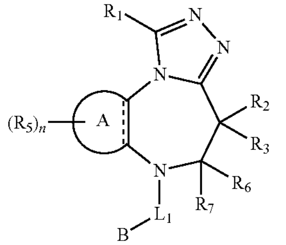

I or a pharmaceutically acceptable salt thereof, wherein:

$R_1$ is alkyl, alkenyl, alkynyl, aralkyl, aryl, cycloalkyl, heteroaryl, heterocycloalkyl, or halo, each of which is optionally substituted; or CN, $OR_A$, $NR_AR_B$, $N(R_C)S(O)_qR_AR_B$, $N(R_A)C(O)R_B$, $N(R_C)C(O)NR_AR_B$, $N(R_A)C(O)OR_A$, $N(R_C)C(S)NR_AR_B$, $S(O)_qR_A$, $C(O)R_A$, $C(O)OR_A$, $OC(O)R_A$, or $C(O)NR_AR_B$;

each $R_A$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

each $R_B$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; or $R_A$ and $R_B$, together with the atoms to which each is attached, can form a heterocycloalkyl or a heteroaryl; each of which is optionally substituted;

each $R_C$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Ring A is cycloalkyl, aryl, heterocycloalkyl, or heteroaryl;

$L^1$ is a covalent bond or an optionally substituted bivalent $C_{1-6}$ hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—;

B is alkyl, alkenyl, alkynyl, cycloalkyl, aryl, heterocycloalkyl, or heteroaryl, each optionally substituted with 1-5 independently selected $R^4$, or H;

$R_2$ and $R_3$, are each independently H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, —OC(O)N(R')(R"), or —$(CH_2)_pR_x$; or $R_2$ and $R_3$ together with the atoms to which each is attached, forms an optionally substituted 3-7 membered saturated or unsaturated spiro-fused ring having 0-3 heteroatoms independently selected from nitrogen, oxygen, or sulfur;

$R_6$ and $R_7$ are each independently H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, —OC(O)N(R')(R"), or —$(CH_2)_pR_x$;

or $R_6$ and $R_7$ together with the atoms to which each is attached, forms an optionally substituted 3-7 membered saturated or unsaturated spiro-fused ring having 0-3 heteroatoms independently selected from nitrogen, oxygen, or sulfur;

or any one of $R_2$ and $R_3$, together with any one of $R_6$ and $R_7$, together with the atoms to which each is attached, may form an optionally substituted aryl, optionally substituted cycloalkyl, optionally substituted heteroaryl, or optionally substituted heterocycloalkyl;

each $R_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R");

each R is independently hydrogen, optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl;

each R' is independently —R, —C(O)R, —C(S)R, —$CO_2$R, —C(O)N$(R)_2$, —C(S)N$(R)_2$, —S(O)R, —$SO_2$R, —$SO_2$N$(R)_2$, or two R groups on the same nitrogen are taken together with their intervening atoms to form an optionally substituted heteroaryl or heterocycloalkyl group;

each R" is independently —R, —C(O)R, —C(S)R, —$CO_2$R, —C(O)N$(R)_2$, —C(S)N$(R)_2$, —S(O)R, —$SO_2$R, —$SO_2$N$(R)_2$, or two R groups on the same nitrogen are taken together with their intervening atoms to form an optionally substituted heteroaryl or heterocycloalkyl group; or R' and R", together with the atoms to which each is attached, can form a cycloalkyl, a heterocycloalkyl, an aryl, or a heteroaryl; each of which is optionally substituted;

each $R_4$ is independently optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, halogen, —OR, —SR, —N(R')(R"), —CN, —$NO_2$, —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(=N(R'))N(R')(R"), —C=NN(R')(R"), —C=NOR, —C(=N(R'))N(R')(R"), —OC(O)R, or —OC(O)N(R')(R");

each $R_5$ is independently —R, halogen, —OR, —SR, —N(R')(R"), —CN, —$NO_2$, —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(=N(R'))N(R')(R"), —C=NN(R')(R"), —C=NOR, —C(=N(R'))N(R')(R"), —OC(O)R, or —OC(O)N(R')(R");

n is 0-5;

each q is independently 0, 1, or 2; and each p is independently an integer selected from 1-6.

In another aspect, the invention provides for a composition comprising a compound described herein (e.g., any formulae herein), and a pharmaceutically acceptable adjuvant, carrier, or vehicle.

In another aspect, the invention provides a method for inhibiting activity of a bromodomain-containing protein, or a mutant thereof, in a biological sample comprising the step of contacting said biological sample with a compound of the invention (e.g., any formulae herein).

In another aspect, the invention provides a method for inhibiting activity of a bromodomain-containing protein, or a mutant thereof, in a patient comprising the step of administering to said patient a compound of the invention (e.g., any formulae herein).

In another aspect, the invention provides a method for treating a bromodomain-containing protein-mediated disorder in a patient in need thereof, comprising the step of administering to said patient a compound of the invention (e.g., any formulae herein).

Provided compounds, and pharmaceutically acceptable compositions thereof, are useful for treating a variety of diseases, disorders or conditions associated with abnormal cellular responses triggered by events mediated by bromodomain-containing proteins. Such diseases, disorders, or conditions include those described herein.

Provided compounds are also useful for the study of bromodomain-containing proteins in biological and pathological phenomena, the study of intracellular signal transduction pathways mediated by bromodomain-containing proteins, and the comparative evaluation of new inhibitors of bromodomain-containing proteins.

DETAILED DESCRIPTION

Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., a inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

The number of carbon atoms in a hydrocarbyl substituent can be indicated by the prefix "$C_x$—$C_y$," where x is the minimum and y is the maximum number of carbon atoms in the substituent.

The prefix "halo" indicates that the substituent to which the prefix is attached is substituted with one or more independently selected halogen radicals. For example, "haloalkyl" means an alkyl substituent wherein at least one hydrogen radical is replaced with a halogen radical.

If a linking element in a depicted structure is "absent", then the left element in the depicted structure is directly linked to the right element in the depicted structure. For example, if a chemical structure is depicted as X-L-Y wherein L is absent, then the chemical structure is X—Y.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Aliphatic groups include, but are not limited to, alkyl, alkenyl, alkynyl, carbocycle. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic or bicyclic ring systems, as described herein, having from 3 to 18 carbon ring atoms, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl, tetrahydronaphthyl, decalin, or bicyclo[2.2.2]octane, where the radical or point of attachment is on an aliphatic ring.

As used herein, the term "cycloalkylene" refers to a bivalent cycloalkyl group. In certain embodiments, a cycloalkylene group is a 1,1-cycloalkylene group (i.e., a spiro-fused ring). Exemplary 1,1-cycloalkylene groups include

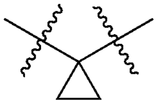

.

In other embodiments, a cycloalkylene group is a 1,2-cycloalkylene group or a 1,3-cycloalkylene group. Exemplary 1,2-cycloalkylene groups include

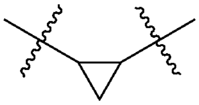

and

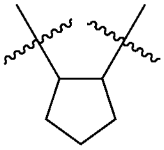

.

The term "alkyl" as used herein, refers to a saturated, straight- or branched-chain hydrocarbon radical typically containing from 1 to 20 carbon atoms. For example, "$C_1$-$C_8$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds and typically from 2 to 20 carbon atoms. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds and typically from 2 to 20 carbon atoms. For example, "$C_2$-$C_8$ alkynyl" contains from two to eight carbon atoms. Representative alkynyl groups include, but are not limited to, for example, ethynyl, 1-propynyl, 1-butynyl, heptynyl, octynyl and the like.

The term "aryl" used alone or as part of a larger moiety as in "aralkyl", "aralkoxy", or "aryloxyalkyl", refers to monocyclic, bicyclic, and tricyclic ring systems having a total of five to 15 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. The term "aralkyl" or "arylalkyl" refers to an alkyl residue attached to an aryl ring. Examples of aralkyl include, but are not limited to, benzyl, phenethyl and the like. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 18 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heteroaryl may be a single ring, or two or more fused rings. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. Examples include, but are not limited to, pyridinylmethyl, pyrimidinylmethyl and the like.

As used herein, the terms "heterocycle", "heterocyclyl", "heterocyclic radical", and "heterocyclic ring" are used interchangeably and refer to a stable 3- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}$NR (as in N-substituted pyrrolidinyl). Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

The term "bivalent hydrocarbon" refers to a bivalent saturated or unsaturated hydrocarbon group. Such bivalent hydrocarbon groups include alkylene, alkenylene, and alkynylene groups.

The term "alkylene" refers to a divalent group derived from a straight or branched saturated hydrocarbyl chain typically containing from 1 to 20 carbon atoms, more typically from 1 to 8 carbon atoms. Examples of an "alkylene" include a polymethylene group, i.e., $-(CH_2)_n-$, wherein n is a positive integer, preferably from 1 to 6, from 1 to 4, from 1 to 3, from 1 to 2, or from 2 to 3; or $-CH_2-$, $-CH_2CH_2-$, $-CH_2CH_2CH_2-$, $-CH_2CH_2CH_2CH_2-$, and $-CH_2CH(CH_3)CH_2-$. A substituted alkylene chain is a polymethylene group in which one or more methylene hydrogen atoms are replaced with a substituent. Suitable substituents include those described below for a substituted aliphatic group.

The term "alkenylene" refers to a divalent unsaturated hydrocarbyl group which may be linear or branched and which has at least one carbon-carbon double bond. An alkenylene group typically contains 2 to 20 carbon atoms, more typically from 2 to 8 carbon atoms. Non-limiting examples of alkenylene groups include $-C(H){=}C(H)-$, $-C(H){=}C(H)-CH_2-$, $-C(H){=}C(H)-CH_2-CH_2-$, $-CH_2-C(H){=}C(H)-CH_2-$, $-C(H){=}C(H)-CH(CH_3)-$, and $-CH_2-C(H){=}C(H)-CH(CH_2CH_3)-$.

The term "alkynylene" refers to a divalent unsaturated hydrocarbon group which may be linear or branched and which has at least one carbon-carbon triple bond. Representative alkynylene groups include, by way of example, $-C{\equiv}C-$, $-C{\equiv}C-CH_2-$, $-C{\equiv}C-CH_2-CH_2-$, $-CH_2-C{\equiv}C-CH_2-$, $-C{\equiv}C-CH(CH_3)-$, and $-CH_2-C{\equiv}C-CH(CH_2CH_3)-$.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

The terms "optionally substituted", "optionally substituted alkyl," "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with substituents including, but not limited to:

—F, —Cl, —Br, —I,

—OH, protected hydroxy, alkoxy, oxo, thiooxo, $-NO_2$, —CN, $CF_3$, $N_3$, $-NH_2$, protected amino, —NH-alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl, $-CONH_2$, —CONH-alkyl, —CONH-alkenyl, —CONH-alkynyl, —CONH-cycloalkyl, —CONH-aryl, —CONH-heteroaryl, —CONH-heterocycloalkyl, $-OCO_2$-alkyl, $-OCO_2$-alkenyl, $-OCO_2$-alkynyl, $-OCO_2$-cycloalkyl, $-OCO_2$-aryl, $-OCO_2$-heteroaryl, $-OCO_2$-heterocycloalkyl, $-OCONH_2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, $-NHCO_2$-alkyl, $-NHCO_2$-alkenyl, $-NHCO_2$-alkynyl, $-NHCO_2$-cycloalkyl, $-NHCO_2$-aryl, $-NHCO_2$-heteroaryl, $-NHCO_2$-heterocycloalkyl, $-NHC(O)NH_2$, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, $NHC(S)NH_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, $-NHC(NH)NH_2$, —NHC(NH)NH-alkyl, —NHC(NH)NH-alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl $-SO_2NH_2$, $-SO_2NH$-alkyl, $-SO_2NH$-alkenyl, $-SO_2NH$-alkynyl, $-SO_2NH$-cycloalkyl, $-SO_2NH$-aryl, $-SO_2NH$-heteroaryl, $-SO_2NH$-heterocycloalkyl, $-NHSO_2$-alkyl, $-NHSO_2$-alkenyl, $-NHSO_2$-alkynyl, $-NHSO_2$-cycloalkyl, $-NHSO_2$-aryl, $-NHSO_2$-heteroaryl, $-NHSO_2$-heterocycloalkyl, $-CH_2NH_2$, $-CH_2SO_2CH_3$, -alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

In certain embodiments, suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_{H2})_{0-4}O(CH_2)_{0-1}Ph$ which may be substituted with $R^\circ$; —CH═CHPh, which may be substituted with $R^\circ$; $-NO_2$; —CN; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)$ $OR^{\circ}$; $-(CH_2)_{0-4}C(O)SR^{\circ}$; $-(CH_2)_{0-4}C(O)OSiR^{\circ}_3$; $-(CH_2)_{0-4}OC(O)R^{\circ}$; $-OC(O)(CH_2)_{0-4}SR-$, $SC(S)SR^{\circ}$; $-(CH_2)_{0-4}SC(O)R^{\circ}$; $-(CH_2)_{0-4}C(O)NR^{\circ}_2$; $-C(S)NR^{\circ}_2$; $-C(S)SR^{\circ}$; $-SC(S)SR^{\circ}$, $-(CH_2)_{0-4}OC(O)NR^{\circ}_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR^{\circ}$; $-(CH_2)_{0-4}OS(O)_2R^{\circ}$; $-S(O)_2NR^{\circ}_2$; $-(CH_2)_{0-4}S(O)R^{\circ}$; $-N(R^{\circ})S(O)_2NR^{\circ}_2$; $-N(R^{\circ})S(O)_2R^{\circ}$; $-N(OR^{\circ})R^{\circ}$; $-C(NH)NR^{\circ}_2$; $-P(O)_2R^{\circ}$; $-P(O)R^{\circ}_2$; $-OP(O)R^{\circ}_2$; $-OP(O)(OR^{\circ})_2$; $-SiR^{\circ}_3$; $-(C_{1-4}$ straight or branched)alkylene)$O-N(R^{\circ})_2$; or $-(C_{1-4}$ straight or branched)alkylene)$C(O)O-N(R^{\circ})_2$, wherein each $R^{\circ}$ may be substituted as defined below and is independently hydrogen, $C_{1-6}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), are independently halogen, $-(CH_2)_{0-2}R^{\bullet}$, -(halo$R^{\bullet}$), $-(CH_2)_{0-2}OH$, $-(CH_2)_{0-2}OR^{\bullet}$, $-(CH_2)_{0-2}CH(OR^{\bullet})_2$; $-O$(halo$R^{\bullet}$), $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, $-(C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include $=O$ and $=S$.

Suitable divalent substituents on a saturated carbon atom of an "optionally substituted" group include the following: $=O$, $=S$, $=NNR^*_2$, $-NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^{\bullet}$, -(halo$R^{\bullet}$), $-OH$, $-OR^{\bullet}$, $-O$(halo$R^{\bullet}$), $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^{\dagger}$, $-NR^{\dagger}_2$, $-C(O)R^{\dagger}$, $-C(O)OR^{\dagger}$, $-C(O)C(O)R^{\dagger}$, $-C(O)CH_2C(O)R^{\dagger}$, $-S(O)_2R^{\dagger}$, $-S(O)_2NR^{\dagger}_2$, $-C(S)NR^{\dagger}_2$, $-C(NH)NR^{\dagger}_2$, or $-N(R^{\dagger})S(O)_2R^{\dagger}$; wherein each $R^{\dagger}$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, $-R^{\bullet}$, -(halo$R^{\bullet}$), $-OH$, $-OR^{\bullet}$, $-O$(halo$R^{\bullet}$), $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

As used herein, the term "suitable amino protecting group," includes those described in detail in *Protecting Groups in Organic Synthesis*, T. W. Greene and P. G. M. Wuts, 3$^{rd}$ edition, John Wiley & Sons, 1999.

Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

As used herein, the term "inhibitor" is defined as a compound that binds to and/or inhibits the target bromodomain-containing protein (such as a BET protein, e.g., BRD2, BRD3, BRD4, and/or BRDT) with measurable affinity. In certain embodiments, an inhibitor has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in activity of at least one bromodomain-containing protein between a sample comprising a provided compound, or composition thereof, and at least one histone methyltransferase, and an equivalent sample comprising at least one bromodomain-containing protein, in the absence of said compound, or composition thereof.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Description of Exemplary Compounds

In one aspect, the invention provides a compound of formula I:

I

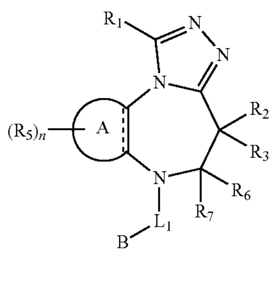

or a pharmaceutically acceptable salt thereof, wherein:

$R_1$ is alkyl, alkenyl, alkynyl, aralkyl, aryl, cycloalkyl, heteroaryl, heterocycloalkyl, or halo, each of which is optionally substituted; or CN, $OR_A$, $NR_AR_B$, $N(R_C)S(O)_qR_AR_B$, $N(R_A)C(O)R_B$, $N(R_C)C(O)NR_AR_B$, $N(R_A)C(O)OR_A$, $N(R_C)C(S)NR_AR_B$, $S(O)_qR_A$, $C(O)R_A$, $C(O)OR_A$, $OC(O)R_A$, or $C(O)NR_AR_B$;

each $R_A$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

each $R_B$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; or $R_A$ and $R_B$, together with the atoms to which each is attached, can form a heterocycloalkyl or a heteroaryl; each of which is optionally substituted;

each $R_C$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Ring A is cycloalkyl, aryl, heterocycloalkyl, or heteroaryl;

$L^1$ is a covalent bond or an optionally substituted bivalent $C_{1-6}$ hydrocarbon chain wherein one or two methylene units is optionally replaced by —NR'—, —N(R')C(O)—, —C(O)N(R')—, —N(R')$SO_2$—, —$SO_2$N(R')—, —O—, —C(O)—, —OC(O)—, —C(O)O—, —S—, —SO— or —$SO_2$—;

B is alkyl, alkenyl, alkynyl, cycloalkyl, aryl, heterocycloalkyl, or heteroaryl, each optionally substituted with 1-5 independently selected $R^4$, or H;

$R_2$ and $R_3$, are each independently H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, —OC(O)N(R')(R"), or —$(CH_2)_pR_x$; or $R_2$ and $R_3$ together with the atoms to which each is attached, forms an optionally substituted 3-7 membered saturated or unsaturated spiro-fused ring having 0-3 heteroatoms independently selected from nitrogen, oxygen, or sulfur;

$R_6$ and $R_7$ are each independently H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')

C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, —OC(O)N(R')(R"), or —$(CH_2)_pR_x$;

or $R_6$ and $R_7$ together with the atoms to which each is attached, forms an optionally substituted 3-7 membered saturated or unsaturated spiro-fused ring having 0-3 heteroatoms independently selected from nitrogen, oxygen, or sulfur;

or any one of $R_2$ and $R_3$, together with any one of $R_6$ and $R_7$, together with the atoms to which each is attached, may form an optionally substituted aryl, optionally substituted cycloalkyl, optionally substituted heteroaryl, or optionally substituted heterocycloalkyl;

each $R_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, —OC(O)N(R')(R");

each R is independently hydrogen, optionally substituted alkyl, optionally substituted alkenyl, optionally substituted alkynyl, optionally substituted aryl, optionally substituted aralkyl, optionally substituted cycloalkyl, optionally substituted heteroaryl, or optionally substituted heterocycloalkyl;

each R' is independently —R, —C(O)R, —C(S)R, —$CO_2$R, —C(O)N$(R)_2$, —C(S)N$(R)_2$, —S(O)R, —$SO_2$R, —$SO_2$N$(R)_2$, or two R groups on the same nitrogen are taken together with their intervening atoms to form an optionally substituted heteroaryl or heterocycloalkyl group;

each R" is independently —R, —C(O)R, —C(S)R, —$CO_2$R, —C(O)N$(R)_2$, —C(S)N$(R)_2$, —S(O)R, —$SO_2$R, —$SO_2$N$(R)_2$, or two R groups on the same nitrogen are taken together with their intervening atoms to form an optionally substituted heteroaryl or heterocycloalkyl group; or R' and R", together with the atoms to which each is attached, can form a cycloalkyl, a heterocycloalkyl, an aryl, or a heteroaryl; each of which is optionally substituted;

each $R_4$ is independently optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, halogen, —OR, —SR, —N(R')(R"), —CN, —$NO_2$, —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, or —OC(O)N(R')(R");

each $R_5$ is independently —R, halogen, —OR, —SR, —N(R')(R"), —CN, —$NO_2$, —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, or —OC(O)N(R')(R");

n is 0-5;

each q is independently 0, 1, or 2; and each p is independently an integer selected from 1-6.

In one embodiment, Ring A is benzo or a 5-6 membered fused heteroaryl ring having 1-2 heteroatoms independently selected from nitrogen, oxygen, or sulfur.

In another embodiment, B is a 3-7 membered aryl ring; 3-7 membered saturated or partially unsaturated carbocyclic ring; or a 4-7 membered saturated or partially unsaturated heterocyclic ring having 1-2 heteroatoms independently selected from nitrogen, oxygen, and sulfur; and is optionally substituted with 1 to 5 independently selected $R_4$ groups. In one aspect of this embodiment, L is a bond; and B is selected from hydrogen, optionally substituted alkyl, a 3-7 membered aryl ring; or a 3-7 membered heteroaryl ring having 1-2 heteroatoms independently selected from nitrogen, oxygen, and sulfur; and wherein the aryl or heteroaryl is optionally substituted with 1 to 5 independently selected $R_4$ groups.

In certain embodiments, $R_2$ is H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —$CO_2$R, —C(O)N(R')(R"), —C(O)SR, or —$(CH_2)_pR_x$.

In various embodiments, $R_3$ is H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —$CO_2$R, —C(O)N(R')(R"), —C(O)SR, or —$(CH_2)_pR_x$.

In another embodiment, $R_2$ and $R_3$, together with the atoms to which each is attached, forms an optionally substituted 3-7 membered saturated or partially unsaturated spiro-fused ring having 0-3 heteroatoms independently selected from nitrogen, oxygen, or sulfur.

In a more specific embodiment, each of $R_2$ and $R_3$ is independently selected from H, optionally substituted alkyl, and —$(CH_2)_pR_x$; or $R_2$ and $R_3$ are taken together with the atoms to which each is attached, to form a 3-7 membered cycloalkyl ring optionally substituted with alkyl, wherein any alkyl substituent is optionally further substituted.

In still other embodiments, $R_6$ is H, halogen, optionally substituted alkyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —$CO_2$R, —C(O)N(R')(R"), or —$(CH_2)_pR_x$.

In yet another embodiment, $R_7$ is H, halogen, optionally substituted alkyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —$CO_2$R, —C(O)N(R')(R"), or —$(CH_2)_pR_x$.

In a more specific embodiment, each of $R_6$ and $R_7$ is independently selected from H, optionally substituted alkyl, and —$(CH_2)_pR_x$.

In certain embodiments, $R_1$ is alkyl, aralkyl, aryl, heteroaryl, halo, CN, $OR_A$, $NR_AR_B$, $N(R_A)S(O)_qR_AR_B$, $N(R_A)C$ (O)$R_B$, N($R_A$)C(O)N$R_A R_B$, N($R_A$)C(O)O$R_A$, N($R_A$)C(S)N-$R_A R_B$, S(O)$_q R_A$, C(O)$R_A$, C(O)O$R_A$, OC(O)$R_A$, or C(O)N$R_A R_B$.

In another embodiment, the invention provides a compound of formula II:

II

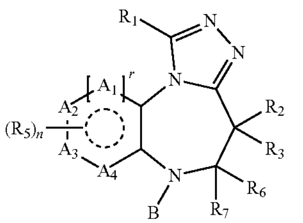

or a pharmaceutically acceptable salt thereof, wherein:

$R_1$ is alkyl, alkenyl, alkynyl, aralkyl, aryl, cycloalkyl, heteroaryl, heterocycloalkyl, or halo, each of which is optionally substituted; or CN, O$R_A$, N$R_A R_B$, N($R_C$)S(O)$_q R_A R_B$, N($R_A$)C(O)$R_B$, N($R_A$)C(O)N$R_A R_B$, N($R_A$)C(O)O$R_A$, N($R_A$)C(S)N$R_A R_B$, S(O)$_q R_A$, C(O)$R_A$, C(O)O$R_A$, OC(O)$R_A$, or C(O)N$R_A R_B$;

each $R_A$ is independently optionally substituted alkyl, containing 0, 1, 2, or 3 heteroatoms selected from O, S, or N; optionally substituted aryl; optionally substituted heteroaryl; optionally substituted heterocyclic; optionally substituted carbocyclic; or hydrogen;

each $R_B$ is independently optionally substituted alkyl, containing 0, 1, 2, or 3 heteroatoms selected from O, S, or N; optionally substituted aryl; optionally substituted heteroaryl; optionally substituted heterocyclic; optionally substituted carbocyclic; or hydrogen;

each $R_C$ is independently optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

each of $A_1$, $A_2$, $A_3$, and $A_4$ is independently CR, N, NR, O, or S; or $A_1$ is absent;

B is a 3-7 membered saturated, partially unsaturated or completely unsaturated carbocyclic ring; or a 3-7 membered aryl ring, wherein B is optionally substituted with 1 to 5 independently selected $R_4$ groups; or H;

$R_2$ and $R_3$ are each independently H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —$CO_2$R, C(O)N(R')(R"), —C(O)SR, or —$(CH_2)_p R_x$; or $R_2$ and $R_3$ together with the atoms to which each is attached, forms an optionally substituted 3-7 membered saturated or partially unsaturated spiro-fused ring having 0-3 heteroatoms independently selected from nitrogen, oxygen, or sulfur;

$R_6$ is H, halogen, optionally substituted alkyl, optionally substituted aryl, optionally substituted aralkyl, optionally substituted heteroaryl —OR, —SR, —N(R')(R"), —C(O)R, —$CO_2$R, —C(O)N(R')(R"), or —$(CH_2)_p R_x$;

$R_7$ is H, halogen, optionally substituted alkyl, optionally substituted aryl, optionally substituted aralkyl, optionally substituted heteroaryl, —OR, —SR, —N(R')(R"), —C(O)R, —$CO_2$R, —C(O)N(R')(R"), or —$(CH_2)_p R_x$;

or $R_6$ and $R_7$ together with the atoms to which each is attached, forms an optionally substituted 3-7 membered saturated or unsaturated spiro-fused ring having 0-3 heteroatoms independently selected from nitrogen, oxygen, or sulfur;

or any one of $R_2$ and $R_3$, together with any one of $R_6$ and $R_7$, together with the atoms to which each is attached, may form an optionally substituted aryl, optionally substituted cycloalkyl, optionally substituted heteroaryl, or optionally substituted heterocycloalkyl;

each $R_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(=N(R'))N(R')(R"), —C=NN(R')(R"), —C=NOR, —C(=N(R'))N(R')(R"), —OC(O)R, —OC(O)N(R')(R");

each R is independently hydrogen, $C_{1-6}$ aliphatic, a 5-6 membered aryl ring, a 3-7 membered saturated, partially unsaturated, or completely unsaturated carbocyclic ring, a 7-12 membered bicyclic saturated, partially unsaturated, or completely unsaturated carbocyclic ring, a 3-7 membered monocyclic heteroaryl ring having 1-3 heteroatoms independently selected from nitrogen, oxygen, and sulfur, a 3-7 membered saturated, partially unsaturated, or completely unsaturated heterocyclic ring having 1-2 heteroatoms independently selected from nitrogen, oxygen, and sulfur, a 7-12 membered bicyclic saturated, partially unsaturated, or completely unsaturated heterocyclic ring having 1-4 heteroatoms independently selected from nitrogen, oxygen, and sulfur, or a 7-12 membered bicyclic heteroaryl ring having 1-4 heteroatoms independently selected from nitrogen, oxygen, and sulfur; each of which is optionally substituted;

each R' is independently —R, —C(O)R, —C(S)R, —$CO_2$R, —C(O)N$(R)_2$, —C(S)N$(R)_2$, —S(O)R, —$SO_2$R, —$SO_2$N$(R)_2$, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;

each R" is independently —R, —C(O)R, —C(S)R, —$CO_2$R, —C(O)N$(R)_2$, —C(S)N$(R)_2$, —S(O)R, —$SO_2$R, —$SO_2$N$(R)_2$, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted; or R' and R", together with the atoms to which each is attached, can form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;

each $R_4$ is independently optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, halogen, —OR, —SR, —N(R')(R"), —CN, —$NO_2$, —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, or —OC(O)N(R')(R");

each $R_5$ is independently —R, halogen, —OR, —SR, —N(R')(R"), —CN, —$NO_2$, —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, or —OC(O)N(R')(R");

r is 0 or 1;

n is 0-5;

each q is independently 0, 1, or 2; and each p is independently an integer selected from 1-6.

In one embodiment, the ring formed by $A_1$, $A_2$, $A_3$, $A_4$, and the atoms to which each is attached, is phenyl, pyridino, pyrimidino, pyrazino, or pyridazino.

In other embodiments, the ring formed by $A_1$, $A_2$, $A_3$, $A_4$, and the atoms to which each is attached, is furanyl, thiopheno, pyrrolo, isoxazolo, or isothiazolo.

In another embodiment, B is phenyl or a 4-7 membered saturated or partially unsaturated heterocyclic ring having 1-2 heteroatoms independently selected from nitrogen, oxygen, and sulfur; and is optionally substituted with 1 to 5 independently selected $R_4$ groups.

In a further embodiment, B is piperidinyl, morpholinyl, or piperazinyl; and is optionally substituted with 1 to 5 independently selected $R_4$ groups.

In other embodiments, $R_1$ is halo, alkyl, aralkyl, aryl, or heteroaryl.

In a further embodiment, $R_1$ is methyl, ethyl, propyl, i-propyl, butyl, s-butyl, t-butyl, pentyl, hexyl, or heptyl.

In certain embodiments, $R_2$ is H, methyl, ethyl, propyl, i-propyl, butyl, s-butyl, pentyl, hexyl, —OR, —SR, —CN, —N(R')(R"), —C(O)R, —C(S)R, —$CO_2$R, —C(O)N(R')(R"), —C(O)SR, or —$(CH_2)_pR_x$.

In a further embodiment, $R_2$ is H, methyl, or —$(CH_2)_pR_x$.

In another further embodiment, $R_x$ is —N(R')(R"), —C(O)R, —C(S)R, —$CO_2$R, —C(O)N(R')(R"), —C(S)N(R')(R"), —S(O)R, —$SO_2$R, —$SO_2$N(R')(R"), —N(R')C(O)R, —N(R')$SO_2$R, —OC(O)R, —OC(O)N(R')(R"), methyl, ethyl, propyl, i-propyl, butyl, s-butyl, pentyl or hexyl.

In other embodiments, $R_3$ is H, methyl, ethyl, propyl, i-propyl, butyl, s-butyl, pentyl, hexyl, —OR, —SR, —CN, —N(R')(R"), —C(O)R, —C(S)R, —$CO_2$R, —C(O)N(R')(R"), —C(O)SR, or —$(CH_2)_pR_x$.

In a further embodiment, $R_3$ is H, methyl, or —$(CH_2)_pR_x$.

In a further embodiment, $R_x$ is —N(R')(R"), —C(O)R, —C(S)R, —$CO_2$R, —C(O)N(R')(R"), —C(S)N(R')(R"), —S(O)R, —$SO_2$R, —$SO_2$N(R')(R"), —N(R')C(O)R, —N(R')$SO_2$R, —OC(O)R, —OC(O)N(R')(R"), methyl, ethyl, propyl, i-propyl, butyl, s-butyl, pentyl or hexyl.

In still other embodiments, $R_2$ and $R_3$ together with the atoms to which each is attached, forms an optionally substituted 3-7 membered saturated or partially unsaturated spiro-fused ring having 0-3 heteroatoms independently selected from nitrogen, oxygen, or sulfur.

In a further embodiment, $R_2$ and $R_3$ together with the atoms to which each is attached, forms a cyclopropyl, cyclobutyl, cyclopentyl, cyclohexyl, azetidine, oxetane, tetrahydrofuran, or pyrrolidine; each of which is optionally substituted.

In other further embodiments, $R_2$ and $R_3$ are optionally substituted by halogen, alkyl, alkenyl, alkynyl, aryl, aralkyl, cycloalkyl, heteroaryl, heterocycloalkyl, each of which is further optionally substituted; or $R_2$ and $R_3$ are optionally substituted by —OR, —SR, —CN, —N(R')(R"), —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, —OC(O)N(R')(R"), or —$(CH_2)_pR_x$.

In another embodiment, $R_6$ is H, methyl, ethyl, propyl, i-propyl, butyl, s-butyl, pentyl, hexyl, —OR, —SR, —N(R')(R"), —C(O)R, —$CO_2$R, —C(O)N(R')(R"), or —$(CH_2)_pR_x$.

In still another embodiment, $R_7$ is H, methyl, ethyl, propyl, i-propyl, butyl, s-butyl, pentyl, hexyl, —OR, —SR, —N(R')(R"), —C(O)R, —$CO_2$R, —C(O)N(R')(R"), or —$(CH_2)_pR_x$.

In each of the following embodiments of B, B is optionally substituted with 1-5 independently selected $R^4$.

In some embodiments, B is phenyl.

In some embodiments, B is a 3-7 membered saturated or partially unsaturated carbocyclic ring. In certain embodiments, B is cyclopropyl, cyclobutyl, cyclopentyl, cyclohexyl, or cycloheptyl. In certain embodiments, B is cyclopentenyl, cyclohexenyl, or cycloheptenyl.

In some embodiments, B is a 4-7 membered saturated or partially unsaturated heterocyclic ring having 1-2 heteroatoms independently selected from nitrogen, oxygen, and sulfur. In certain embodiments, B is a 5-6 membered saturated or partially unsaturated heterocyclic ring having 1-2 heteroatoms independently selected from nitrogen, oxygen, and sulfur. In certain embodiments, B is tetrahydrofuranyl, tetrahydrothienyl, tetrahydropyranyl, tetrahydrothiopyranyl, pyrrolidinyl, pyrrolidonyl, piperidinyl, pyrrolinyl, oxazolidinyl, piperazinyl, dioxanyl, dioxolanyl, diazepinyl, oxazepinyl, thiazepinyl, or morpholinyl.

In some embodiments, B is a 5-6 membered monocyclic heteroaryl ring having 1-3 heteroatoms independently selected from nitrogen, oxygen, and sulfur.

In certain embodiments, B is 6-membered heteroaryl ring having 1-3 nitrogen atoms. In other embodiments, B is a 6-membered heteroaryl ring having 1 nitrogen atom. In certain other embodiments, B is a 6-membered heteroaryl ring having 2 nitrogen atoms. In yet other embodiments, B is a 6-membered heteroaryl ring having 3 nitrogen atoms.

In other embodiments, B is a 5-membered heteroaryl ring having 1-3 heteroatoms independently selected from nitrogen, oxygen, or sulfur. In certain embodiments, B is a 5-membered heteroaryl ring having 1 heteroatom independently selected from nitrogen, oxygen, or sulfur. In certain embodiments, B is a 5-membered heteroaryl ring having 2 heteroatoms independently selected from nitrogen, oxygen, or sulfur. In other embodiments, B is a 5-membered heteroaryl ring having 2 heteroatoms independently selected from nitrogen and oxygen. In some embodiments, B is a 5-membered heteroaryl ring having 2 heteroatoms independently selected from nitrogen and sulfur. In other embodiments, B is a 5-membered heteroaryl ring having 1-3 nitrogen atoms. In certain embodiments, B is thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, or pyrazinyl.

In some embodiments, B is a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur. In certain embodiments, B is a 5,5-fused-, 5,6-fused, or 6,6-fused saturated, partially unsaturated, or aromatic bicyclic ring. In some embodiments, B is a 5,5-fused, 5,6-fused, or 6,6-fused aromatic bicyclic ring. In other embodiments, B is a naphthalenyl, indanyl or indenyl group.

In some embodiments, B is a 7-10 membered bicyclic saturated or partially unsaturated heterocyclic ring having 1-4 heteroatoms independently selected from nitrogen, oxygen, and sulfur. In certain embodiments, B is a 7-8 membered bicyclic saturated heterocyclic ring having 1-3 heteroatoms independently selected from nitrogen, oxygen, and sulfur. In certain embodiments, B is a 7-8 membered bicyclic partially unsaturated heterocyclic ring having 1-3 heteroatoms independently selected from nitrogen, oxygen, and sulfur. In certain embodiments, B is a 9-10 membered bicyclic saturated heterocyclic ring having 1-3 heteroatoms independently selected from nitrogen, oxygen, and sulfur. In certain embodiments, B is a 9-10 membered bicyclic partially unsaturated heterocyclic ring having 1-3 heteroatoms independently selected from nitrogen, oxygen, and sulfur. In certain embodiments, B is tetrahydroquinolinyl, tetrahydroisoquinolinyl, decahydroquinolinyl, or quinuclidinyl. In certain embodiments, B is indolinyl, 3H-indolyl, chromanyl, phenanthridinyl, 2-azabicyclo[2.2.1]heptanyl, octahydroindolyl, or tetrahydroquinolinyl.

In some embodiments, B is a 8-10 membered bicyclic heteroaryl ring having 1-4 heteroatoms independently selected from nitrogen, oxygen, and sulfur.

In some embodiments, B is a 5,5-fused, 5,6-fused, or 6,6-fused saturated, partially unsaturated, or aromatic bicyclic ring having 1-4 heteroatoms, independently selected from nitrogen, oxygen, or sulfur. In other embodiments, B is a 5,5-fused, 5,6-fused, or 6,6-fused heteroaryl ring having 1-4 heteroatoms, independently selected from nitrogen, oxygen, or sulfur. In certain embodiments, B is a 5,5-fused, 5,6-fused, or 6,6-fused heteroaryl ring having 1-4 nitrogen atoms. In other embodiments, B is a 5,6-fused heteroaryl ring having 1-4 nitrogen atoms. In certain embodiments, B is pyrrolizinyl, indolyl, quinolinyl, isoquinolinyl, benzimidazolyl, imidazopyridinyl, indazolyl, purinyl, cinnolinyl, quinazolinyl, phthalazinyl, naphthridinyl, quinoxalinyl, thianaphtheneyl, or benzofuranyl. In certain embodiments, B is a indolizinyl, purinyl, naphthyridinyl, or pteridinyl.

In yet another embodiment, the invention provides a compound of Formula III:

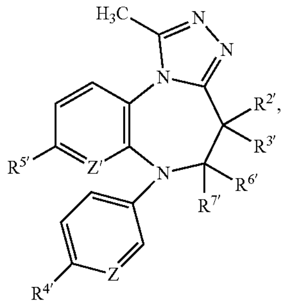

or a pharmaceutically acceptable salt thereof, wherein:

each of Z and Z' is independently selected from N or CH;

$R^{2'}$ and $R^{3'}$ are independently selected from hydrogen and methyl; or $R^{2'}$ and $R^{3'}$ are taken together with the carbon atom to which they are bound to form cyclopropyl optionally substituted with an optionally substituted alkyl;

$R^{4'}$ is selected from chloro, —$NH_2$, —CN, —$C(O)NH_2$, —$S(O)_2CH_3$, and $CF_3$;

$R^{5'}$ is selected from phenyl, pyrazolyl, pyridinyl, triazolyl, pyrazinyl, pyridinonyl, pyrimidinyl, oxadiazolyl, —$OCH_3$, —$C(O)NH_2$, —$C(O)NH$—$CH_2CH_2OH$, —C≡C—$C(CH_3)_2OH$, —C≡C—$C(CH_3)_2NH_2$, and bromo, wherein the phenyl, pyrazolyl, pyridinyl, triazolyl, pyrazinyl, pyridinonyl, pyrimidinyl, or oxadiazolyl is optionally substituted with one or more substituents independently selected from optionally substituted alkyl, —$NH_2$, COOH, $C(O)NH_2$, and $CH_2CONH_2$; and each of $R^{6'}$ and $R^{7'}$ is independently selected from methyl and hydrogen.

In one specific aspect of Formula III:

each of Z and Z' is CH;

$R^{4'}$ is selected from chloro, —CN, —$C(O)NH_2$, —$S(O)_2CH_3$, $CF_3$; and $R^{5'}$ is selected from phenyl, pyrazolyl, pyridinyl, triazolyl, pyrazinyl, pyridinonyl, pyrimidinyl, oxadiazolyl, —$C(O)NH_2$, wherein the phenyl, pyrazolyl, pyridinyl, triazolyl, pyrazinyl, pyridinonyl, pyrimidinyl, or oxadiazolyl is optionally substituted with one or more of —$CH_3$, —$NH_2$, COOH, $C(O)NH_2$, $CH_2CONH_2$, or $CH_2CH_2OH$.

In a more specific aspect of Formula III:

$R^{2'}$ is (R)-methyl, $R^{3'}$ is hydrogen;

$R^{4'}$ is chloro;

$R^{5'}$ is selected from pyridinyl, triazolyl, pyrimidinyl or pyrazinyl, wherein $R^{5'}$ is substituted with methyl or $NH_2$; and each of $R^{6'}$ and $R^{7'}$ is hydrogen.

Exemplary compounds of the invention are set forth in Table 1 below.

TABLE 1

| Exemplary Compounds<br>Compounds of the invention include the following: | | | |
|---|---|---|---|
| Cmpd No. | Structure | NMR Data | LRMS Data |
| 1 | 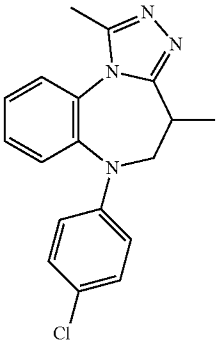 [SMILES: Cc1nnc2n1-c1ccccc1N(c1ccc(Cl)cc1)CC2C] | $^{1}H$ NMR (300 MHz, $CD_3OD$): δ 7.67-7.69 (m, 1H), 7.53-7.59 (m, 2H), 7.35-7.38 (m, 1H), 7.15-7.18 (m, 2H), 6.75-6.78 (m, 2H), 4.03-4.08 (m, 1H), 3.63 (t, J = 10.5 Hz, 1H), 3.16-3.25 (m, 1H), 2.71 (s, 3H), 1.55 (d, J = 6.6 Hz, 3H). | calcd 324.11; found 324 |
| 2 | 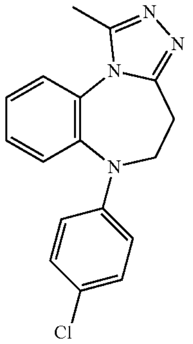 [SMILES: Cc1nnc2n1-c1ccccc1N(c1ccc(Cl)cc1)CC2] | $^{1}H$ NMR (300 MHz, $CD_3OD$): δ 7.54-7.51 (m, 1H), 7.40-7.37 (m, 2H), 7.24-7.20 (m, 1H), 7.03-7.00 (m, 2H), 6.61-6.58 (m, 2H), 3.83 (t, J = 6.6 Hz, 2H), 2.96 (s, 2H), 2.46 (s, 3H). | calcd: 310.10; found 310 |
| 3 | 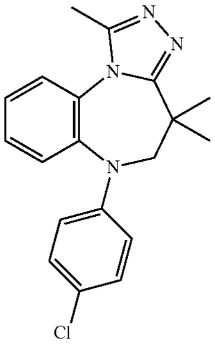 [SMILES: Cc1nnc2n1-c1ccccc1N(c1ccc(Cl)cc1)CC2(C)C] | $^{1}H$ NMR (300 MHz, $CD_3OD$): δ 7.61-7.64 (m, 1H), 7.50-7.53 (m, 2H), 7.28-7.31 (m, 1H), 7.09-7.12 (m, 2H), 6.68 (d, J = 9 Hz, 2H), 3.83 (s, 2H), 2.52 (s, 3H), 1.29 (s, 6H). | calcd 338.13, found 338; |
| 4 | 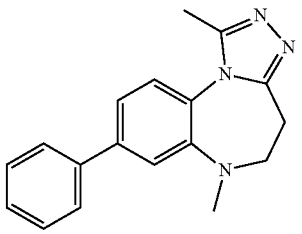 [SMILES: Cc1nnc2n1-c1ccc(-c3ccccc3)cc1N(C)CC2] | $^{1}H$ NMR (300 MHz, d6-DMSO): δ 7.39-7.51 (m, 5H), 7.71-7.74 (m, 2H), 7.53-7.56 (d, J = 8.4 Hz, 1H), 3.32-3.33 (m, 2H), 2.81-2.86 (m, 2H), 2.80 (s, 3H), 2.39 (s, 3H). | 290 m/z |
| 5 | 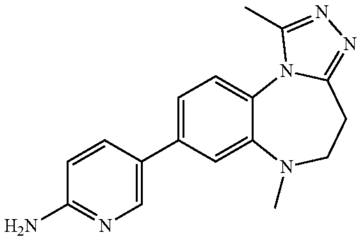 [SMILES: Cc1nnc2n1-c1ccc(-c3ccc(N)nc3)cc1N(C)CC2] | $^{1}H$ NMR (300 MHz, d6-DMSO): δ 8.30-8.31 (d, J = 2.4 Hz, 1H), 7.75-7.78 (m, 1H), 7.45-7.48 (d, J = 7.8 Hz, 1H), 7.33-7.38 (m, 2H), 6.52-6.55 (d, J = 8.7 Hz, 1H), 6.16-6.17 (m, 2H), 3.29-3.30 (m, 2H), 2.82-2.84 (m, 2H), 2.78 (s, 3H), 2.37 (s, 3H). | 306 m/z. |

TABLE 1-continued
| Exemplary Compounds<br>Compounds of the invention include the following: | | | |
|---|---|---|---|
| Cmpd No. | Structure | NMR Data | LRMS Data |
| 6 | 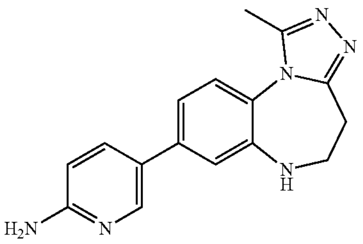 [SMILES: Cc1nnc2n1-c1ccc(-c3ccc(N)nc3)cc1NCC2] | $^1$H NMR (300 MHz, d6-DMSO): δ 8.20-8.21 (d, J = 2.4 Hz, 1H), 7.63-7.67 (m, 1H), 7.36-7.39 (d, J = 8.4 Hz, 1H), 7.27-7.28 (d, J = 2.1 Hz, 1H), 7.12-7.15 (m, 1H), 6.51-6.54 (d, J = 8.7 Hz, 1H), 5.58 (s, 1H), 3.50-3.53 (m, 2H), 2.90-2.94 (t, J = 6.3 Hz, 2H), 2.40 (s, 3H). | 292 m/z. |
| 7 | 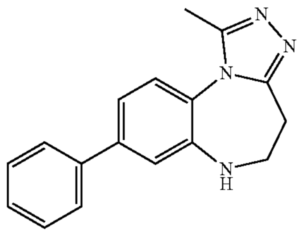 [SMILES: Cc1nnc2n1-c1ccc(-c3ccccc3)cc1NCC2] | $^1$H NMR (300 MHz, d6-DMSO): δ 7.61-7.63 (d, J = 7.8 Hz, 2H), 7.37-7.49 (m, 5H), 7.20-7.23 (m, 1H), 5.76 (s, 1H), 3.51-3.56 (m, 2H), 2.92-2.96 (t, J = 6.3 Hz, 2H), 2.41 (s, 3H). | 276 m/z. |
| 8 | 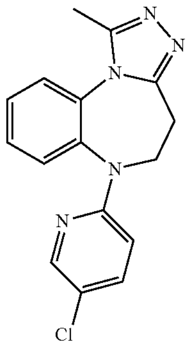 [SMILES: Cc1nnc2n1-c1ccccc1N(c1ccc(Cl)cn1)CC2] | $^1$H NMR (300 MHz, $CD_3OD$): δ 8.07 (s, 1H), 7.41-7.75 (m, 5H), 6.37 (d, J = 9.0 Hz, 1H), 4.08-4.71 (m, 2H), 3.01-3.12 (m, 2H), 2.55 (s, 3H). | 311 m/z. |
| 9 | 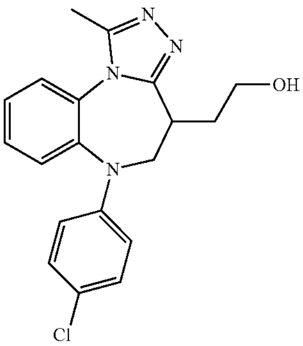 [SMILES: Cc1nnc2n1-c1ccccc1N(c1ccc(Cl)cc1)CC2CCO] | $^1$H NMR (300 MHz, $CD_3OD$): δ 7.61-7.69 (m, 1H), 7.49-7.58 (m, 2H), 7.34-7.41 (m, 1H), 7.09-7.18 (m, 2H), 6.72-6.83 (m, 2H), 4.02-4.07 (m, 1H), 3.64-3.80 (m, 3H), 3.21-3.26 (m, 1H), 2.59 (s, 3H), 2.32-2.44 (m, 1H), 1.96-2.09 (m, 1H). | 354 m/z. |

TABLE 1-continued
| Exemplary Compounds<br>Compounds of the invention include the following: | | | |
|---|---|---|---|
| Cmpd No. | Structure | NMR Data | LRMS Data |
| 10 | 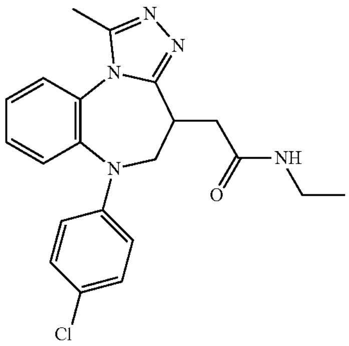 [SMILES: CCNC(=O)CC1CN(c2ccc(Cl)cc2)c2ccccc2-n2c(C)nnc21] | $^1$H NMR (300 MHz, $CDCl_3$): δ 7.44-7.52 (m, 3H), 7.33-7.35 (m, 1H), 7.14-7.17 (m, 2H), 6.83 (s, 1H), 6.61-6.64 (m, 2H), 4.06-4.07 (m, 1H), 3.68-3.69 (m, 2H), 2.24-3.27 (m, 3H), 2.69-2.73 (m, 4H), 1.14 (t, J = 7.5 Hz, 3H). | 395 m/z. |
| 11 | 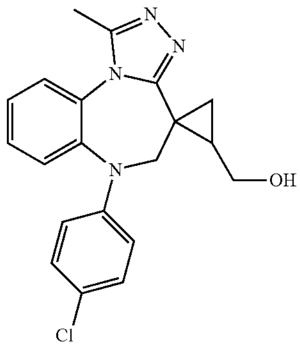 [SMILES: Cc1nnc2n1-c1ccccc1N(c1ccc(Cl)cc1)CC21CC1CO] | $^1$H NMR (300 MHz, $CD_3OD$): δ 7.48-7.51 (m, 1H), 7.38-7.41 (m, 2H), 7.23-7.25 (m, 1H), 7.00-7.03 (m, 2H), 6.58-6.61 (m, 2H), 4.47 (s, 2H), 2.89 (s, 1H), 2.75 (s, 1H), 2.44 (s, 3H), 0.60-0.81 (m, 3H), | 366 m/z. |
| 12 | 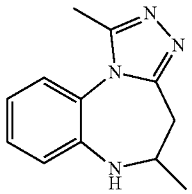 [SMILES: Cc1nnc2n1-c1ccccc1NC(C)C2] | $^1$H NMR (300 MHz, $CD_3OD$): δ 7.32-7.44 (m, 2H), 7.15-7.21 (m, 2H), 3.92-3.97 (m, 1H), 2.98-3.05 (m, 1H), 2.65-2.71 (m, 1H), 2.49 (s, 3H), 1.25 (d, J = 6.0 Hz, 3H). | 214 m/z. |
| 13 | 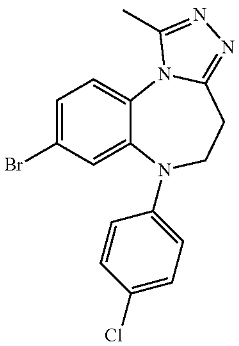 [SMILES: Cc1nnc2n1-c1ccc(Br)cc1N(c1ccc(Cl)cc1)CC2] | $^1$H NMR (300 MHz, $CD_3OD$): δ 7.61-7.64 (m, 1H), 7.54-7.57 (m, 1H), 7.43-7.44 (d, J = 2.1 Hz, 2H), 7.16-7.19 (m, 2H), 6.75-6.78 (m, 2H), 3.92-3.96 (t, J = 6.6 Hz, 2H), 3.07-3.11 (m, 2H), 2.60 (s, 3H). | 388 m/z. |

TABLE 1-continued
| Exemplary Compounds<br>Compounds of the invention include the following: | | | |
|---|---|---|---|
| Cmpd No. | Structure | NMR Data | LRMS Data |
| 14 | 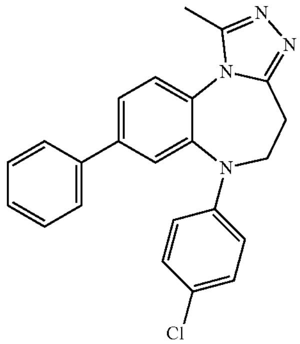 [SMILES: Cc1nnc2n1-c1ccc(-c3ccccc3)cc1N(c1ccc(Cl)cc1)CC2] | $^1$H NMR (300 MHz, $CD_3OD$): δ 7.70-7.72 (m, 2H), 7.51-7.54 (m, 3H), 7.36-7.44 (m, 3H), 7.12-7.16 (m, 2H), 6.75-6.78 (m, 2H), 3.95-4.00 (m, 2H), 3.11-3.13 (m, 2H), 2.60 (s, 3H). | 386 m/z. |
| 15 | 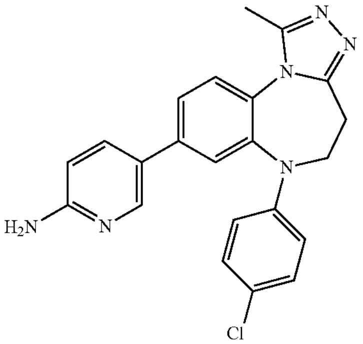 [SMILES: Cc1nnc2n1-c1ccc(-c3ccc(N)nc3)cc1N(c1ccc(Cl)cc1)CC2] | $^1$H NMR (300 MHz, $CD_3OD$): δ 8.09-8.21 (m, 2H), 7.66-7.76 (m, 3H), 7.48 (s, 1H), 7.13-7.16 (m, 2H), 6.67-6.79 (m, 3H), 3.96-4.00 (m, 2H), 3.09-3.14 (m, 2H), 2.59 (s, 3H). | 402 m/z. |
| 16 | 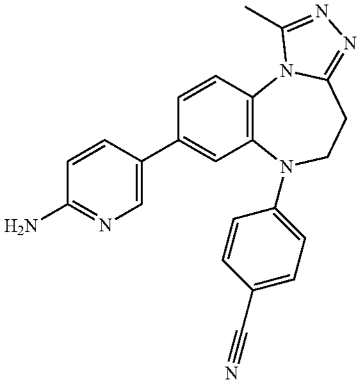 [SMILES: Cc1nnc2n1-c1ccc(-c3ccc(N)nc3)cc1N(c1ccc(C#N)cc1)CC2] | $^1$H NMR (300 MHz, $CD_3OD$): δ 8.16 (s, 1H), 7.85-7.71 (m, 3H), 7.60 (s, 1H), 7.50-7.44 (m, 2H), 6.82-6.79 (m, 2H), 6.72-6.64 (m, 1H), 4.10-4.06 (m, 2H), 3.13-3.11 (m, 2H), 2.58 (s, 3H). | calcd 393.17; found 393. |
| 17 | 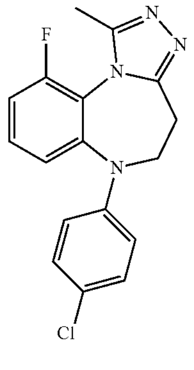 [SMILES: Cc1nnc2n1-c1c(F)cccc1N(c1ccc(Cl)cc1)CC2] | $^1$H NMR (400 MHz, d6-DMSO) δ 7.55 (dt, J = 6.44, 8.31 Hz, 1H), 7.46 (ddd, J = 1.25, 8.62, 10.08 Hz, 1H), 7.18-7.24 (m, 2H), 7.11-7.15 (m, 1H), 6.75-6.81 (m, 2H), 3.76-3.93 (m, 2H), 3.27 (dd, J = 4.78, 15.16 Hz, 1H), 2.82 (ddd, J = 7.06, 12.41, 15.01 Hz, 1H), 2.41 (d, J = 3.12 Hz, 3H). | m/z: 329 |

TABLE 1-continued

Exemplary Compounds
Compounds of the invention include the following:

| Cmpd No. | Structure | NMR Data | LRMS Data |
|---|---|---|---|
| 18 | 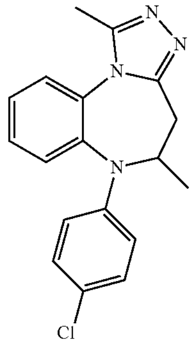 [SMILES: Cc1nnc2n1-c1ccccc1N(c1ccc(Cl)cc1)C(C)C2] | $^1$H NMR (400 MHz, d6-DMSO) δ 7.81 (dd, J = 3.43, 6.13 Hz, 1H), 7.58-7.65 (m, 2H), 7.41 (dd, J = 3.53, 5.61 Hz, 1H), 7.07-7.15 (m, 2H), 6.51 (d, J = 8.93 Hz, 2H), 4.51-4.63 (m, 1H), 3.36 (dd, J = 6.02, 14.96 Hz, 1H), 2.51-2.55 (m, 3H), 2.40 (dd, J = 11.11, 14.85 Hz, 1H), 1.28 (d, J = 6.02 Hz, 3H). | m/z: 325 |
| 19 | 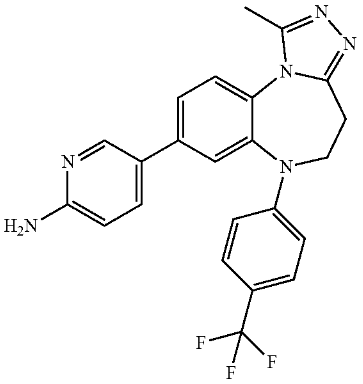 [SMILES: Cc1nnc2n1-c1ccc(-c3ccc(N)nc3)cc1N(c1ccc(C(F)(F)F)cc1)CC2] | $^1$H NMR (300 MHz, $CD_3OD$): δ 8.14 (s, 1H), 7.71-7.69 (m, 3H), 7.56 (s, 1H), 7.43-7.40 (m, 2H), 6.86-6.83 (m, 2H), 6.65-6.62 (m, 1H), 4.10-4.06 (m, 2H), 3.14-3.13 (m, 2H), 2.59 (s, 3H). | calcd 436.16; found 436. |
| 20 | 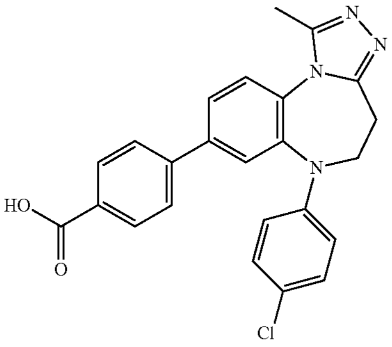 [SMILES: Cc1nnc2n1-c1ccc(-c3ccc(C(=O)O)cc3)cc1N(c1ccc(Cl)cc1)CC2] | $^1$H NMR (300 MHz, d6-DMSO): δ 13.04 (br. s, 1H), 8.00-7.98 (m, 2H), 7.82 (s, 2H), 7.76-7.73 (m, 2H), 7.62 (s, 1H), 7.19-7.16 (m, 2H), 6.76-6.73 (m, 2H), 3.92-3.90 (m, 2H), 3.04-3.03 (m, 2H), 2.52 (s, 3H). | calcd 430.12; found 430. |
| 21 | 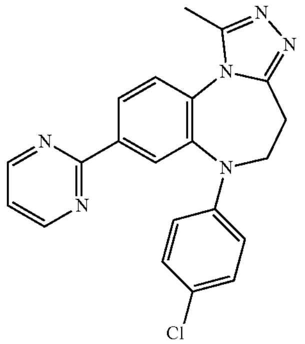 [SMILES: Cc1nnc2n1-c1ccc(-c3ncccn3)cc1N(c1ccc(Cl)cc1)CC2] | $^1$H NMR (300 MHz, $CD_3OD$): δ 8.78 (d, J = 4.8 Hz, 2H), 8.47-8.41 (m, 2H), 7.45 (d, J = 8.4 Hz, 2H), 7.12-7.10 (m, 2H), 6.67-6.63 (m, 2H), 3.99-3.95 (m, 2H), 3.15-3.11 (m, 2H), 2.61 (s, 3H). | calcd 388.12; found 388. |

TABLE 1-continued

Exemplary Compounds
Compounds of the invention include the following:

| Cmpd No. | Structure | NMR Data | LRMS Data |
|---|---|---|---|
| 22 | 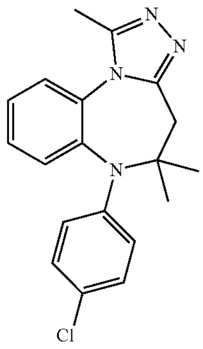 [SMILES: Cc1nnc2n1-c1ccccc1N(c1ccc(Cl)cc1)C(C)(C)C2] | $^1$H NMR (400 MHz, d6-DMSO) δ 7.62-7.71 (m, 1H), 7.39 (s, 2H), 7.17 (d, J = 8.93 Hz, 2H), 7.07-7.12 (m, 1H), 6.86 (d, J = 8.93 Hz, 2H), 2.72-2.89 (m, 2H), 2.57 (s, 3H), 1.42 (br. s., 6H). | m/z: 339. |
| 23 | 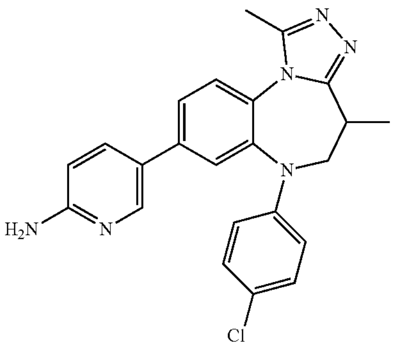 [SMILES: Cc1nnc2n1-c1ccc(-c3ccc(N)nc3)cc1N(c1ccc(Cl)cc1)CC2C] | $^1$H NMR (300 MHz, $CDCl_3$): δ 8.21 (s, 1H), 7.61-7.60 (m, 3H), 7.41 (s, 1H), 7.18 (d, J = 8.7 Hz, 2H), 6.71 (d, J = 8.7 Hz, 2H), 6.46 (d, J = 8.7 Hz, 1H), 6.19 (s, 2H), 4.02-3.98 (m, 1H), 3.51-3.46 (m, 1H), 3.13-3.05 (m, 1H), 2.49 (s, 3H), 1.41 (d, J = 6.9 Hz, 3H). | calcd 416.15; found 416. |
| 24 | 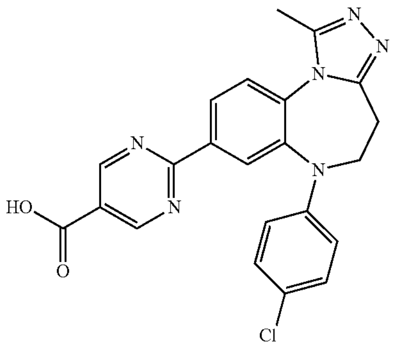 [SMILES: Cc1nnc2n1-c1ccc(-c3ncc(C(=O)O)cn3)cc1N(c1ccc(Cl)cc1)CC2] | $^1$H NMR (300 MHz, $CD_3OD$): δ 9.29 (s, 2H), 8.63 (d, J = 5.1 Hz, 1H), 8.51 (s, 1H), 7.83 (d, J = 8.4 Hz, 1H), 7.21 (d, J = 9.0 Hz, 2H), 6.84 (d, J = 9.0 Hz, 2H), 4.05 (t, J = 6.9 Hz, 2H), 3.21-3.15 (m, 2H), 2.67 (s, 3H). | calcd 432.11; found 432. |
| 25 | 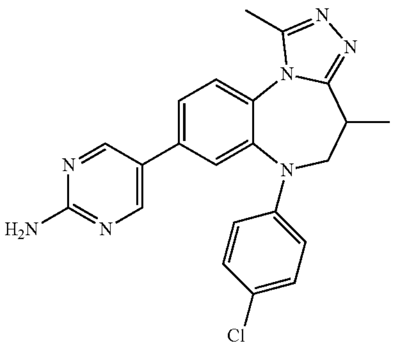 [SMILES: Cc1nnc2n1-c1ccc(-c3cnc(N)nc3)cc1N(c1ccc(Cl)cc1)CC2C] | $^1$H NMR (300 MHz, d6-DMSO): δ 8.55 (s, 2H), 7.74-7.73 (m, 2H), 7.56 (s, 1H), 7.17 (d, J = 9.0 Hz, 2H), 6.88 (s, 2H), 6.72 (d, J = 9.0 Hz, 2H), 3.98-3.93 (m, 1H), 3.56-3.48 (m, 1H), 3.05-3.01 (m, 1H), 2.49 (s, 3H), 1.41 (d, J = 6.0 Hz, 3H). | calcd 417.15; found 417. |

TABLE 1-continued

Exemplary Compounds
Compounds of the invention include the following:

| Cmpd No. | Structure | NMR Data | LRMS Data |
|---|---|---|---|
| 26 | 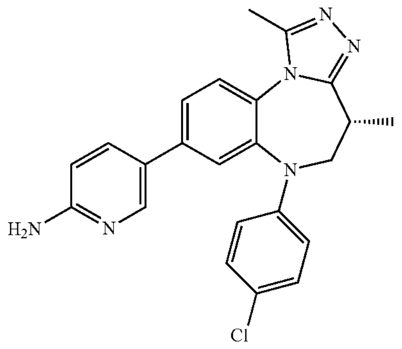 [SMILES: Cc1nnc2n1-c1ccc(-c3ccc(N)nc3)cc1N(c1ccc(Cl)cc1)C[C@H]2C] | $^1$H NMR (300 MHz, $CDCl_3$): δ 8.21 (s, 1H), 7.61-7.60 (m, 3H), 7.41 (s, 1H), 7.18 (d, J = 8.7 Hz, 2H), 6.71 (d, J = 8.7 Hz, 2H), 6.46 (d, J = 8.7 Hz, 1H), 6.19 (s, 2H), 4.02-3.98 (m, 1H), 3.51-3.46 (m, 1H), 3.13-3.05 (m, 1H), 2.49 (s, 3H), 1.41 (d, J = 6.9 Hz, 3H). | calcd 416.15; found 416. |
| 27 | 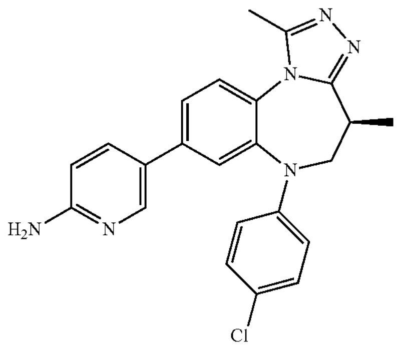 [SMILES: Cc1nnc2n1-c1ccc(-c3ccc(N)nc3)cc1N(c1ccc(Cl)cc1)C[C@@H]2C] | $^1$H NMR (300 MHz, $CDCl_3$): δ 8.21 (s, 1H), 7.61-7.60 (m, 3H), 7.41 (s, 1H), 7.18 (d, J = 8.7 Hz, 2H), 6.71 (d, J = 8.7 Hz, 2H), 6.46 (d, J = 8.7 Hz, 1H), 6.19 (s, 2H), 4.02-3.98 (m, 1H), 3.51-3.46 (m, 1H), 3.13-3.05 (m, 1H), 2.49 (s, 3H), 1.41 (d, J = 6.9 Hz, 3H). | calcd 416.15; found 416. |
| 28 | 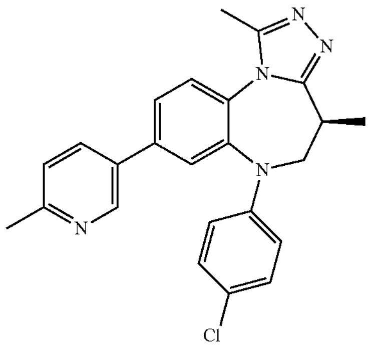 | $^1$H NMR (300 MHz, $CDCl_3$): δ 8.58 (s, 1H), 7.64-7.69 (m, 1H), 7.51-7.38 (m, 3H), 7.18-7.15 (m, 1H), 7.08 (d, J = 9.0 Hz, 2H), 6.63 (d, J = 9.0 Hz, 2H), 3.96-3.91 (m, 1H), 3.59-3.51 (m, 1H), 3.02-3.06 (m, 1H), 2.57 (s, 3H), 2.55 (s, 3H), 1.57 (d, J = 6.9 Hz, 3H). | calcd 415.16; found 415. |
| 29 | 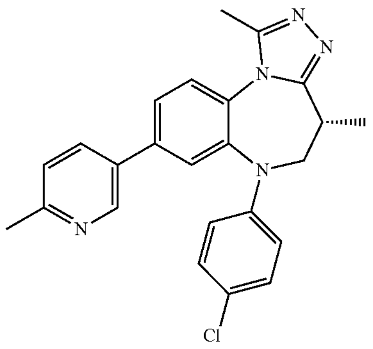 | $^1$H NMR (300 MHz, $CDCl_3$): δ 8.58 (s, 1H), 7.64-7.69 (m, 1H), 7.51-7.38 (m, 3H), 7.18-7.15 (m, 1H), 7.08 (d, J = 9.0 Hz, 2H), 6.63 (d, J = 9.0 Hz, 2H), 3.96-3.91 (m, 1H), 3.59-3.51 (m, 1H), 3.02-3.06 (m, 1H), 2.57 (s, 3H), 2.55 (s, 3H), 1.57 (d, J = 6.9 Hz, 3H). | calcd 415.16; found 415. |

TABLE 1-continued

Exemplary Compounds
Compounds of the invention include the following:

| Cmpd No. | Structure | NMR Data | LRMS Data |
|---|---|---|---|
| 30 | 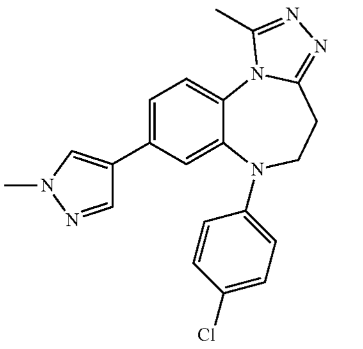 [SMILES: Cc1nnc2n1-c1ccc(-c3cnn(C)c3)cc1N(c1ccc(Cl)cc1)CC2] | $^1$H NMR (300 MHz, $CDCl_3$): δ 7.68 (s, 1H), 7.55 (s, 1H), 7.47-7.31 (m, 3H), 7.13 (d, J = 9.0 Hz, 2H), 6.65 (d, J = 9.0 Hz, 2H), 3.96-3.91 (m, 2H), 3.13-3.11 (m, 2H), 2.59 (s, 3H). | calcd 390.14; found 390. |
| 31 | 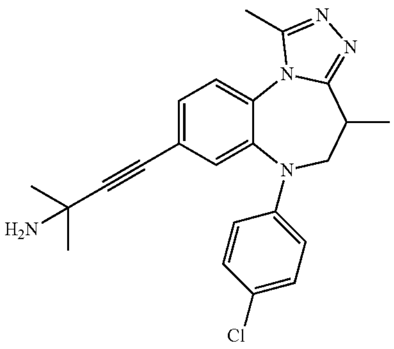 [SMILES: Cc1nnc2n1-c1ccc(C#CC(C)(C)N)cc1N(c1ccc(Cl)cc1)CC2C] | $^1$H NMR (300 MHz, $CDCl_3$): δ 7.42-7.27 (m, 3H), 7.14 (d, J = 8.4 Hz, 2H), 6.61 (d, J = 8.4 Hz, 2H), 5.90 (s, 2H), 3.93-3.88 (m, 1H), 3.58-3.51 (m, 1H), 3.03-2.94 (m, 1H), 2.56 (s, 3H), 1.58-1.56 (m, 9H). | calcd 405.17; found 405. |
| 32 | 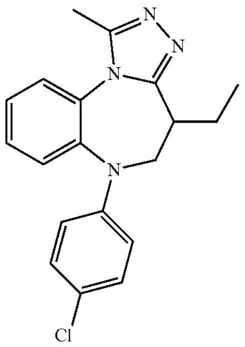 [SMILES: CCC1CN(c2ccc(Cl)cc2)c2ccccc2-n2c(C)nnc21] | $^1$H NMR (300 MHz, $CD_3OD$): δ 7.70-7.67 (m, 1H), 7.58-7.51 (m, 2H), 7.38-7.35 (m, 1H), 7.19-7.14 (m, 2H), 6.76-6.71 (m, 2H), 4.10-4.04 (m, 1H), 3.66-3.34 (m, 1H), 2.96-2.90 (m, 1H), 2.59 (s, 3H), 2.18-2.13 (m, 1H), 1.91-1.82 (m, 1H), 1.12-1.07 (m, 3H). | calcd 338.13; found 338. |
| 33 | 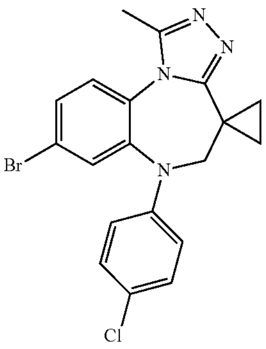 [SMILES: Cc1nnc2n1-c1ccc(Br)cc1N(c1ccc(Cl)cc1)CC21CC1] | $^1$H NMR (300 MHz, $CDCl_3$): δ 7.48 (dd, J = 8.4 Hz, J = 2.1 Hz, 1H), 7.41 (d, J = 1.8 Hz, 1H), 7.17-7.13 (m, 3H), 6.63-6.60 (m, 2H), 3.74-3.72 (m, 2H), 2.57 (s, 3H), 1.09-1.07 (m, 2H), 0.79-0.77 (m, 2H). | calcd 414.02; found 414. |

TABLE 1-continued

Exemplary Compounds
Compounds of the invention include the following:

| Cmpd No. | Structure | NMR Data | LRMS Data |
|---|---|---|---|
| 34 | 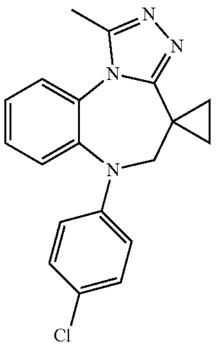 [SMILES: Cc1nnc2n1-c1ccccc1N(c1ccc(Cl)cc1)CC21CC1] | $^1$H NMR (300 MHz, $CDCl_3$): δ 7.40-7.37 (m, 2H), 7.31-7.26 (m, 2H), 7.12-7.09 (m, 2H), 6.60-6.57 (m, 2H), 3.78-3.75 (m, 2H), 2.60 (s, 3H), 1.07-1.04 (m, 2H), 0.75-0.73 (m, 2H). | calcd 336.11; found 336. |
| 35 | 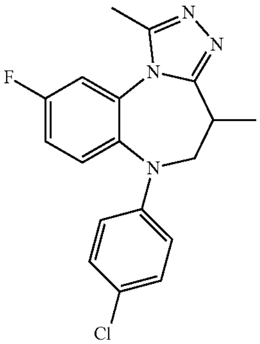 [SMILES: Cc1nnc2n1-c1cc(F)ccc1N(c1ccc(Cl)cc1)CC2C] | $^1$H NMR (300 MHz, $CDCl_3$) δ 7.32-7.26 (m, 1H), 7.16-7.05 (m, 4H), 6.59-6.54 (m, 2H), 3.93-3.88 (m, 1H), 3.60-3.53 (m, 1H), 3.05-2.96 (m, 1H), 2.59 (s, 3H), 1.59 (d, J = 6.9 Hz, 3H). | calcd 342.10; found 342. |
| 36 | 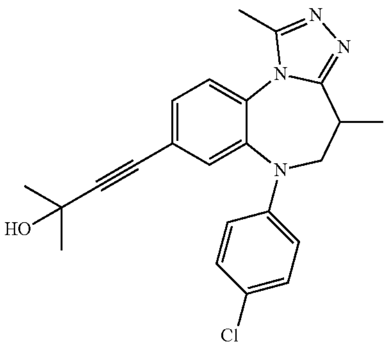 [SMILES: Cc1nnc2n1-c1ccc(C#CC(C)(C)O)cc1N(c1ccc(Cl)cc1)CC2C] | $^1$H NMR (300 MHz, $CDCl_3$): δ 7.39-7.34 (m, 3H), 7.14 (d, J = 8.4 Hz, 2H), 6.61 (d, J = 8.4 Hz, 2H), 3.91-3.88 (m, 1H), 3.58-3.50 (m, 1H), 3.01-2.97 (m, 1H), 2.57 (m, 3H), 1.59 (m, 9H). | calcd 406.16; found 406. |
| 37 | 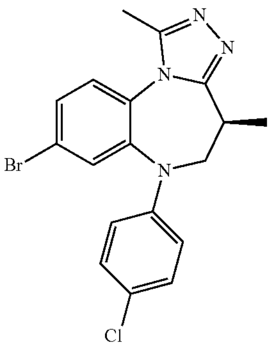 [SMILES: Cc1nnc2n1-c1ccc(Br)cc1N(c1ccc(Cl)cc1)C[C@@H]2C] | $^1$H NMR (300 MHz, $CD_3OD$): δ 7.59-7.40 (m, 3H), 7.15 (d, J = 8.7 Hz, 2H), 6.75 (d, J = 8.7 Hz, 2H), 4.04-3.98 (m, 1H), 3.54-3.47 (m, 1H), 3.14-3.05 (m, 1H), 2.55 (s, 3H), 1.49 (d, J = 6.9 Hz, 3H). | calcd 402.02; found 402. |

TABLE 1-continued

Exemplary Compounds

Compounds of the invention include the following:

| Cmpd No. | Structure | NMR Data | LRMS Data |
|---|---|---|---|
| 38 | 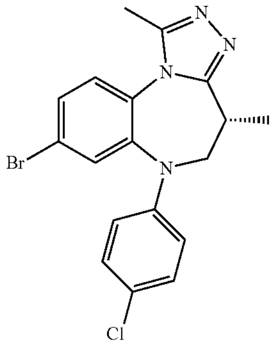 [SMILES: Cc1nnc2n1-c1ccc(Br)cc1N(c1ccc(Cl)cc1)C[C@H]2C] | $^1$H NMR (300 MHz, $CD_3OD$): δ 7.59-7.40 (m, 3H), 7.15 (d, J = 8.7 Hz, 2H), 6.75 (d, J = 8.7 Hz, 2H), 4.04-3.98 (m, 1H), 3.54-3.47 (m, 1H), 3.14-3.05 (m, 1H), 2.55 (s, 3H), 1.49 (d, J = 6.9 Hz, 3H). | calcd 402.02; found 402. |
| 39 | 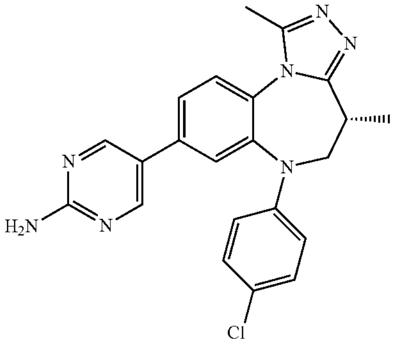 [SMILES: Cc1nnc2n1-c1ccc(-c3cnc(N)nc3)cc1N(c1ccc(Cl)cc1)C[C@H]2C] | $^1$H NMR (300 MHz, $CD_3OD$): δ 8.52 (s, 2H), 7.73-7.72 (m, 2H), 7.55 (s, 1H), 7.20 (d, J = 8.4 Hz, 2H), 6.80 (d, J = 8.4 Hz, 2H), 4.10-4.06 (m, 1H), 3.67-3.59 (m, 1H), 3.36-3.33 (m, 1H), 2.62 (s, 3H), 1.57 (d, J = 6.9 Hz, 3H). | calcd 417.15; found 417. |
| 40 | 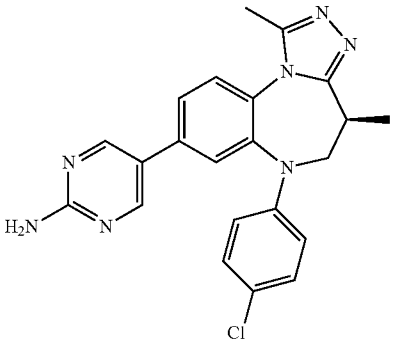 [SMILES: Cc1nnc2n1-c1ccc(-c3cnc(N)nc3)cc1N(c1ccc(Cl)cc1)C[C@@H]2C] | $^1$H NMR (300 MHz, $CD_3OD$): δ 8.52 (s, 2H), 7.73-7.72 (m, 2H), 7.55 (s, 1H), 7.20 (d, J = 8.4 Hz, 2H), 6.80 (d, J = 8.4 Hz, 2H), 4.10-4.06 (m, 1H), 3.67-3.59 (m, 1H), 3.36-3.33 (m, 1H), 2.62 (s, 3H), 1.57 (d, J = 6.9 Hz, 3H). | calcd 417.15; found 417. |
| 41 | 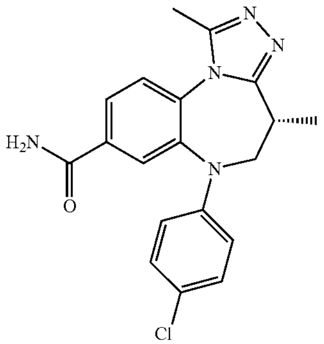 [SMILES: Cc1nnc2n1-c1ccc(C(N)=O)cc1N(c1ccc(Cl)cc1)C[C@H]2C] | $^1$H NMR (300 MHz, $CD_3OD$): δ 8.03-7.99 (m, 1H), 7.90 (s, 1H), 7.76 (d, J = 8.4 Hz, 1H), 7.20 (d, J = 9.3 Hz, 2H), 6.80 (d, J = 9 Hz, 2H), 4.11-4.05 (m, 1H), 3.65-3.58 (m, 1H), 3.19-3.13 (m, 1H), 2.63 (s, 3H), 1.56 (d, J = 6.9 Hz, 3H). | calcd 367.12; found 367. |

TABLE 1-continued

| Exemplary Compounds<br>Compounds of the invention include the following: | | | |
|---|---|---|---|
| Cmpd No. | Structure | NMR Data | LRMS Data |
| 42 | 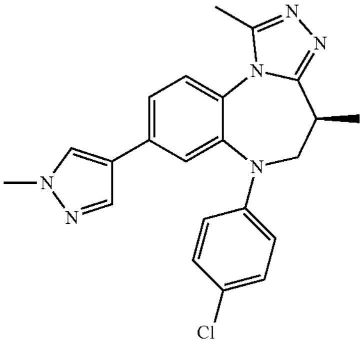 | $^1$H NMR (300 MHz, $CD_3OD$): δ 7.99 (s, 1H), 7.83 (s, 1H), 7.69-7.62 (m, 2H), 7.53-7.52 (m, 1H), 7.18 (d, J = 9 Hz, 2H), 6.78 (d, J = 9 Hz, 2H), 4.09-4.03 (m, 1H), 3.93 (s, 3H), 3.66-3.58 (m, 1H), 3.36-3.34 (m, 1H), 2.61 (s, 3H), 1.56 (d, J = 6.6 Hz, 3H). | calcd 404.15; found 404. |
| 43 | 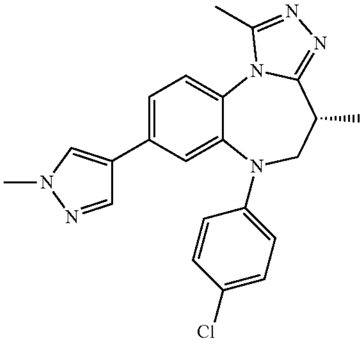 | $^1$H NMR (300 MHz, $CD_3OD$): δ 7.99 (s, 1H), 7.83 (s, 1H), 7.69-7.62 (m, 2H), 7.53-7.52 (m, 1H), 7.18 (d, J = 9 Hz, 2H), 6.78 (d, J = 9 Hz, 2H), 4.09-4.03 (m, 1H), 3.93 (s, 3H), 3.66-3.58 (m, 1H), 3.36-3.34 (m, 1H), 2.61 (s, 3H), 1.56 (d, J = 6.6 Hz, 3H). | calcd 404.15; found 404. |
| 44 | 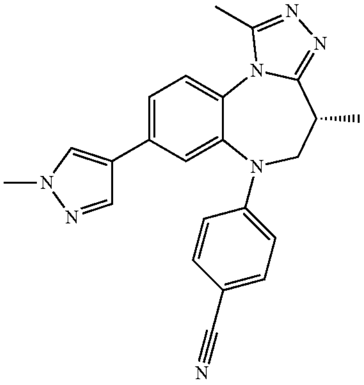 | $^1$H NMR (300 MHz, $CDCl_3$): δ 7.70 (s, 1H), 7.59-7.53 (m, 2H), 7.42-7.34 (m, 4H), 6.67 (d, J = 8.7 Hz, 2H), 3.98-3.93 (m, 4H), 3.72-3.65 (m, 1H), 3.13-3.05 (m, 1H), 2.56 (s, 3H), 1.59 (d, J = 6.6 Hz, 3H). | calcd 395.19; found 395. |
| 45 | 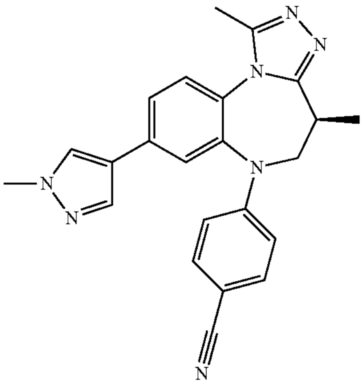 | $^1$H NMR (300 MHz, $CDCl_3$): δ 7.70 (s, 1H), 7.59-7.53 (m, 2H), 7.42-7.34 (m, 4H), 6.67 (d, J = 8.7 Hz, 2H), 3.98-3.93 (m, 4H), 3.72-3.65 (m, 1H), 3.13-3.05 (m, 1H), 2.56 (s, 3H), 1.59 (d, J = 6.6 Hz, 3H). | calcd 395.19; found 395. |

TABLE 1-continued

Exemplary Compounds

Compounds of the invention include the following:

| Cmpd No. | Structure | NMR Data | LRMS Data |
|---|---|---|---|
| 46 | 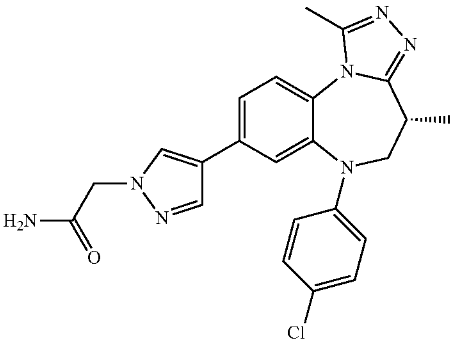 [SMILES: Cc1nnc2n1-c1ccc(-c3cnn(CC(N)=O)c3)cc1N(c1ccc(Cl)cc1)C[C@H]2C] | $^1$H NMR (300 MHz, $CDCl_3$): δ 7.82 (s, 1H), 7.69 (s, 1H), 7.48-7.45 (m, 1H), 7.39-7.34 (m, 2H), 7.14 (d, J = 9 Hz, 2H), 6.65 (d, J = 9 Hz, 2H), 6.23 (br, 1H), 5.48 (br, 1H), 4.83 (s, 2H), 3.98-3.93 (m, 1H), 3.63-3.55 (m, 1H), 3.11-3.03 (m, 1H), 2.62 (s, 3H), 1.60 (d, J = 6.9 Hz, 3H). | calcd 447.16; found 447. |
| 47 | 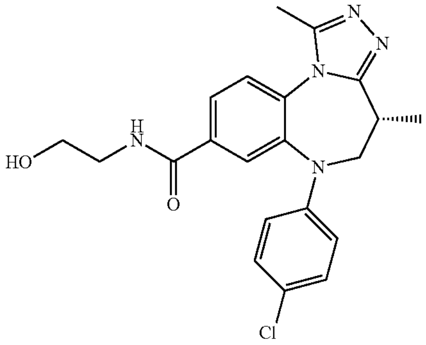 [SMILES: Cc1nnc2n1-c1ccc(C(=O)NCCO)cc1N(c1ccc(Cl)cc1)C[C@H]2C] | $^1$H NMR (300 MHz, $CD_3OD$): δ 7.96-7.92 (m, 1H), 7.83-7.82 (m, 1H), 7.72 (d, J = 8.1 Hz, 1H), 7.16 (d, J = 9 Hz, 2H), 6.76-6.73 (m, 2H), 4.07-4.01 (m, 1H), 3.70-3.66 (m, 2H), 3.60-3.56 (m, 1H), 3.49-3.45 (m, 2H), 3.32-3.26 (m, 1H), 2.59 (s, 3H), 1.52 (d, J = 6.9 Hz, 3H). | calcd 411.15; found 411. |
| 48 | 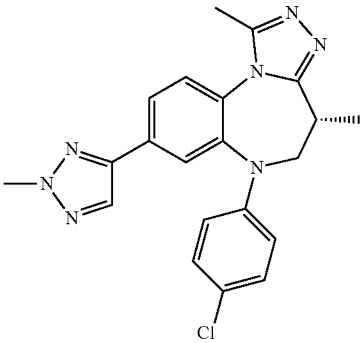 | $^1$H NMR (300 MHz, $CDCl_3$): δ 7.76-7.71 (m, 3H), 7.38 (d, J = 8.4 Hz, 1H), 7.13 (d, J = 9.0 Hz, 2H), 6.64 (d, J = 9.0 Hz, 2H), 4.21 (s, 3H), 3.98-3.93 (m, 1H), 3.62-3.55 (m, 1H), 3.09-3.01 (m, 1H), 2.59 (s, 3H), 1.59 (d, J = 6.6 Hz, 3H). | calcd 405.15; found 405. |
| 49 | 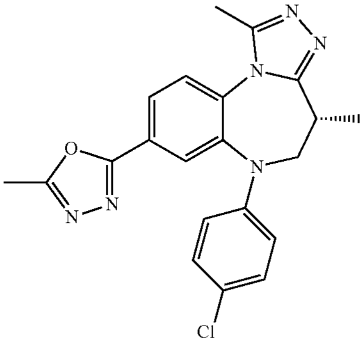 | $^1$H NMR (300 MHz, $CD_3OD$): δ 8.11-8.07 (m, 1H), 7.91 (s, 1H), 7.82 (d, J = 8.4 Hz, 1H), 7.18 (d, J = 8.7 Hz, 2H), 6.81 (d, J = 9 Hz, 2H), 4.11-4.06 (m, 1H), 3.62-3.54 (m, 1H), 3.29-3.21 (m, 1H), 2.61 (s, 3H), 2.59 (s, 3H), 1.54 (d, J = 6.9 Hz, 3H). | calcd. 406.13; found 406. |

TABLE 1-continued

Exemplary Compounds
Compounds of the invention include the following:

| Cmpd No. | Structure | NMR Data | LRMS Data |
|---|---|---|---|
| 50 | 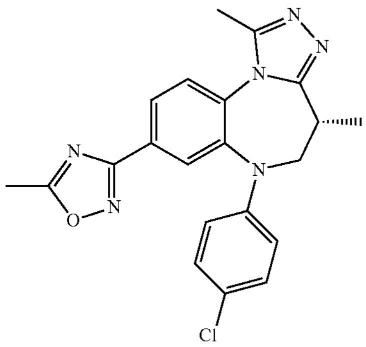 | $^1$H NMR (300 MHz, $CD_3OD$): δ 8.13-8.09 (m, 1H), 7.95 (s, 1H), 7.77 (d, J = 8.1 Hz, 1H), 7.19-7.16 (m, 2H), 6.81-6.78 (m, 2H), 4.10-4.05 (m, 1H), 3.62-3.54 (m, 1H), 3.30-3.25 (m, 1H), 2.63 (s, 3H), 2.61 (s, 3H), 1.54 (d, J = 6.9 Hz, 3H). | calcd. 406.13; found 406. |
| 51 | 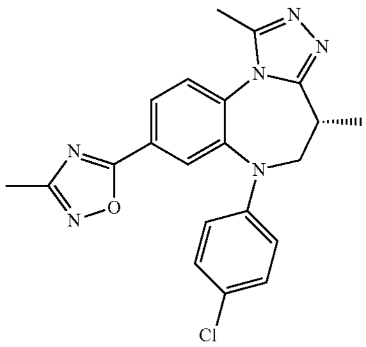 | $^1$H NMR (300 MHz, $CD_3OD$): δ 8.17-8.14 (m, 1H), 8.00 (s, 1H), 7.84 (d, J = 8.4 Hz, 1H), 7.19 (d, J = 9 Hz, 2H), 6.82 (d, J = 9 Hz, 2H), 4.10-4.05 (m, 1H), 3.62-3.54 (m, 1H), 3.30-3.25 (m, 1H), 2.62 (s, 3H), 2.41 (s, 3H), 1.54 (d, J = 6.9 Hz, 3H). | calcd. 406.13; found 406. |
| 52 | 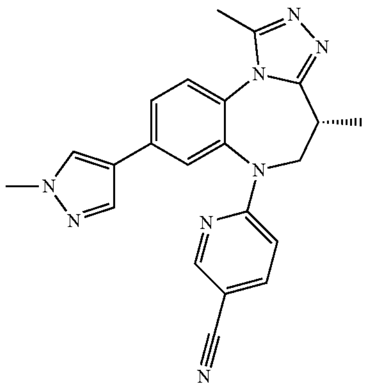 | $^1$H NMR (300 MHz, $CDCl_3$): δ 8.45-8.44 (m, 1H), 7.75 (s, 1H), 7.65-7.62 (m, 2H), 7.51-7.40 (m, 3H), 6.27 (d, J = 9.0 Hz, 1H), 4.62-4.55 (m, 1H), 3.96 (s, 3H), 3.89-3.84 (m, 1H), 3.09-3.05 (m, 1H), 2.55 (s, 3H), 1.61 (d, J = 6.3 Hz, 3H). | calcd 396.18; found 396. |
| 53 | 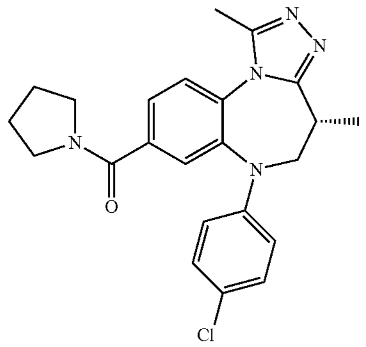 [SMILES: Cc1nnc2n1-c1ccc(C(=O)N3CCCC3)cc1N(c1ccc(Cl)cc1)C[C@H]2C] | $^1$H NMR (300 MHz, $CDCl_3$): δ 7.54-7.34 (m, 3H), 7.13 (d, J = 9.0 Hz, 2H), 6.63 (d, J = 9.0 Hz, 2H), 3.96-3.90 (m, 1H), 3.62-3.44 (m, 3H), 3.38-3.26 (m, 2H), 3.04-2.96 (m, 1H), 2.58 (s, 3H), 1.97-1.87 (m, 4H), 1.58 (d, J = 6.6 Hz, 3H). | calcd 421.17; found 421. |

TABLE 1-continued

Exemplary Compounds
Compounds of the invention include the following:

| Cmpd No. | Structure | NMR Data | LRMS Data |
|---|---|---|---|
| 54 | 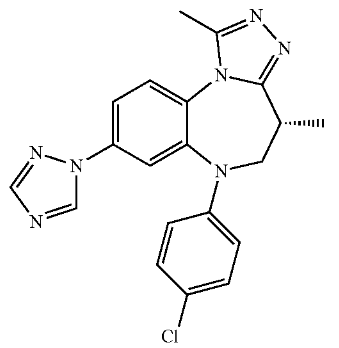 [SMILES: Cc1nnc2n1-c1ccc(-n3cncn3)cc1N(c1ccc(Cl)cc1)C[C@H]2C] | $^1$H NMR (300 MHz, $CDCl_3$): δ 8.52 (s, 1H), 8.10 (s, 1H), 7.71-7.66 (m, 2H), 7.54-7.51 (m, 1H), 7.17 (d, J = 8.7 Hz, 2H), 6.70 (d, J = 9 Hz, 2H), 4.04-3.99 (m, 1H), 3.64-3.57 (m, 1H), 3.11-3.07 (m, 1H), 2.66 (s, 3H), 1.62 (d, J = 6.6 Hz, 3H). | calcd 391.13; found 391. |
| 55 | 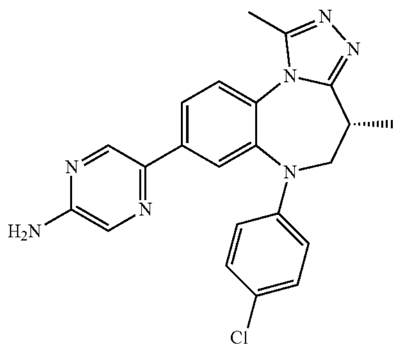 [SMILES: Cc1nnc2n1-c1ccc(-c3cnc(N)cn3)cc1N(c1ccc(Cl)cc1)C[C@H]2C] | $^1$H NMR (300 MHz, $CDCl_3$): δ 8.35 (s, 1H), 8.02 (s, 1H), 7.83-7.81 (m, 2H), 7.43-7.41 (m, 1H), 7.12 (d, J = 9.0 Hz, 2H), 6.64 (d, J = 9.0 Hz, 2H), 4.78 (s, 2H), 3.99-3.94 (m, 1H), 3.64-3.56 (m, 1H), 3.08-3.06 (m, 1H), 2.62 (s, 3H), 1.61-1.59 (d, J = 6.0 Hz, 3H). | calcd 417.15; found 417. |
| 56 | 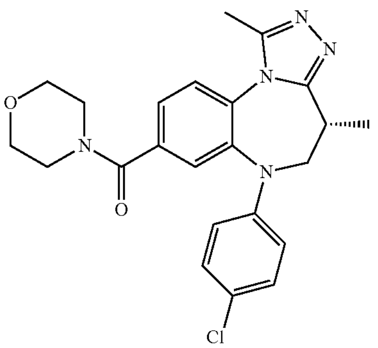 [SMILES: Cc1nnc2n1-c1ccc(C(=O)N3CCOCC3)cc1N(c1ccc(Cl)cc1)C[C@H]2C] | $^1$H NMR (300 MHz, $CDCl_3$): δ 7.41-7.31 (m, 3H), 7.14 (d, J = 9.0 Hz, 2H), 6.64 (d, J = 9.0 Hz, 2H), 3.98-3.93 (m, 1H), 3.76-3.30 (m, 9H), 3.06-2.98 (m, 1H), 2.60 (s, 3H), 1.59 (d, J = 6.6 Hz, 3H). | calcd 437.16; found 437. |
| 58 | 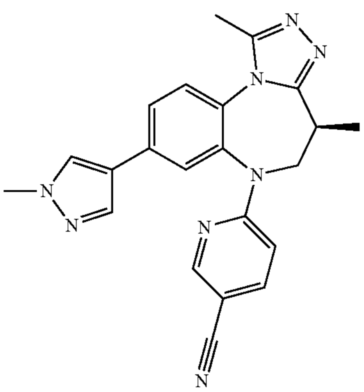 | $^1$H NMR (300 MHz, $CDCl_3$): δ 8.45-8.44 (m, 1H), 7.75 (s, 1H), 7.65-7.62 (m, 2H), 7.51-7.40 (m, 3H), 6.27 (d, J = 9.0 Hz, 1H), 4.62-4.55 (m, 1H), 3.96 (s, 3H), 3.89-3.84 (m, 1H), 3.09-3.05 (m, 1H), 2.55 (s, 3H), 1.61 (d, J = 6.3 Hz, 3H). | calcd 396.18; found 396. |

TABLE 1-continued

| Exemplary Compounds<br>Compounds of the invention include the following: | | | |
|---|---|---|---|
| Cmpd No. | Structure | NMR Data | LRMS Data |
| 59 | 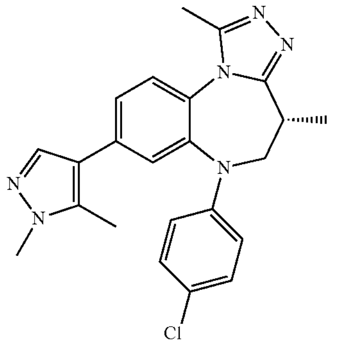 [SMILES: Cc1c(-c2ccc3c(c2)N(c2ccc(Cl)cc2)C[C@@H](C)c2nnc(C)n2-3)cnn1C] | $^1H$ NMR (300 MHz, $CDCl_3$): δ 7.50 (s, 1H), 7.35 (s, 2H), 7.25 (s, 1H), 7.13 (d, J = 8.1 Hz, 2H), 6.68 (d, J = 11.4 Hz, 2H), 3.97-3.92 (m, 1H), 3.84 (s, 3H), 3.63-3.55 (m, 1H), 3.14-3.09 (m, 1H), 2.62 (s, 3H), 2.30 (s, 3H), 1.61 (d, J = 1.2 Hz, 3H). | calcd 418.17; found 418. |
| 60 | 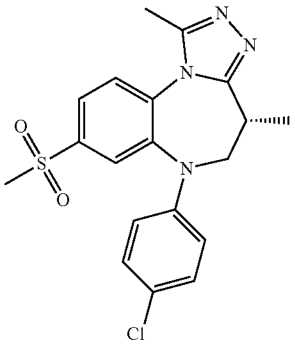 | $^1H$ NMR (300 MHz, $CDCl_3$): δ 7.91-7.88 (m, 2H), 7.53-7.50 (m, 1H), 7.18-7.15 (m, 2H), 6.68-6.64 (m, 2H), 4.04-3.99 (m, 1H), 3.62-3.54 (m, 1H), 3.08-2.97 (m, 4H), 2.59 (s, 3H), 1.60 (d, J = 6.9 Hz, 3H). | calcd 402.09; found 402. |
| 61 | 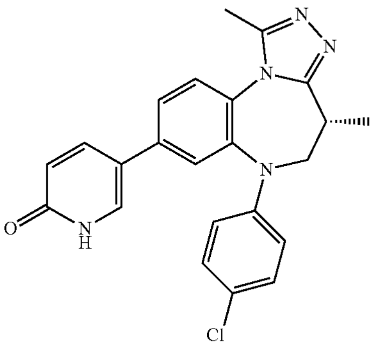 [SMILES: Cc1nnc2n1-c1ccc(-c3ccc(=O)[nH]c3)cc1N(c1ccc(Cl)cc1)C[C@H]2C] | $^1H$ NMR (300 MHz, $CDCl_3$): δ 7.68-7.64 (m, 1H), 7.54-7.53 (m, 1H), 7.41 (s, 2H), 7.36 (s, 1H), 7.17 (d, J = 9 Hz, 2H), 6.71-6.66 (m, 3H), 4.00-3.95 (m, 1H), 3.64-3.57 (m, 1H), 3.14-3.06 (m, 1H), 2.64 (s, 3H), 1.62 (d, J = 6 Hz, 3H). | calcd 417.14, found 417 |
| 62 | 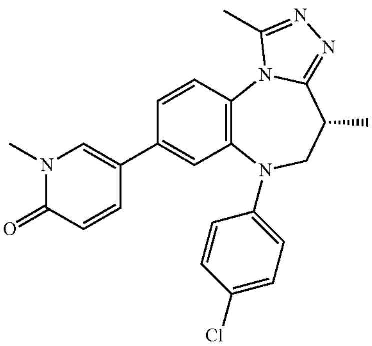 [SMILES: Cc1nnc2n1-c1ccc(-c3ccc(=O)n(C)c3)cc1N(c1ccc(Cl)cc1)C[C@H]2C] | $^1H$ NMR (300 MHz, $CDCl_3$): δ 7.53-7.49 (m, 1H), 7.46-7.45 (m, 1H), 7.40 (s, 2H), 7.34 (s, 1H), 7.16 (d, J = 9 Hz, 2H), 6.69-6.65 (m, 3H), 3.99-3.94 (m, 1H), 3.64-3.57 (m, 1H), 3.62 (s, 3H), 3.09-3.05 (m, 1H), 2.64 (s, 3H), 1.61 (d, J = 6 Hz, 3H). | calcd 431.15, found 431 |

TABLE 1-continued

| Cmpd No. | Structure | NMR Data | LRMS Data |
|---|---|---|---|
| | Exemplary Compounds Compounds of the invention include the following: | | |
| 63 | 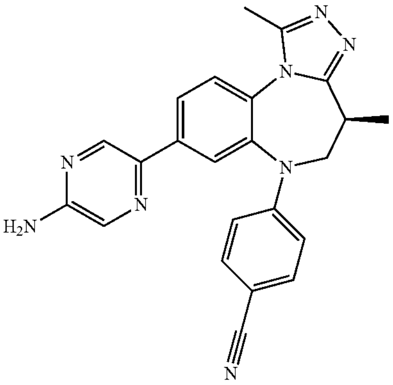 [SMILES: Cc1nnc2n1-c1ccc(-c3cnc(N)cn3)cc1N(c1ccc(C#N)cc1)C[C@@H]2C] | $^1$H NMR (300 MHz, $CD_3OD$) δ 8.41 (s, 1H), 8.10 (d, J = 8.4 Hz, 1H), 8.00 (dd, J = 1.6, 6.6 Hz, 2H), 7.72 (d, J = 8.4 Hz, 1H), 7.47 (d, J = 9.0 Hz, 2H), 6.82 (d, J = 9.0 Hz, 2H), 4.11-4.05 (m, 1H), 3.80-3.73 (m, 1H), 3.35-3.30 (m, 1H), 2.60 (s, 3H), 1.55 (d, J = 3.9 Hz, 3H). | cald. 408; found 408. |
| 64 | 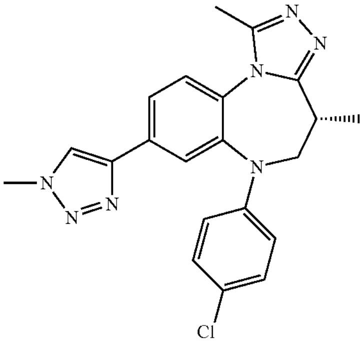 | $^1$H NMR (400 MHz, $CDCl_3$): δ 7.86-7.82 (m, 1H), 7.74-7.72 (m, 2H), 7.38 (m, J = 10.8 Hz, 1H), 7.12-7.09 (m, 2H), 6.67-6.63 (m, 2H), 4.14 (s, 3H), 3.97-3.92 (m, 1H), 3.54-3.61 (m, 1H), 3.09-3.01 (m, 1H), 2.59 (s, 3H), 1.59 (d, J = 7.2 Hz, 3H). | calcd 405.15; found 405. |
| 65 | 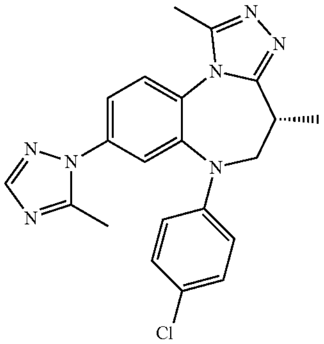 [SMILES: Cc1ncnn1-c1ccc2c(c1)N(c1ccc(Cl)cc1)C[C@@H](C)c1nnc(C)n1-2] | $^1$H NMR (300 MHz, $CDCl_3$): δ 7.92 (s, 1H), 7.49-7.48 (m, 3H), 7.19-7.15 (m, 2H), 6.73-6.69 (m, 2H), 4.02-3.99 (m, 1H), 3.63-3.55 (m, 1H), 3.13-3.06 (m, 1H), 2.62 (s, 3H), 2.51 (s, 3H), 1.62 (d, J = 6.9 Hz, 3H). | calcd 405.15; found 405 |
| 66 | 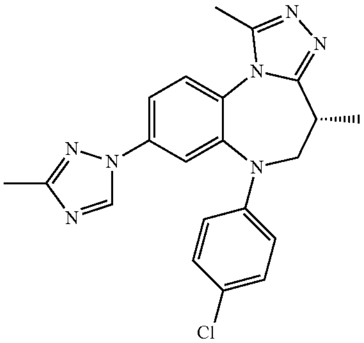 | $^1$H NMR (300 MHz, $CDCl_3$): δ 8.39 (s, 1H), 7.65-7.62 (m, 2H), 7.46-7.44 (m, 1H), 7.18-7.15 (m, 2H), 6.69-6.66 (m, 2H), 4.01-3.96 (m, 1H), 3.63-3.55 (m, 1H), 3.08-3.05 (m, 1H), 2.60 (s, 3H), 2.47 (s, 3H), 1.61 (d, J = 6.9 Hz, 3H). | calcd 405.15; found 405 |

TABLE 1-continued

Exemplary Compounds
Compounds of the invention include the following:

| Cmpd No. | Structure | NMR Data | LRMS Data |
|---|---|---|---|
| 67 | 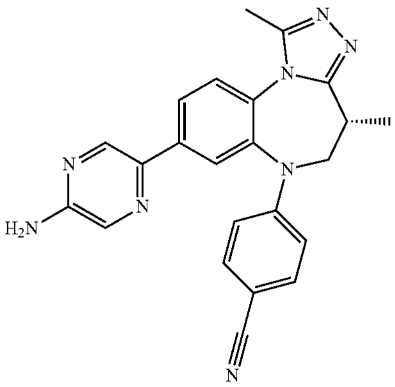 [SMILES: Cc1nnc2n1-c1ccc(-c3cnc(N)cn3)cc1N(c1ccc(C#N)cc1)C[C@H]2C] | $^{1}H$ NMR (300 MHz, $CD_3OD$) δ 8.41 (s, 1H), 8.10 (d, J = 8.4 Hz, 1H), 8.00 (dd, J = 1.6, 6.6 Hz, 2H), 7.72 (d, J = 8.4 Hz, 1H), 7.47 (d, J = 9.0 Hz, 2H), 6.82 (d, J = 9.0 Hz, 2H), 4.11-4.05 (m, 1H), 3.80-3.73 (m, 1H), 3.35-3.30 (m, 1H), 2.60 (s, 3H), 1.55 (d, J = 3.9 Hz, 3H). | |
| 68 | 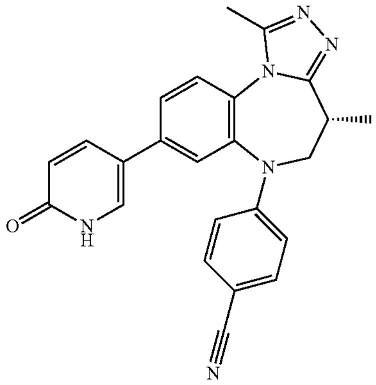 [SMILES: Cc1nnc2n1-c1ccc(-c3ccc(=O)[nH]c3)cc1N(c1ccc(C#N)cc1)C[C@H]2C] | $^{1}H$ NMR (300 MHz, $CDCl_3$): δ 7.73-7.70 (m, 1H), 7.63 (m, 1H), 7.55-7.45 (m, 5H), 6.73-6.71 (m, 3H ), 4.02-3.99 (m, 1H), 3.76-3.73 (m, 1H), 3.14-3.12 (m, 1H), 2.64 (s, 3H), 1.65 (d, J = 6 Hz, 3H). | calcd 408.17, found 408 |
| 69 | 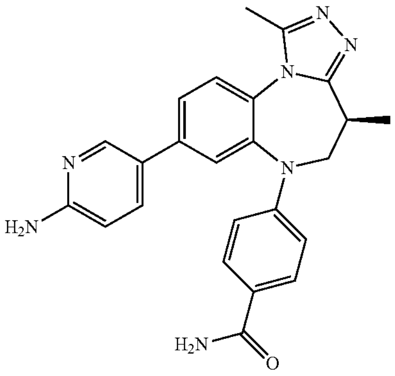 [SMILES: Cc1nnc2n1-c1ccc(-c3ccc(N)nc3)cc1N(c1ccc(C(N)=O)cc1)C[C@@H]2C] | $^{1}H$ NMR (300 MHz, d6-DMSO): δ 8.23 (s, 1H), 7.75-7.64 (m, 5H), 7.51 (s, 1H), 7.04 (br, 1H), 6.71 (d, J = 8.7 Hz, 2H), 6.50 (d, J = 8.7 Hz, 1H), 6.18 (br, 2H), 4.02-3.98 (m, 1H), 3.67-3.60 (m, 1H), 3.13-3.05 (m, 1H), 2.49 (s, 3H), 1.44 (d, J = 6.6 Hz, 3H). | calcd 425.20; found 425. |
| 70 | 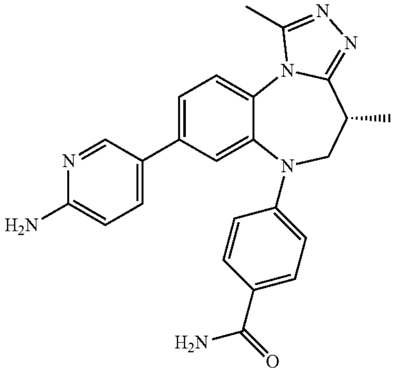 [SMILES: Cc1nnc2n1-c1ccc(-c3ccc(N)nc3)cc1N(c1ccc(C(N)=O)cc1)C[C@H]2C] | $^{1}H$ NMR (300 MHz, d6-DMSO): δ 8.23 (s, 1H), 7.75-7.64 (m, 5H), 7.51 (s, 1H), 7.04 (br, 1H), 6.71 (d, J = 8.7 Hz, 2H), 6.50 (d, J = 8.7 Hz, 1H), 6.18 (br, 2H), 4.02-3.98 (m, 1H), 3.67-3.60 (m, 1H), 3.13-3.05 (m, 1H), 2.49 (s, 3H), 1.44 (d, J = 6.6 Hz, 3H). | |

TABLE 1-continued

Exemplary Compounds
Compounds of the invention include the following:

| Cmpd No. | Structure | NMR Data | LRMS Data |
|---|---|---|---|
| 71 | 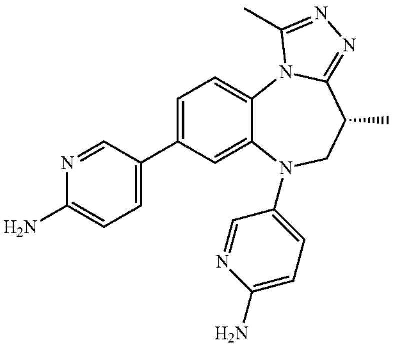 [SMILES: Cc1nnc2n1-c1ccc(-c3ccc(N)nc3)cc1N(c1ccc(N)nc1)C[C@H]2C] | $^1$H NMR (300 MHz, CDCl3): δ 8.14-8.13 (m, 1H), 7.60-7.49 (m, 3H), 7.20-7.19 (m, 1H), 7.98 (dd, J = 3.0 Hz, 9.0 Hz, 1H), 6.49 (d, J = 8.7 Hz, 1H), 6.38 (d, J = 11.7 Hz, 1H), 6.17 (s, 2H), 5.76 (s, 2H), 4.03-3.98 (m, 1H), 3.33 (d, J = 8.4 Hz, 1H), 3.04-2.98 (m, 1H), 2.50 (s, 3H), 1.41 (d, J = 6.6 Hz, 3H). | calcd 398.2; found 398. |
| 72 | 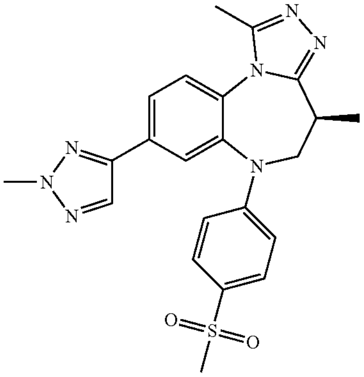 | $^1$H NMR (400 MHz, $CDCl_3$): δ 7.87-7.80 (m, 3H), 7.69 (d, J = 6.6 Hz, 2H), 7.45 (d, J = 6 Hz, 1H), 6.74 (d, J = 6 Hz, 2H), 4.23 (s, 3H), 4.03-3.99 (m, 1H), 3.76-3.70 (m, 1H), 3.13-3.07 (m, 1H), 2.99 (s, 3H), 2.59 (s, 3H), 1.61 (d, J = 5.1 Hz, 3H). | calcd 449.16; found 449. |
| 73 | 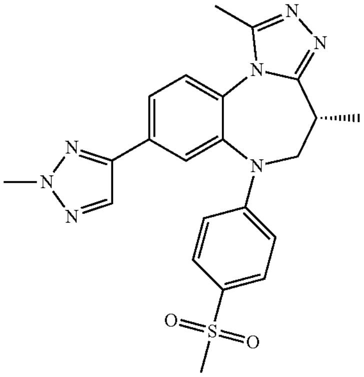 | $^1$H NMR (400 MHz, $CDCl_3$): δ 7.87-7.80 (m, 3H), 7.69 (d, J = 6.6 Hz, 2H), 7.45 (d, J = 6 Hz, 1H), 6.74 (d, J = 6 Hz, 2H), 4.23 (s, 3H), 4.03-3.99 (m, 1H), 3.76-3.70 (m, 1H), 3.13-3.07 (m, 1H), 2.99 (s, 3H), 2.59 (s, 3H), 1.61 (d, J = 5.1 Hz, 3H). | |
| 74 | 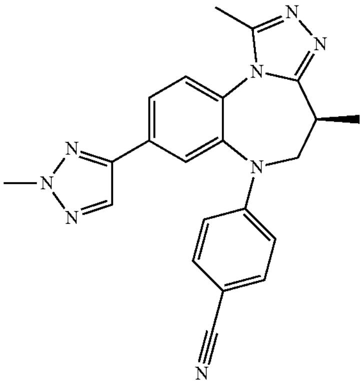 | $^1$H NMR (400 MHz, $CDCl_3$): δ 7.86-7.78 (m, 3H), 7.46-7.41 (m, 3H), 6.67 (d, J = 9.2 Hz, 2H), 4.22 (s, 3H), 3.99-3.95 (m, 1H), 3.70 (t, J = 11.2 Hz, 1H), 3.11-3.05 (m, 1H), 2.59 (s, 3H), 1.60 (d, J = 6.8 Hz, 3H). | calcd 396.2; found 396. |

TABLE 1-continued

Exemplary Compounds
Compounds of the invention include the following:

| Cmpd No. | Structure | NMR Data | LRMS Data |
|---|---|---|---|
| 75 | 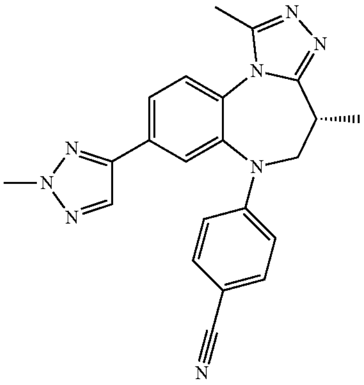 | $^1$H NMR (400 MHz, $CDCl_3$): δ 7.86-7.78 (m, 3H), 7.46-7.41 (m, 3H), 6.67 (d, J = 9.2 Hz, 2H), 4.22 (s, 3H), 3.99-3.95 (m, 1H), 3.70 (t, J = 11.2 Hz, 1H), .11-3.05 (m, 1H), 2.59 (s, 3H), 1.60 (d, J = 6.8 Hz, 3H). | |
| 76 | 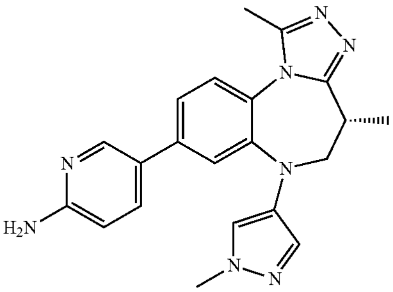 [SMILES: Cc1nnc2n1-c1ccc(-c3ccc(N)nc3)cc1N(c1cnn(C)c1)C[C@H]2C] | $^1$H NMR (400 MHz, $CDCl_3$): δ 8.15 (s, 1H), 7.62 (dd, J = 2.4 Hz, 8.8 Hz, 1H), 7.54 (d, J = 2.0 Hz, 1H), 7.37-7.36 (m, 1H), 7.34-7.31 (m, 1H), 7.12 (s, 1H), 7.05 (s, 1H), 6.62 (d, J = 8.8 Hz, 1H), 5.35 (s, 2H), 3.84-3.78 (m, 4H), 3.50-3.45 (m, 1H), 3.10-3.04 (m, 1H), 2.59 (s, 3H), 1.57 (d, J = 6.8 Hz, 3H). | calcd 386.20; found 386. |
| 77 | 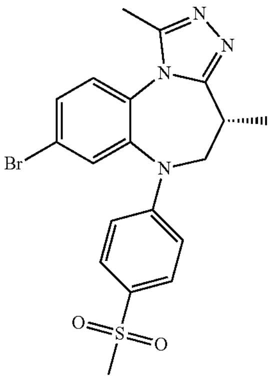 [SMILES: Cc1nnc2n1-c1ccc(Br)cc1N(c1ccc(S(C)(=O)=O)cc1)C[C@H]2C] | $^1$H NMR (400 MHz, $CDCl_3$): δ 7.71 (d, J = 9.2 Hz, 2H), 7.62-7.60 (m, 1H), 7.52 (s, 1H), 7.29-7.26 (m, 1H), 6.75-6.71 (m, 2H), 4.00-3.96 (m, 1H), 3.70-3.65 (m, 1H), 3.08-3.02 (m, 1H), 2.97 (s, 3H), 2.57 (s, 3H), 1.60 (d, J = 6.8 Hz, 3H). | calcd. 446.04, found 446.8. |
| 78 | 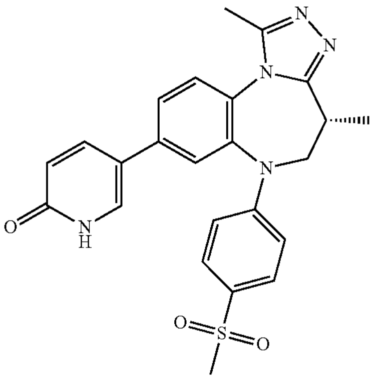 [SMILES: Cc1nnc2n1-c1ccc(-c3ccc(=O)[nH]c3)cc1N(c1ccc(S(C)(=O)=O)cc1)C[C@H]2C] | $^1$H NMR (400 MHz, $CDCl_3$): δ 7.70-7.66 (m, 3H), 7.63 (m, 1H), 7.54-7.51 (m, 1H), 7.44 (m, 2H), 6.74 (d, J = 8.8 Hz, 2H), 6.67-6.64 (d, J = 9.2 Hz, 1H), 4.02-3.98 (m, 1H), 3.75-3.69 (t, J = 10.8 Hz, 1H), 3.12-3.08 (m, 1H), 2.99 (s, 3H), 2.59 (s, 3H), 1.60 (d, J = 6.8 Hz, 3H). | calcd 461.15, found 461.9. |

TABLE 1-continued

Exemplary Compounds
Compounds of the invention include the following:

| Cmpd No. | Structure | NMR Data | LRMS Data |
|---|---|---|---|
| 79 | 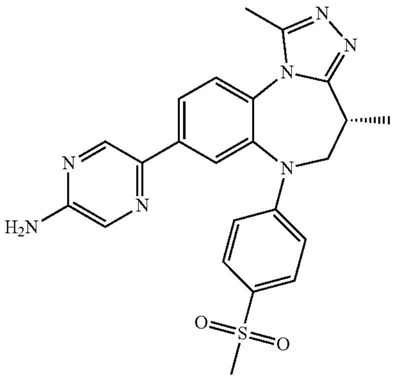 [SMILES: Cc1nnc2n1-c1ccc(-c3cnc(N)cn3)cc1N(c1ccc(S(C)(=O)=O)cc1)C[C@H]2C] | $^1$H NMR (400 MHz, $CDCl_3$): δ 8.40 (s, 1H) 8.03 (s, 1H) 7.97 (m, 2H), 7.68-7.65 (m, 2H), 7.46 (d, J = 8.4 Hz, 1H), 6.75-6.73 (m, 2H), 5.01 (s, 2H), 4.03-3.99 (m, 1H), 3.75-3.70 (m, 1H), 3.13-3.07 (m, 1H), 2.98 (s, 3H), 2.59 (s, 3H), 1.60 (d, J = 2.4 Hz, 3H). | calcd 461.16, found 461.9. |
| 80 | 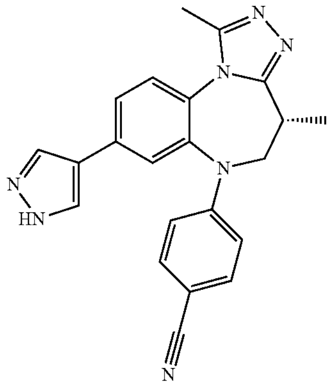 [SMILES: Cc1nnc2n1-c1ccc(-c3cn[nH]c3)cc1N(c1ccc(C#N)cc1)C[C@H]2C] | 1H-NMR (400 MHz, $CDCl_3$): δ 7.84 (s, 2H), 7.62-7.60 (dd, J = 2.0 Hz, 8.0 Hz, 1H), 7.48-7.40 (m, 4H), 7.25-7.15 (m, 1H), 6.70-6.68 (d, J = 8.8 Hz, 2H), 4.00-3.96 (m, 1H), 3.74-3.69 (m, 1H), 3.08-3.15 (m, 1H), 2.61 (s, 3H), 1.63-1.61 (d, J = 6.8 Hz, 3H). | calcd 381.17, found 382.0. |
| 81 | 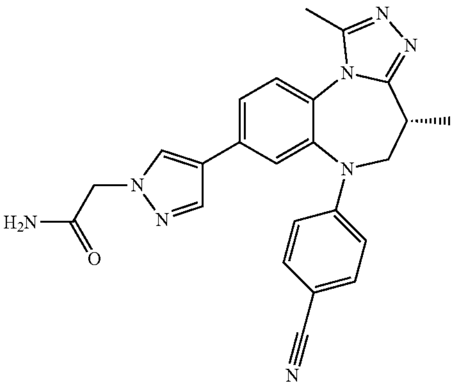 [SMILES: Cc1nnc2n1-c1ccc(-c3cnn(CC(N)=O)c3)cc1N(c1ccc(C#N)cc1)C[C@H]2C] | $^1$H NMR (400 MHz, $CDCl_3$): δ 7.83 (s, 1H), 7.74 (s, 1H), 7.58-7.55 (m, 1H), 7.45-7.38 (m, 4H), 6.68-6.66 (d, J = 7.2 Hz, 2H), 6.30 (s, 1H), 5.73 (s, 1H), 4.84-4.83 (d, J = 1.2 Hz, 2H), 3.98-3.94 (m, 1H), 3.72-3.67 (t, J = 10.8 Hz, 1H), 3.11-3.05 (m, 1H), 2.57 (s, 3H), 1.61-1.59 (d, J = 6.4 Hz, 3H). | calcd 438.19; found 438.9. |
| 82 | 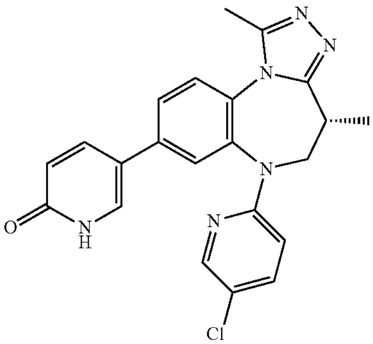 [SMILES: Cc1nnc2n1-c1ccc(-c3ccc(=O)[nH]c3)cc1N(c1ccc(Cl)cn1)C[C@H]2C] | $^1$H NMR (400 MHz, $CDCl_3$): δ 8.08 (s, 1H), 7.71-7.62 (m, 2H), 7.52-7.33 (m, 4H), 6.68-6.65 (d, J = 9.6 Hz, 1H), 6.31-6.28 (d, J = 8.8 Hz, 2H), 4.23-4.17 (t, J = 12.0 Hz, 1H), 3.93-3.89 (m, 1H), 3.06-3.00 (m, 1H), 2.55 (s, 3H), 1.57-1.56 (d, J = 6.8 Hz, 3H). | calcd 418.13, found 418.8. |

TABLE 1-continued

Exemplary Compounds
Compounds of the invention include the following:

| Cmpd No. | Structure | NMR Data | LRMS Data |
|---|---|---|---|
| 83 | 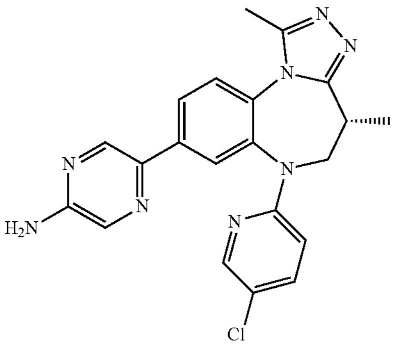 [SMILES: Cc1nnc2n1-c1ccc(-c3cnc(N)cn3)cc1N(c1ccc(Cl)cn1)C[C@H]2C] | $^1$H NMR (400 MHz, $CDCl_3$): δ 8.37 (s, 1H) 8.05-8.03 (m, 2H), 7.95-7.91 (m, 2H), 7.41 (d, J = 8.4 Hz, 1H), 7.21-7.18 (m, 1H), 6.26 (d, J = 8.8 Hz, 1H), 5.38 (s, 2H), 4.30-4.24 (m, 1H), 3.90 (m, 1H), 3.06-3.00 (m, 1H), 2.53 (s, 3H), 1.54 (d, J = 6.8 Hz, 3H). | calcd 418.14, found 418.9. |
| 84 | 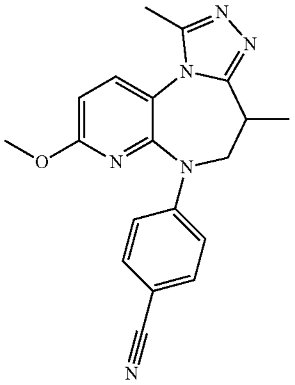 | $^1$H NMR (400 MHz, $CD_3OD$): δ 7.98-8.00 (d, J = 6.0 Hz, 1H), 7.53-7.56 (m, 2H), 6.92-6.96 (m, 3H), 4.17-4.21 (m, 1H), 3.74-3.75 (m, 3H), 3.68-3.73 (m, 1H), 3.25-3.32 (m, 1H), 2.56 (s, 3H), 1.57-1.58 (d, J = 6.8 Hz, 3H). | calcd 346.15; found 346.9. |
| 85 | 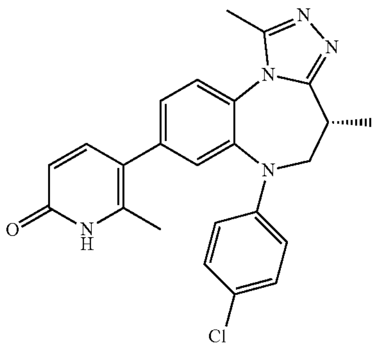 [SMILES: Cc1[nH]c(=O)ccc1-c1ccc2c(c1)N(c1ccc(Cl)cc1)C[C@@H](C)c1nnc(C)n1-2] | $^1$H NMR (400 MHz, $CD_3OD$): δ 7.67 (d, J = 8.0 Hz, 1H), 7.48 (d, J = 9.2 Hz, 1H), 7.41 (dd, J = 2.4, 8.4 Hz, 1H), 7.22 (d, J = 2.0 Hz, 1H), 7.15 (m, 2H), 6.77 (m, 2H), 6.42 (dd, J = 0.8, 9.6 Hz, 1H), 4.01 (dd, J = 6.0, 10.4 Hz, 1H), 3.55 (dd, J = 10.8, 11.6 Hz, 1H), 3.14 (m, 1H), 2.59 (s, 3H), 2.21 (s, 3H), 1.52 (d, J = 6.8 Hz, 3H). | calcd 431.15, found 432.1. |
| 86 | 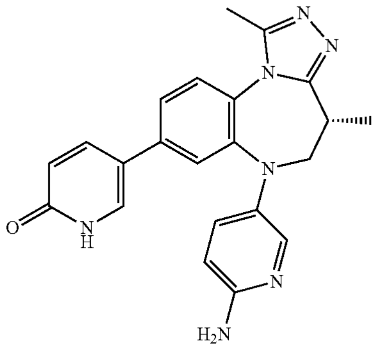 [SMILES: Cc1nnc2n1-c1ccc(-c3ccc(=O)[nH]c3)cc1N(c1ccc(N)nc1)C[C@H]2C] | | |

TABLE 1-continued
| Exemplary Compounds<br>Compounds of the invention include the following: | | | |
|---|---|---|---|
| Cmpd No. | Structure | NMR Data | LRMS Data |
| 87 | 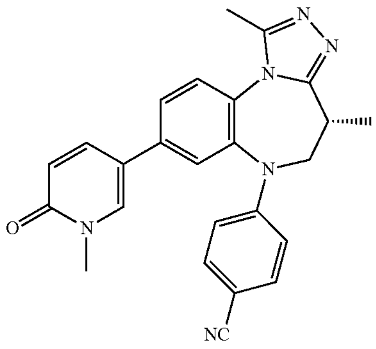 [SMILES: Cc1nnc2n1-c1ccc(-c3ccc(=O)n(C)c3)cc1N(c1ccc(C#N)cc1)C[C@H]2C] | | |
| 88 | 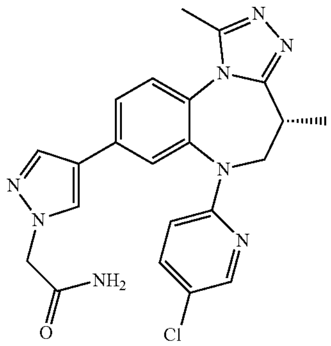 [SMILES: Cc1nnc2n1-c1ccc(-c3cnn(CC(N)=O)c3)cc1N(c1ccc(Cl)cn1)C[C@H]2C] | | |
| 89 | 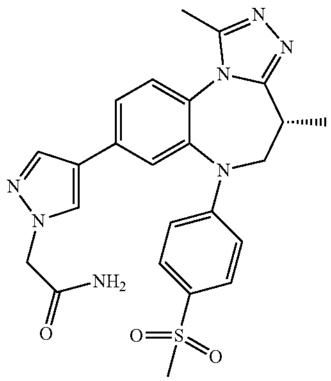 [SMILES: Cc1nnc2n1-c1ccc(-c3cnn(CC(N)=O)c3)cc1N(c1ccc(S(C)(=O)=O)cc1)C[C@H]2C] | | |
| 90 | 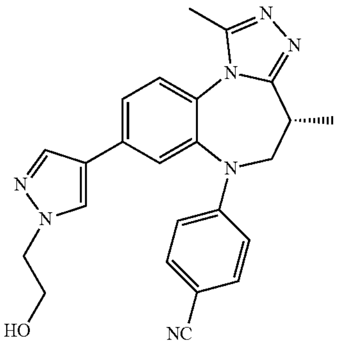 [SMILES: Cc1nnc2n1-c1ccc(-c3cnn(CCO)c3)cc1N(c1ccc(C#N)cc1)C[C@H]2C] | | |

TABLE 1-continued
| Exemplary Compounds Compounds of the invention include the following: | | | |
|---|---|---|---|
| Cmpd No. | Structure | NMR Data | LRMS Data |
| 91 | 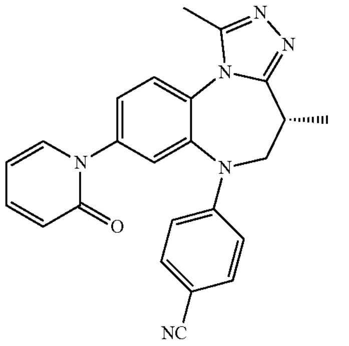 [SMILES: Cc1nnc2n1-c1ccc(-n3ccccc3=O)cc1N(c1ccc(C#N)cc1)C[C@H]2C] | | |
| 93 | 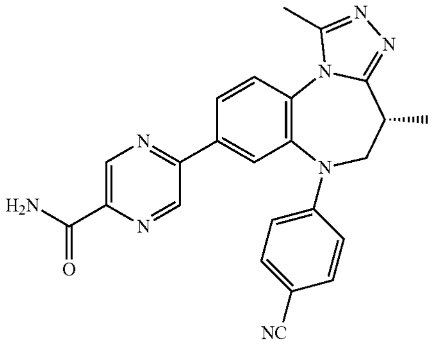 [SMILES: Cc1nnc2n1-c1ccc(-c3cnc(C(N)=O)cn3)cc1N(c1ccc(C#N)cc1)C[C@H]2C] | | |
| 94 | 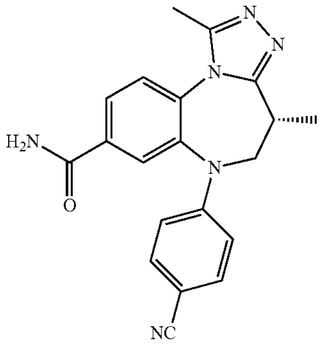 [SMILES: Cc1nnc2n1-c1ccc(C(N)=O)cc1N(c1ccc(C#N)cc1)C[C@H]2C] | | |
| 95 | 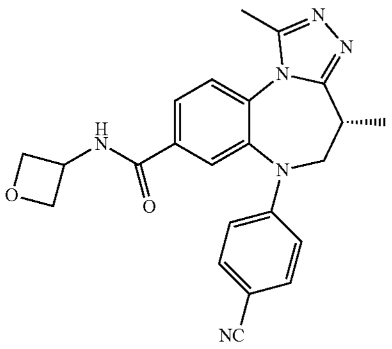 [SMILES: Cc1nnc2n1-c1ccc(C(=O)NC3COC3)cc1N(c1ccc(C#N)cc1)C[C@H]2C] | | |

TABLE 1-continued
| Exemplary Compounds Compounds of the invention include the following: | | | |
|---|---|---|---|
| Cmpd No. | Structure | NMR Data | LRMS Data |
| 96 | 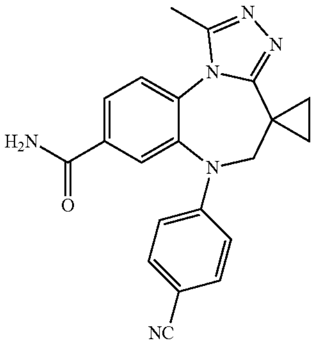 [SMILES: Cc1nnc2n1-c1ccc(C(N)=O)cc1N(c1ccc(C#N)cc1)CC21CC1] | | |
| 97 | 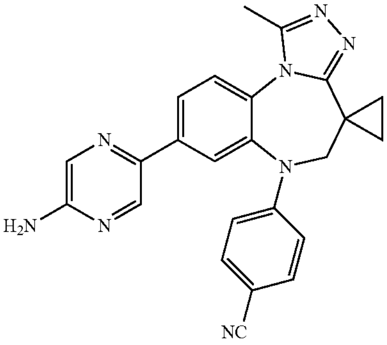 [SMILES: Cc1nnc2n1-c1ccc(-c3cnc(N)cn3)cc1N(c1ccc(C#N)cc1)CC21CC1] | | |
| 98 | 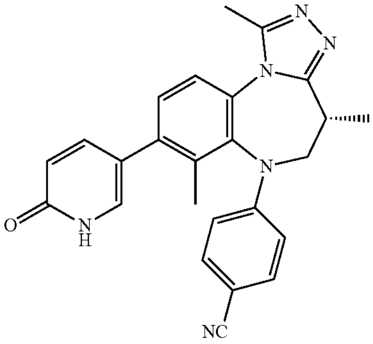 [SMILES: Cc1c(-c2ccc(=O)[nH]c2)ccc2c1N(c1ccc(C#N)cc1)C[C@@H](C)c1nnc(C)n1-2] | | |
| 99 | 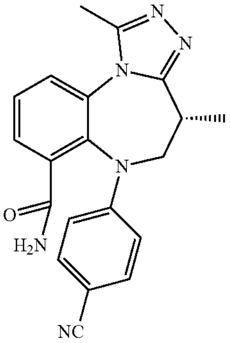 [SMILES: Cc1nnc2n1-c1cccc(C(N)=O)c1N(c1ccc(C#N)cc1)C[C@H]2C] | | |

TABLE 1-continued
| Cmpd No. | Structure | NMR Data | LRMS Data |
|---|---|---|---|
| 100 | 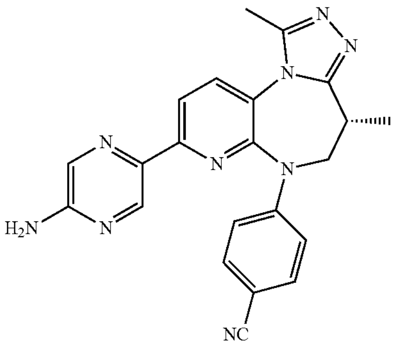 [SMILES: Cc1nnc2n1-c1ccc(-c3cnc(N)cn3)nc1N(c1ccc(C#N)cc1)C[C@H]2C] | | |
| 101 | 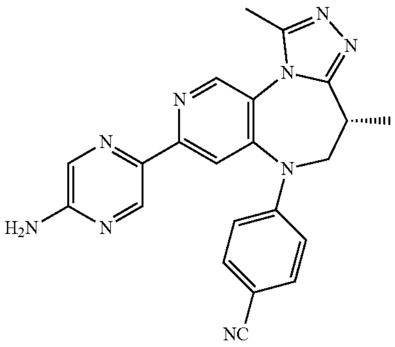 [SMILES: Cc1nnc2n1-c1cnc(-c3cnc(N)cn3)cc1N(c1ccc(C#N)cc1)C[C@H]2C] | | |
| 102 | 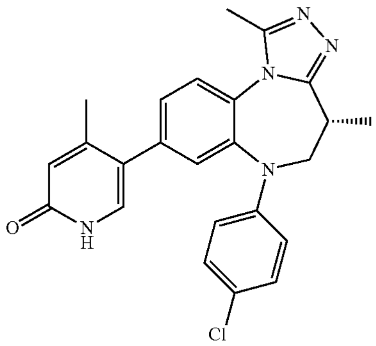 [SMILES: Cc1cc(=O)[nH]cc1-c1ccc2c(c1)N(c1ccc(Cl)cc1)C[C@@H](C)c1nnc(C)n1-2] | | |
| 103 | 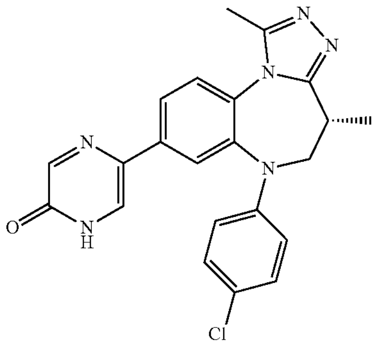 [SMILES: Cc1nnc2n1-c1ccc(-c3c[nH]c(=O)cn3)cc1N(c1ccc(Cl)cc1)C[C@H]2C] | | |
Exemplary Compounds
Compounds of the invention include the following:

TABLE 1-continued
Exemplary Compounds
Compounds of the invention include the following:
| Cmpd No. | Structure | NMR Data | LRMS Data |
|---|---|---|---|
| 104 | 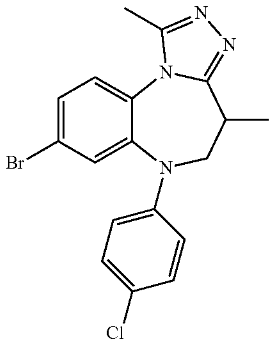 [SMILES: Cc1nnc2n1-c1ccc(Br)cc1N(c1ccc(Cl)cc1)CC2C] | | |
| 105 | 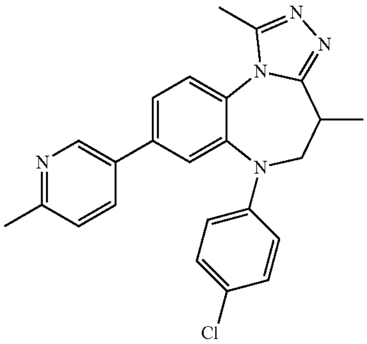 | $^1$H NMR (300 MHz, $CDCl_3$): δ 8.58 (s, 1H), 7.64-7.69 (m, 1H), 7.51-7.38 (m, 3H), 7.18-7.15 (m, 1H), 7.08 (d, J = 9.0 Hz, 2H), 6.63 (d, J = 9.0 Hz, 2H), 3.96-3.91 (m, 1H), 3.59-3.51 (m, 1H), 3.02-3.06 (m, 1H), 2.57 (s, 3H), 2.55 (s, 3H), 1.57 (d, J = 6.9 Hz, 3H). | calcd 415.16; found 415. |
| 106 | 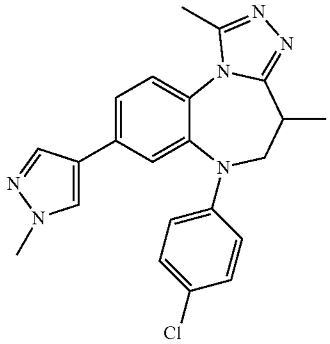 [SMILES: Cc1nnc2n1-c1ccc(-c3cnn(C)c3)cc1N(c1ccc(Cl)cc1)CC2C] | $^1$H NMR (300 MHz, $CD_3OD$): δ 7.99 (s, 1H), 7.83 (s, 1H), 7.69-7.62 (m, 2H), 7.53-7.52 (m, 1H), 7.18 (d, J = 9 Hz, 2H), 6.78 (d, J = 9 Hz, 2H), 4.09-4.03 (m, 1H), 3.93 (s, 3H), 3.66-3.58 (m, 1H), 3.36-3.34 (m, 1H), 2.61 (s, 3H), 1.56 (d, J = 6.6 Hz, 3H). | calcd 404.15; found 404. |
| 107 | 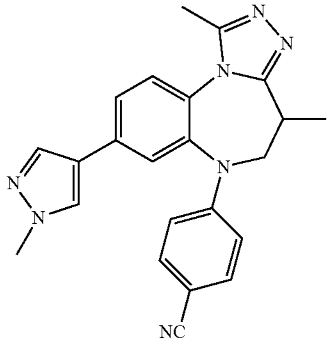 [SMILES: Cc1nnc2n1-c1ccc(-c3cnn(C)c3)cc1N(c1ccc(C#N)cc1)CC2C] | $^1$H NMR (300 MHz, $CDCl_3$): δ 7.70 (s, 1H), 7.59-7.53 (m, 2H), 7.42-7.34 (m, 4H), 6.67 (d, J = 8.7 Hz, 2H), 3.98-3.93 (m, 4H), 3.72-3.65 (m, 1H), 3.13-3.05 (m, 1H), 2.56 (s, 3H), 1.59 (d, J = 6.6 Hz, 3H). | calcd 395.19; found 395. |

TABLE 1-continued

Exemplary Compounds
Compounds of the invention include the following:

| Cmpd No. | Structure | NMR Data | LRMS Data |
|---|---|---|---|
| 108 | 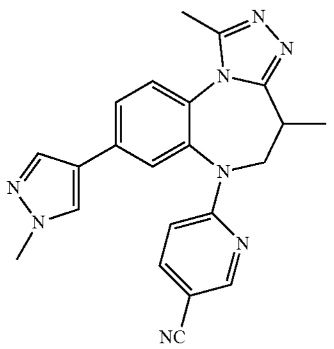 [SMILES: Cc1nnc2n1-c1ccc(-c3cnn(C)c3)cc1N(c1ccc(C#N)cn1)CC2C] | $^1$H NMR (300 MHz, $CDCl_3$): δ 8.45-8.44 (m, 1H), 7.75 (s, 1H), 7.65-7.62 (m, 2H), 7.51-7.40 (m, 3H), 6.27 (d, J = 9.0 Hz, 1H), 4.62-4.55 (m, 1H), 3.96 (s, 3H), 3.89-3.84 (m, 1H), 3.09-3.05 (m, 1H), 2.55 (s, 3H), 1.61 (d, J = 6.3 Hz, 3H). | calcd 396.18; found 396. |
| 109 | 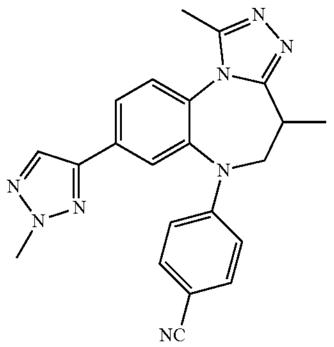 [SMILES: Cc1nnc2n1-c1ccc(-c3cnn(C)n3)cc1N(c1ccc(C#N)cc1)CC2C] | $^1$H NMR (400 MHz, $CDCl_3$): δ 7.86-7.78 (m, 3H), 7.46-7.41 (m, 3H), 6.67 (d, J = 9.2 Hz, 2H), 4.22 (s, 3H), 3.99-3.95 (m, 1H), 3.70 (t, J = 11.2 Hz, 1H), .11-3.05 (m, 1H), 2.59 (s, 3H), 1.60 (d, J = 6.8 Hz, 3H). | calcd 396.2; found 396. |
| 110 | 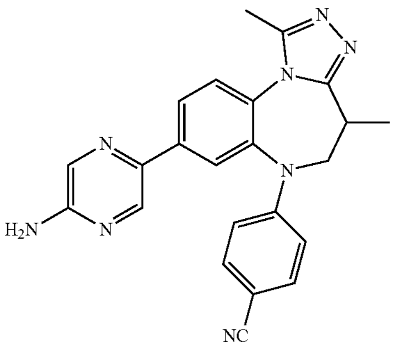 [SMILES: Cc1nnc2n1-c1ccc(-c3cnc(N)cn3)cc1N(c1ccc(C#N)cc1)CC2C] | $^1$H NMR (300 MHz, CD3OD) δ 8.41 (s, 1H), 8.10 (d, J = 8.4 Hz, 1H), 8.00 (dd, J = 1.6, 6.6 Hz, 2H), 7.72 (d, J = 8.4 Hz, 1H), 7.47 (d, J = 9.0 Hz, 2H), 6.82 (d, J = 9.0 Hz, 2H), 4.11-4.05 (m, 1H), 3.80-3.73 (m, 1H), 3.35-3.30 (m, 1H), 2.60 (s, 3H), 1.55 (d, J = 3.9 Hz, 3H). | cald. 408; found 408. |
| 111 | 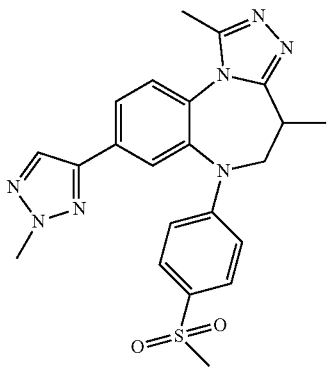 [SMILES: Cc1nnc2n1-c1ccc(-c3cnn(C)n3)cc1N(c1ccc(S(C)(=O)=O)cc1)CC2C] | $^1$H NMR (400 MHz, $CDCl_3$): δ 7.87-7.80 (m, 3H), 7.69 (d, J = 6.6 Hz, 2H), 7.45 (d, J = 6 Hz, 1H), 6.74 (d, J = 6 Hz, 2H), 4.23 (s, 3H), 4.03-3.99 (m, 1H), 3.76-3.70 (m, 1H), 3.13-3.07 (m, 1H), 2.99 (s, 3H), 2.59 (s, 3H), 1.61 (d, J = 5.1 Hz, 3H). | calcd 449.16; found 449. |

TABLE 1-continued

| Exemplary Compounds Compounds of the invention include the following: | | | |
|---|---|---|---|
| Cmpd No. | Structure | NMR Data | LRMS Data |
| 112 | 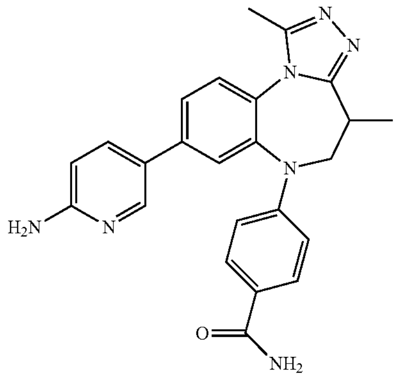 [SMILES: Cc1nnc2n1-c1ccc(-c3ccc(N)nc3)cc1N(c1ccc(C(N)=O)cc1)CC2C] | $^1$H NMR (300 MHz, d6-DMSO): δ 8.23 (s, 1H), 7.75-7.64 (m, 5H), 7.51 (s, 1H), 7.04 (br, 1H), 6.71 (d, J = 8.7 Hz, 2H), 6.50 (d, J = 8.7 Hz, 1H), 6.18 (br, 2H), 4.02-3.98 (m, 1H), 3.67-3.60 (m, 1H), 3.13-3.05 (m, 1H), 2.49 (s, 3H), 1.44 (d, J = 6.6 Hz, 3H). | calcd 425.20; found 425. |

In certain embodiments, the present invention provides a method of inhibiting a bromodomain-containing protein (such as a BET protein, e.g., BRD2, BRD3, BRD4, and/or BRDT) comprising contacting said bromodomain-containing protein with any compound depicted in Table 1, above, or a pharmaceutically acceptable salt or composition thereof.

Uses, Formulation and Administration

Pharmaceutically Acceptable Compositions

In another aspect, the invention provides for a composition comprising a compound of any of the formulae herein, and a pharmaceutically acceptable adjuvant, carrier, or vehicle.

In one embodiment, the invention provides for a composition, in combination with an additional therapeutic agent.

According to another embodiment, the present invention provides a method of inhibiting a bromodomain-containing protein (such as a BET protein, e.g., BRD2, BRD3, BRD4, and/or BRDT) using a composition comprising a compound of the invention or a pharmaceutically acceptable derivative thereof and a pharmaceutically acceptable carrier, adjuvant, or vehicle. The amount of a compound of the invention in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, the amount of compound in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, a provided composition is formulated for administration to a patient in need of such composition. In some embodiments, a provided composition is formulated for oral administration to a patient.

The term "patient," as used herein, means an animal, such as a mammal, such as a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitory active metabolite or residue thereof.

As used herein, the term "inhibitory active metabolite or residue thereof" means that a metabolite or residue thereof is also an inhibitor of one or more bromodomain-containing proteins (such as a BET protein, e.g., BRD2, BRD3, BRD4, and/or BRDT), or a mutant thereof.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration. Provided compositions may be formulate such that a dosage of between 0.01-100 mg/kg body weight/day of the inhibitor can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

In another aspect, the invention provides a method for inhibiting activity of a bromodomain-containing protein, or a mutant thereof, in a biological sample comprising the step of contacting said biological sample with a compound as described herein (e.g. any formulae herein).

In one embodiment, the bromodomain-containing protein is a BET protein.

In a further embodiment, the BET protein is BRD4.

In another aspect, the invention provides a method for inhibiting activity of a bromodomain-containing protein, or a mutant thereof, in a patient comprising the step of administering to said patient a compound as described herein (e.g. any formulae herein).

In one embodiment, the bromodomain-containing protein is a BET protein.

In other embodiments, the BET protein is BRD4.

In another aspect, the invention provides a method for treating a bromodomain-containing protein-mediated disorder in a patient in need thereof, comprising the step of administering to said patient a compound as described herein (e.g. any formulae herein).

In one embodiment, the bromodomain-containing protein is a BET protein.

In a further embodiment, the BET protein is BRD4.

In another embodiment, the disorder is a proliferative disorder, inflammatory disease, sepsis, autoimmune disease, or viral infection.

In a further embodiment, the proliferative disorder is cancer.

In certain embodiments, the cancer is adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

Compounds and compositions described herein are generally useful for the inhibition of activity of one or more proteins involved in epigenetic regulation. Thus, in some embodiments, the present invention provides a method of inhibiting one or more proteins involved in epigenetic regulation, such as proteins containing acetyl-lysine recognition motifs, also known as bromodomains (e.g., BET proteins, such as BRD2, BRD3, BRD4, and/or BRDT), by administering a provided compound or composition.

Epigenetics is the study of heritable changes in gene expression caused by mechanisms other than changes in the underlying DNA sequence. Molecular mechanisms that play a role in epigenetic regulation include DNA methylation and chromatin/histone modifications. Chromatin recognition, in particular, is critical in many epigenetic phenomena.

Chromatin, the organized assemblage of nuclear DNA and histone proteins, is the basis for a multitude of vital nuclear processes including regulation of transcription, replication, DNA-damage repair and progression through the cell cycle. A number of factors, such as chromatin-modifying enzymes, have been identified that play an important role in maintaining the dynamic equilibrium of chromatin (Margueron, et al. (2005) *Curr. Opin. Genet. Dev.* 15:163-176).

Histones are the chief protein components of chromatin. They act as spools around which DNA winds, and they play a role in gene regulation. There are a total of six classes of histones (H1, H2A, H2B, H3, H4, and H5) organized into two super classes: core histones (H2A, H2B, H3, and H4) and linker histones (H1 and H5). The basic unit of chromatin is the nucleosome, which consists of about 147 base pairs of DNA wrapped around the histone octamer, consisting of two copies each of the core histones H2A, H2B, H3, and H4 (Luger, et al. (1997) *Nature* 389:251-260).

Histones, particularly residues of the amino termini of histones H3 and H4 and the amino and carboxyl termini of histones H2A, H2B and H1, are susceptible to a variety of post-translational modifications including acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

One type of histone modification, lysine acetylation, is recognized by bromodomain-containing proteins. Bromodomain-containing proteins are components of transcription factor complexes and determinants of epigenetic memory (Dey, et al. (2009) *Mol. Biol. Cell* 20:4899-4909). There are 46 human proteins containing a total of 57 bromodomains discovered to date. One family of bromodomain-containing proteins, BET proteins (BRD2, BRD3, BRD4, and BRDT) have been used to establish proof-of-concept for targeting protein-protein interactions of epigenetic "readers," as opposed to chromatin-modifying enzymes, or so-called epigenetic "writers" and "erasers" (Filippakopoulos, et al. "Selective Inhibition of BET Bromodomains," *Nature* (published online Sep. 24, 2010); Nicodeme, et al. "Suppression of Inflammation by a Synthetic Histone Mimic," *Nature* (published online Nov. 10, 2010)).

Examples of proteins inhibited by the compounds and compositions described herein and against which the methods described herein are useful include bromodomain-containing proteins, such as BET proteins, such as BRD2, BRD3, BRD4, and/or BRDT, or an isoform or mutant thereof.

The activity of a provided compound, or composition thereof, as an inhibitor of a bromodomain-containing protein, such as a BET protein, such as BRD2, BRD3, BRD4, and/or BRDT, or an isoform or mutant thereof, may be assayed in vitro, in vivo, or in a cell line. In vitro assays include assays that determine inhibition of bromodomain-containing proteins, such as BET proteins, such as BRD2, BRD3, BRD4, and/or BRDT, or a mutant thereof. Alternatively, inhibitor binding may be determined by running a competition experiment where a provided compound is incubated with a bromodomain-containing protein, such as a BET protein, such as BRD2, BRD3, BRD4, and/or BRDT bound to known ligands, labeled or unlabeled. Detailed conditions for assaying a provided compound as an inhibitor of a bromodomain-containing protein, such as a BET protein, such as BRD2, BRD3, BRD4, and/or BRDT or a mutant thereof, are set forth in the Examples below.

The invention provides for a method of treating a subject with a MYC-dependent cancer, comprising: identifying a subject in need of treatment; administering to the subject a BET inhibitor; determining at least one of MYC mRNA expression, MYC protein expression and tumor mass, and wherein following administration, there is a decrease in at least one of myc mRNA expression, MYC protein expression and tumor mass, thereby treating the disease.

In one embodiment, the identification step comprises determining whether the subject has at least one of a MYC translocation, a genetic rearrangement of MYC, MYC amplification, MYC over-expression and at least one cellular function that facilitates cellular and/or tumor growth and is altered upon reduction of myc mRNA or protein expression.

The invention also provides for a method of treating a subject with a MYC-dependent cancer, comprising: determining in a subject at least one of MYC mRNA expression, MYC protein expression and tumor mass; administering to the subject a BET inhibitor; and comparing at least one of MYC mRNA expression, MYC protein expression and tumor mass in the subject before and after administration of the BET inhibitor.

The invention also provides a method of treating a subject with a MYC-dependent cancer, comprising: administering to the subject a BET inhibitor that is identified as capable of decreasing at least one of myc mRNA expression, MYC protein expression and tumor mass; and determining at least one of myc mRNA expression, MYC protein expression and tumor mass; wherein following the administration, there is a decrease in at least one of myc mRNA expression, MYC protein expression and tumor mass, thereby treating the disease.

The invention also provides for a method of treating a subject with a disease, comprising: administering a BET inhibitor that is identified as capable of decreasing at least one of myc mRNA expression, MYC protein expression and tumor mass, wherein following the administration, there is a decrease in at least one of myc mRNA expression, MYC protein expression and tumor mass, thereby treating the disease.

Acetylated histone recognition and bromodomain-containing proteins (such as BET proteins) have been implicated in proliferative disease. BRD4 knockout mice die shortly after implantation and are compromised in their ability to maintain an inner cell mass, and heterozygotes display pre- and postnatal growth defects associated with reduced proliferation rates. BRD4 regulates genes expressed during M/G1, including growth-associated genes, and remains bound to chromatin throughout the cell cycle (Dey, et al. (2009) *Mol. Biol. Cell* 20:4899-4909). BRD4 also physically associates with Mediator and P-TEFb (CDK9/cyclin T1) to facilitate transcriptional elongation (Yang, et al. (2005) *Oncogene* 24:1653-1662; Yang, et al. (2005) *Mol. Cell* 19:535-545). CDK9 is a validated target in chronic lymphocytic leukemia (CLL), and is linked to c-Myc-dependent transcription (Phelps, et al. *Blood* 113:2637-2645; Rahl, et al. (2010) *Cell* 141:432-445).

BRD4 is translocated to the NUT protein in patients with lethal midline carcinoma, an aggressive form of human squamous carcinoma (French, et al. (2001) *Am. J. Pathol.* 159: 1987-1992; French, et al. (2003) *Cancer Res.* 63:304-307). In vitro analysis with RNAi supports a causal role for BRD4 in this recurrent t(15;19) chromosomal translocation. Pharmacologic inhibition of the BRD4 bromodomains results in growth arrest/differentiation of BRD4-NUT cell lines in vitro and in vivo (Filippakopoulos, et al. "Selective Inhibition of BET Bromodomains," *Nature* (published online Sep. 24, 2010)).

Bromodomain-containing proteins (such as BET proteins) have also been implicated in inflammatory diseases. BET proteins (e.g., BRD2, BRD3, BRD4, and BRDT) regulate assembly of histone acetylation-dependent chromatin complexes that control inflammatory gene expression (Hargreaves, et al. (2009) *Cell* 138:129-145; LeRoy, et al. (2008) *Mol. Cell* 30:51-60; Jang, et al. (2005) *Mol. Cell* 19:523-534; Yang, et al. (2005) *Mol. Cell* 19:535-545). Key inflammatory genes (secondary response genes) are down-regulated upon bromodomain inhibition of the BET subfamily, and non-responsive genes (primary response genes) are poised for transcription. BET bromodomain inhibition protects against LPS-induced endotoxic shock and bacteria-induced sepsis in vivo (Nicodeme, et al. "Suppression of Inflammation by a Synthetic Histone Mimic," *Nature* (published online Nov. 10, 2010)).

Bromodomain-containing proteins (such as BET proteins) also play a role in viral disease. For example, BRD4 is implicated in human papilloma virus (HPV). In the primary phase of HPV infection of basal epithelia, the viral genome is maintained in an extra-chromosomal episome. In some strains of HPV, BRD4 binding to the HPV E2 protein functions to tether the viral genome to chromosomes. E2 is critical for both the repression of E6/E7 and the activation of HPV viral genes. Disruption of BRD4 or the BRD4-E2 interaction blocks E2-dependent gene activation. BRD4 also functions to tether other classes of viral genomes to host chromatin (e.g., Herpesvirus, Epstein-Barr virus).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In certain embodiments, a provided compound inhibits one or more of BRD2, BRD3, BRD4, BRDT, and/or another member of the bromodomain-containing proteins, or a mutant thereof. In some embodiments, a provided compound inhibits two or more of BRD2, BRD3, BRD4, BRDT, and/or another member of the bromodomain-containing proteins, or a mutant thereof. Provided compounds are inhibitors of one of more of the bromodomain-containing proteins, such as BRD2, BRD3, BRD4, and/or BRDT and are therefore useful for treating one or more disorders associated with activity of one or more of the bromodomain-containing proteins, such as BRD2, BRD3, BRD4, and/or BRDT. Thus, in certain embodiments, the present invention provides a method for treating an bromodomain-containing protein-mediated disorder, such as a BET-mediated, a BRD2-mediated, a BRD3-mediated, a BRD4-mediated disorder, and/or a BRDT-mediated disorder comprising the step of inhibiting a bromodomain-containing protein, such as a BET protein, such as BRD2, BRD3, BRD4, and/or BRDT, or a mutant thereof, by administering to a patient in need thereof a provided compound, or a pharmaceutically acceptable composition thereof.

As used herein, the terms "bromodomain-containing protein-mediated", "BET-mediated", "BRD2-mediated", "BRD3-mediated", "BRD4-mediated", and/or "BRDT-mediated" disorders or conditions means any disease or other deleterious condition in which one or more of the bromodomain-containing proteins, such as BET proteins, such as BRD2, BRD3, BRD4 and/or BRDT, or a mutant thereof, are known to play a role. Accordingly, another embodiment of the present invention relates to treating or lessening the severity of one or more diseases in which one or more of the bromodomain-containing proteins, such as BET proteins, such as BRD2, BRD3, BRD4, and/or BRDT, or a mutant thereof, are known to play a role.

Diseases and conditions treatable according to the methods of this invention include, but are not limited to, cancer and other proliferative disorders, inflammatory diseases, sepsis, autoimmune disease, and viral infection. Thus one aspect is a method of treating a subject having a disease, disorder, or symptom thereof the method including administration of a compound or composition herein to the subject. In one embodiment, a human patient is treated with a compound of the invention and a pharmaceutically acceptable carrier, adjuvant, or vehicle, wherein said compound is present in an amount to measurably inhibit bromodomain-containing protein activity (such as BET protein, e.g., BRD2, BRD3, BRD4, and/or BRDT) in the patient.

The invention further relates to a method for treating or ameliorating cancer or another proliferative disorder by administration of an effective amount of a compound according to this invention to a mammal, in particular a human in need of such treatment. In some aspects of the invention, the disease to be treated by the methods of the present invention is cancer. Examples of cancers treated using the compounds and methods described herein include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In some embodiments, the present invention provides a method of treating a benign proliferative disorder. Such benign proliferative disorders include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The invention further relates to a method for treating infectious and noninfectious inflammatory events and autoimmune and other inflammatory diseases by administration of an effective amount of a provided compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleroderma, mycosis fungoides, acute inflammatory responses (such as acute respiratory distress syndrome and ischemia/reperfusion injury), and Graves' disease.

In some embodiments, the present invention provides a method of treating systemic inflammatory response syndromes such as LPS-induced endotoxic shock and/or bacteria-induced sepsis by administration of an effective amount of a provided compound to a mammal, in particular a human in need of such treatment.

The invention further relates to a method for treating viral infections and diseases by administration of an effective amount of a provided compound to a mammal, in particular a human in need of such treatment. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

The invention further provides a method of treating a subject, such as a human, suffering from one of the abovementioned conditions, illnesses, disorders or diseases. The method comprises administering a therapeutically effective amount of one or more provided compounds, which function by inhibiting a bromodomain and, in general, by modulating gene expression, to induce various cellular effects, in particular induction or repression of gene expression, arresting cell proliferation, inducing cell differentiation and/or inducing apoptosis, to a subject in need of such treatment.

The invention further provides a therapeutic method of modulating protein methylation, gene expression, cell proliferation, cell differentiation and/or apoptosis in vivo in diseases mentioned above, in particular cancer, inflammatory disease, and/or viral disease comprising administering to a subject in need of such therapy a pharmacologically active and therapeutically effective amount of one or more provided compounds.

The invention further provides a method of regulating endogenous or heterologous promoter activity by contacting a cell with a provided compound.

In certain embodiments, the invention provides a method of treating a disorder (as described above) in a subject, comprising administering to the subject identified as in need thereof, a compound of the invention. The identification of those patients who are in need of treatment for the disorders described above is well within the ability and knowledge of one skilled in the art. Certain of the methods for identification of patients which are at risk of developing the above disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a disorder by methods well known in the art (e.g., determining tumor size or screening for tumor markers where the cell proliferative disorder is cancer) and then administering a therapeutically effective amount of a compound of the invention, to the subject. After an appropriate period of time after the administration of the compound (e.g., 1 day, 1 week, 2 weeks, one month, six months), the extent of the disorder is determined again. The modulation (e.g., decrease) of the extent or invasiveness of the disorder indicates efficacy of the treatment. The extent or invasiveness of the disorder may be determined periodically throughout treatment. For example, the extent or invasiveness of the disorder may be checked every few hours, days or weeks to assess the further efficacy of the treatment. A decrease in extent or invasiveness of the disorder indicates that the treatment is efficacious. The method described may be used to screen or select patients that may benefit from treatment with a compound of the invention.

The invention further relates to the use of provided compounds for the production of pharmaceutical compositions which are employed for the treatment and/or prophylaxis and/or amelioration of the diseases, disorders, illnesses and/or conditions as mentioned herein.

The invention further relates to the use of provided compounds for the production of pharmaceutical compositions which are employed for the treatment and/or prophylaxis of diseases and/or disorders responsive or sensitive to the inhibition of bromodomain-containing proteins, particularly those diseases mentioned above, such as e.g. cancer, inflammatory disease, viral disease.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

Compounds or compositions described herein may be administered using any amount and any route of administration effective for treating or lessening the severity of cancer or other proliferative disorder. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

According to some embodiments, the invention relates to a method of inhibiting bromodomain-containing proteins in a biological sample comprising the step of contacting said biological sample with a provided compound, or a composition thereof.

According to some embodiments, the invention relates to a method of inhibiting a bromodomain-containing protein, such as a BET protein, such as BRD2, BRD3, BRD4 and/or BRDT, or a mutant thereof, activity in a biological sample comprising the step of contacting said biological sample with a provided compound, or a composition thereof.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition of activity of an protein, e.g., a bromodomain-containing protein, such as a BET protein, such as BRD2, BRD3, BRD4 and/or BRDT, or a mutant thereof, in a biological sample is useful for a variety of purposes that are known to one of skill in the art. Examples of such purposes include, but are not limited to, blood transfusion, organ-transplantation, biological specimen storage, and biological assays.

According to another embodiment, the invention relates to a method of inhibiting activity of one or more bromodomain-containing protein, such as a BET protein, such as BRD2, BRD3, BRD4, and/or BRDT, or a mutant thereof, in a patient comprising the step of administering to said patient a provided compound, or a composition comprising said compound. In certain embodiments, the present invention provides a method for treating a disorder mediated by one or more bromodomain-containing proteins, such as a BET protein, such as BRD2, BRD3, BRD4, and/or BRDT, or a mutant thereof, in a patient in need thereof, comprising the step of administering to said patient a provided compound or pharmaceutically acceptable composition thereof. Such disorders are described in detail herein.

Depending upon the particular condition, or disease, to be treated, additional therapeutic agents that are normally administered to treat that condition may also be present in the compositions of this disclosure or administered separately as a part of a dosage regimen. As used herein, additional therapeutic agents that are normally administered to treat a particular disease, or condition, are known as "appropriate for the disease, or condition, being treated."

In some embodiments, the additional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

Other therapies, chemotherapeutic agents, or other antiproliferative agents may be combined with a provided compound to treat proliferative diseases and cancer. Examples of therapies or anticancer agents that may be used in combination with compounds of formula I include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effects (e.g., an antiemetic), and any other approved chemotherapeutic drug.

A provided compound may also be used to advantage in combination with one or more antiproliferative compounds. Such antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carotenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Exemplary aromatase inhibitors include steroids, such as atamestane, exemestane and formestane, and non-steroids, such as aminoglutethimide, rogletimide, pyridoglutethimide, trilostane, testolactone, ketoconazole, vorozole, fadrozole, anastrozole and letrozole.

Exemplary anti-estrogens include tamoxifen, fulvestrant, raloxifene and raloxifene hydrochloride. Anti-androgens include, but are not limited to, bicalutamide. Gonadorelin agonists include, but are not limited to, abarelix, goserelin and goserelin acetate.

Exemplary topoisomerase I inhibitors include topotecan, gimatecan, irinotecan, camptothecin and its analogues, 9-nitrocamptothecin and the macromolecular camptothecin conjugate PNU-166148. Topoisomerase II inhibitors include, but are not limited to, the anthracyclines such as doxorubicin, daunorubicin, epirubicin, idarubicin and nemorubicin, the anthraquinones mitoxantrone and losoxantrone, and the podophillotoxins etoposide and teniposide.

Exemplary microtubule active agents include microtubule stabilizing, microtubule destabilizing compounds and microtubulin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; colchicine and epothilones and derivatives thereof.

Exemplary alkylating agents include cyclophosphamide, ifosfamide, melphalan or nitrosoureas such as carmustine and lomustine.

Exemplary cyclooxygenase inhibitors include Cox-2 inhibitors, 5-alkyl substituted 2-arylaminophenylacetic acid and derivatives, such as celecoxib, rofecoxib, etoricoxib, valdecoxib or a 5-alkyl-2-arylaminophenylacetic acid, such as lumiracoxib.

Exemplary matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary mTOR inhibitors include compounds that inhibit the mammalian target of rapamycin (mTOR) and possess antiproliferative activity such as sirolimus, everolimus, CCI-779, and ABT578.

Exemplary antimetabolites include 5-fluorouracil (5-FU), capecitabine, gemcitabine, DNA demethylating compounds, such as 5-azacytidine and decitabine, methotrexate and edatrexate, and folic acid antagonists such as pemetrexed.

Exemplary platin compounds include carboplatin, cis-platin, cisplatinum, and oxaliplatin.

Exemplary methionine aminopeptidase inhibitors include bengamide or a derivative thereof and PPI-2458.

Exemplary bisphosphonates include etidronic acid, clodronic acid, tiludronic acid, pamidronic acid, alendronic acid, ibandronic acid, risedronic acid and zoledronic acid.

Exemplary antiproliferative antibodies include trastuzumab, trastuzumab-DM1, cetuximab, bevacizumab, rituximab, PRO64553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary heparanase inhibitors include compounds that target, decrease or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras; for example, a farnesyl transferase inhibitor such as L-744832, DK8G557, tipifarnib, and lonafarnib.

Exemplary telomerase inhibitors include compounds that target, decrease or inhibit the activity of telomerase, such as compounds which inhibit the telomerase receptor, such as telomestatin.

Exemplary proteasome inhibitors include compounds that target, decrease or inhibit the activity of the proteasome including, but not limited to, bortezomib.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and busulfan; and ALK inhibitors, which are compounds which target, decrease or inhibit anaplastic lymphoma kinase.

Exemplary Flt-3 inhibitors include PKC412, midostaurin, a staurosporine derivative, SU11248 and MLN518.

Exemplary HSP90 inhibitors include compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing or inhibiting the activity of the platelet-derived growth factor-receptors (PDGFR), such as a compound which targets, decreases, or inhibits the activity of PDGFR, such as an N-phenyl-2-pyrimidine-amine derivatives, such as imatinib, SU101, SU6668 and GFB-111; b) a compound targeting, decreasing or inhibiting the activity of the fibroblast growth factor-receptors (FGFR); c) a compound targeting, decreasing or inhibiting the activity of the insulin-like growth factor receptor I (IGF-IR), such as a compound which targets, decreases, or inhibits the activity of IGF-IR; d) a compound targeting, decreasing or inhibiting the activity of the Trk receptor tyrosine kinase family, or ephrin B4 inhibitors; e) a compound targeting, decreasing or inhibiting the activity of the Ax1 receptor tyrosine kinase family; f) a compound targeting, decreasing or inhibiting the activity of the Ret receptor tyrosine kinase; g) a compound targeting, decreasing or inhibiting the activity of the Kit/SCFR receptor tyrosine kinase, such as imatinib; h) a compound targeting, decreasing or inhibiting the activity of the c-Kit receptor tyrosine kinases, such as imatinib; i) a compound targeting, decreasing or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; ISIS 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) a compound targeting, decreasing or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, C1-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing or inhibiting the activity of the c-Met receptor.

Exemplary compounds that target, decrease or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g. thalidomide and TNP-470.

Additional exemplary chemotherapeutic compounds, one or more of which may be used in combination with provided compounds, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugen; FLT-4 inhibitors, FLT-3 inhibitors, VEGFR-2 IgGI antibody, RPI 4610, bevacizumab, porfimer sodium, anecortave, triamcinolone, hydrocortisone, 11-α-epihydrocotisol, cortexolone, 17α-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA or siRNA, or a miscellaneous compound or compound with other or unknown mechanism of action.

For a more comprehensive discussion of updated cancer therapies see, *The Merck Manual*, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

The above-mentioned compounds, one or more of which can be used in combination with a provided compound, can be prepared and administered as described in the art.

Provided compounds can be administered alone or in combination with one or more other therapeutic compounds, possible combination therapy taking the form of fixed combinations or the administration of a provided compound and one or more other therapeutic compounds being staggered or given independently of one another, or the combined administration of fixed combinations and one or more other therapeutic compounds. Provided compounds can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Such additional agents may be administered separately from a composition containing a provided compound, as part of a multiple dosage regimen. Alternatively, those agents may be part of a single dosage form, mixed together with a provided compound in a single composition. If administered as part of a multiple dosage regimen, the two active agents may be submitted simultaneously, sequentially or within a period of time from one another normally within five hours from one another.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present invention comprise administration to a patient in need of such treatment from about 10 mg to about 1000 mg of the compound(s) of this invention per day in single or multiple doses.

As used herein, the term "combination," "combined," and related terms refers to the simultaneous or sequential administration of therapeutic agents in accordance with this invention. For example, a provided compound may be administered with another therapeutic agent simultaneously or sequentially in separate unit dosage forms or together in a single unit dosage form. Accordingly, an embodiment of the invention provides a single unit dosage form comprising a provided compound, an additional therapeutic agent, and a pharmaceutically acceptable carrier, adjuvant, or vehicle for use in the methods of the invention.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions should be formulated such that a dosage of between 0.01-100 mg/kg body weight/day of a provided compound can be administered.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Provided compounds, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a provided compound. Implantable devices coated with a compound of this invention are another embodiment of the present invention.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

In another aspect, the invention provides a method of method of synthesizing a compound of any formulae as described herein. Another embodiment is a method of making a compound of any of the formulae herein using any one, or combination of, reactions delineated herein. The method can include the use of one or more intermediates or chemical reagents delineated herein.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. In addition, it will also be appreciated that certain intermediates formed in the synthesis exemplified below are also compounds of the invention, even if not designated by a compound number.

Example 1

Synthesis of 6-(4-chlorophenyl)-1,4-dimethyl-5,6-dihydro-4H-benzo[b][1,2,4]triazolo[4,3-d][1,4]diazepine (Compound 1)

N-(4-chlorophenyl)-2-nitrobenzenamine

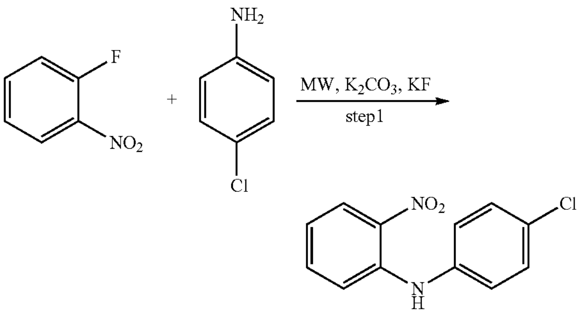

A mixture of 2-fluoronitrobenzene (3.5 g, 24.8 mmol), 4-chlorobenzenamine (3.05 g, 24.0 mmol), $K_2CO_3$ (3.45 g, 25.0 mmol) and KF (1.5 g, 25.8 mmol) was heated at 220° C. for 28 min under microwave condition. The solid was dissolved in DCM (150 mL), washed with water (50 mL×3), dried over $Na_2SO_4$. The solvent was evaporated in vacuo, and then the mixture was purified by Combi-flash (PE:EA=20:1) to give N-(4-chlorophenyl)-2-nitrobenzenamine (3.2 g, 52%) as a scarlet solid. $^1H$ NMR (300 MHz, $CD_3OD$): δ 6.82-6.87 (m, 1H), 7.27-7.31 (m, 2H), 7.41-7.45 (m, 3H), 7.70-7.73 (m, 1H), 8.15-8.18 (m, 1H).

$N^1$-(4-chlorophenyl)benzene-1,2-diamine

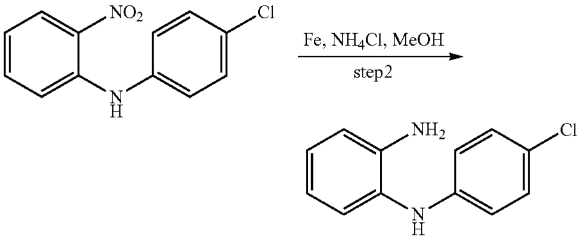

To a mixture of EtOH (100 ml) and $NH_4Cl$ saturated solution (15 ml), N-(4-chlorophenyl)-2-nitrobenzenamine (5.0 g, 20.1 mmol) was added, followed by iron powder (4.0 g). The reaction mixture was heated at 70° C. for 2 h. The solid was filtered and the filtrate was extracted by EA (100 mL×3), dried over $Na_2SO_4$. After the solvent was removed, the mixture was purified by Combi-flash (PE:EA=5:1) to give $N^1$-(4-chlorophenyl)benzene-1,2-diamine (4.1 g, 93.2%) as a light yellow solid. LRMS (M+H$^+$) m/z: calcd 218.06. found 218.

$^1H$ NMR (300 MHz, $CD_3OD$): δ 6.52-6.59 (m, 3H), 6.70-6.74 (m, 1H), 6.81-6.87 (m, 1H), 6.90-6.99 (m, 3H).

1-(4-chlorophenyl)-1H-benzo[b][1,4]diazepine-2,4(3H,5H)-dione

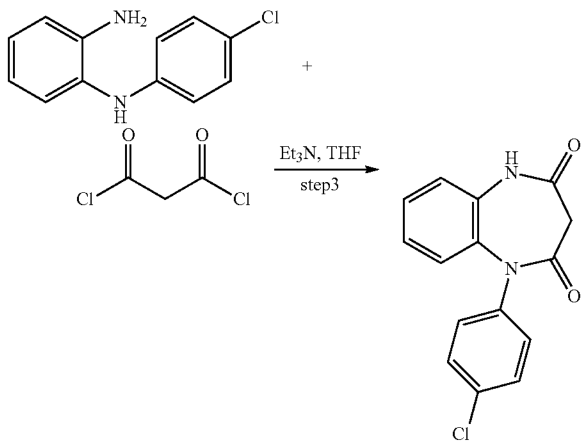

To a stirred refluxing solution of $N^1$-(4-chlorophenyl)benzene-1,2-diamine (100.0 mg, 0.46 mmol) in toluene (20 mL) was added dropwise a solution of malonyl dichloride (65.00 mg, 0.46 mmol). After addition was completed, the reaction mixture was refluxed for 1 h. The solvent was removed in vacuo, the mixture was stirred with water (20 mL), extracted with DCM (10 mL*3), and then was purified by Prep-TLC (DCM:MeOH=30:1) to give 1-(4-chlorophenyl)-1H-benzo[b][1,4]diazepine-2,4(3H,5H)-dione (80.00 mg, 60%) as a white solid. LRMS ($M+H^+$) m/z: calcd 286.05. found 286.

1-(4-chlorophenyl)-4-thioxo-4,5-dihydro-1H-benzo[b][1,4]diazepin-2(3H)-one

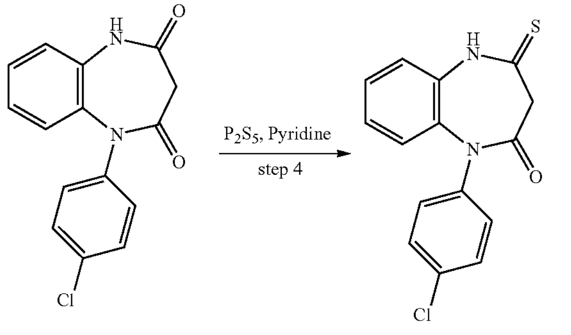 [SMILES: O=C1CC(=O)N(c2ccc(Cl)cc2)c2ccccc2N1 ; O=C1CC(=S)Nc2ccccc2N1c1ccc(Cl)cc1]

A solution of 1-(4-chlorophenyl)-1H-benzo[b][1,4]diazepine-2,4(3H,5H)-dione (2.00 g, 7.0 mmol) and $P_2S_5$ (1.87 g, 8.4 mmol) in pyridine (40 ml) was refluxed, with stirring for 1 h under $N_2$ atmosphere. The solvent was evaporated in vacuo to afford a residue. The residue was purified by column chromatography (silica-gel, DCM:MEOH=40:1) to give 1-(4-chlorophenyl)-4-thioxo-4,5-dihydro-1H-benzo[b][1,4]diazepin-2(3H)-one (1.05 g, 49%). LRMS ($M+H^+$) m/z: calcd 302.03. found 302.

6-(4-chlorophenyl)-1-methyl-4H-benzo[b][1,2,4]triazolo[4,3-d][1,4]diazepin-5(6H)-one

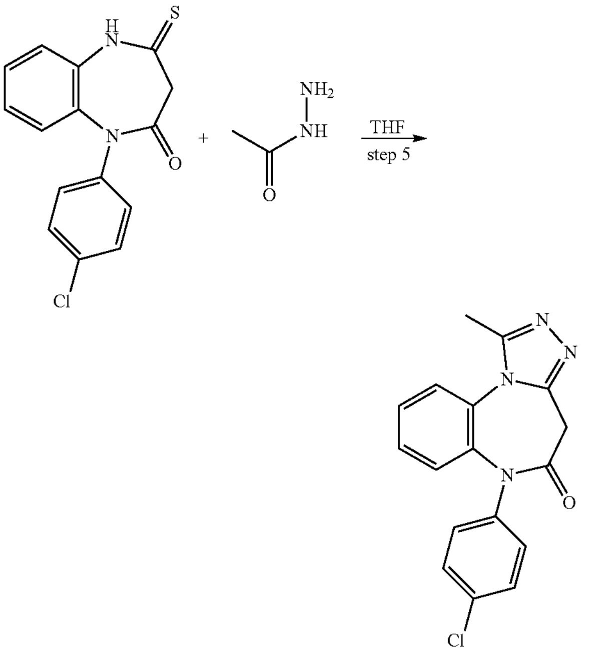

A solution of 1-(4-chlorophenyl)-4-thioxo-4,5-dihydro-1H-benzo[b][1,4]diazepin-2(3H)-one (1.0 g, 3.3 mmol) and acetohydrazide (1.23 g, 16.6 mmol) in n-butanol (20 ml) was refluxed for 24 h under $N_2$ atmosphere. The solvent was evaporated in vacuo and partitioned between DCM (100 mL) and water (50 mL). The organic phase was dried over $Na_2SO_4$ and the solvent was evaporated in vacuo to afford a residue. The residue was purified by column chromatography (silica-gel, DCM:MEOH=30:1) to give 6-(4-chlorophenyl)-1-methyl-4H-benzo[b][1,2,4]triazolo[4,3-d][1,4]diazepin-5(6H)-one (430.0 mg, 40%). LRMS ($M+H^+$) m/z: calcd 324.08. found 324. $^1H$ NMR (300 MHz, $CD_3OD$): δ 2.72 (s, 3H), 3.94 (q, J=14.1 Hz, 2H), 7.15-7.24 (m, 3H), 7.40-7.52 (m, 4H), 7.70-7.73 (m, 1H).

6-(4-chlorophenyl)-1,4-dimethyl-4H-benzo[b][1,2,4]triazolo[4,3-d][1,4]diazepin-5(6H)-one

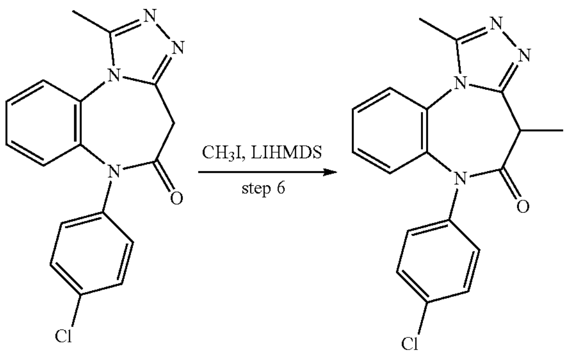 [SMILES: Cc1nnc2n1-c1ccccc1N(c1ccc(Cl)cc1)C(=O)C2 ; Cc1nnc2n1-c1ccccc1N(c1ccc(Cl)cc1)C(=O)C2C]

To a solution of 6-(4-chlorophenyl)-1-methyl-4H-benzo[b][1,2,4]triazolo[4,3-d][1,4]diazepin-5(6H)-one (100 mg, 0.31 mmol) in THF was added LiHMDS (0.17 mL, 0.33 mmol) at −78° C. The mixture was stirred at the same temperature for 1 h, and then $CH_3I$ (84.00 mg, 0.59 mmol) was added. The mixture was stirred at −78° C. for 2 h, then warmed to room temperature, and maintained at room temperature for 2 h. $NH_4Cl$ aqueous (15 mL) was added, and then extracted with DCM (10 mL*3). The product was purified by column chromatography (silica-gel, DCM:MEOH=30:1) to give 6-(4-chlorophenyl)-1,4-dimethyl-4H-benzo[b][1,2,4]triazolo[4,3-d][1,4]diazepin-5(6H)-one (40.0 mg, 38%). LRMS ($M+H^+$) m/z: calcd 338.09. found 338.

6-(4-chlorophenyl)-1,4-dimethyl-5,6-dihydro-4H-benzo[b][1,2,4]triazolo[4,3-d][1,4]diazepine (Compound 1)

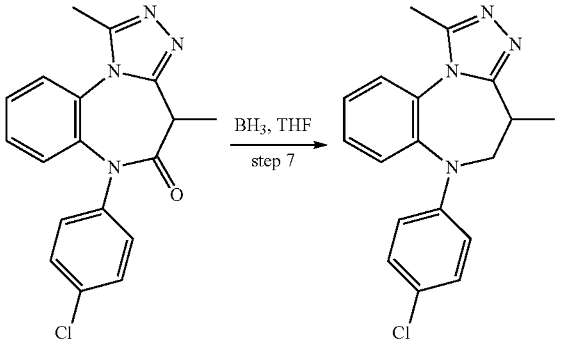 [SMILES: Cc1nnc2n1-c1ccccc1N(c1ccc(Cl)cc1)C(=O)C2C ; Cc1nnc2n1-c1ccccc1N(c1ccc(Cl)cc1)CC2C]

To a solution of 6-(4-chlorophenyl)-1,4-dimethyl-4H-benzo[b][1,2,4]triazolo[4,3-d][1,4]diazepin-5(6H)-one (40.0 mg, 0.12 mmol) in THF (5 ml) was added $BH_3$-THF solution (1 mL, 1M in THF) slowly, the resulting mixture was stirred under reflux overnight, concentrated, the residue was purified by Prep-HPLC (column: Gemini 5u C18 250*21.5 mm; mobile: $H_2O$ (0.1% TFA)-ACN(0.1% TFA)) to give 6-(4-chlorophenyl)-1,4-dimethyl-5,6-dihydro-4H-benzo[b][1,2,4]triazolo[4,3-d][1,4]diazepine as an off-white solid (3.0 mg, 7.8%).

Example 2

Synthesis of 6-(4-chlorophenyl)-1-methyl-5,6-dihydro-4H-benzo[b][1,2,4]triazolo[4,3-d][1,4]diazepine (Compound 2)

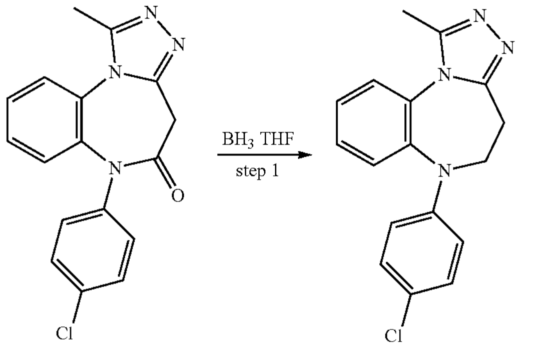 [SMILES: Cc1nnc2n1-c1ccccc1N(c1ccc(Cl)cc1)C(=O)C2 ; Cc1nnc2n1-c1ccccc1N(c1ccc(Cl)cc1)CC2 ; "BH3 THF"]

To a THF (5 ml) solution of 6-(4-chlorophenyl)-1-methyl-4H-benzo[b][1,2,4]triazolo[4,3-d][1,4]diazepin-5(6H)-one (20.0 mg, 0.06 mmol) was added $BH_3$ THF complex (1 mL, 1M in THF) slowly. The resulting solution was stirred at room temperature for 2 h, concentrated. The residue was purified by Prep-TLC (pure EA) to give 6-(4-chlorophenyl)-1-methyl-5,6-dihydro-4H-benzo[b][1,2,4]triazolo[4,3-d][1,4]diazepine as an off-white solid (3.0 mg, 16%).

Example 3

Synthesis of 6-(4-chlorophenyl)-1,4,4-trimethyl-5,6-dihydro-4H-benzo[b][1,2,4]triazolo[4,3-d][1,4]diazepine (Compound 3)

1-(4-chlorophenyl)-3,3-dimethyl-1H-benzo[b][1,4]diazepine-2,4(3H,5H)-dione

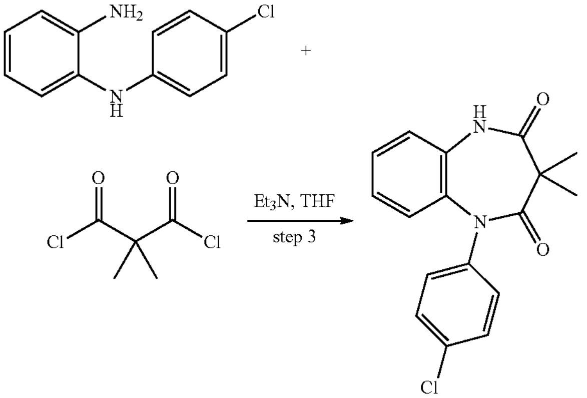

To a stirred refluxing solution of $N^1$-(4-chlorophenyl)benzene-1,2-diamine (200 mg, 0.92 mmol) in toluene (20 mL) was added drop-wise a solution of 2,2-dimethylmalonyl dichloride (155 mg, 0.92 mmol). Then the mixture was refluxed for 1 h. The solvent was removed in vacuum, stirred with water (20 mL), extracted with DCM (20 mL×3). The combined organic layer was dried over $Na_2SO_4$. The mixture was concentrated in vacuum and the residue was purified by column chromatography (silica-gel, DCM: methanol=40:1) to give 1-(4-chlorophenyl)-3,3-dimethyl-1H-benzo[b][1,4]diazepine-2,4(3H,5H)-dione as a yellow solid (167.5 mg, 58%). LRMS ($M+H^+$) m/z: calcd 314.08. found 314.

6-(4-chlorophenyl)-1,4,4-trimethyl-4H-benzo[b][1,2,4]triazolo[4,3-d][1,4]diazepin-5(6H)-one

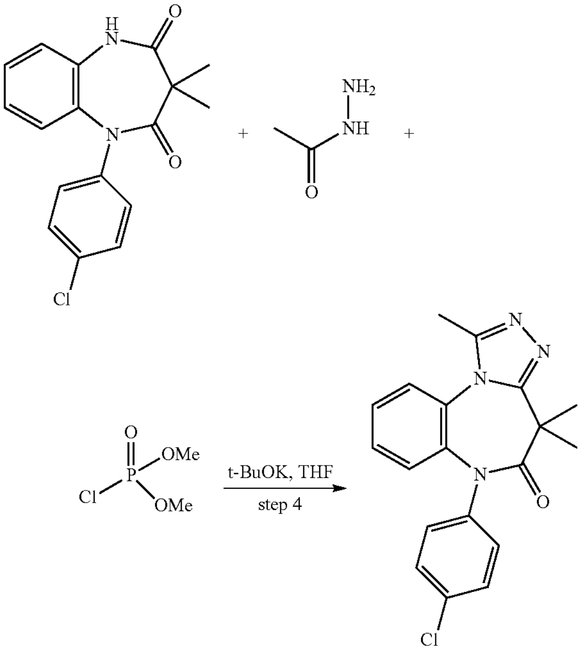

To a solution of 1-(4-chlorophenyl)-3,3-dimethyl-1H-benzo[b][1,4]diazepine-2,4(3H,5H)-dione (100 mg, 0.32 mmol) in THF (10 mL) was added a solution of t-BuOK (35.8 mg, 0.32 mmol) dropwise at −78° C. over 10 min. The solution was slowly warmed up to 0° C. in 30 min and recooled to −78° C. for the addition of dimethyl phosphorochloridate (55 mg, 0.38 mmol). The mixture was warmed up to 0° C. over 30 min and stirred for 1 hour at room temperature. The solution was cooled to −78° C. and a solution of acetohydrazide (28 mg, 0.38 mmol) in THF (5 mL) was added. The mixture was heated to reflux for 3 hours. The crude solution was diluted with water (20 mL) and extracted with ethyl acetate (20 mL*3). The combined organic layers were dried over $Na_2SO_4$, concentrated in vacuo and the residue was purified by column chromatography (silica-gel, DCM: methanol=20: 1) to give 6-(4-chlorophenyl)-1,4,4-trimethyl-4H-benzo[b][1,2,4]triazolo[4,3-d][1,4]diazepin-5(6H)-one as a white solid (51 mg, yield 44%) LRMS (M+H$^+$) m/z: calcd 352.11. found 352.

6-(4-chlorophenyl)-1,4,4-trimethyl-5,6-dihydro-4H-benzo[b][1,2,4]triazolo[4,3-d][1,4]diazepine (Compound 3)

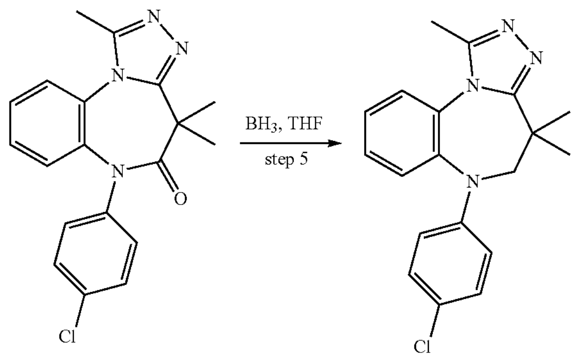 [SMILES: Cc1nnc2n1-c1ccccc1N(c1ccc(Cl)cc1)C(=O)C2(C)C ; Cc1nnc2n1-c1ccccc1N(c1ccc(Cl)cc1)CC2(C)C]

To a THF (5 ml) solution of 6-(4-chlorophenyl)-1,4,4-trimethyl-4H-benzo[b][1,2,4]triazolo[4,3-d][1,4]diazepin-5(6H)-one of (51 mg, 0.14 mmol) was added $BH_3$-THF complex (1 mL, 1M in THF) drop-wise at 0° C. The resulting mixture was heated at reflux overnight, then the mixture was concentrated in vacuo and the residue was purified by Prep-TLC (silica-gel, DCM:methanol=10:1) to give 6-(4-chlorophenyl)-1,4,4-trimethyl-5,6-dihydro-4H-benzo[b][1,2,4]triazolo[4,3-d][1,4]diazepine as a white solid (5.0 mg, yield 10.4%).

Example 4

Synthesis of 1,6-dimethyl-8-phenyl-5,6-dihydro-4H-benzo[b][1,2,4]triazolo[4,3-d][1,4]diazepine Compound 4 was synthesized according to the Scheme below.

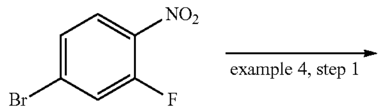

-continued

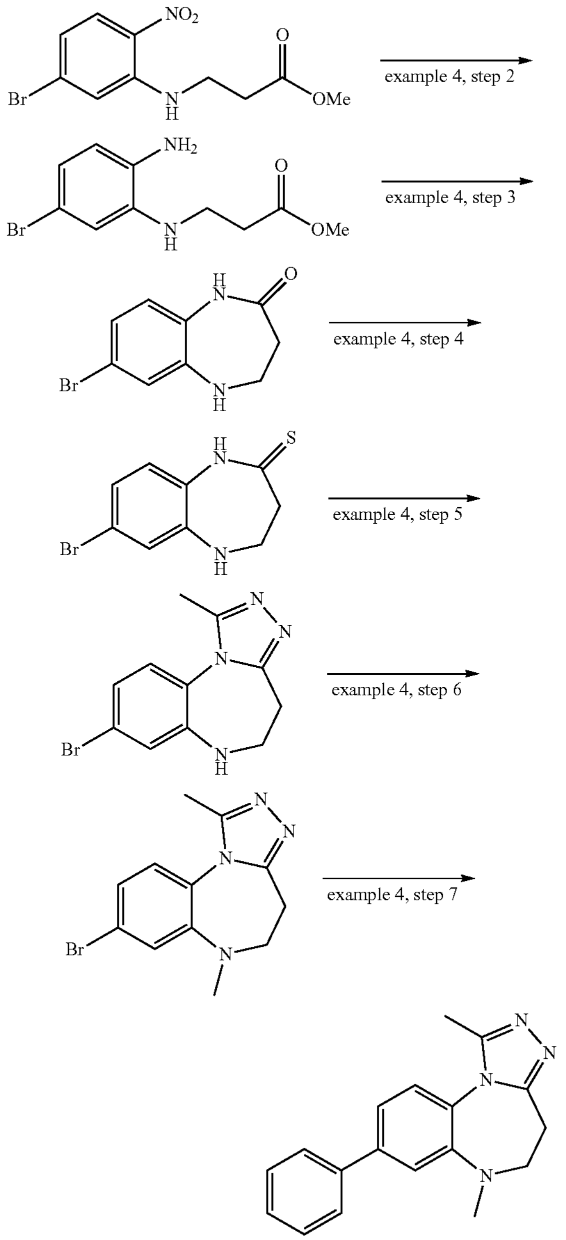

Methyl 3-((5-bromo-2-nitrophenyl)amino)propanoate (Step 1)

A solution of 4-bromo-2-fluoro-1-nitrobenzene (10 g, 45.5 mol), methyl 3-aminopropanoate hydrochloride (6.4 g, 45.5 mol) and $K_2CO_3$ (19 g, 136.5 mol) in THF (250 mL) was heated at 100° C. for 4 hrs. The mixture was extracted with ethyl acetate (100 mL), washed with brine (150 mL), dried and concentrated to give the residue, which was purified by CombiFlash (PE:EA=2:1) to give methyl 3-((5-bromo-2-nitrophenyl)amino)propanoate (12 g, yield 88%). $^1$H NMR (300 MHz, $CDCl_3$) δ 2.70-2.75 (t, J=6.6 Hz, 2H), 3.58-3.65 (m, 2H), 3.74 (s, 3H), 6.76-6.80 (m, 1H), 7.02-7.03 (d, J=2.1 Hz, 1H), 8.01-8.04 (d, J=9.0 Hz, 2H), 8.20-8.22 (br, 1H).

Methyl 3-((2-amino-5-bromophenyl)amino)propanoate (Step 2)

Iron powder (7 g, 0.12 mol) was added to a mixture of methyl 3-(5-bromo-2-nitrophenylamino)propanoate (12 g, 0.04 mol) in aq. $NH_4Cl$ solution (50 mL) and ethanol (100 mL). After heating at 60° C. for 2 h, the mixture solution was filtered. The filtrate was evaporated, diluted with water (100 mL), extracted with ethyl acetate (150 mL), dried and concentrated to give the crude product, which was purified by CombiFlash to afford methyl 3-((2-amino-5-bromophenyl) amino)propanoate (9.4 g, yield 84%). LRMS $(M+H)^+$: 272 m/z. $^1H$ NMR (300 MHz, $CDCl_3$) δ 2.67-2.72 (d, 2H, J=6.3 Hz), 3.40-3.44 (d, 2H, J=6.3 Hz), 3.72 (s, 3H), 4.58 (br, 3H), 6.67-6.70 (d, 2H, J=8.1 Hz), 6.80-6.82 (m, 2H).

7-bromo-4,5-dihydro-1H-benzo[b][1,4]diazepin-2(3H)-one (Step 3)

Sodium (2.4 g, 104 mmol) was added in portions to 50 mL of methanol until it dissolved. The solution was then added dropwise to a cooled solution of methyl 3-((2-amino-5-bromophenyl)amino)propanoate (9.4 g, 34.6 mmol) in 50 mL of methanol at 0° C. After additional, the mixture was stirred at room temperature overnight. It was concentrated, added with water (50 mL), extracted with ethyl acetate (50 mL) and purified by CombiFlash (PE:EA=5:1) to give 7-bromo-4,5-dihydro-1H-benzo[b][1,4]diazepin-2(3H)-one (2 g, yield 24%). LRMS $(M+H)^+$: 240 m/z. $^1H$ NMR (300 MHz, $CDCl_3$) δ 2.68-2.72 (t, J=6.0 Hz, 2H), 3.68-3.72 (t, J=6.0 Hz, 2H), 6.79-6.82 (d, J=8.7 Hz, 2H), 6.98-7.06 (m, 2H), 8.00 (br, 1H).

7-bromo-4,5-dihydro-1H-benzo[b][1,4]diazepine-2(3H)-thione (Step 4)

A solution of 7-bromo-4,5-dihydro-1H-benzo[b][1,4]diazepin-2(3H)-one (3) (1.5 g, 6.25 mmol) and Lawesson's Reagent (2.5 g, 12.5 mmol) in THF (50 mL) was heated at 80° C. overnight. The mixture was evaporated, water (50 mL) was added and the solution was extracted with ethyl acetate (100 mL), washed with water (50 mL), dried and concentrated to give the residue, which was purified by CombiFlash (PE:EA=5:1) to afford 7-bromo-4,5-dihydro-1H-benzo[b][1,4]diazepine-2(3H)-thione (1.2 g, yield 75%). LRMS $(M+H)^+$: 256 m/z. $^1H$ NMR (300 MHz, $CDCl_3$) δ 3.13-3.17 (t, J=5.4 Hz, 2H), 3.75-3.79 (t, J=5.4 Hz, 2H), 6.77-6.80 (m, 1H), 6.95-6.98 (m, 2H).

8-bromo-1-methyl-5,6-dihydro-4H-benzo[b][1,2,4]triazolo[4,3-d][1,4]diazepine (Step 5)

A solution of 7-bromo-4,5-dihydro-1H-benzo[b][1,4]diazepine-2(3H)-thione (1.2 g, 4.69 mmol) and acetohydrazide (693 mg, 9.38 mmol) in n-BuOH (20 mL) was heated at 130° C. overnight. The reaction mixture was evaporated, extracted with ethyl acetate (15 mL), washed with water (15 mL), dried and concentrated to give the crude product, which was purified by CombiFlash (DCM:MeOH=20:1) to afford bromo-1-methyl-5,6-dihydro-4H-benzo[b][1,2,4]triazolo[4,3-d][1,4] diazepine (1 g, yield 77%). LRMS $(M+H)^+$: calcd 278.02. found 278. $^1H$ NMR (300 MHz, $CDCl_3$) δ 2.51 (s, 3H), 3.08-3.12 (m, 2H), 3.72-3.77 (t, J=6.3 Hz, 2H), 7.02-7.05 (d, J=8.4 Hz, 1H), 7.16-7.26 (m, 2H).

8-bromo-1,6-dimethyl-5,6-dihydro-4H-benzo[b][1,2,4]triazolo[4,3-d][1,4]diazepine (Step 6)

A solution of bromo-1-methyl-5,6-dihydro-4H-benzo[b][1,2,4]triazolo[4,3-d][1,4]diazepine (250 mg, 0.90 mmol) in formic acid (4 mL) and formaldehyde (4 mL) was heated at 100° C. for 2 hrs. The reaction mixture was evaporated, added with $NaHCO_3$ solution (5 mL), extracted with ethyl acetate (10 mL), concentrated to give the crude product, which was purified by prep-TLC (DCM:MeoH=7:1) to afford 8-bromo-1,6-dimethyl-5,6-dihydro-4H-benzo[b][1,2,4]triazolo[4,3-d][1,4]diazepine (240 mg, yield 92%). LRMS $(M+H)^+$: 292 m/z. $^1H$ NMR (300 MHz, $CD_3C1$): δ 2.03 (s, 3H), 2.77 (s, 3H), 2.80-2.95 (m, 2H), 3.38-3.40 (m, 2H), 7.02-7.05 (d, J=8.1 Hz, 1H), 7.26-7.31 (m, 2H).

1,6-dimethyl-8-phenyl-5,6-dihydro-4H-benzo[b][1,2,4]triazolo[4,3-d][1,4]diazepine (Step 7) (Compound 4)

A solution of bromo-1-methyl-5,6-dihydro-4H-benzo[b][1,2,4]triazolo[4,3-d][1,4]diazepine (50 mg, 0.17 mmol), phenylboronic acid (42 mg, 0.34 mmol), tetrakis(triphenylphosphine)palladium (10 mg) and $Cs_2CO_3$ (110 mg, 0.34 mmol) in dioxane (5 mL) and water (1 mL) was heated at 120° C. under microwave for 20 min. The reaction mixture was concentrated to give the crude product, which was purified by prep-TLC (DCM:MeOH=10:1) to afford 1,6-dimethyl-8-phenyl-5,6-dihydro-4H-benzo[b][1,2,4]triazolo[4,3-d][1,4] diazepine (20 mg, yield 41%).

Example 5

Synthesis of 5-(1,6-dimethyl-5,6-dihydro-4H-benzo[b][1,2,4]triazolo[4,3-d][1,4]diazepin-8-yl)pyridin-2-amine. (Compound 5)

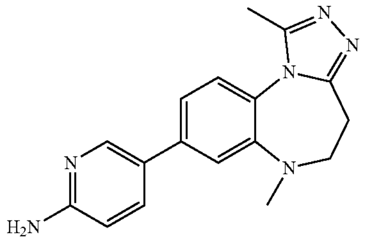 [SMILES: Cc1nnc2n1-c1ccc(-c3ccc(N)nc3)cc1N(C)CC2]

A solution of bromo-1-methyl-5,6-dihydro-4H-benzo[b][1,2,4]triazolo[4,3-d][1,4]diazepine (50 mg, 0.17 mmol), 5-(4,4,5,5-tetramethyl-1,3,2-dioxaborolan-2-yl)pyridin-2-amine (75 mg, 0.34 mmol), Tetrakis(triphenylphosphine)palladium(0)(10 mg) and $Cs_2CO_3$ (110 mg, 0.34 mmol) in dioxane (5 mL) and water (1 mL) was heated at 120° C. under microwave for 20 min. The reaction mixture was concentrated to give the crude product, which was purified by prep-TLC (DCM:MeOH=10:1) to afford 5-(1,6-dimethyl-5,6-dihydro-4H-benzo[b][1,2,4]triazolo[4,3-d][1,4]diazepin-8-yl) pyridin-2-amine (20 mg, yield 38%).

Example 6

Synthesis of 5-(1-methyl-5,6-dihydro-4H-benzo[b][1,2,4]triazolo[4,3-d][1,4]diazepin-8-yl)pyridin-2-amine (Compound 6)

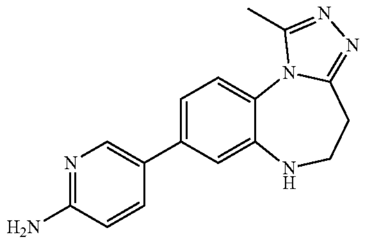 [SMILES: Cc1nnc2n1-c1ccc(-c3ccc(N)nc3)cc1NCC2]

A solution of bromo-1-methyl-5,6-dihydro-4H-benzo[b][1,2,4]triazolo[4,3-d][1,4]diazepine (30 mg, 0.11 mmol), 5-(4,4,5,5-tetramethyl-1,3,2-dioxaborolan-2-yl)pyridin-2-amine (48 mg, 0.22 mmol), Tetrakis(triphenylphosphine)palladium(0) (10 mg) and $Cs_2CO_3$ (72 mg, 0.22 mmol) in dioxane (5 mL) and water (1 mL) was heated at 120° C. under microwave for 20 min. The reaction mixture was concentrated to give the crude product, which was purified by prep-TLC (DCM:MeOH=10:1) to afford 5-(1-methyl-5,6-dihydro-4H-benzo[b][1,2,4]triazolo[4,3-d][1,4]diazepin-8-yl)pyridin-2-amine (21 mg, yield 55%).

Example 7

Synthesis of 1-methyl-8-phenyl-5,6-dihydro-4H-benzo[b][1,2,4]triazolo[4,3-d][1,4]diazepine (Compound 7)

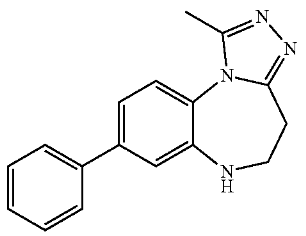 [SMILES: Cc1nnc2n1-c1ccc(-c3ccccc3)cc1NCC2]

A solution of bromo-1-methyl-5,6-dihydro-4H-benzo[b][1,2,4]triazolo[4,3-d][1,4]diazepine (30 mg, 0.11 mmol), phenylboronic acid (26 mg, 0.22 mmol), Tetrakis(triphenylphosphine)palladium(0) (10 mg) and $Cs_2CO_3$ (72 mg, 0.22 mmol) in dioxane (5 mL) and water (1 mL) was heated at 120° C. under microwave for 20 min. The reaction mixture was concentrated to give the crude product, which was purified by prep-TLC (DCM:MeOH=10:1) to afford 1-methyl-8-phenyl-5,6-dihydro-4H-benzo[b][1,2,4]triazolo[4,3-d][1,4]diazepine (16 mg, yield 55%).

Example 8

Synthesis of 6-(5-chloropyridin-2-yl)-1-methyl-5,6-dihydro-4H-benzo[b][1,2,4]triazolo[4,3-d][1,4]diazepine (Compound 8)

Compound 8 was synthesized according to the following Scheme.

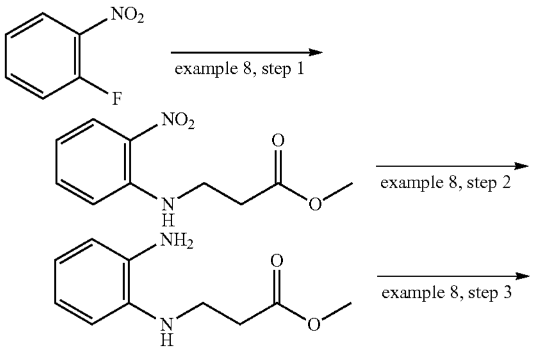

-continued

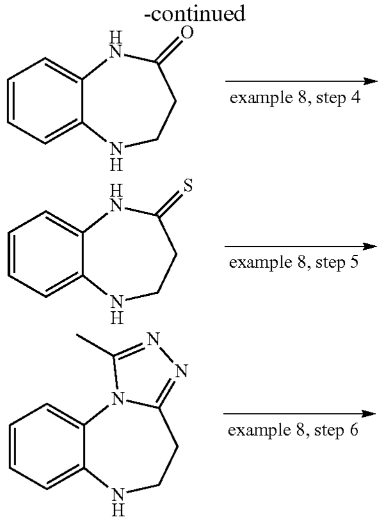

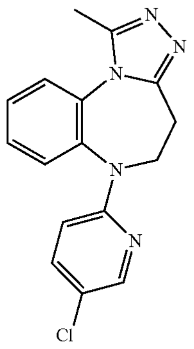

Methyl 3-((2-nitrophenyl)amino)propanoate (Step 1)

A mixture of methyl 3-aminopropanoate hydrochloride (15 g, 0.107 mol), 1-fluoro-2-nitrobenzene (14.9 g, 0.107 mol) and $K_2CO_3$ (36.6 g, 0.265 mol) in THF (50 mL) was heated at 90° C. and stirred overnight. After cooled to room temperature, water (20 mL) and ethyl acetate (40 mL) were added, and the separated organic layer was dried over $Na_2SO_4$, concentrated, and the resulting residue was purified by CombiFlash (PE:EA=4:1) to give methyl 3-((2-nitrophenyl)amino)propanoate (21.4 g, 90%). $^1H$ NMR (300 MHz, $CD_3OD$): δ 2.72 (t, J=6.6 Hz, 2H), 3.64-3.69 (m, 5H), 6.64-6.70 (m, 1H), 7.01-7.04 (m, 1H), 7.46-7.52 (m, 1H), 8.09-8.13 (m, 1H).

Methyl 3-((2-aminophenyl)amino)propanoate (Step 2)

A mixture of methyl 3-((2-nitrophenyl)amino)propanoate (11 g, 48.9 mmol) and Pd/C (3.3 g, 10%) in 300 mL of MeOH and 20 mL of EtOAc was stirred overnight under $H_2$ atmosphere at room temperature. The mixture was filtered off, and the filtrate was concentrated to give methyl 3-((2-aminophenyl)amino)propanoate as a yellow oil. (9.3 g, 98%). LRMS $(M+H)^+$: 193 m/z.

4,5-dihydro-1H-benzo[b][1,4]diazepin-2(3H)-one (Step 3)

Sodium (1.8 g, 77.2 mmol) was added in portions to methanol (50 mL), and the mixture was stirred for 1 h. The resulting mixture was added dropwise to a solution of methyl 3-((2- aminophenyl)amino)propanoate (9.4 g, 48.2 mmol) in methanol (150 mL) at 0° C. Once addition was completed, the mixture was stirred at room temperature overnight. The mixture was concentrated, and the residue was purified by CombiFlash (PE:EA=5:1) to give 4,5-dihydro-1H-benzo[b][1,4] diazepin-2(3H)-one as a yellow solid (3.9 g, 50%). LRMS $(M+H)^+$: 161 m/z. $^1H$ NMR (300 MHz, $CD_3OD$): δ 2.61 (t, J=6.0 Hz, 2H), 3.62 (t, J=6.0 Hz, 2H), 6.76-6.86 (m, 2H), 6.90-6.99 (m, 2H).

4,5-dihydro-1H-benzo[b][1,4]diazepine-2(3H)-thione (Step 4)

A solution of 4,5-dihydro-1H-benzo[b][1,4]diazepin-2 (3H)-one (3.2 g, 19.6 mmol) and $P_2S_5$ (5.2 g, 23.5 mmol) in pyridine (100 mL) was heated at 120° C. and stirred for 30 min. After being cooled to room temperature, water (100 mL) and ethyl acetate (200 mL) were added, the separated organic layer was dried over $Na_2SO_4$, concentrated in vacuum, and the residue was purified by CombiFlash (DCM:MeOH=20:1) to give 4,5-dihydro-1H-benzo[b][1,4]diazepine-2(3H)-thione as a yellow solid (2.1 g, 59%). LRMS $(M+H)^+$: 177 m/z.

1-methyl-5,6-dihydro-4H-benzo[b][1,2,4]triazolo[4, 3-d][1,4]diazepine (Step 5)

A solution of compound 4 (200 mg, 1.12 mmol) and acetohydrazide (165 mg, 2.24 mmol) in n-BuOH (10 mL) was heated at 130° C. and stirred overnight. After cooling to room temperature, the reaction mixture was concentrated, and then water (10 mL) and ethyl acetate (10 mL) were added, the separated organic layer was dried over $Na_2SO_4$ and concentrated. The residue was purified by Prep-TLC to give 1-methyl-5,6-dihydro-4H-benzo[b][1,2,4]triazolo[4,3-d][1,4]diazepine as a yellow solid (50 mg, 22.3%). LRMS $(M+H)^+$: 199 m/z. $^1H$ NMR (300 MHz, $CDCl_3$): δ 2.51 (s, 3H), 3.03-3.07 (t, J=6.3 Hz, 1H), 3.71-3.75 (m, J=6.3 Hz, 1H), 7.00-7.03 (m, 1H), 7.06-7.12 (m, 1H), 7.17-7.20 (m, 1H), 7.28-7.31 (m, 1H).

6-(5-chloropyridin-2-yl)-1-methyl-5,6-dihydro-4H-benzo[b][1,2,4]triazolo[4,3-d][1,4]diazepine (Step 6) (Compound 8)

A mixture of 1-methyl-5,6-dihydro-4H-benzo[b][1,2,4] triazolo[4,3-d][1,4]diazepine (300 mg, 1.5 mmol), 5-chloro-2-fluoropyridine (600 mg, 4.5 mmol) and $K_2CO_3$ (621 mg, 4.5 mmol) in 10 mL of DMF was stirred at 170° C. for 30 min. After the solvent was removed in vacuo, the product was purified by flash chromatography eluting with DCM: MeOH=10:1 to give 6-(5-chloropyridin-2-yl)-1-methyl-5,6-dihydro-4H-benzo[b][1,2,4]triazolo[4,3-d][1,4]diazepine as a yellow solid. (50 mg, 11.3%).

Example 9

Synthesis of 2-(6-(4-chlorophenyl)-1-methyl-5,6-dihydro-4H-benzo[b][1,2,4]triazolo[4,3-d][1,4]diazepin-4-yl)ethanol (Compound 9)

Compound 9 was synthesized by the Scheme set forth below.

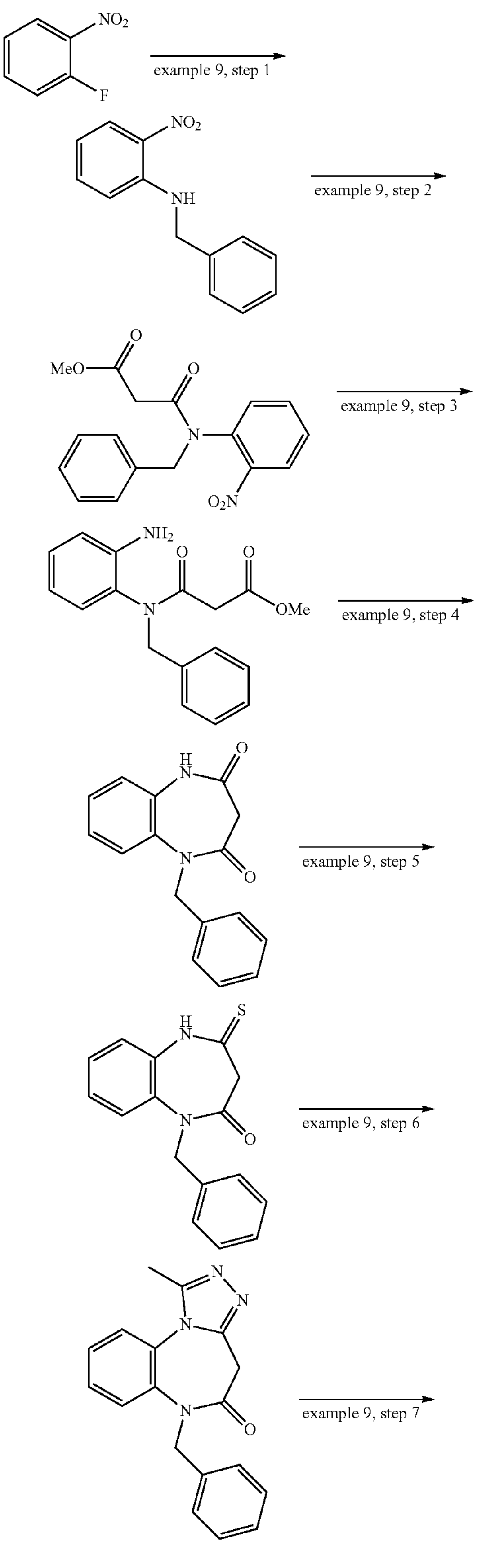

-continued

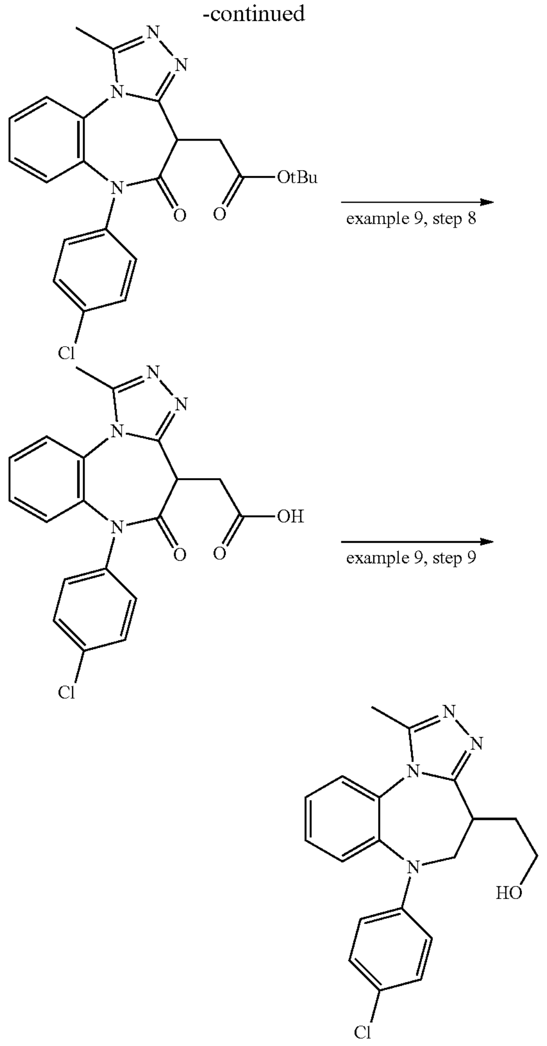

N-benzyl-2-nitroaniline (Step 1)

2-nitrobenzenamine (5.0 g, 36.2 mmol) was dissolved in 100 mL of THF under $N_2$ atmosphere, 60% NaH (1.7 g, 43.4 mmol) was added at 0° C., and the mixture was stirred for 30 min at room temperature. (Bromomethyl)benzene (7.4 g, 43.4 mmol) was added at 0° C. and the reaction was stirred at 80° C. overnight. The solvent was evaporated in vacuo and the residue was purified by combi-flash (PE:EA=2:1) to give N-benzyl-2-nitroaniline as a yellow solid (2.92 g, 36%). $^1$H NMR (300 MHz, $CD_3OD$): δ 4.65 (d, J=6 Hz, 2H), 6.69 (t, J=7.2 Hz, 1H), 6.94 (d, J=9 Hz, 1H), 7.25-7.50 (m, 5H), 8.09 (d, J=8.4 Hz, 1H), 8.62-8.68 (m, 1H).

Methyl 3-(benzyl(2-nitrophenyl)amino)-3-oxopropanoate (Step 2)

A mixture of N-benzyl-2-nitroaniline (1.62 g, 7.1 mmol) and methyl 3-chloro-3-oxopropanoate (1.17 mg, 8.5 mmol), $Et_3N$ (1.8 g, 17.8 mmol) in 50 mL of $CH_2Cl_2$ was stirred at 80° C. for 2 days. The solvent was evaporated, and the residue was purified by combi-flash to give methyl 3-(benzyl(2-nitrophenyl)amino)-3-oxopropanoate as a yellow solid. LRMS $(M+H)^+$: 328 m/z.

Methyl 3-((2-aminophenyl)(benzyl)amino)-3-oxopropanoate (Step 3)

Iron powder (3 g) was added to a solution of methyl 3-(benzyl(2-nitrophenyl)amino)-3-oxopropanoate (400 mg, 1.22 mmol) in EtOH (10 mL) and $NH_4Cl$ (10 mL). The reaction mixture was heated at 70° C. for 2 h. The mixture was filtered off and the filtrate was extracted by EA (50 mL), the separated organic layer was dried over $Na_2SO_4$. After the solvent was removed in vacuum, the residue was purified by combi-flash to give methyl 3-((2-aminophenyl)(benzyl)amino)-3-oxopropanoate as a yellow solid (200 mg, 55%). LRMS $(M+H)^+$: 298 m/z.

1-benzyl-1H-benzo[b][1,4]diazepine-2,4(3H,5H)-dione (Step 4)

methyl 3-((2-aminophenyl)(benzyl)amino)-3-oxopropanoate (200 mg, 0.67 mmol) was dissolved in 10 mL of EtOH and cooled to 0° C., and Na metal (25 mg, 1.07 mmol) was added. The reaction mixture was warmed to room temperature and stirred for 1 h. The mixture was concentrated and the residue was purified by prep-TLC to give 1-benzyl-1H-benzo[b][1,4]diazepine-2,4(3H,5H)-dione (160 mg, 89%). $^1$H NMR (300 MHz, DMSO): δ 2.89 (d, J=9.9 Hz, 1H), 3.03 (d, J=10.2 Hz, 1H), 3.46 (q, J=21 Hz, 2H), 6.68 (t, J=8.1 Hz, 1H), 6.84-6.91 (m, 2H), 7.08-7.28 (m, 6H).

1-benzyl-4-thioxo-4,5-dihydro-1H-benzo[b][1,4]diazepin-2(3H)-one (Step 5)

A solution of 1-benzyl-1H-benzo[b][1,4]diazepine-2,4(3H,5H)-dione (160 mg, 0.60 mmol) and $P_2S_5$ (140 mg, 0.63 mmol) in 20 mL of pyridine was heated to reflux and stirred for 1 h under $N_2$ atmosphere. The solvent was evaporated in vacuo, the residue was purified by prep-TLC (DCM:MeOH=50:1) to give 1-benzyl-4-thioxo-4,5-dihydro-1H-benzo[b][1,4]diazepin-2(3H)-one (50 mg, 30%). $^1$H NMR (300 MHz, DMSO): δ 3.74 (q, J=12.3 Hz, J=12.3 Hz, 1H), 5.12 (q, J=15.6 Hz, J=15.9 Hz, 1H), 7.03-7.06 (m, 2H), 7.17-7.27 (m, 6H), 7.48 (d, J=7.5 Hz, 1H).

6-benzyl-1-methyl-4H-benzo[b][1,2,4]triazolo[4,3-d][1,4]diazepin-5(6H)-one (Step 6)

A solution of 1-benzyl-4-thioxo-4,5-dihydro-1H-benzo[b][1,4]diazepin-2(3H)-one (50 mg, 0.18 mmol) and acetohydrazide (40 mg, 0.53 mmol) in 20 mL of n-butanol was heated to reflux, and stirred for 24 h under $N_2$ atmosphere. The solvent was evaporated in vacuo and the residue was purified by prep-TLC (DCM:MeOH=25:1) to give 6-benzyl-1-methyl-4H-benzo[b][1,2,4]triazolo[4,3-d][1,4]diazepin-5(6H)-one (20 mg, 38%). $^1$H NMR (300 MHz, $CD_3OD$): δ 2.36 (s, 3H), 3.77 (d, J=14.1 Hz, 1H), 3.98 (d, J=14.1 Hz, 1H), 4.69 (d, J=15 Hz, 1H), 5.64 (d, J=15 Hz, 1H), 6.77-6.80 (m, 2H), 7.13-7.16 (m, 3H), 7.49-7.62 (m, 3H), 7.82-7.85 (m, 1H). LRMS $(M+H)^+$: 304 m/z.

tert-butyl 2-(6-(4-chlorophenyl)-1-methyl-5-oxo-5,6-dihydro-4H-benzo[b][1,2,4]triazolo[4,3-d][1,4]diazepin-4-yl)acetate (Step 7)

To a solution of 6-(4-chlorophenyl)-1-methyl-4H-benzo[b][1,2,4]triazolo[4,3-d][1,4]diazepin-5(6H)-one (200 mg, 0.62 mmol) in THF was added LiHMDS (0.9 mL, 0.9 mmol) at −78° C. The mixture was stirred at the same temperature for 1 h, and then tert-butyl 2-bromoacetate (180 mg, 0.92 mmol)

was added, the mixture was warmed to room temperature and stirred overnight. $NH_4Cl$ aqueous (15 mL) was added, and then extracted with DCM (3×10 mL3). The combined organic layers were dried over $Na_2SO_4$, and the solvent was removed in vacuum. The residue was purified by column chromatography (silica-gel, DCM:MeOH=20:1) to give tert-butyl 2-(6-(4-chlorophenyl)-1-methyl-5-oxo-5,6-dihydro-4H-benzo[b][1,2,4]triazolo[4,3-d][1,4]diazepin-4-yl)acetate as a yellow solid (140 mg, 51.4%). LRMS $(M+H)^+$: 324 m/z. $^1H$ NMR (300 MHz, $CD_3OD$): δ 1.46 (s, 9H), 2.72 (s, 3H), 3.08-3.15 (m, 1H), 3.31-3.39 (m, 1H), 4.10-4.15 (m, 1H), 7.15-7.23 (m, 3H), 7.40-7.43 (m, 2H), 7.50-7.54 (m, 2H), 7.74-7.79 (m, 1H).

2-(6-(4-chlorophenyl)-1-methyl-5-oxo-5,6-dihydro-4H-benzo[b][1,2,4]triazolo[4,3-d][1,4]diazepin-4-yl) acetic acid (Step 8)

To a solution of tert-butyl 2-(6-(4-chlorophenyl)-1-methyl-5-oxo-5,6-dihydro-4H-benzo[b][1,2,4]triazolo[4,3-d][1,4]diazepin-4-yl)acetate (90 mg, 0.21 mmol) in 5 mL of DCM, was added TFA (1 mL). The mixture was stirred at room temperature for 2 h. The solvent was removed in vacuo and the residue was purified by flash chromatography eluting with DCM:MeOH=20:1 to give 2-(6-(4-chlorophenyl)-1-methyl-5-oxo-5,6-dihydro-4H-benzo[b][1,2,4]triazolo[4,3-d][1,4]diazepin-4-yl)acetic acid as a yellow solid (68 mg, 87%). LRMS $(M+H)^+$: 382 m/z.

2-(6-(4-chlorophenyl)-1-methyl-5,6-dihydro-4H-benzo[b][1,2,4]triazolo[4,3-d][1,4]diazepin-4-yl) ethanol (Step 9) (Compound 9)

To a solution of 2-(6-(4-chlorophenyl)-1-methyl-5-oxo-5,6-dihydro-4H-benzo[b][1,2,4]triazolo[4,3-d][1,4]diazepin-4-yl)acetic acid (500 mg, 1.32 mmol) in THF (300 ml) was added $BH_3$ solution in THF (1 M, 6.5 mL) dropwise, the resulting mixture was stirred at room temperature overnight. $NH_4Cl$ aqueous (15 mL) was added, and then extracted with DCM (3×30 mL), the combined organic layers were dried over $Na_2SO_4$, and the solvent was removed in vacuum. The residue was purified by flash chromatography eluting with DCM:MeOH=40:1 to give 2-(6-(4-chlorophenyl)-1-methyl-5,6-dihydro-4H-benzo[b][1,2,4]triazolo[4,3-d][1,4]diazepin-4-yl)ethanol as an off-white solid (90 mg, 18.5%).

Example 10

Synthesis of 2-(6-(4-chlorophenyl)-1-methyl-5,6-dihydro-4H-benzo[b][1,2,4]triazolo[4,3-d][1,4]diazepin-4-yl)-N-ethylacetamide (Compound 10)

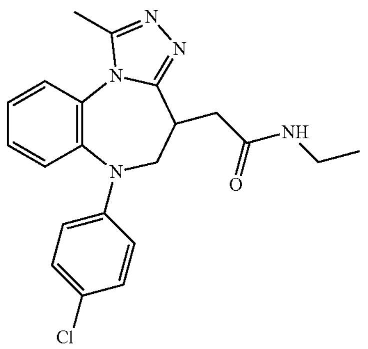 [SMILES: CCNC(=O)CC1CN(c2ccc(Cl)cc2)c2ccccc2-n2c(C)nnc21]

A mixture of 2-(6-(4-chlorophenyl)-1-methyl-5-oxo-5,6-dihydro-4H-benzo[b][1,2,4]triazolo[4,3-d][1,4]diazepin-4-yl)acetic acid (15 mg, 0.04 mmol), ethanamine (4 mg, 1.12 mmol), HATU (19 mg, 0.05 mmol), DIEA (8 mg, 0.06 mmol) in DCM (5 mL) was stirred overnight at room temperature. The mixture was concentrated and purified by prep-HPLC to give 2-(6-(4-chlorophenyl)-1-methyl-5,6-dihydro-4H-benzo[b][1,2,4]triazolo[4,3-d][1,4]diazepin-4-yl)-N-ethylacetamide as a white solid (4 mg).

Example 11

Synthesis of (6-(4-chlorophenyl)-1-methyl-5,6-dihydrospiro[benzo[b][1,2,4]triazolo[4,3-d][1,4]diazepine-4,1'-cyclopropan]-2'-yl)methanol (Compound 11)

Compound 11 was synthesized by the Scheme set forth below.

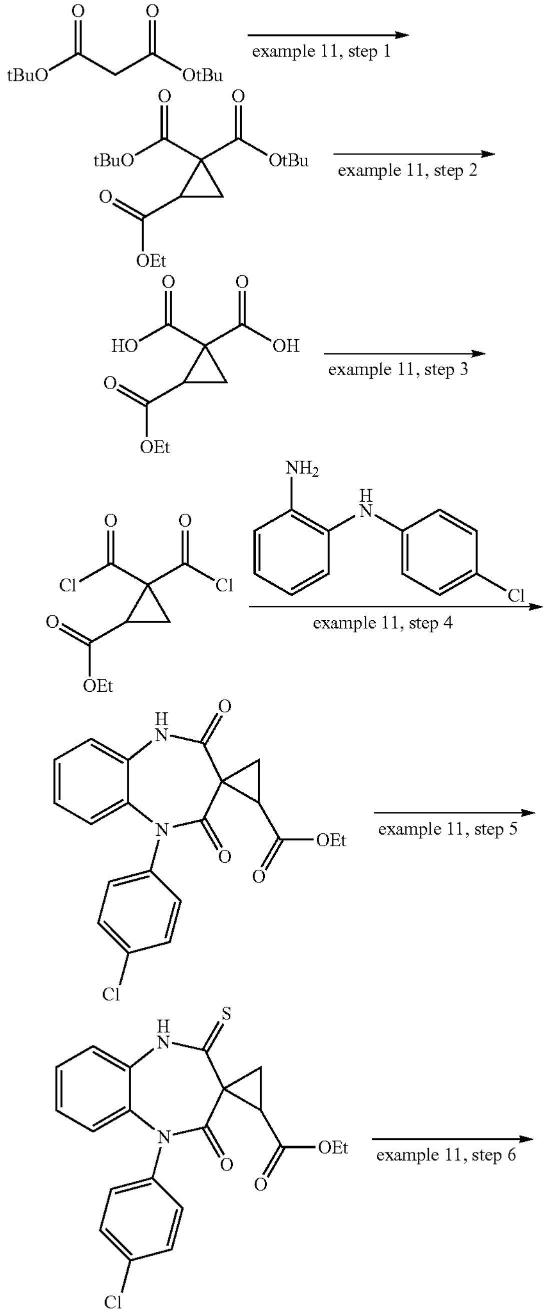

-continued

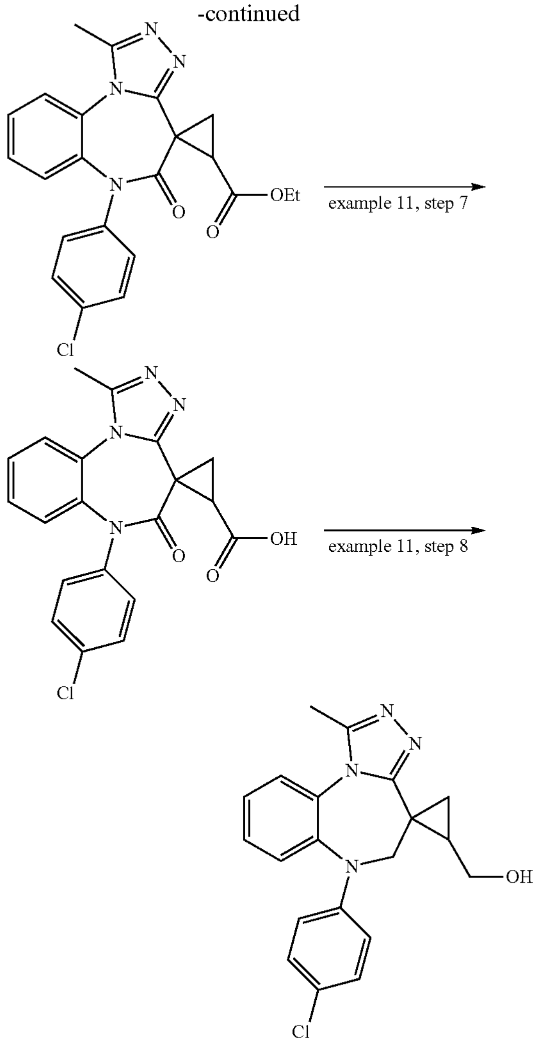

1,1-di-tert-butyl 2-ethyl cyclopropane-1,1,2-tricarboxylate (Step 1)

To a THF (200 mL) solution of t-BuOK (11.4 g, 102 mmol) at −30° C. was added slowly di-tert-butyl malonate (20 g, 92.6 mmol). The internal temperature was maintained between −30° C. and −10° C. After 30 min, ethyl 2,3-dibromopropanoate (29 g, 111.1 mmol) was added. The cooling bath was removed. After 1.5 h, the reaction mixture was cooled to −10° C. for addition of t-BuOK (11.4 g, 102 mmol). The cooling mixture was removed and the mixture was stirred overnight. The solution was evaporated and the residue was extracted with ethyl acetate (600 mL), dried and purified by CombiFlash (PE:EA=15:1) to afford 1,1-di-tert-butyl 2-ethyl cyclopropane-1,1,2-tricarboxylate (18 g, 62%). $^1$H NMR (300 MHz, $CDCl_3$): δ 1.34-1.51 (t, J=7.2 Hz, 3H), 1.54-1.56 (d, J=4.4 Hz, 18H), 1.58-1.60 (m, 1H), 1.90-1.94 (m, 1H), 2.52-2.57 (m, 1H), 4.21-4.31 (m, 2H).

2-(ethoxycarbonyl)cyclopropane-1,1-dicarboxylic acid (Step 2)

TFA (4.5 g, 39.7 mmol) was added into a solution of 1,1-di-tert-butyl 2-ethyl cyclopropane-1,1,2-tricarboxylate (4.9 g, 13.2 mmol) in dichloromethane (20 mL) and the mixture was stirred at room temperature for 48 h. The solvent was evaporated in vacuo and the excess TFA was lyophilized to afford 2-(ethoxycarbonyl)cyclopropane-1,1-dicarboxylic acid (3.3 g, 100%). $^1$H NMR (300 MHz, $CD_3OD$): δ 1.23-1.29 (t, J=6.9 Hz, 3H), 1.60-1.64 (m, 1H), 1.85-1.88 (m, 1H), 2.48-2.53 (m, 1H), 4.10-4.18 (m, 1H).

Ethyl 2,2-bis(chlorocarbonyl)cyclopropanecarboxylate (Step 3)

$(COCl)_2$ (5 mL) was added dropwise to a solution of 2-(ethoxycarbonyl)cyclopropane-1,1-dicarboxylic acid (2 g, 10 mmol) in dichloromethane (20 mL) and the mixture was stirred at 45° C. overnight. The solution was evaporated to afford crude ethyl 2,2-bis(chlorocarbonyl)cyclopropanecarboxylate, which was used in the next step directly.

Ethyl 1-(4-chlorophenyl)-2,4-dioxo-1,2,4,5-tetrahydrospiro[benzo[b][1,4]diazepine-3,1'-cyclopropane]-2'-carboxylate (Step 4)

Ethyl 2,2-bis(chlorocarbonyl)cyclopropanecarboxylate (2 g, crude product from last step) in dichloromethane (10 mL) was added dropwise to a solution of N1-(4-chlorophenyl)benzene-1,2-diamine (2.2 g, 10 mmol) in toluene (50 mL) and the resulting mixture was heated to 100° C. for 48 h. The solvent was evaporated and the residue was purified by CombiFlash (PE:EA=5:1) to obtained ethyl 1-(4-chlorophenyl)-2,4-dioxo-1,2,4,5-tetrahydrospiro[benzo[b][1,4]diazepine-3,1'-cyclopropane]-2'-carboxylate (500 mg, 13%). LRMS $(M+H)^+$: 384 m/z. $^1$H NMR (300 MHz, $CDCl_3$): δ 1.07-1.12 (t, J=7.2 Hz, 3H), 1.72-1.81 (m, 1H), 2.16-2.18 (m, 1H), 2.41-2.43 (br, 1H), 3.92-4.00 (m, 2H), 7.20-7.25 (m, 1H), 7.42-7.49 (m, 4H), 7.52-7.65 (m, 3H), 8.06-8.08 (m, 1H).

Ethyl 1-(4-chlorophenyl)-2-oxo-4-thioxo-1,2,4,5-tetrahydrospiro[benzo[b][1,4]diazepine-3,1'-cyclopropane]-2'-carboxylate (Step 5)

Lawesson's Reagent (237 mg, 0.58 mmol) was added to a solution of ethyl 1-(4-chlorophenyl)-2,4-dioxo-1,2,4,5-tetrahydrospiro[benzo[b][1,4]diazepine-3,1'-cyclopropane]-2'-carboxylate (150 mg, 0.39 mmol) in THF (20 mL). The resulting mixture was heated at 80° C. overnight. The solution was evaporated and purified by CombiFlash (PE:EA=1:1) to get ethyl 1-(4-chlorophenyl)-2-oxo-4-thioxo-1,2,4,5-tetrahydrospiro[benzo[b][1,4]diazepine-3,1'-cyclopropane]-2'-carboxylate (70 mg, 45%) as brown solid. LRMS $(M+H)^+$: 400 m/z. $^1$H NMR (300 MHz, $CDCl_3$): δ 0.96-1.04 (t, J=7.2 Hz, 3H), 1.19-1.25 (m, 1H), 1.70-1.76 (m, 1H), 2.17-2.19 (m, 1H), 3.73-3.96 (m, 2H), 6.68-6.71 (d, 1H, J=8.1 Hz), 7.11-7.12 (m, 1H), 7.14-7.24 (m, 4H), 7.24-7.26 (m, 2H).

Ethyl 6-(4-chlorophenyl)-1-methyl-5-oxo-5,6-dihydrospiro[benzo[b][1,2,4]triazolo[4,3-d][1,4]diazepine-4,1'-cyclopropane]-2'-carboxylate (Step 6)

A solution of ethyl 1-(4-chlorophenyl)-2-oxo-4-thioxo-1,2,4,5-tetrahydrospiro[benzo[b][1,4]diazepine-3,1'-cyclopropane]-2'-carboxylate (70 mg, 0.17 mmol) and acetohydrazide (60 mg, 0.78 mmol) in n-BuOH (20 mL) was heated at 130° C. overnight. The solution was evaporated and purified by CombiFlash (DCM:MeOH=10:1) to afford ethyl 6-(4-chlorophenyl)-1-methyl-5-oxo-5,6-dihydrospiro[benzo[b][1,2,4]triazolo[4,3-d][1,4]diazepine-4,1'-cyclopropane]-2'-carboxylate (30 mg, 41%). LRMS $(M+H)^+$: 422 m/z. $^1$H NMR (300 MHz, $CD_3OD$): δ 1.04-1.08 (t, J=7.2 Hz, 3H), 1.92-1.97 (m, 1H), 2.10-2.18 (m, 2H), 2.74 (s, 3H), 3.87-4.03 (m, 2H), 6.96-6.99 (m, 1H), 7.23-7.27 (m, 2H), 7.41-7.54 (m, 4H), 7.69-7.72 (m, 1H).

6-(4-chlorophenyl)-1-methyl-5-oxo-5,6-dihydrospiro[benzo[b][1,2,4]triazolo[4,3-d][1,4]diazepine-4,1'-cyclopropane]-2'-carboxylic acid (Step 7)

NaOH (48 mg, 1.2 mmol) was added to a solution of ethyl 6-(4-chlorophenyl)-1-methyl-5-oxo-5,6-dihydrospiro[benzo[b][1,2,4]triazolo[4,3-d][1,4]diazepine-4,1'-cyclopropane]-2'-carboxylate (100 mg, 0.24 mmol) in MeOH (10 mL) and water (4 mL). It was stirred at room temperature overnight. The solution was adjust to pH=5 using HCl solution (1 M), then concentrated, adding dichloromethane (5 mL), filtered and the filtrate was concentrated to give crude 6-(4-chlorophenyl)-1-methyl-5-oxo-5,6-dihydrospiro[benzo[b][1,2,4]triazolo[4,3-d][1,4]diazepine-4,1'-cyclopropane]-2'-carboxylic acid, which was used in the next step directly. LRMS $(M+H)^+$: 394 m/z.

(6-(4-chlorophenyl)-1-methyl-5,6-dihydrospiro[benzo[b][1,2,4]triazolo[4,3-d][1,4]di azepine-4,1'-cyclopropan]-2'-yl)methanol (Step 8)(Compound 11)

$BH_3$-THF complex (1.8 mL, 1M in THF) was added dropwise to a solution of 6-(4-chlorophenyl)-1-methyl-5-oxo-5,6-dihydrospiro[benzo[b][1,2,4]triazolo[4,3-d][1,4]diazepine-4,1'-cyclopropane]-2'-carboxylate (70 mg, 0.18 mmol) in anhydrous THF (10 mL) at 0° C. The resulting mixture was stirred at room temperature for 48 hrs, then quenched with $NH_4Cl$ solution (5 mL), extracted with ethyl acetate (10 mL), dried with $Na_2SO_4$, concentrated and purified with prep-HPLC to afford (6-(4-chlorophenyl)-1-methyl-5,6-dihydrospiro[benzo[b][1,2,4]triazolo[4,3-d][1,4]diazepine-4,1'-cyclopropan]-2'-yl)methanol (2 mg, 3%) as a white solid.

Example 12

Synthesis of 1,5-dimethyl-5,6-dihydro-4H-benzo[b][1,2,4]triazolo[4,3-d][1,4]diazepine (Compound 12)

Compound 12 was synthesized by the Scheme set forth below.

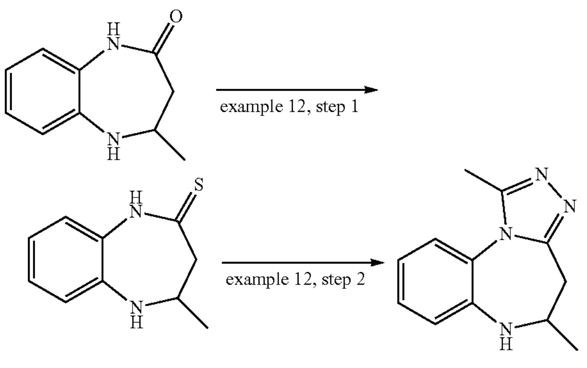

4-methyl-4,5-dihydro-1H-benzo[b][1,4]diazepine-2(3H)-thione (Step 1)

A solution of 4-methyl-4,5-dihydro-1H-benzo[b][1,4]diazepin-2(3H)-one (220 mg, 1.25 mmol) and $P_2S_5$ (444 mg, 2.0 mmol) in pyridine (10 mL) was heated at 120° C. for 30 min. To the mixture, water (10 mL) was added, and then extracted with ethyl acetate (20 mL), dried with $Na_2SO_4$, concentrated and purified by CombiFlash (PE:EA=10:1) to give 4-methyl-4,5-dihydro-1H-benzo[b][1,4]diazepine-2(3H)-thione (200 mg, 83%). LRMS $(M+H)^+$: 192 m/z.

1,5-dimethyl-5,6-dihydro-4H-benzo[b][1,2,4]triazolo[4,3-d][1,4]diazepine (Step 2) (Compound 12)

A solution of 4-methyl-4,5-dihydro-1H-benzo[b][1,4]diazepine-2(3H)-thione (200 mg, 1.04 mmol) and acetohydrazide (150 mg, 2.07 mmol) in n-BuOH (10 mL) was heated at 130° C. overnight. The reaction mixture was evaporated, and then water (10 mL) was added, extracted with ethyl acetate (10 mL), dried with $Na_2SO_4$, and concentrated to give the crude product, which was purified by prep-TLC to give 1,5-dimethyl-5,6-dihydro-4H-benzo[b][1,2,4]triazolo[4,3-d][1,4]diazepine (100 mg, 45%).

Example 13

8-bromo-6-(4-chlorophenyl)-1-methyl-5,6-dihydro-4H-benzo[b][1,2,4]triazolo[4,3-d][1,4]diazepine (Compound 13)

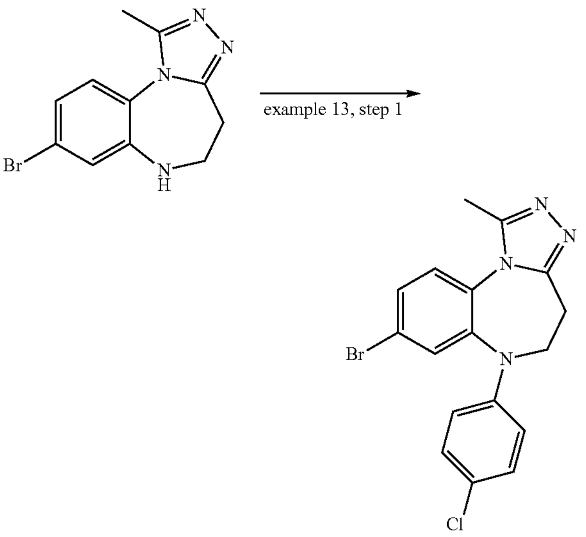

A solution of 8-bromo-1-methyl-5,6-dihydro-4H-benzo[b][1,2,4]triazolo[4,3-d][1,4]diazepine (50 mg, 0.17 mmol), 1-chloro-4-iodobenzene (82 mg, 0.34 mmol), $Pd_2(dba)_3$ (15 mg), 2-dicyclohexylphosphino-2',6'-dimethoxybiphenyl (15 mg) and $Cs_2CO_3$ (110 mg, 0.34 mmol) in toluene (10 mL) was heated at 110° C. overnight. The reaction mixture was evaporated, water (10 mL) was added, extracted with ethyl acetate (20 mL), concentrated to give the crude product, which was purified by prep-TLC (DCM:MeOH=15:1) to afford 8-bromo-6-(4-chlorophenyl)-1-methyl-5,6-dihydro-4H-benzo[b][1,2,4]triazolo[4,3-d][1,4]diazepine (14 mg, yield 20%).

Example 14

6-(4-chlorophenyl)-1-methyl-8-phenyl-5,6-dihydro-4H-benzo[b][1,2,4]triazolo[4,3-d][1,4]diazepine (Compound 14)

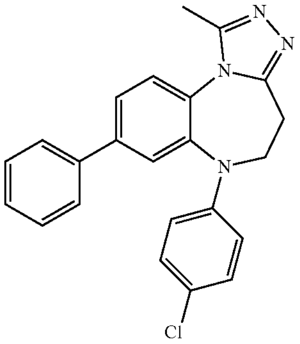 [SMILES: Cc1nnc2n1-c1ccc(-c3ccccc3)cc1N(c1ccc(Cl)cc1)CC2]

A solution of 8-bromo-6-(4-chlorophenyl)-1-methyl-5,6-dihydro-4H-benzo[b][1,2,4]triazolo[4,3-d][1,4]diazepine (30 mg, 0.08 mmol), phenylboronic acid (20 mg, 0.16 mmol), Tetrakis(triphenylphosphine)palladium(0) (10 mg) and $Cs_2CO_3$ (60 mg, 0.16 mmol) in dioxane (5 mL) and water (1 mL) was heated at 120° C. under microwave for 20 min. The reaction mixture was concentrated to give the crude product, which was purified by prep-TLC (DCM:MeOH=12:1) to afford 6-(4-chlorophenyl)-1-methyl-8-phenyl-5,6-dihydro-4H-benzo[b][1,2,4]triazolo[4,3-d][1,4]diazepine (10 mg, yield 33%).

Example 15

Synthesis of 5-(6-(4-chlorophenyl)-1-methyl-5,6-dihydro-4H-benzo[b][1,2,4]triazolo[4,3-d][1,4]diazepin-8-yl)pyridin-2-amine (Compound 15)

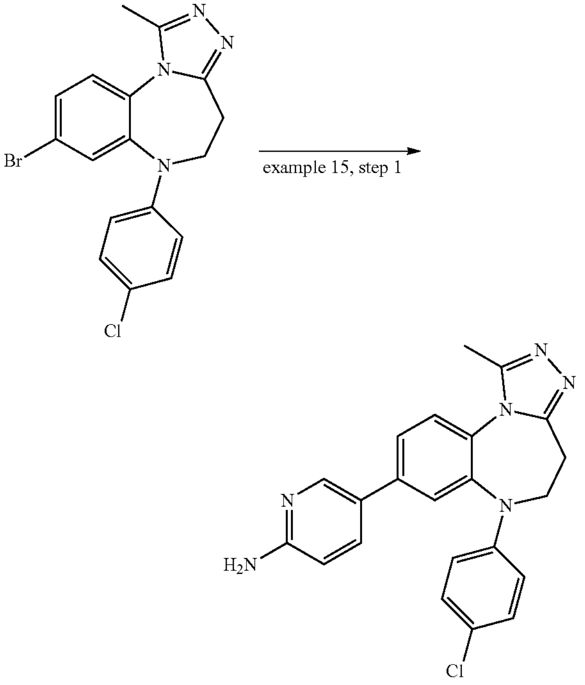

A solution of 8-bromo-6-(4-chlorophenyl)-1-methyl-5,6-dihydro-4H-benzo[b][1,2,4]triazolo[4,3-d][1,4]diazepine (30 mg, 0.08 mmol), 5-(4,4,5,5-tetramethyl-1,3,2-dioxaborolan-2-yl)pyridin-2-amine (35 mg, 0.16 mmol), Tetrakis (triphenylphosphine)palladium(0) (10 mg) and $Cs_2CO_3$ (60 mg, 0.16 mmol) in dioxane (5 mL) and water (1 mL) was heated at 120° C. under microwave for 20 min. The reaction mixture was concentrated to give the crude product, which was purified by prep-TLC (DCM:MeOH=12:1) to afford 5-(6-(4-chlorophenyl)-1-methyl-5,6-dihydro-4H-benzo[b][1,2,4]triazolo[4,3-d][1,4]diazepin-8-yl)pyridin-2-amine (9.3 mg, yield 29%).

Example 16

Synthesis of 4H-[1,2,4]triazolo[4,3-a][1,5]benzodiazepine, 5,6-dihydro-1-methyl-8-(6-aminopyridin-3-yl)-6-(4-cyano-phenyl) (Compound 16)

The title compound is synthesized by the Scheme set forth below.

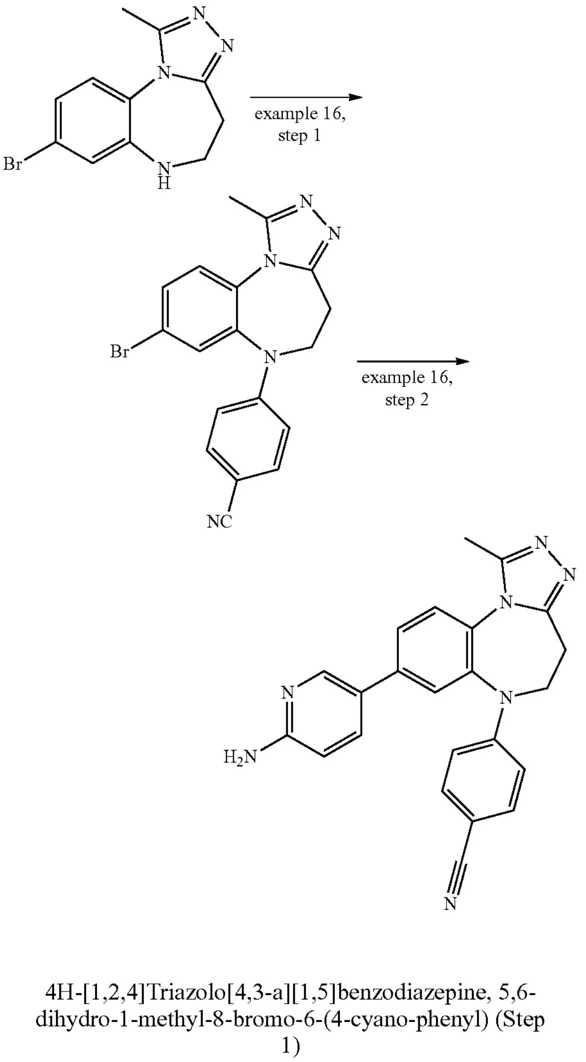

4H-[1,2,4]Triazolo[4,3-a][1,5]benzodiazepine, 5,6-dihydro-1-methyl-8-bromo-6-(4-cyano-phenyl) (Step 1)

A mixture of 4H-[1,2,4]triazolo[4,3-a][1,5]benzodiazepine, 5,6-dihydro-1-methyl-8-bromo (from Example 4, step 5; 300 mg, 1.1 mmol), 4-fluorobenzonitrile (266 mg, 2.2 mmol) and potassium carbonate (455 mg, 3.3 mmol) in N,N-dimethylformamide (5 mL) was heated at 180° C. for 1 hours under microwave (pressure: 17.2 bar, equipment power: 150 W). The reaction mixture was concentrated in vacuo to give a residue. The residue was dissolved in water (10 mL), extracted with ethyl acetate (10 mL*3). The organic phase was dried over anhydrous sodium sulfate, filtered and concentrated to give a residue. The residue was purified by column chromatography (silica gel, dichloromethane/methanol=10:1) to afford 4H-[1,2,4]triazolo[4,3-a][1,5]benzodiazepine, 5,6-dihydro-1-methyl-8-bromo-6-(4-cyano-phenyl) as a white solid (60 mg, 14.7%). $^{1}$H NMR (300 MHz, CD3OD): δ 7.76-7.73 (m, 1H), 7.64-7.60 (m, 2H), 7.51-7.48 (m, 2H), 6.82-6.79 (m, 2H), 4.04 (t, J=6.6 Hz, 2H), 3.13-3.12 (m, 2H), 2.56 (s, 3H).

4H-[1,2,4]triazolo[4,3-a][1,5]benzodiazepine, 5,6-dihydro-1-methyl-8-(6-aminopyridin-3-yl)-6-(4-cyano-phenyl) (Compound 16)

A solution of 4H-[1,2,4]triazolo[4,3-a][1,5]benzodiazepine, 5,6-dihydro-1-methyl-8-bromo-6-(4-cyano-phenyl) (60 mg, 0.16 mmol), 5-(4,4,5,5-tetramethyl-1,3,2-dioxaborolan-2-yl)pyridin-2-amine (70 mg, 0.32 mmol), Tetrakis (triphenylphosphine)palladium(0) (20 mg) and cesium carbonate (156 mg, 0.48 mmol) in mixed solution of dioxane (5 mL) and water (1 mL) was heated at 120° C. under microwave (pressure: 17.2 bar, equipment power: 150 W) for 20 minutes. The reaction mixture was concentrated in vacuo, the residue dissolved in water (10 mL), extracted with ethyl acetate (10 mL*3). The organic phase was washed with brine (10 mL*2), dried over anhydrous sodium sulfate, filtered and concentrated. The residue was purified by preparative-TLC (silica gel, dichloromethane/methanol=10:1) to afford 4H-[1,2,4] triazolo[4,3-a][1,5]benzodiazepine, 5,6-dihydro-1-methyl-8-(6-aminopyridin-3-yl)-6-(4-cyano-phenyl) (20 mg, 32%).

Example 17

Synthesis of 4H-[1,2,4]triazolo[4,3-a][1,5]benzodiazepine,5,6-dihydro-1-methyl-8-(6-amino-pyridin-3-yl)-6-(4-trifluoromethyl-phenyl) (Compound 17)

The title compound is synthesized by the Scheme set forth below.

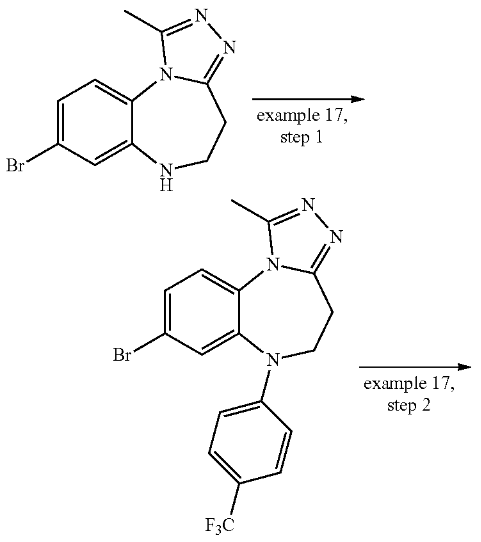

-continued

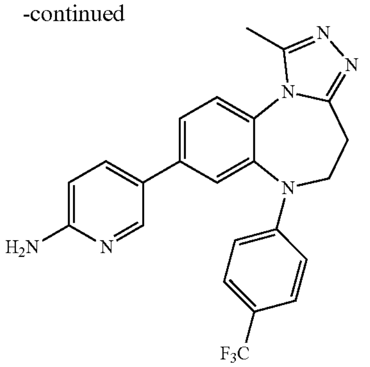

4H-[1,2,4]triazolo[4,3-a][1,5]benzodiazepine,5,6-dihydro-1-methyl-8-bromo-6-(4-trifluoromethyl-phenyl) (Step 1)

A mixture of 4H-[1,2,4]triazolo[4,3-a][1,5]benzodiazepine, 5,6-dihydro-1-methyl-8-bromo (300 mg, 1.07 mmol), 1-iodo-4-(trifluoromethyl)benzene (288 mg, 1.03 mmol), 2-dicyclohexylphosphino-2',6'-dimeth-oxybiphenyl (88 mg, 0.22 mmol), tris(dibenzylideneacetone)dipalladium (76 mg), and cesium carbonate (717 mg, 2.2 mmol) in toluene (10 mL) was heated at 100° C. for 20 minutes under microwave (pressure: 17.2 bar, equipment power: 150 W). The mixture was filtered and the filtrate was concentrated to give a residue, which was purified by column chromatography (silica gel, dichloromethane/methanol=10:1) to afford 4H-[1,2,4]triazolo[4,3-a][1,5]benzodiazepine,5,6-dihydro-1-methyl-8-bromo-6-(4-trifluoromethyl-phenyl) as a white solid (40 mg, 9%). LRMS $(M+H)^{+}$: calcd 422.04. found 422.

Synthesis of 4H-[1,2,4]triazolo[4,3-a][1,5]bienzodiazepine,5,6-dihydro-1-methyl-8-(6-amino-pyridin-3-yl)-6-(4-trifluoromethyl-phenyl) (Compound 17)

A mixture of 4H-[1,2,4]triazolo[4,3-a][1,5]benzodiazepine,5,6-dihydro-1 methyl-8-bromo-6-(4-trifluoro-methyl-phenyl) (40 mg, 0.09 mmol), 5-(4,4,5,5-tetramethyl-1,3,2-dioxaborolan-2-yl)pyridin-2-amine (47 mg, 0.21 mmol), Tetrakis(triphenylphosphine)palladium(0) (5 mg) and cesium carbonate (70 mg, 0.21 mmol) in dioxane (2 mL) and water (0.1 mL) was heated at 120° C. for 20 minutes under microwave (pressure: 17.2 bar, equipment power: 150 W). The mixture was filtered and the filtrate was concentrated to give a residue. To the residue, ethyl acetate was added (15 mL), washed with brine (10 mL*3), dried over anhydrous sodium sulfate and then filtered. The filtrate was concentrated and the residue was purified by column chromatography (silica gel, dichloromethane/methanol=10:1) to afford 4H-[1,2,4]triazolo[4,3-a][1,5]benzodiazepine,5,6-dihydro-1-methyl-8-(6-amino-pyridin-3-yl)-6-(4-trifluoromethyl-phenyl) as a white solid (15 mg, 37%).

Example 18

Synthesis of 6-(4-chlorophenyl)-1-methyl-8-(pyrimidin-2-yl)-5,6-dihydro-4H-benzo[b][1,2,4]triazolo[4,3-d][1,4]diazepine (Compound 21)

The title compound was synthesized by the Scheme set forth below.

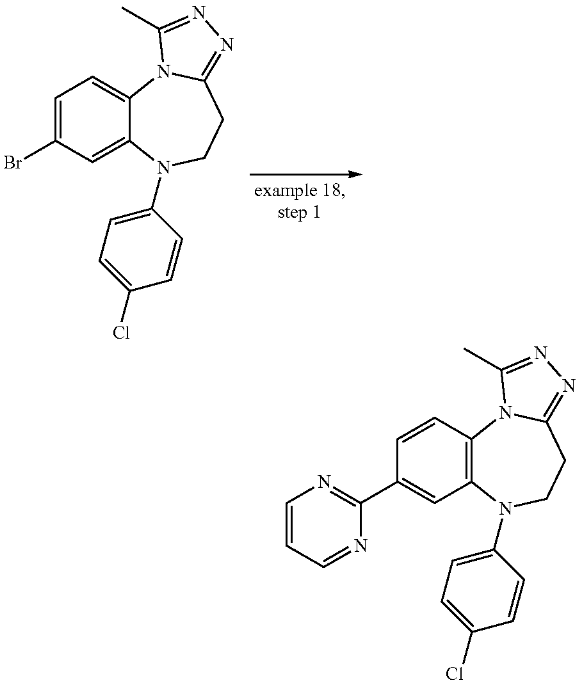

Into a 25 mL sealed-tube evacuated and brimmed with nitrogen, was charged with a mixture of 8-bromo-6-(4-chlorophenyl)-1-methyl-5,6-dihydro-4H-benzo[b][1,2,4]triazolo[4,3-d][1,4]diazepine (Compound 13; 40 mg, 0.10 mmol), 2-(tributylstannyl)pyrimidine (56.8 g, 0.15 mmol), [1,1'-bis(diphenylphosphino)ferrocene]dichloropalladium(II) (7.2 mg, 0.01 mmol), lithium chloride (6.5 mg, 0.15 mmol) and toluene (2 mL). The mixture was heated for 12 hours at 100° C. The mixture was concentrated in vacuo, partitioned with ethyl acetate (10 mL) and water (5 mL). The organic layer was separated, washed with brine, dried over anhydrous sodium sulfate and concentrated to give a residue. The residue was purified by prep-HPLC (Phenomenex $C_{18}$ (150 mm*21.2 mm*5 um), acetonitrile/water=1:100 (0.1% formic acid), flow rate: 30 mL/min) to yield 6-(4-chlorophenyl)-1-methyl-8-(pyrimidin-2-yl)-5,6-dihydro-4H-benzo[b][1,2,4]triazolo[4,3-d][1,4]diazepine as a white solid (2 mg, 5%).

Example 19

Synthesis of 4H-[1,2,4]triazolo[4,3-a][1,5]benzodiazepine,5,6-dihydro-1,4-dimethyl-8-bromo-6-(4-chloro-phenyl) (Compound 104)

The title compound is synthesized by the Scheme set forth below.

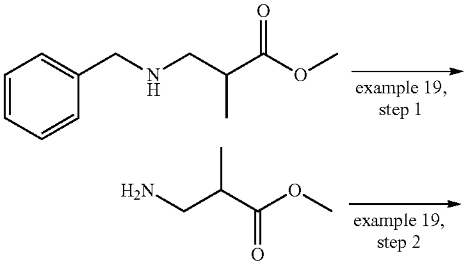

-continued

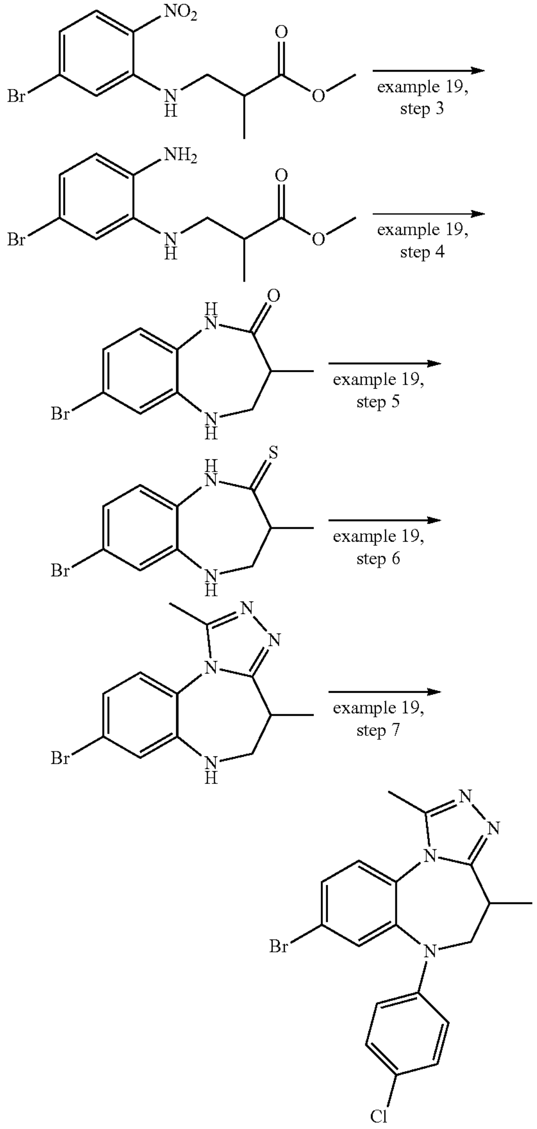

Methyl 3-(benzylamino)-2-methylpropanoate

To a solution of benzylamine (10.7 g, 100 mmol) in methanol (100 mL) was added methyl methacrylate (10 g, 100 mmol). The reaction solution was stirred at room temperature for 12 hours. The reaction mixture was concentrated in vacuo. The residue was purified by column chromatography (silica gel, petroleum ether/ethyl acetate=1:1) to give methyl 3-(benzylamino)-2-methylpropanoate as a light yellow oil (12 g, 57%).

Methyl 3-amino-2-methylpropanoate (Step 1)

A mixture of methyl 3-(benzylamino)-2-methylpropanoate (12 g, 58 mmol) and palladium hydroxide (1.2 g) in methanol (250 mL) was stirred under hydrogen (1 atm) at room temperature for 12 hours. The reaction mixture was filtered and the filtrate was concentrated in vacuo to give methyl 3-amino-2-methylpropanoate as a yellow oil (5 g, 73.6%).

Methyl 3-(5-bromo-2-nitrophenylamino)-2-methylpropanoate (Step 2)

To a solution of 4-bromo-2-fluoro-1-nitrobenzene (9.4 g, 42.7 mmol) in tetrahydrofuran (100 mL) were added methyl 3-amino-2-methylpropanoate (5 g, 42.7 mmol) and potassium carbonate (11.8 g, 85.4 mmol). The reaction mixture was stirred with refluxing for 3 hours. The mixture was diluted with water (100 mL), extracted with ethyl acetate (100 mL×3). The organic layers were separated, combined, dried over anhydrous sodium sulfate, filtered and concentrated to give a residue, which was purified by column chromatography (silica gel, petroleum ether/ethyl acetate=5:1) to give methyl 3-(5-bromo-2-nitrophenylamino)-2-methylpropanoate as a light yellow solid (8 g, 59%).

Methyl 3-(2-amino-5-bromophenylamino)-2-methylpropanoate (Step 3)

Iron powder (7 g, 0.12 mol) was added to a mixture of methyl 3-(5-bromo-2-nitrophenylamino)-2-methyl-propanoate (8 g, 25.2 mmol) in the mixed solvents of ammonium chloride aqueous (50 mL) and ethanol (100 mL). Once addition was completed, the mixture was heated to 60° C. for 2 hours. The mixture was filtered. The filtrate was concentrated, diluted with water (100 mL), extracted with ethyl acetate (150 mL×3). The organic layers were separated, combined, dried over anhydrous sodium sulfate, filtered and concentrated to give a residue. The residue was purified by column chromatography (silica gel, petroleum ether/ethyl acetate=3:1) to afford methyl 3-(2-amino-5-bromophenylamino)-2-methylpropanoate (6 g, 83%).

7-bromo-3-methyl-4,5-dihydro-1H-benzo[b][1,4]diazepin-2(3H)-one (Step 4)

Sodium metal (2.4 g, 104 mmol) was added in portions to methanol (50 mL) and the mixture was stirred at room temperature until sodium metal was dissolved completely. The solution was then added dropwise to a cooled solution of methyl 3-(2-amino-5-bromophenylamino)-2-methylpropanoate (6 g, 20.9 mmol) in methanol (100 mL) at 0° C. After addition, the mixture was stirred at room temperature for 12 hours. The mixture was concentrated in vacuo. To the residue was added water (50 mL). The mixture was extracted with ethyl acetate (100 mL×3). The organic layers were combined, dried over anhydrous sodium sulfate and then filtered. The filtrate was concentrated to give a crude product, which was purified by column chromatography (silica-gel, petroleum ether/ethyl acetate=3:1) to afford 7-bromo-3-methyl-4,5-dihydro-1H-benzo[b][1,4]diazepin-2(3H)-one (1.8 g, 34%).

7-bromo-3-methyl-4,5-dihydro-1H-benzo[b][1,4]diazepine-2(3H)-thione (Step 5)

A solution of 7-bromo-3-methyl-4,5-dihydro-1H-benzo[b][1,4]diazepin-2(3H)-one (1.8 g, 7.1 mmol) and Lawesson's reagent (4.2 g, 10.4 mmol) in tetrahydrofuran (50 mL) was heated at 80° C. for 12 hours. The mixture was concentrated in vacuo. To the residue was added water (50 mL), extracted with ethyl acetate (50 mL×3). The combined layers were washed with brine (50 mL). The organic phase was dried over anhydrous sodium sulfate, filtered and concentrated to give a crude product, which was purified by column chromatography (silica gel, petroleum ether/ethyl acetate=5:1) to afford 7-bromo-3-methyl-4,5-dihydro-1H-benzo[b][1,4]diazepine-2(3H)-thione (1.5 g, 79%).

4H-[1,2,4]triazolo[4,3-a][1,5]benzodiazepine, 5,6-dihydro-1,4-dimethyl-8-bromo (Step 6)

A solution of 7-bromo-3-methyl-4,5-dihydro-1H-benzo[b][1,4]diazepine-2(3H)-thione (1.5 g, 5.5 mmol) and acetohydrazide (693 mg, 9.36 mmol) in n-butanol (20 mL) was heated at 130° C. for 12 hours. The reaction mixture was concentrated in vacuo, diluted with water (20 mL), extracted with ethyl acetate (15 mL×3) and washed with brine (10 mL×3). The combined organic phase was dried over anhydrous sodium sulfate and then filtered. The filtrate was concentrated to give a crude product, which was purified by column chromatography (silica gel, dichloromethane/methanol=20:1) to afford 4H-[1,2,4]triazolo[4,3-a][1,5]benzodiazepine, 5,6-dihydro-1,4-dimethyl-8-bromo as a white solid (1 g, 62%). $^1$H NMR (300 MHz, CDC13): δ 7.19-7.14 (m, 2H), 7.01 (d, J=8.1 Hz, 1H), 3.74-3.64 (m, 1H), 3.43-3.36 (m, 1H), 3.13-3.05 (m, 1H), 2.49 (s, 3H), 1.50 (d, J=6.9 Hz, 3H). LRMS $(M+H)^+$: calcd 292.03. found 292.

4H-[1,2,4]triazolo[4,3-a][1,5]benzodiazepine,5,6-dihydro-1,4-dimethyl-8-bromo-6-(4-chloro-phenyl) (Compound 104)

A mixture of 4H-[1,2,4]triazolo[4,3-a][1,5]benzodiazepine, 5,6-dihydro-1,4-dimethyl-8-bromo (500 mg, 1.7 mmol), 1-chloro-4-iodobenzene (820 mg, 3.4 mmol), tris(dibenzylideneacetone)dipalladium(0) (150 mg), 2-dicyclohexylphosphino-2',6'-dimethoxybiphenyl (150 mg) and cesium carbonate (1.1 g, 0.34 mmol) in toluene (10 mL) was heated at 110° C. for 12 hours under nitrogen atmosphere. The reaction mixture was concentrated in vacuo, and the residue was purified by column chromatography (silica gel, dichloromethane/methanol=15:1) to afford 4H-[1,2,4]triazolo[4,3-a][1,5]benzodiazepine, 5,6-dihydro-1,4-dimethyl-8-bromo-6-(4-chloro-phenyl) (140 mg, 20%).

Example 20

Separation of (S)-4H-[1,2,4]triazolo[4,3-a][1,5]benzodiazepine, 5,6-dihydro-1,4-dimethyl-8-bromo-6-(4-chloro-phenyl) (Compound 37) and (R)-4H-[1,2,4]triazolo[4,3-a][1,5]benzodiazepine,5,6-dihydro-1,4-dimethyl-8-bromo-6-(4-chloro-phenyl) (Compound 38)

4H-[1,2,4]Triazolo[4,3-a][1,5]benzodiazepine,5,6-dihydro-1,4-dimethyl-8-bromo-6-(4-chloro-phenyl) (Compound 104; 100 mg, 0.24 mmol) was separated by chiral HPLC (Daicel AD-H (250 mm×20 mm×5 um), carbon dioxide/methanol=70:30, flow rate: 2.5 g/min, temperature: 38° C., back pressure: 100 bar), then (R or S) 4H-[1,2,4]triazolo[4,3-a][1,5]benzodiazepine,5,6-dihydro-1,4-dimethyl-8-bromo-6-(4-chloro-phenyl). (30 mg, 60%) and (S or R) 4H-[1,2,4]triazolo[4,3-a][1,5]benzodiazepine, 5,6-dihydro-1,4-dimethyl-8-bromo-6-(4-chloro-phenyl) (30 mg, 60%) was obtained. The retention times were 4.51 minute and 5.4 minute respectively in chiral HPLC.

Example 21

Synthesis of 4H-[1,2,4]triazolo[4,3-a][1,5]benzodiazepine,5,6-dihydro-1,4-dimethyl-8-(6-aminopyridin-3-yl)-6-(4-chloro-phenyl) (Compound 23)

A mixture of 4H-[1,2,4]triazolo[4,3-a][1,5]benzodiazepine, 5,6-dihydro-1,4-dimethyl-8-bromo-6-(4-chloro-phenyl) (250 mg, 0.62 mmol), 5-(4,4,5,5-tetramethyl-1,3,2-dioxaborolan-2-yl)pyridin-2-amine (274 mg, 1.24 mmol), tetrakis (triphenylphosphine)palladium(0) (50 mg) and potassium carbonate (350 mg, 2.53 mmol) in mixed solution of tetrahydrofuran (10 mL) and water (1 mL) was heated at 100° C. for 30 minutes under microwave (pressure: 17.2 bar, equipment power: 150 W). The reaction mixture was diluted with ethyl acetate (20 mL) and washed with brine (10 mL×3). The organic phase was separated, dried over anhydrous sodium sulfate and then filtered. The filtrate was concentrated to give a crude product, which was purified by column chromatography (silica gel, dichloromethane/methanol=12:1) to afford 4H-[1,2,4]triazolo[4,3-a][1,5]benzodiazepine,5,6-dihydro-1,4-dimethyl-8-(6-aminopyridin-3-yl)-6-(4-chloro-phenyl) as a light yellow solid (170 mg, 66%).

Example 22

Synthesis of (S)-4H-[1,2,4]triazolo[4,3-a][1,5]benzodiazepine, 5,6-dihydro-1,4-dimethyl-8-(6-aminopyridin-3-yl)-6-(4-chloro-phenyl) (Compound 27) and (R)-4H-[1,2,4]triazolo[4,3-a][1,5]benzodiazepine, 5,6-dihydro-1,4-dimethyl-8-(6-aminopyridin-3-yl)-6-(4-chloro-phenyl) (Compound 28)

4H-[1,2,4]triazolo[4,3-a][1,5]benzodiazepine,5,6-dihydro-1,4-dimethyl-8-(6-aminopyridin-3-yl)-6-(4-chloro-phenyl) (Compound 23; 370 mg, 0.86 mmol) was separated by chiral HPLC (Daicel AD-H (250 mm×20 mm×5 μm), hexane/ethanol (0.2 diethylamine)=30:70, flow rate: 13 mL/min), then (R or S) 4H-[1,2,4]triazolo[4,3-a][1,5]benzodiazepine, 5,6-dihydro-1,4-dimethyl-8-(6-aminopyridin-3-yl)-6-(4-chloro-phenyl) (105 mg, 56%) and (S or R) 4H-[1,2,4]triazolo[4,3-a][1,5]benzodiazepine, 5,6-dihydro-1,4-dimethyl-8-(6-aminopyridin-3-yl)-6-(4-chloro-phenyl) (110 mg, 58%) were obtained. The retention times were 17.275 minute and 20.835 minute respectively in chiral prep-HPLC chromatography.

Example 23

Synthesis of 4H-[1,2,4]triazolo[4,3-a][1,5]benzodiazepine,5,6-dihydro-1-methyl-8-(4-carboxy-phenyl)-6-(4-chloro-phenyl) (Compound 20)

A mixture of 4H-[1,2,4]triazolo[4,3-a][1,5]benzodiazepine,5,6-dihydro-1-methyl-8-bromo-6-(4-chloro-phenyl) (Compound 13; 60 mg, 0.15 mmol), methyl 4-(4,4,5,5-tetramethyl-1,3,2-dioxaborolan-2-yl)benzoate (81 mg, 0.30 mmol), and cesium carbonate (98 mg, 0.30 mmol) in dioxane (2 mL) and water (1 mL) was heated at 120° C. for 20 minutes under microwave (pressure: 17.2 bar, equipment power: 150 W). The solid was filtered and the filtrate was concentrated to give a residue. To the residue, ethyl acetate (30 mL) was added and the mixture was washed with brine (20 mL×3). The organic phase was dried over anhydrous sodium sulfate and then filtered. The filtrate was concentrated to give a residue, which was purified by column chromatography (silica gel, dichloromethane/methanol=10:1) to afford 4H-[1,2,4]Triazolo[4,3-a][1,5]benzodiazepine, 5,6-dihydro-1-methyl-8-(4-carboxy-phenyl)-6-(4-chloro-phenyl) as a white solid (30 mg, 47%).

Example 24

Synthesis of 6-(4-chlorophenyl)-1-methyl-4H-benzo[b][1,2,4]triazolo[4,3-d][1,4]diazepin-5(6H)-one (Compound 32)

The title compound was synthesized by the scheme set forth below:

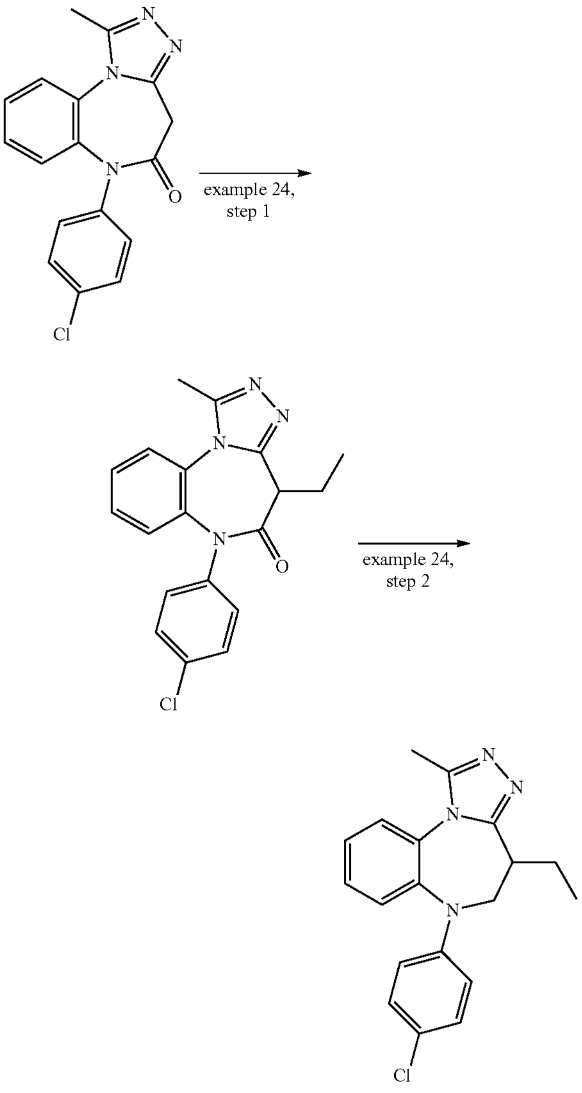

6-(4-chlorophenyl)-4-ethyl-1-methyl-4H-benzo[b][1,2,4]triazolo[4,3-d][1,4]diazepin-5(6H)-one (Step 1)

Into a 50 mL flask evacuated and brimmed with dry nitrogen, was charged with a solution of 6-(4-chlorophenyl)-1-methyl-4H-benzo[b][1,2,4]triazolo[4,3-d][1,4]diazepin-5(6H)-one (Example 1, step 5; 100 mg, 0.31 mmol) in anhydrous tetrahydrofuran (10 mL). To this mixture, was added lithium bis(trimethylsilyl)amide (tetrahydrofuran solution) (0.17 mL, 0.33 mmol) at −78° C. The mixture was stirred at the same temperature for 1 hour, and then warmed to room temperature, maintained at the same temperature for 2 hours. Iodoethane (92.04 mg, 0.59 mmol) was added. The mixture was stirred at room temperature for another 2 hours. The reaction was quenched by ammonium chloride aqueous (5 mL), extracted with ethyl acetate (5 mL*3). The crude product was purified by column chromatography (silica gel, dichloromethane/methanol=25:1) to give 6-(4-chlorophenyl)-4-ethyl-1-methyl-4H-benzo[b][1,2,4]triazolo[4,3-d][1,4]diazepin-5(6H)-one as a light yellow solid (20.0 mg, 18%). LRMS $(M+H)^+$: calcd 352.11. found 352.

Synthesis of 6-(4-chlorophenyl)-1-methyl-4H-benzo[b][1,2,4]triazolo[4,3-d][1,4]diazepin-5(6H)-one (Compound 32)

Into a 50 mL flask evacuated and brimmed with dry nitrogen, was charged with a solution of 6-(4-chlorophenyl)-4-ethyl-1-methyl-4H-benzo[b][1,2,4]triazolo[4,3-d][1,4]diazepin-5(6H)-one (10.0 mg, 0.028 mmol) in tetrahydrofuran (5 mL). To this mixture was added borane-tetrahydrofuran complex solution (1 mol/L, 1 mL) slowly. The mixture was stirred for 12 hours at reflux, quenched by hydrochloric acid aqueous (1.0 mol/L, 1 mL) to adjust pH>7 and extracted with ethyl acetate (5 mL*3). The organic layer was concentrated to give a residue. The residue was purified by prep-HPLC (Phenomenex $C_{18}$ (150 mm*21.2 mm*5 um), acetonitrile/water=1:100 (0.1% formic acid), flow rate: 30 mL/min) to give 6-(4-chlorophenyl)-1-methyl-4H-benzo[b][1,2,4]triazolo[4,3-d][1,4]diazepin-5(6H)-one as an off-white solid (1.2 mg, 12%).

Example 25

Synthesis of 4H-[1,2,4]triazolo[4,3-a][1,5]benzodiazepine, 5,6-dihydro-1-methyl-8-(5-(carboxy)pyrimidin-2-yl)-6-(4-chloro-phenyl) (Compound 24)

The title compound was synthesized by the scheme set forth below:

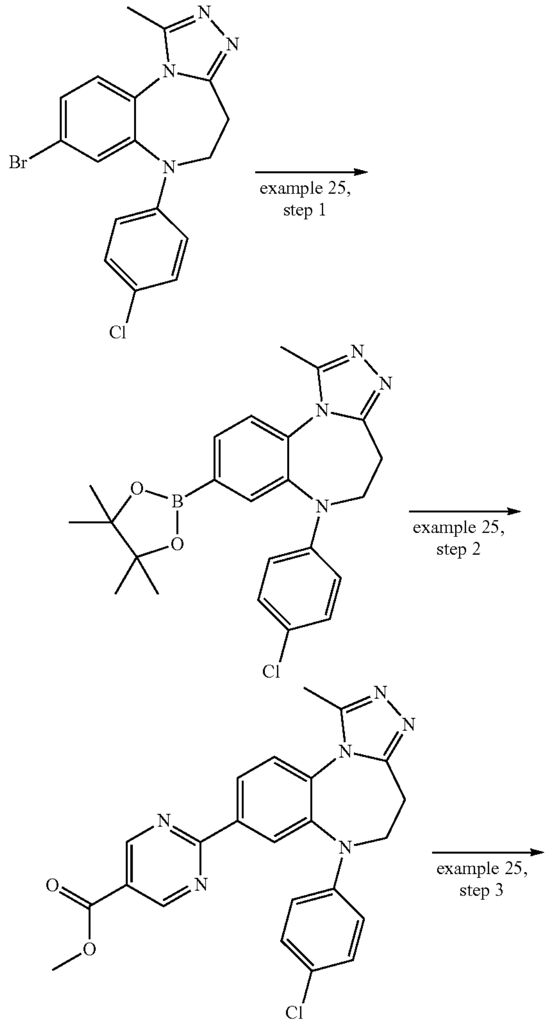

-continued

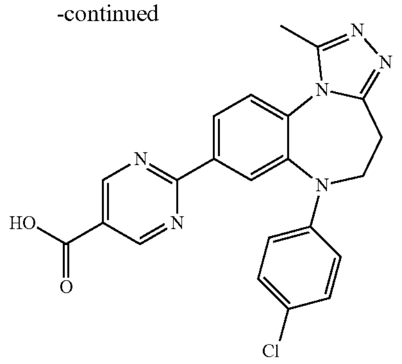

4H-[1,2,4]triazolo[4,3-a][1,5]benzodiazepine, 5,6-dihydro-1methyl-8-(4,4,5,5-tetramethyl-1,3,2-dioxaborolan-2-yl)-6-(4-chloro-phenyl) (Step 1)

A mixture of 4H-[1,2,4]triazolo[4,3-a][1,5]benzodiazepine, 5,6-dihydro-1methyl-8-bromo-6-(4-chloro-phenyl) (30 mg, 0.08 mmol), 4,4,4',4',5,5,5',5'-octamethyl-2,2'-bi(1,3,2-dioxaborolane) (30 mg, 0.118 mmol), [1,1'-bis(diphenyl phosphino)ferrocene]dichloropalladium(II) (10 mg) and potassium acetate (23 mg, 0.24 mmol) in N,N-dimethylformamide (5 mL) was heated at 110° C. for 15 minutes under microwave (pressure: 17.2 bar, equipment power: 150 W). The solvent was evaporated in vacuo. The residue was dissolved in ethyl acetate (20 mL) and washed with brine (10 mL×2). The separated organic layer was dried over anhydrous sodium sulfate and then filtered. The filtrate was concentrated and the residue was purified by preparative-TLC (silica gel, dichloromethane/methanol=10:1) to yield 4H-[1,2,4]triazolo[4,3-a][1,5]benzodiazepine,5,6-dihydro-1methyl-8-(4,4,5,5-tetramethyl-1,3,2-dioxaborolan-2-yl)-6-(4-chloro-phenyl) as yellow solid (10 mg, 29.1%).

4H-[1,2,4]triazolo[4,3-a][1,5]benzodiazepine, 5,6-dihydro-1-methyl-8-(5-(methoxy carbonyl)pyrimidin-2-yl)-6-(4-chloro-phenyl) (Step 2)

A mixture of 4H-[1,2,4]triazolo[4,3-a][1,5]benzodiazepine,5,6-dihydro-1methyl-8-(4,4,5,5-tetramethyl-1,3,2-dioxaborolan-2-yl)-6-(4-chloro-phenyl) (75 mg, 0.17 mmol), methyl 2-chloropyrimidine-5-carboxylate (36 mg, 0.21 mmol), Tetrakis(triphenylphosphine)palladium(0) (20 mg) and potassium carbonate (50 mg, 0.36 mmol) in N,N-Dimethylformamide (8 mL) degassed by nitrogen three times, and then the mixture was heated at 50° C. for 12 hours. The solvent was evaporated in vacuo. The residue was dissolved in ethyl acetate (20 mL) and washed with brine (10 mL×2). The separated organic layer was dried over anhydrous sodium sulfate and then filtered. The filtrate was concentrated and the residue was purified by preparative-TLC (silica gel, dichloromethane/methanol=10:1) to yield 4H-[1,2,4]triazolo[4,3-a][1,5]benzodiazepine,5,6-dihydro-1-methyl-8-(5-(methoxycarbonyl)pyrimidin-2-yl)-6-(4-chloro-phenyl) as a white solid (30 mg, 39%). LRMS $(M+H)^+$: calcd 446.13. found 446.

4H-[1,2,4]triazolo[4,3-a][1,5]benzodiazepine, 5,6-dihydro-1-methyl-8-(5-(carboxy)pyrimidin-2-yl)-6-(4-chloro-phenyl) (Compound 24)

To a solution of 4H-[1,2,4]triazolo[4,3-a][1,5]benzodiazepine, 5,6-dihydro-1-methyl-8-(5-(methoxy carbonyl)pyrimidin-2-yl)-6-(4-chloro-phenyl) (10 mg, 0.02 mmol) in tetrahydrofuran (5 mL) and water (0.5 mL) was added lithium hydroxide (3 mg, 0.07 mmol). The resultant mixture was stirred at room temperature for 1 hour. After the solvent was evaporated in vacuo, the residue was dissolved in water (10 mL). Hydrochloride acid aqueous (1 N) was added to adjust pH to 1. The water layer was extracted with dichloromethane (5 mL×2). The combined organic layers were dried over anhydrous sodium sulfate and then filtered. The filtrate was concentrated and the residue was purified by preparative-TLC (silica gel, dichloromethane/methanol=8:1) to yield 4H-[1,2,4]triazolo[4,3-a][1,5]benzodiazepine,5,6-dihydro-1-methyl-8-(5-(carboxy)pyrimidin-2-yl)-6-(4-chloro-phenyl) as a white solid (2 mg, 23%).

Example 26

Synthesis of 8-bromo-6-(4-chlorophenyl)-1-methyl-5,6-dihydrospiro[benzo[b][1,2,4]triazolo[4,3-d][1,4]diazepine-4,1'-cyclopropane] (Compound 33)

The title compound was synthesized by the following scheme:

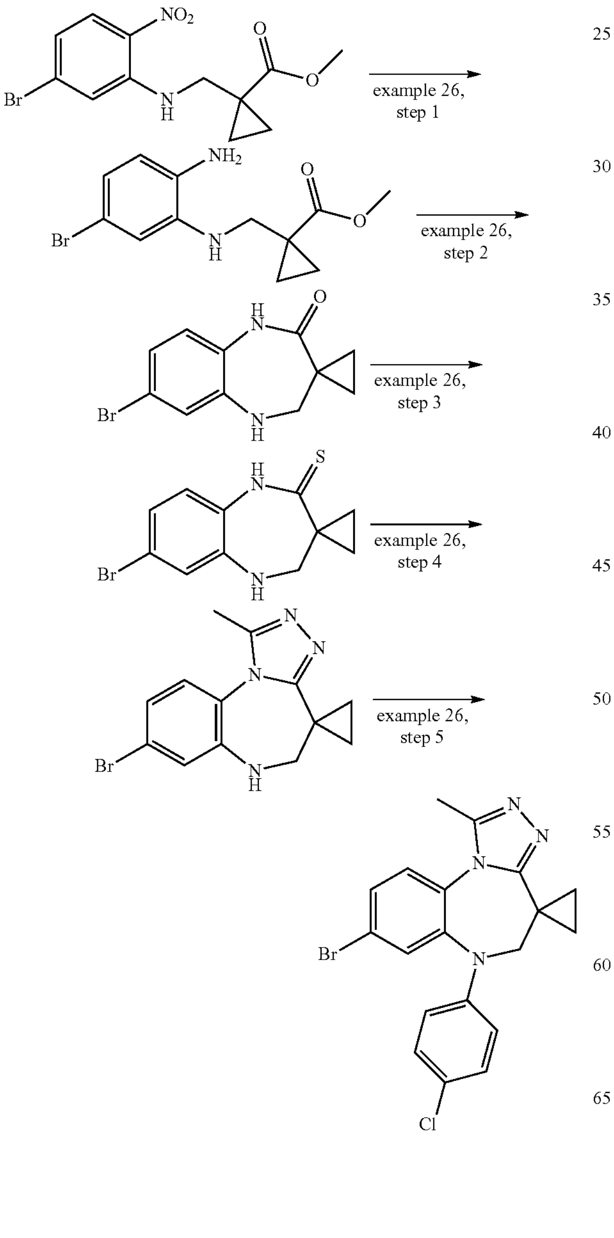

Ethyl 1-((5-bromo-2-nitrophenylamino)methyl)cyclopropanecarboxylate

To a solution of 4-bromo-2-fluoro-1-nitrobenzene (792 mg, 3.6 mmol) in tetrahydrofuran (30 mL) was added ethyl 1-(aminomethyl)cyclopropanecarboxylate (441 mg, 3.0 mmol) and potassium carbonate (621 mg, 4.5 mmol). The reaction mixture was stirred at reflux for 15 hours. The mixture was diluted with water (50 mL) and extracted with ethyl acetate (50 mL). The organic phase was separated, concentrated and the residue was purified by column chromatography (silica gel, petroleum ether/ethyl acetate=5:1) to give ethyl 1-((5-bromo-2-nitrophenylamino)methyl)cyclopropanecarboxylate as a light yellow solid (832 mg, 67%).

Ethyl 1-((2-amino-5-bromophenylamino)methyl) cyclopropanecarboxylate (Step 1)

Iron powder (448 mg, 8.0 mmol) was added to a mixture of ethyl 1-((5-bromo-2-nitrophenylamino)methyl)cyclopropanecarboxylate (684 mg, 2.0 mmol), ammonium chloride aqueous (6 mL) and ethanol (20 mL). The reaction was heated to 70° C. and maintained at the 70° C. for 2 hours. The mixture solution was filtered. The filtrate was evaporated, diluted with water (100 mL), extracted with ethyl acetate (100 mL), and dried by sodium sulfate. The mixture was filtered. The filtrate was concentrated and purified by column chromatography (silica gel, petroleum ether/ethyl acetate=5:1) to give ethyl 1-((2-amino-5-bromophenylamino)methyl)cyclopropanecarboxylate (474 mg, 76%) as off-white solid.

7-bromo-4,5-dihydrospiro[benzo[b][1,4]diazepine-3,1'-cyclopropan]-2(1H)-one (Step 2)

To a stirred solution of ethyl 1-((2-amino-5-bromophenylamino)methyl)cyclopropanecarboxylate (624 mg, 2.0 mmol) in toluene (15 mL) was added dropwise tetraisopropoxytitanium (1.2 g, 4.0 mmol). After addition was complete, the reaction was stirred for 12 hours at 90° C. The mixture was diluted with water (200 mL), extracted with ethyl acetate (200 mL). The organic layer was separated, dried by sodium sulfate, filtered and concentrated to give the crude 7-bromo-4,5-dihydrospiro[benzo[b][1,4]diazepine-3,1'-cyclopropan]-2(1H)-one (400 mg, 75%) as white solid, used for the next step without further purification.

7-bromo-4,5-dihydrospiro[benzo[b][1,4]diazepine-3,1'-cyclopropane]-2(1H)-thione (Step 3)

A solution of 7-bromo-4,5-dihydrospiro[benzo[b][1,4]diazepine-3,1'-cyclopropan]-2(1H)-one (267 mg, 1.0 mmol) and Lawesson's reagent (606 mg, 1.5 mmol) in tetrahydrofuran (15 mL) was heated to 80° C., and maintained at the same temperature for 1 hours. The mixture was concentrated. To the residue was added water (50 mL), extracted with ethyl acetate (50 mL). The organic phase was washed with water (50 mL*2), dried by sodium sulfate, filtered and concentrated to give a residue. The residue was purified by column chromatography (silica gel, petroleum ether/ethyl acetate=6:1) to afford 7-bromo-4,5-dihydrospiro[benzo[b][1,4]diazepine-3,1'-cyclopropane]-2(1H)-thione (125 mg, 44%).

8-bromo-1-methyl-5,6-dihydrospiro[benzo[b][1,2,4]triazolo[4,3-d][1,4]diazepine-4,1'-cyclopropane] (Step 4)

A solution of 7-bromo-4,5-dihydrospiro[benzo[b][1,4]diazepine-3,1'-cyclopropane]-2(1H)-thione (500 mg, 1.77 mmol) and acetohydrazide (1.05 g, 14.2 mmol) in n-butanol (15 mL) was heated to 130° C., and maintained at the same temperature for 12 hours. The reaction mixture was concentrated, extracted with ethyl acetate (15 mL), washed with water (25 mL*2). The organic phase was separated, dried by sodium sulfate, filtered and concentrated to give the crude product, which was purified by column chromatography (silica gel, dichloromethane/methanol=30:1) to afford 8-bromo-1-methyl-5,6-dihydrospiro[benzo[b][1,2,4]triazolo[4,3-d][1,4]diazepine-4,1'-cyclopropane] (286 mg, 53%). $^1$H NMR (300 MHz, d6-DMSO): δ 7.31-7.28 (m, 2H), 7.11 (dd, J=6.0 Hz, J=2.4 Hz, 1H), 5.80-5.78 (m, 1H), 3.36-3.35 (m, 2H), 2.37 (s, 3H), 0.88-0.86 (m, 2H), 0.77-0.73 (m, 2H). LRMS $(M+H)^+$: calcd 304.03. found 304.

8-bromo-6-(4-chlorophenyl)-1-methyl-5,6-dihydrospiro[benzo[b][1,2,4]triazolo[4,3-d][1,4]diazepine-4,1'-cyclopropane] (Compound 33)

A solution of 8-bromo-1-methyl-5,6-dihydrospiro[benzo[b][1,2,4]triazolo[4,3-d][1,4]diazepine-4,1'-cyclopropane] (150 mg, 0.49 mmol), 1-chloro-4-iodobenzene (468 mg, 2.0 mmol), tris(dibenzylideneacetone)dipalladium(0) (35 mg, 0.049 mmol), 2-dicyclohexylphosphino-2',6'-dimethoxybiphenyl (40 mg, 0.098 mmol) and cesium carbonate anhydrous (320 mg, 0.98 mmol) in toluene (10 mL) was heated to 110° C., and maintained at the same temperature for 12 hours. The reaction mixture was concentrated. Water was added (20 mL), and the mixture was extracted with ethyl acetate (20 mL). The organic phase was separated, and concentrated to give the crude product, which was purified by preparative-TLC (silica-gel, dichloromethane:methanol=30:1) to afford 8-bromo-6-(4-chlorophenyl)-1-methyl-5,6-dihydrospiro[b][1,2,4]triazolo[4,3-d][1,4]diazepine-4,1'-cyclopropane] (14 mg, 6.9%).

Example 27

Synthesis of 6-(4-chlorophenyl)-1-methyl-5,6-dihydrospiro[benzo[b][1,2,4]triazolo[4,3-d][1,4]diazepine-4,1'-cyclopropane] (Compound 34)

The title compound was synthesized by the following scheme:

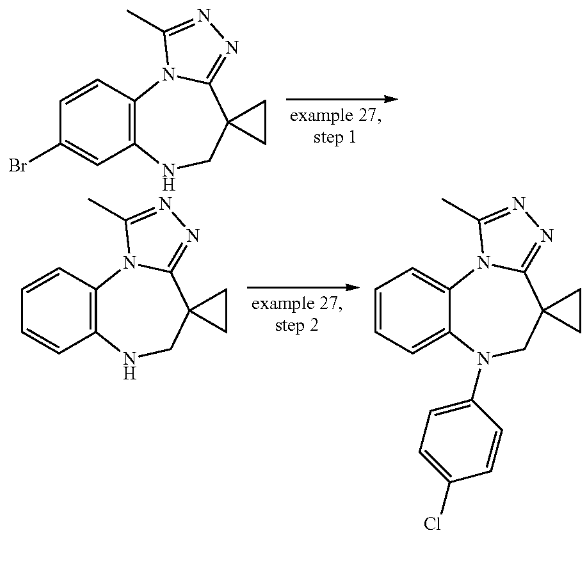

1-methyl-5,6-dihydrospiro[benzo[b][1,2,4]triazolo[4,3-d][1,4]diazepine-4,1'-cyclopropane] (Step 1)

A mixture of 8-bromo-1-methyl-5,6-dihydrospiro[benzo[b][1,2,4]triazolo[4,3-d][1,4]diazepine-4,1'-cyclopropane] (150 mg, 0.49 mmol) and palladium on carbon (40 mg) in methanol (10 mL) was stirred for 2 hours at 40° C. under hydrogen atmosphere. The solid was filtered and the filtrate was concentrated to give crude 1-methyl-5,6-dihydrospiro[benzo[b][1,2,4]triazolo[4,3-d][1,4]diazepine-4,1'-cyclopropane] (100 mg, 91%) as yellow oil, used for the next step without further purification. LRMS $(M+H+)^+$: calcd 226.12. found 226.

6-(4-chlorophenyl)-1-methyl-5,6-dihydrospiro[benzo[b][1,2,4]triazolo[4,3-d][1,4]diazepine-4,1'-cyclopropane] (Compound 34)

A solution of 1-methyl-5,6-dihydrospiro[benzo[b][1,2,4]triazolo[4,3-d][1,4]diazepine-4,1'-cyclopropane] (111 mg, 0.49 mmol), 1-chloro-4-iodobenzene (468 mg, 2.0 mmol), tris(dibenzylideneacetone)dipalladium(0) (35 mg, 0.049 mmol), 2-dicyclohexylphosphino-2',6'-dimethoxybiphenyl (40 mg, 0.098 mmol) and cesium carbonate anhydrous (320 mg, 0.98 mmol) in toluene (10 mL) was heated to 110° C., and maintained at the same temperature for 12 hours. The reaction mixture was concentrated, added with water (20 mL), extracted with ethyl acetate (20 mL). The organic phase was separated, and concentrated to give a crude product, which was purified by preparative-TLC (silica-gel, dichloromethane/methanol=30:1) to afford 6-(4-chlorophenyl)-1-methyl-5,6-dihydrospiro[benzo[b][1,2,4]triazolo[4,3-d][1,4]diazepine-4,1'-cyclopropane] (8 mg, 4.8%).

Example 28

Synthesis of 4H-[1,2,4]triazolo[4,3-a][1,5]benzodiazepine, 5,6-dihydro-1,4-dimethyl-8-(6-methylpyridin-3-yl)-6-(4-chloro-phenyl) (Compound 105) and its (S) and (R) enantiomers (Compounds 28 and 29)

A mixture of 4H-[1,2,4]triazolo[4,3-a][1,5]benzodiazepine, 5,6-dihydro-1,4-dimethyl-8-bromo-6-(4-chloro-phenyl) (Compound 104; 340 mg, 0.84 mmol), 2-methyl-5-(4,4,5,5-tetramethyl-1,3,2-dioxaborolan-2-yl)pyridine (390 mg, 1.78 mmol), tetrakis(triphenylphosphine)palladium(0) (98 mg) and potassium carbonate (466 mg, 3.37 mmol) tetrahydrofuran (10 mL) and water (2 mL) was heated at 100° C. for 30 minutes under microwave (pressure: 17.2 bar, equipment power: 150 W). The reaction mixture was diluted with ethyl acetate (20 mL) and washed with brine (10 mL×3). The organic phase was separated, dried over anhydrous sodium sulfate and then filtered. The filtrate was concentrated to give the crude product, which was purified by column chromatography (silica gel, dichloromethane/methanol=12:1) to afford 4H-[1,2,4]triazolo[4,3-a][1,5]benzodiazepine,5,6-dihydro-1,4-dimethyl-8-(6-methylpyridin-3-yl)-6-(4-chloro-phenyl) as a light yellow solid (260 mg, 74%).

(R)-4H-[1,2,4]triazolo[4,3-a][1,5]benzodiazepine, 5,6-dihydro-1,4-dimethyl-8-(6-methylpyridin-3-yl)-6-(4-chloro-phenyl)(Compound 29) and (S)-4H-[1,2,4]triazolo[4,3-a][1,5]benzodiazepine, 5,6-dihydro-1,4-dimethyl-8-(6-methylpyridin-3-yl)-6-(4-chloro-phenyl) (Compound 28)

4H-[1,2,4]Triazolo[4,3-a][1,5]benzodiazepine,5,6-dihydro-1,4-dimethyl-8-(6-methylpyridin-3-yl)-6-(4-chlorophenyl) (450 mg, 1.08 mmol) was separated by chiral prep-HPLC (Daicel AD-H (250 mm×20 mm×5 μm), hexane/ethanol (0.2 diethylamine)=40:60, flow rate: 13 mL/min), then (S)-4H-[1,2,4]triazolo[4,3-a][1,5]benzodiazepine,5,6-dihydro-1,4-dimethyl-8-(6-methylpyridin-3-yl)-6-(4-chloro-phenyl) (130 mg, 58%) and (R)-4H-[1,2,4]triazolo[4,3-a][1,5]benzodiazepine, 5,6-dihydro-1,4-dimethyl-8-(6-methylpyridin-3-yl)-6-(4-chloro-phenyl) (120 mg, 54%) were obtained. The retention times were 7.287 minute and 13.686 minute respectively in chiral prep-HPLC chromatography.

Example 29

Synthesis of 4H-[1,2,4]triazolo[4,3-a][1,5]benzodiazepine,5,6-dihydro-1,4-dimethyl-8-(5-aminopyrimidin-2-yl)-6-(4-chloro-phenyl) (Compound 25) and its (S) and (R) enantiomers (Compounds 40 and 39)

A solution of 4H-[1,2,4]triazolo[4,3-a][1,5]benzodiazepine,5,6-dihydro-1,4-dimethyl-8-bromo-6-(4-chloro-phenyl) (Compound 104; 30 mg, 0.07 mmol), 5-(4,4,5,5-tetramethyl-1,3,2-dioxaborolan-2-yl)pyridin-2-amine (31 mg, 0.14 mmol), Tetrakis(triphenylphosphine)palladium(0) (10 mg) and potassium carbonate (39 mg, 0.28 mmol) in mixed solution of tetrahydrofuran (2 mL) and water (0.2 mL) was degassed by nitrogen three times, and then the mixture was heated at 100° C. under microwave (pressure: 17.2 bar, equipment power: 150 W) for 20 minutes. After cooling to room temperature, dichloromethane (50 mL) was added. The organic layer was separated, dried over anhydrous sodium sulfate, filtered and concentrated in vacuo. The residue was purified by column chromatography (silica gel, dichloromethane/methane=10:1) to give 4H-[1,2,4]triazolo[4,3-a][1,5]benzodiazepine,5,6-dihydro-1,4-dimethyl-8-(5-aminopyrimidin-2-yl)-6-(4-chloro-phenyl) as a white solid (15 mg, 48%).

(R)-4H-[1,2,4]triazolo[4,3-a][1,5]benzodiazepine,5,6-dihydro-1,4-dimethyl-8-(2-aminopyrimidin-5-yl)-6-(4-chloro-phenyl) (Compound 39) and (S)-4H-[1,2,4]triazolo[4,3-a][1,5]benzodiaze-pine,5,6-dihydro-1,4-dimethyl-8-(2-aminopyrimidin-5-yl)-6-(4-chloro-phenyl) (Compound 40)

4H-[1,2,4]Triazolo[4,3-a][1,5]benzodiazepine,5,6-dihydro-1,4-dimethyl-8-(2-aminopyrimidin-5-yl)-6-(4-chloro-phenyl) (50 mg, 0.12 mmol) was separated by chiral prep-HPLC (Daicel OJ-H (250 mm×20 mm×5 um), carbon dioxide/ethanol (0.2% diethylamine)=70:30, flow rate: 13 g/min, 38° C.), then (R)-4H-[1,2,4]triazolo[4,3-a][1,5]benzodiazepine,5,6-dihydro-1,4-dimethyl-8-(2-aminopyrimidin-5-yl)-6-(4-chloro-phenyl) (20 mg, 80%) and (S) 4H-[1,2,4]-triazolo[4,3-a][1,5]benzodiaze-pine,5,6-dihy-dro-1,4-dimethyl-8-(2-aminopyrimidin-5-yl)-6-(4-chloro-phenyl) (20 mg, 80%).

Example 30

Synthesis of 4H-[1,2,4]triazolo[4,3-a][1,5]benzodiazepine,5,6-dihydro-1,4-dimethyl-8-(3-hydroxy-3-methylbut-1-ynyl)-6-(4-chloro-phenyl) (Compound 36)

Into a 100 mL flask evacuated and purged with nitrogen, was charged a mixture of 4H-[1,2,4]triazolo[4,3-a][1,5]benzodiazepine,5,6-dihydro-1,4-dimethyl-8-bromo-6-(4-chloro-phenyl) (60 mg, 0.15 mmol), 2-methylbut-3-yn-2-ol (600 mg, 7.14 mmol), bis(triphenylphosphine)palladium(II) chloride (25 mg), copper (I) iodide (25 mg), triethylamine (300 mg, 3 mmol) in tetrahydrofuran (20 mL). The mixture was heated for 12 hours at 75° C. The mixture was concentrated in vacuo, water (5 mL) was added, and then extracted with ethyl acetate (10 mL). The organic layer was washed with brine (10 mL), separated, dried over anhydrous sodium sulfate, filtered and concentrated to give a residue. The residue was purified by preparative-TLC (silica-gel, dichloromethane/methanol=15:1) to yield 4H-[1,2,4]triazolo[4,3-a][1,5]benzodiazepine, 5,6-dihydro-1,4-dimethyl-8-(3-hydroxy-3-methylbut-1-ynyl)-6-(4-chloro-phenyl) as a yellow oil (10 mg, 16%).

Example 31

Synthesis of 4H-[1,2,4]triazolo[4,3-a][1,5]benzodiazepine,5,6-dihydro-1,4-dimethyl-8-(3-amino-3-methylbut-1-ynyll)-6-(4-chloro-phenyl) (Compound 31)

A mixture of 4H-[1,2,4]triazolo[4,3-a][1,5]benzodiazepine, 5,6-dihydro-1,4-dimethyl-8-bromo-6-(4-chloro-phenyl) (60 mg, 0.15 mmol), 2-methylbut-3-yn-2-amine (62 mg, 0.75 mmol), tetrakis(triphenylphosphine)palladium (9 mg), copper (I) iodide (2 mg) and triethylamine (3 mL) was stirred at 100° C. for 30 minutes under microwave (pressure: 17.2 bar, equipment power: 150 W). The mixture was concentrated in vacuo, the residue was partitioned with ethyl acetate (10 mL) and water (5 mL). The separated organic layer was washed with brine (5 mL×2), dried over anhydrous sodium sulfate and then filtered. The filtrate was concentrated and the residue was purified by column chromatography (silica gel, dichloromethane/methanol=10:1) to afford 4H-[1,2,4]triazolo[4,3-a][1,5]benzodiazepine, 5,6-dihydro-1,4-dimethyl-8-(3-amino-3-methylbut-1-ynyll)-6-(4-chloro-phenyl) as a white solid (25 mg, 42%).

Example 32

Synthesis of 4H-[1,2,4]triazolo[4,3-a][1,5]benzodiazepine,5,6-dihydro-1,4-dimethyl-9-fluoro-6-(4-chloro-phenyl) (Compound 35)

The title compound was produced by the following scheme:

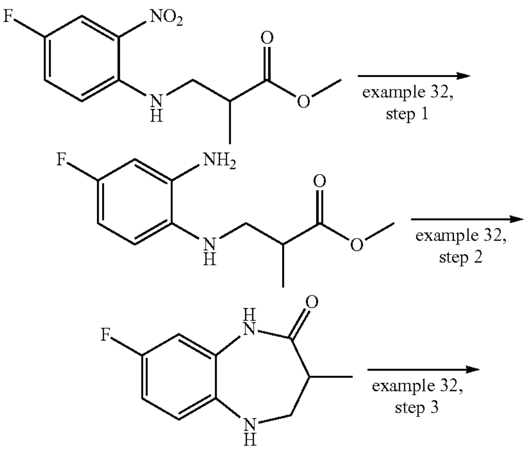

-continued

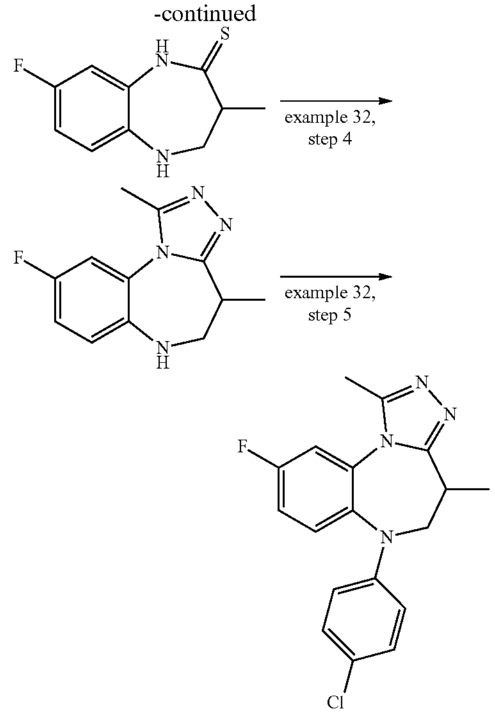

Methyl 3-(4-fluoro-2-nitrophenylamino)-2-methylpropanoate

To a solution of 1,4-difluoro-2-nitrobenzene (14.3 g, 90 mmol) in tetrahydrofuran (250 mL) was added methyl 3-amino-2-methylpropanoate (10.5 g, 90 mmol) and potassium carbonate (24.8 g, 180 mmol). The reaction mixture was heated to reflux and stirred for 15 hours. Then the mixture was concentrated in vacuo, and the residue was dissolved in water (250 mL), extracted with ethyl acetate (100 mL*3). The combined organic layers was separated, dried over anhydrous sodium sulfate, and concentrated to give a residue. The residue was purified by column chromatography (silica gel, petroleum ether/ethyl acetate=5:1) to afford methyl 3-(4-fluoro-2-nitrophenylamino)-2-methylpropanoate as a red solid (14.0 g, 61%).

Methyl 3-(2-amino-4-fluorophenylamino)-2-methylpropanoate (Step 1)

To a solution of methyl 3-(4-fluoro-2-nitrophenylamino)-2-methylpropanoate (14.0 g, 54.6 mmol) in ethanol (250 mL) were added zinc powder (14.2 g, 218 mmol) and saturated ammonium chloride (28.4 mL) at 0° C. Once addition was completed, the reaction mixture was stirred at reflux for 1 hour. Then the mixture was cooled to room temperature, filtered, and washed with ethanol (200 mL). The organic phase was concentrated in vacuo, dissolved in water (250 mL), and extracted with ethyl acetate (200 mL*3). The combined organic layers was separated, dried over anhydrous sodium sulfate, and concentrated to give a residue. The residue was purified by column chromatography (silica gel, petroleum ether/ethyl acetate=2:1) to afford methyl 3-(2-amino-4-fluorophenylamino)-2-methylpropanoate as a black solid (10.0 g, 81%).

8-fluoro-3-methyl-4,5-dihydro-1H-benzo[b][1,4]diazepin-2(3H)-one (Step 2)

To a solution of methyl 3-(2-amino-4-fluorophenylamino)-2-methylpropanoate (10.0 g, 44.2 mmol) in toluene (200 mL) was added titanium tetraisopropanolate (18.8 g, 66.3 mmol). The mixture was stirred at 90° C. for 15 hours. The resultant mixture was concentrated in vacuo, and dissolved in tetrahydrofuran (200 mL), filtered through celite, and washed with tetrahydrofuran (100 mL). The filtrate was concentrated in vacuo, and the residue was purified by column chromatography (silica gel, petroleum ether/ethyl acetate=2:1) to afford 8-fluoro-3-methyl-4,5-dihydro-1H-benzo[b][1,4]diazepin-2(3H)-one as a black solid (6.5 g, 76%).

8-fluoro-3-methyl-4,5-dihydro-1H-benzo[b][1,4]diazepine-2(3H)-thione (Step 3)

A solution of 8-fluoro-3-methyl-4,5-dihydro-1H-benzo[b][1,4]diazepin-2(3H)-one (6.2 g, 32 mmol) and Lawesson's reagent (25.9 g, 64 mmol) in tetrahydrofuran (300 mL) was heated at 80° C. for 1 hour. The mixture was concentrated in vacuo, and the residue was purified by column chromatography (silica gel, petroleum ether/ethyl acetate=5:1-2:1) to afford 8-fluoro-3-methyl-4,5-dihydro-1H-benzo[b][1,4]diazepine-2(3H)-thione as a pale green solid (10.0 g, crude).

4H-[1,2,4]triazolo[4,3-a][1,5]benzodiazepine, 5,6-dihydro-1,4-dimethyl-9-fluoro-(Step 4)

A solution of 8-fluoro-3-methyl-4,5-dihydro-1H-benzo[b][1,4]diazepine-2(3H)-thione (5.0 g, 23.8 mmol) and acetohydrazide (2.64 g, 35.7 mmol) in n-butanol (60 mL) was heated at 130° C. for 15 hours. The mixture was concentrated in vacuo, and the residue was purified by column chromatography (silica gel, petroleum ether/ethyl acetate=5:1-2:1) to afford 4H-[1,2,4]triazolo[4,3-a][1,5]benzodiazepine, 5,6-dihydro-1,4-dimethyl-9-fluoro-as an off-white solid (1.9 g, 34%). LRMS $(M+H)^+$: calcd 232.11. found 232.

4H-[1,2,4]triazolo[4,3-a][1,5]benzodiazepine,5,6-dihydro-1,4-dimethyl-9-fluoro-6-(4-chloro-phenyl) (Compound 35)

A solution of 4H-[1,2,4]triazolo[4,3-a][1,5]benzodiazepine, 5,6-dihydro-1,4-dimethyl-9-fluoro- (400 mg, 1.7 mmol), 1-chloro-4-iodobenzene (2.03 g, 8.5 mmol), tris(dibenzylideneacetone)dipalladium(0) (150 mg), 2-dicyclohexylphosphino-2',6'-dimethoxy biphenyl (150 mg) and cesium carbonate (1.1 g, 0.34 mmol) in toluene (20 mL) was heated at 120° C. for 15 hours under nitrogen atmosphere, then filtered through celite, and washed with methanol (20 mL). The filtrate was concentrated in vacuo, and the residue was purified by column chromatography (silica gel, petroleum ether/ethyl acetate=2:1) to afford 4H-[1,2,4]triazolo[4,3-a][1,5]benzodiazepine,5,6-dihydro-1,4-dimethyl-9-fluoro-6-(4-chloro-phenyl) as an off-white solid (300 mg, 51%).

Example 33

Synthesis of 4H-[1,2,4]triazolo[4,3-a][1,5]benzodiazepine,5,6-dihydro-1methyl-8-(1-methyl-1H-pyrazol-4-yl)-6-(4-chloro-phenyl) (Compound 30)

A mixture of 4H-[1,2,4]triazolo[4,3-a][1,5]benzodiazepine,5,6-dihydro-1 methyl-8-bromo-6-(4-chloro-phenyl) (40 mg, 0.1 mmol), 1-methyl-4-(4,4,5,5-tetramethyl-1,3,2-dioxaborolan-2-yl)-1H-pyrazole (43 mg, 0.2 mmol), Tetrakis(triphenylphosphine)palladium(0) (12 mg) and potassium carbonate (57 mg, 0.41 mmol) in tetrahydrofuran (5 mL) and water (0.2 mL) was heated at 100° C. under microwave (pressure: 17.2 bar, equipment power: 150 W) for 30 minutes. The reaction mixture was concentrated in vacuo. Water (10 mL) was added to the residue and the mixture was extracted with ethyl acetate (10 mL×3), washed with brine (10 mL×2), dried over anhydrous sodium sulfate and then filtered. The filtrate was concentrated and the residue was purified by column chromatography (silica gel, dichloromethane/methanol=10:1) to afford 4H-[1,2,4]triazolo[4,3-a][1,5]benzodiazepine,5,6-dihydro-1methyl-8-(1-methyl-1H-pyrazol-4-yl)-6-(4-chloro-phenyl) as a white solid (20 mg, 51%).

Example 34

Synthesis of Synthesis of 4H-[1,2,4]Triazolo[4,3-a][1,5]benzodiazepine,5,6-dihydro-1,4-dimethyl-8-(1-methyl-1H-pyrazol-4-yl)-6-(4-chloro-phenyl) (Compound 106) and its (R) and (S) enantiomers (Compounds 43 and 42)

A suspension of 4H-[1,2,4]triazolo[4,3-a][1,5]benzodiazepine,5,6-dihydro-1,4-dimethyl-8-bromo-6-(4-chloro-phenyl) (Compound 104; 100 mg, 0.25 mmol), (1-methyl-4-(4,4,5,5-tetramethyl-1,3,2-dioxaborolan-2-yl)-1H-pyrazole) (110 mg, 0.5 mmol), potassium carbonate (70 mg, 0.5 mmol), and tetrakis(triphenylphosphine)palladium(0) (10 mg) in tetrahydrofuran (20 mL) and water (0.25 mL) was degassed by nitrogen three times, and then the mixture was heated at 100° C. for 20 minutes under microwave (pressure: 17.2 bar, equipment power: 150 W). After cooling to room temperature, the organic layer was separated, dried over anhydrous sodium sulfate, filtered and concentrated in vacuo. The residue was purified by column chromatography (silica gel, dichloromethane/methanol=50:1) to afford 4H-[1,2,4]triazolo[4,3-a][1,5]benzodiazepine,5,6-dihydro-1,4-dimethyl-8-(1-methyl-1H-pyrazol-4-yl)-6-(4-chloro-phenyl) as an off-white solid (50 mg, 48%).

(S)-4H-[1,2,4]triazolo[4,3-a][1,5]benzodiazepine, 5,6-dihydro-1,4-dimethyl-8-(1-methyl-1H-pyrazol-4-yl)-6-(4-chloro-phenyl) (Compound 42) and (R)-(4H-[1,2,4]triazolo[4,3-a][1,5]benzodiazepine,5,6-dihydro-1,4-dimethyl-8-(1-methyl-1H-pyrazol-4-yl)-6-(4-chloro-phenyl)) (Compound 43)

4H-[1,2,4]triazolo[4,3-a][1,5]benzodiazepine,5,6-dihydro-1,4-dimethyl-8-(1-methyl-1H-pyrazol-4-yl)-6-(4-chloro-phenyl) (50 mg, 0.12 mmol) was separated by chiral prep-HPLC (Daicel AD-H (250 mm×20 mm×5 um), hexane/i-PrOH (0.2% diethylamine+0.2% formic acid)=50:50, flow rate: 13 mL/min), then (S)-4H-[1,2,4]triazolo[4,3-a][1,5]benzodiazepine, 5,6-dihydro-1,4-dimethyl-8-(1-methyl-1H-pyrazol-4-yl)-6-(4-chloro-phenyl) (20 mg, 80%) and (R)-4H-[1,2,4]triazolo[4,3-a][1,5]benzodiazepine,5,6-dihydro-1,4-dimethyl-8-(1-methyl-1H-pyrazol-4-yl)-6-(4-chloro-phenyl) (20 mg, 80%) was obtained. The retention times were 7.05 minute and 9.73 minute respectively in chiral HPLC chromatography.

Example 35

Synthesis of 4H-[1,2,4]Triazolo[4,3-a][1,5]benzodiazepine, 5,6-dihydro-1,4-dimethyl-8-(1-methyl-1H-pyrazol-4-yl)-6-(4-cyano-phenyl) (Compound 107) and its (R) and (S) enantiomers (Compounds 44 and 45)

Compound 107 is prepared by the following scheme:

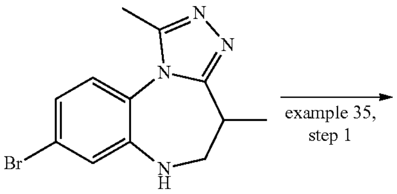

-continued

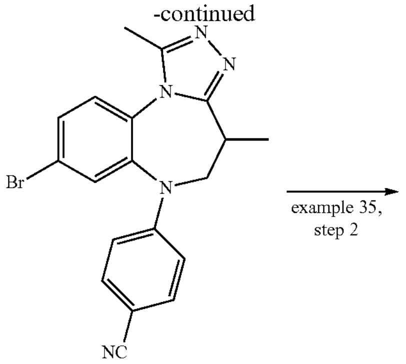

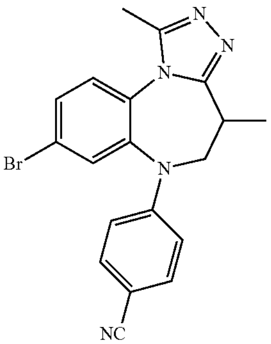

4H-[1,2,4]triazolo[4,3-a][1,5]benzodiazepine,5,6-dihydro-1,4-dimethyl-8-bromo-6-(4-cyano-phenyl) (Step 1)

A mixture of 4H-[1,2,4]triazolo[4,3-a][1,5]benzodiazepine, 5,6-dihydro-1,4-dimethyl-8-bromo (100 mg, 0.34 mmol), 4-fluorobenzonitrile (83 mg, 0.68 mmol) and potassium carbonate (140 mg, 1.02 mmol) in N,N-dimethylformamide (3 mL) was heated at 180° C. for 30 minutes under microwave (pressure: 17.2 bar, equipment power: 150 W). The reaction mixture was concentrated in vacuo. The residue was re-dissolved in ethyl acetate (30 mL), washed by brine (15 mL×3), dried over anhydrous sodium sulfate and then filtered. The filtrate was concentrated and the residue was purified by preparative-TLC (silica gel, dichloromethane/methanol=10:1) to afford 4H-[1,2,4]triazolo[4,3-a][1,5]benzodiazepine,5,6-dihydro-1,4-dimethyl-8-bromo-6-(4-cyano-phenyl) as a brown solid (12 mg, 9.0%). LRMS $(M+H)^+$: calcd 393.06. found 393.

4H-[1,2,4]Triazolo[4,3-a][1,5]benzodiazepine, 5,6-dihydro-1,4-dimethyl-8-(1-methyl-1H-pyrazol-4-yl)-6-(4-cyano-phenyl) (Compound 107)

A solution of 4H-[1,2,4]triazolo[4,3-a][1,5]benzodiazepine, 5,6-dihydro-1,4-dimethyl-8-bromo-6-(4-cyano-phenyl) (110 mg, 0.28 mmol), 1-methyl-4-(4,4,5,5-tetramethyl-1,3,2-dioxaborolan-2-yl)-1H-pyrazole (116 mg, 0.55 mmol), tetrakis(triphenylphosphine)palladium(0) (33 mg), potassium carbonate (155 mg, 1.12 mmol), tetrahydrofuran (10 mL) and water (0.5 mL) was reacted at 100° C. for 30 minutes under microwave (pressure: 17.2 bar, equipment power: 150 W). The reaction mixture was diluted with ethyl acetate (50 mL), washed with brine (15 mL×3). The organic phase was dried over anhydrous sodium sulfate and then filtered. The filtrate was concentrated and the residue was purified by column chromatography (silica gel, dichloromethane/methanol=10:1) to afford 4H-[1,2,4]Triazolo[4,3-a][1,5]benzodiazepine, 5,6-dihydro-1,4-dimethyl-8-(1-methyl-1H-pyrazol-4-yl)-6-(4-cyano-phenyl) as a white solid (70 mg, 63.6%).

(R)-4H-[1,2,4]triazolo[4,3-a][1,5]benzodiazepine, 5,6-dihydro-1,4-dimethyl-8-(1-methyl-1H-pyrazol-4-yl)-6-(4-cyano-phenyl) (Compound 44) and (S)-4H-[1,2,4]triazolo[4,3-a][1,5]benzodiazepine,5,6-dihydro-1,4-dimethyl-8-(1-methyl-1H-pyrazol-4-yl)-6-(4-cyano-phenyl) (Compound 45)

4H-[1,2,4]Triazolo[4,3-a][1,5]benzodiazepine,5,6-dihydro-1,4-dimethyl-8-(1-methyl-1H-pyrazol-4-yl)-6-(4-cyano-phenyl) (70 mg, 0.18 mmol) was separated by chiral HPLC (Daicel OJ-H (20 mm*250 mm*5 um), carbon dioxide/ethanol=70:30, flow rate: 40 mL/minute, temperature: 36° C., back pressure: 100 bar), then (R)-4H-[1,2,4]triazolo[4,3-a][1,5]benzodiazepine,5,6-dihydro-1,4-dimethyl-8-(1-methyl-1H-pyrazol-4-yl)-6-(4-cyano-phenyl) (20 mg, 56%) and (S)-4H-[1,2,4]triazolo[4,3-a][1,5]benzodiazepine, 5,6-dihydro-1,4-dimethyl-8-(1-methyl-1H-pyrazol-4-yl)-6-(4-cyano-phenyl) (25 mg, 72%) were obtained. The retention times were 3.98 minute and 4.82 minute respectively in chiral HPLC chromatography.

Example 36

Synthesis of 4-R-4H-[1,2,4]Triazolo[4,3-a][1,5]benzodiazepine,5,6-dihydro-1,4-dimethyl-8-carbamoyl-6-(4-chloro-phenyl) (Compound 41)

Compound 41 is prepared by the following scheme:

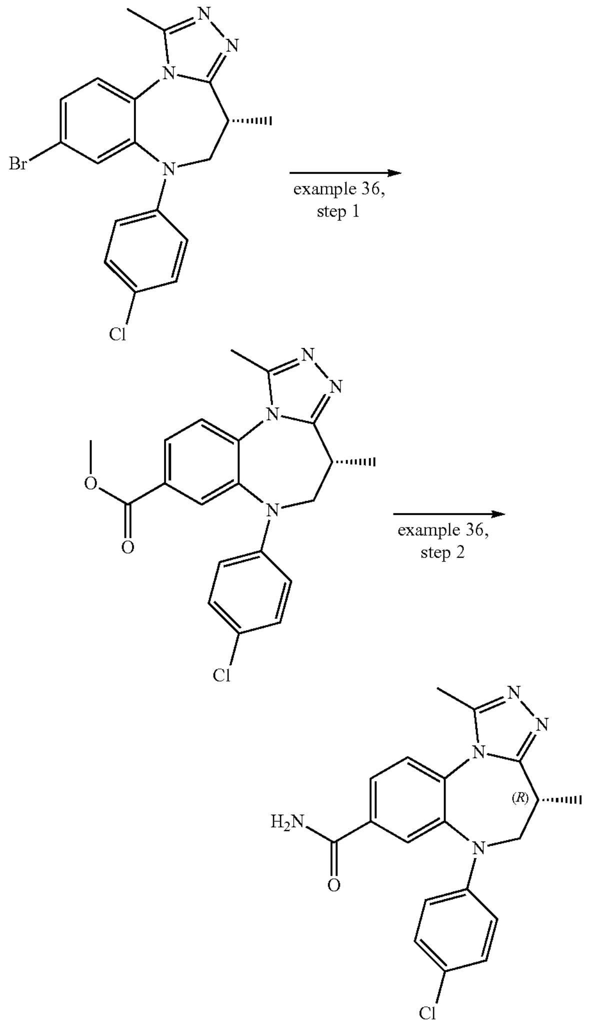

4-R-4H-[1,2,4]triazolo[4,3-a][1,5]benzodiazepine, 5,6-dihydro-1,4-dimethyl-8-methyl-oxycarbonyl-6-(4-chloro-phenyl)(Step 1)

To a sealed tube, was charged with a mixture of 4-R-4H-[1,2,4]triazolo[4,3-a][1,5]benzodiazepine, 5,6-dihydro-1,4-dimethyl-8-bromo-6-(4-chloro-phenyl) (Compound 38; 50 mg, 0.12 mmol), 1,3-bis(diphenylphosphino) propane (20 mg), palladium acetate (10 mg), triethylamine (300 mg, 3 mmol) and methanol (20 mL). The mixture was heated at 90° C. for 12 hours under carbon monoxide. The mixture was concentrated in vacuo. The residue was purified by column chromatography (silica gel, dichloromethane/methanol=20:1) to yield 4-R-4H-[1,2,4]triazolo[4,3-a][1,5]benzodiazepine,6-dihydro-1,4-dimethyl-8-methoxycarbonyl-6-(4-chloro-phenyl) as a yellow oil (35 mg, 78%). $^1$H NMR (300 MHz, CD3OD): δ 8.13-8.09 (m, 1H), 7.95 (s, 1H), 7.77 (d, J=8.4 Hz, 1H), 7.20 (d, J=9 Hz, 2H), 6.80 (d, J=9 Hz, 2H), 4.10-4.05 (m, 1H), 3.91 (s, 3H), 3.63-3.56 (m, 1H), 3.17-3.10 (m, 1H), 2.63 (s, 3H), 1.55 (d, J=6.6 Hz, 3H).

4-R-4H-[1,2,4]Triazolo[4,3-a][1,5]benzodiazepine,5,6-dihydro-1,4-dimethyl-8-carbamoyl-6-(4-chloro-phenyl) (Compound 41)

Into a sealed tube, was charged with a mixture of 4-R-4H-[1,2,4]triazolo[4,3-a][1,5]benzodiazepine,5,6-dihydro-1,4-dimethyl-8-methoxycarbonyl-6-(4-chloro-phenyl) (35 mg, 0.10 mmol) and ammonia in methanol (5 mL). The mixture was heated for 12 hours at 90° C. The mixture was concentrated in vacuo, and then the residue was purified by preparative-TLC (silica-gel, dichloromethane/methanol=15:1) to yield 4-R-4H-[1,2,4]triazolo[4,3-a][1,5]benzodiazepine,5,6-dihydro-1,4-dimethyl-8-carbamoyl-6-(4-chloro-phenyl) as a yellow oil (20 mg, 49%).

Example 37

Synthesis of 4H-[1,2,4]triazolo[4,3-a][1,5]benzodiazepine,5,6-dihydro-(4R)-1,4-dimethyl-8-(1-(2-amino-2-oxoethyl)-1H-pyrazol-4-yl)-6-(4-chloro-phenyl) (Compound 46)

The title compound was prepared by the following scheme:

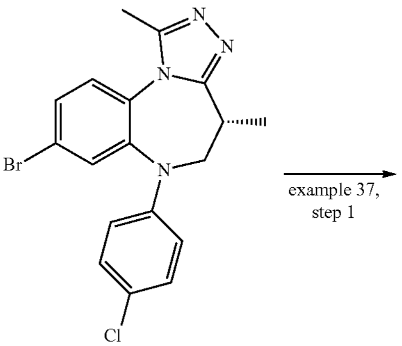

-continued

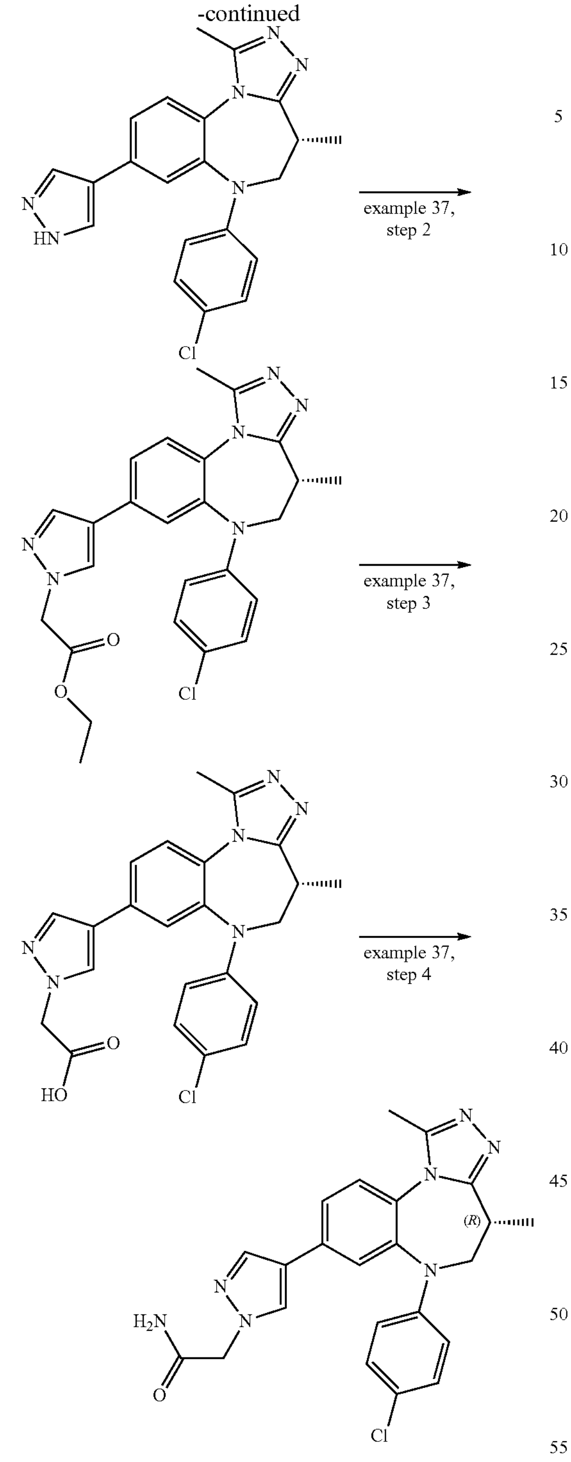

4H-[1,2,4]triazolo[4,3-a][1,5]benzodiazepine,5,6-dihydro-(4R)-1,4-dimethyl-8-(1H-pyrazol-4-yl)-6-(4-chloro-phenyl) (Step 1)

To a mixed solution of tetrahydrofuran (6 mL) and water (1.5 mL), 4H-[1,2,4]triazolo[4,3-a][1,5]benzodiazepine,5,6-dihydro-(4R)-1,4-dimethyl-8-bromo-6-(4-chloro-phenyl) (402 mg, 1 mmol), 4-(4,4,5,5-tetramethyl-1,3,2-dioxaborolan-2-yl)-1H-pyrazole (214 mg, 1.1 mmol), tetrakis(triphenylphosphine)palladium(0) (115 mg, 0.1 mmol) and potassium carbonate (276 mg, 2 mmol) was added. The mixture was stirred at 90° C. for 10 hours under nitrogen atmosphere. The resultant mixture was filtered. The filtrate was diluted with water (10 mL) and extracted with ethyl acetate (30 mL*3). The organic phase was separated, dried over sodium sulfate and then concentrated in vacuo. The residue was purified by column chromatography (silica gel, dichloromethane/methanol=10:1) to give 4H-[1,2,4]triazolo[4,3-a][1,5]benzodiazepine, 5,6-dihydro-(4R)-1,4-dimethyl-8-(1H-pyrazol-4-yl)-6-(4-chloro-phenyl) as a yellow solid (241 mg, 62%). LRMS $(M+H)^+$: calcd 390.14. found 390.

4H-[1,2,4]triazolo[4,3-a][1,5]benzodiazepine,5,6-dihydro-(4R)-1,4-dimethyl-8-(1-(2-ethoxy-2-oxoethyl)-1H-pyrazol-4-yl)-6-(4-chloro-phenyl) (Step 2)

A mixture of 4H-[1,2,4]triazolo[4,3-a][1,5]benzodiazepine,5,6-dihydro-(4R)-1,4-dimethyl-8-(1H-pyrazol-4-yl)-6-(4-chloro-phenyl) (241 mg, 0.62 mmol), ethyl 2-bromoacetate (154 mg, 0.93 mmol) and potassium carbonate (257 mg, 1.86 mmol) in N,N-dimethylformamide (5.0 mL) was stirred at 90° C. for 4 hours under nitrogen atmosphere. The resultant mixture was diluted with ethyl acetate (40 mL) and washed with water (20 mL*3). The organic layer was separated, dried over anhydrous sodium sulfate, filtered and concentrated in vacuo and then the residue was purified by column chromatography (silica gel, dichloromethane/methanol=10:1) to give 4H-[1,2,4]triazolo[4,3-a][1,5]benzodiazepine,5,6-dihydro-(4R)-1,4-dimethyl-8-(1-(2-ethoxy-2-oxoethyl)-1H-pyrazol-4-yl)-6-(4-chloro-phenyl) as a yellow solid (203 mg, 69%). LRMS $(M+H)^+$: calcd 476.17. found 476.

4H-[1,2,4]Triazolo[4,3-a][1,5]benzodiazepine,5,6-dihydro-(4R)-1,4-dimethyl-8-(1-(carboxymethyl)-1H-pyrazol-4-yl)-6-(4-chloro-phenyl) (Step 3)

To a mixed solution of methanol (4 mL) and water (4 mL), 4H-[1,2,4]triazolo[4,3-a][1,5]benzodiazepine,5,6-dihydro-(4R)-1,4-dimethyl-8-(1-(2-ethoxy-2-oxoethyl)-1H-pyrazol-4-yl)-6-(4-chloro-phenyl) (203 mg, 0.43 mmol) and lithium hydroxide (31 mg, 1.29 mmol) was added. The mixture was stirred at room temperature for 4 hours. The resultant mixture was concentrated and hydrochloride acid aqueous (5 mL, 1N) was added. The mixture was extracted with ethyl acetate (20 mL*3). The combined organic layers was separated, dried over anhydrous sodium sulfate, filtered and concentrated in vacuo to give 4H-[1,2,4]triazolo[4,3-a][1,5]benzodiazepine, 5,6-dihydro-(4R)-1,4-dimethyl-8-(1-(carboxymethyl)-1H-pyrazol-4-yl)-6-(4-chloro-phenyl) as a white solid (94 mg, 49%). LRMS $(M+H)^+$: calcd 448.14. found 448.

4H-[1,2,4]triazolo[4,3-a][1,5]benzodiazepine,5,6-dihydro-(4R)-1,4-dimethyl-8-(1-(2-amino-2-oxoethyl)-1H-pyrazol-4-yl)-6-(4-chloro-phenyl) (Compound 46)

To a solution of 4H-[1,2,4]triazolo[4,3-a][1,5]benzodiazepine,5,6-dihydro-(4R)-1,4-dimethyl-8-(1-(carboxymethyl)-1H-pyrazol-4-yl)-6-(4-chloro-phenyl) (94 mg, 0.21 mmol) in anhydrous dichloromethane (5 mL) was added thionyl chloride (2 mL) dropwise at 0° C. The mixture was stirred at room temperature for 4 hours. Then the resultant mixture was concentrated in vacuo to give 4H-[1,2,4]triazolo[4,3-a][1,5]benzodiazepine,5,6-dihydro-(4R)-1,4-dimethyl-8-(1-(2-chloro-2-oxoethyl)-1H-pyrazol-4-yl)-6-(4-chloro-phenyl) as a yellow oil (97 mg, 99%). To the solution of 4H-[1,2,4]triazolo[4,3-a][1,5]benzodiazepine, 5,6-dihydro-(4R)-1, 4-dimethyl-8-(1-(2-chloro-2-oxoethyl)-1H-pyrazol-4-yl)-6-(4-chloro-phenyl) (97 mg, 0.21 mmol) in anhydrous dichloromethane (5 mL) was added saturated ammonia aqueous (2 mL). The mixture was stirred for 1 hour and then concentrated in vacuo. The residue was purified by column chromatography (silica gel, dichloromethane/methanol=10:1) to give 4H-[1,2,4]triazolo[4,3-a][1,5]benzodiazepine, 5,6-dihydro-(4R)-1,4-dimethyl-8-(1-(2-amino-2-oxoethyl)-1H-pyrazol-4-yl)-6-(4-chloro-phenyl) as a white solid (25 mg, 26%).

Example 38

Synthesis of 4-R-4H-[1,2,4]triazolo[4,3-a][1,5]benzodiazepine,5,6-dihydro-1,4-dimethyl-8-(5-methyl-1,3,4-oxadiazol-2-yl)-6-(4-chloro-phenyl) (Compound 49)

The title compound was prepared by the following scheme:

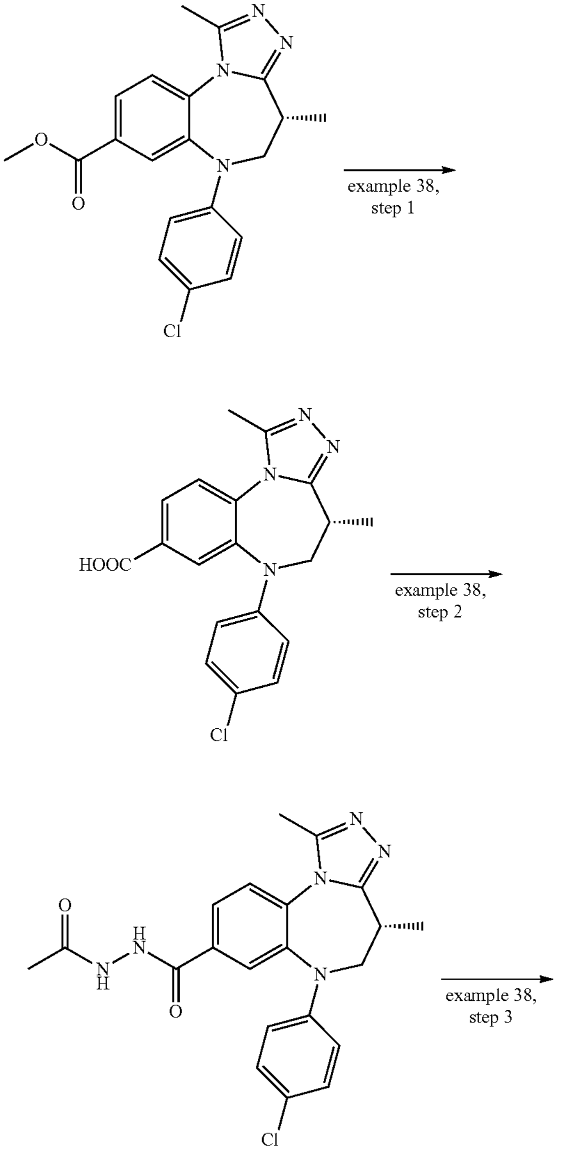

-continued

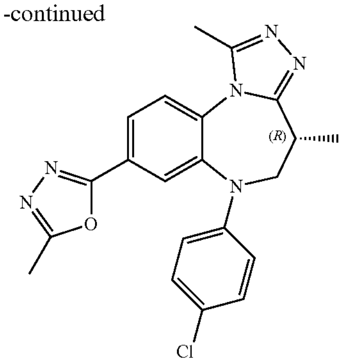

4-R-4H-[1,2,4]triazolo[4,3-a][1,5]benzodiazepine,5,6-dihydro-1,4-dimethyl-8-carboxy-6-(4-chloro-phenyl) (Step 1)

A mixture of 4-R-4H-[1,2,4]triazolo[4,3-a][1,5]benzodiazepine,5,6-dihydro-1,4-dimethyl-8-methoxycarbonyl-6-(4-chloro-phenyl) (Example 36, Step 1; 294 mg, 0.77 mmol), sodium hydroxide (200 mg+E73, 5 mmol), methanol (8 mL) and water (20 mL) was stirred at 60° C. for 5 hours. The mixture was neutralized to pH=1 with concentrated hydrochloric acid (1 N, 6 mL) and then extracted with ethyl ether (15 mL*3). The combined organic layers was separated, dried over anhydrous sodium sulfate, filtered and concentrated in vacuo to give crude 4-R-4H-[1,2,4]triazolo[4,3-a][1,5]benzodiazepine, 5,6-dihydro-1,4-dimethyl-8-car-boxy-6-(4-chloro-phenyl) as a white solid (270 mg). LRMS $(M+H)^+$: calcd. 368.1. found 368.

4-R-4H-[1,2,4]triazolo[4,3-a][1,5]benzodiazepine,5,6-dihydro-1,4-dimethyl-8-(2-acetylhydrazinecarbonyl)-6-(4-chloro-phenyl) (Step 2)

A mixture of 4-R-4H-[1,2,4]triazolo[4,3-a][1,5]benzodiazepine, 5,6-dihydro-1,4-dimethyl-8-carboxy-6-(4-chloro-phenyl) (100 mg, 0.27 mmol), acethydrazide (100 mg, 1.4 mmol), o-(7-azabenzotriazol-1-yl)-N, N,N',N'-tetramethyluronium hexafluorophosphate (420 mg, 1.11 mmol), and triethylamine (1 mL) in dichloromethane (15 mL) was stirred at room temperature for 14 hours. The mixture was diluted with dichloromethane (20 mL), washed with water (20 mL*3), dried over anhydrous sodium sulfate, filtered, and concentrated to give a residue. The residue was purified by column chromatography (silica gel, dichloromethane/methanol=30:1) to give 4-R-4H-[1,2,4]triazolo[4,3-a][1,5]benzodiazepine, 5,6-dihydro-1,4-dimethyl-8-(2-acetylhydrazinecarbonyl)-6-(4-chloro-phenyl) as a color less oil (60 mg, 60%).

4-R-4H-[1,2,4]triazolo[4,3-a][1,5]benzodiazepine,5,6-dihydro-1,4-dimethyl-8-(5-methyl-1,3,4-oxadiazol-2-yl)-6-(4-chloro-phenyl) (Compound 49)

A mixture of 4-R-4H-[1,2,4]triazolo[4,3-a][1,5]benzodiazepine, 5,6-dihydro-1,4-dimethyl-8-(2-acetylhydrazinecarbonyl)-6-(4-chloro-phenyl) (30 mg, 0.07 mmol), triphenylphosphine (52 mg, 0.2 mmol), N,N-diisopropylethylamine (1 mL), and hexachloroethane (47 mg, 0.2 mmol) in dichloromethane (15 mL) was stirred at room temperature for 14 hours. The mixture was diluted with dichloromethane (20 mL), washed with water (20 mL*3), dried over anhydrous sodium sulfate, filtered, and concentrated in vacuo to give a residue. The residue was purified by column chromatography (silica gel, dichloromethane/methanol=30:1) to give 4-R-4H-[1,2,4]Triazolo[4,3-a][1,5]benzodiazepine, 5,6-dihydro-1,4-dimethyl-8-(5-methyl-1,3,4-oxadiazol-2-yl)-6-(4-chloro-phenyl) as a colorless oil (8 mg, 26%).

Example 39

Synthesis of 4-R-4H-[1,2,4]triazolo[4,3-a][1,5]benzodiazepine,5,6-dihydro-1,4-dimethyl-8-(2-hydroxyethylcarbamoyl)-6-(4-chloro-phenyl) (Compound 47)

The title compound was prepared by the following scheme:

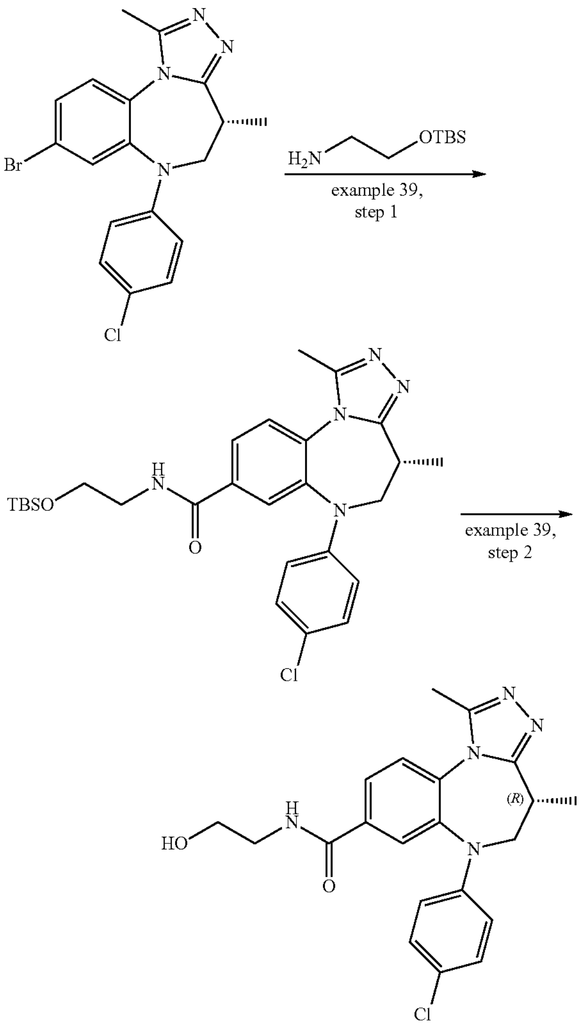

2-(tert-butyldimethylsilyloxy)ethanamine

To a solution of 2-aminoethanol (5 g, 82 mmol) and tert-butylchlorodimethylsilane (18 g, 123 mmol) in dichloromethane (200 mL) was added triethyl amine (16 g, 158 mmol) dropwise at 0° C. Once addition was completed, the resultant mixture was stirred at room temperature for 4 hours. The mixture was concentrated in vacuo to give a residue, and the residue was purified by column chromatography (silica gel, petroleum ether/ethyl acetate=5:1) to give 2-(tert-butyldimethylsilyloxy)ethanamine as a colorless oil (12 g, 84%).

4H-[1,2,4]triazolo[4,3-a][1,5]benzodiazepine,5,6-dihydro-(4R)-1,4-dimethyl-8-(2-(tert-butyldimethylsilyloxy)ethylcarbamoyl)-6-(4-chloro-phenyl) (Step 1)

To a solution of 4H-[1,2,4]triazolo[4,3-a][1,5]benzodiazepine,5,6-dihydro-(4R)-1,4-dimethyl-8-bromo-6-(4-chlorophenyl) (300 mg, 0.7 mmol) in triethylamine (30 mL) was added 2-(tert-butyldimethylsilyloxy)ethanamine (250 mg, 1.4 mmol), 1,3-bis(diphenylphosphino) propane (20 mg) and palladium acetate (10 mg). The mixture was stirred for 12 hours at 90° C. under carbon monoxide atmosphere (1 atm). The mixture was concentrated in vacuo, and then the residue was purified by preparative-TLC (silica-gel, dichloromethane/methanol=15:1) to yield 4H-[1,2,4]triazolo[4,3-a][1,5]benzodiazepine,5,6-dihydro-(4R)-1,4-dimethyl-8-(2-(tert-butyldimethylsilyloxy)ethylcarbamoyl)-6-(4-chlorophenyl) as a white solid (200 mg, 51%).

4H-[1,2,4]triazolo[4,3-a][1,5]benzodiazepine,5,6-dihydro-(4R)-1,4-dimethyl-8-(2-hydroxyethylcarbamoyl)-6-(4-chloro-phenyl) (Compound 47)

To a solution of 4H-[1,2,4]triazolo[4,3-a][1,5]benzodiazepine,5,6-dihydro-(4R)-1,4-dimethyl-8-(2-(tert-butyldimethylsilyloxy)ethylcarbamoyl)-6-(4-chloro-phenyl) (200 mg, 0.38 mmol) in ethanol (10 mL) was added concentrated hydrochloride acid (1 mL). The resultant mixture was stirred at room temperature for 12 hours. The reaction was quenched with sodium bicarbonate aqueous (20 mL), extracted with dichloromethane (100 mL*3). The organic layers were separated, combined, dried over anhydrous sodium sulfate, filtered and concentrated in vacuo. The residue was purified by column chromatography (silica gel, dichloromethane/methanol=10:1) to give 4H-[1,2,4]triazolo[4,3-a][1,5]benzodiazepine,5,6-dihydro-(4R)-1,4-dimethyl-8-(2-hydroxyethylcarbamoyl)-6-(4-chloro-phenyl) as a white solid (50 mg, 32%).

Example 40

Synthesis of 4-R-4H-[1,2,4]triazolo[4,3-a][1,5]benzodiazepine,5,6-dihydro-1,4-dimethyl-8-(2-hydroxyethylcarbamoyl)-6-(4-chloro-phenyl) (Compound 48)

The title compound was prepared by the following scheme:

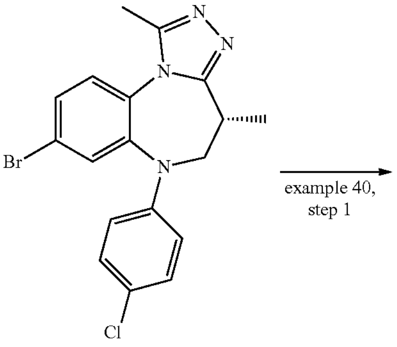

-continued

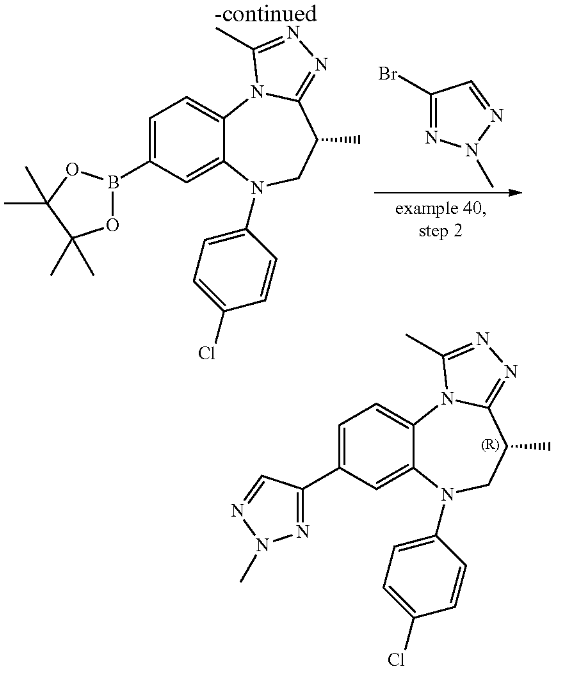

A. Synthesis of 4-bromo-2-methyl-2H-1,2,3-triazole 4,5-dibromo-2H-1,2,3-triazole Bromine (15 mL) was added dropwise to a stirred solution of 2H-1,2,3-triazole (15.0 g, 217 mmol) in water (200 mL) at 0° C. Once addition was completed, the mixture was stirred for 12 hours at room temperature. The resultant mixture was filtered off and washed with water, dried over sodium sulfate and recrystallized from methanol to afford 4,5-dibromo-2H-1,2,3-triazole as a dark brown solid (29.8 g, 60.8%).

4,5-dibromo-2-methyl-2H-1,2,3-triazole

Iodomethane (19.0 g, 133.8 mmol) was added to a solution of 4,5-dibromo-2H-1,2,3-triazole (15.0 g, 66.7 mmol) and potassium carbonate (18.1 g, 131.2 mmol) in N,N-dimethylformamide (100 mL) at −10° C. The mixture was warmed to room temperature and stirred for 12 hours. The reaction mixture was concentrated to give a residue. The residue was dissolved in ethyl acetate (200 mL), washed by brine (50 mL×3), dried over anhydrous sodium sulfate and then filtered. The filtrate was concentrated and the residue was purified by column chramtography (silica gel, dichloromethane/methanol=15:1) to afford 4,5-dibromo-2-methyl-2H-1,2,3-triazole as a white solid (5.9, 36.9%).

4-bromo-2-methyl-2H-1,2,3-triazole n-Butyllithium (8.3 mL) was added dropwise to a solution of 4,5-dibromo-2-methyl-2H-1,2,3-triazole (2.0 g, 8.37 mmol) in tetrahydrofuran (50 mL) under −78° C., Once addition was completed, the mixture was stirred for another 30 minutes at −78° C. The reaction was quenched with water, extracted with ethyl acetate (50 mL×3), washed by brine (30 mL×3). The organic phase was dried over anhydrous sodium sulfate and then filtered. The filtrate was concentrated in vacuo to afford 4-bromo-2-methyl-2H-1,2,3-triazole.

B. Synthesis of Compound 48

4-R-4H-[1,2,4]triazolo[4,3-a][1,5]benzodiazepine, 5,6-dihydro-1,4-dimethyl-8-(4,4,5,5-tetramethyl-1,3,2-dioxaborolan-2-yl)-6-(4-chloro-phenyl) (Step 1)

A mixture of 4-R-4H-[1,2,4]triazolo[4,3-a][1,5]benzodiazepine, 5,6-dihydro-1,4-dimethyl-8-bromo-6-(4-chloro-phenyl) (200 mg, 0.50 mmol), 4,4,4',4',5,5,5',5'-octamethyl-2,2'-bi(1,3,2-dioxaborolane) (95 mg, 0.37 mmol), [1,1'-bis(diphenylphosphino)ferrocene]dichloropalladium(II) (10 mg), potassium acetate (74 mg, 0.75 mmol) in N,N-dimethylformamide (10 mL) was heated at 110° C. for 20 minutes under microwave (pressure: 17.2 bar, equipment power: 150 W). The reaction mixture was concentrated to give a residue. The residue was dissolved in ethyl acetate (100 mL) and washed by brine (20 mL×3). The organic phase was dried over sodium sulfate anhydrous and then filtered. The filtrate was concentrated and the residue was purified by column chramtography (silica gel, dichloromethane/methanol=10:1) to afford 4-R-4H-[1,2,4]triazolo[4,3-a][1,5]benzodiazepine, 5,6-dihydro-1,4-dimethyl-8-(4,4,5,5-tetramethyl-1,3,2-dioxaborolan-2-yl)-6-(4-chloro-phenyl) as a dark yellow solid (200 mg, 89.0%).

4H-[1,2,4]triazolo[4,3-a][1,5]benzodiazepine, 5,6-dihydro-(4R)-1,4-dimethyl-8-(2-methyl-2H-1,2,3-triazole-4-yl)-6-(4-chloro-phenyl) (Compound 48)

A mixture of 4-R-4H-[1,2,4]triazolo[4,3-a][1,5]benzodiazepine, 5,6-dihydro-1,4-dimethyl-8-(4,4,5,5-tetramethyl-1,3,2-dioxaborolan-2-yl)-6-(4-chloro-phenyl) (200 mg, 0.44 mmol), 4-bromo-2-methyl-2H-1,2,3-triazole (72 mg, 0.44 mmol), tetrakis(triphenylphosphine)palladium(0) (51 mg) and potassium carbonate (243 mg, 1.76 mmol) in mixed solution of tetrahydrofuran (10 mL) and water (2 mL) was heated at 100° C. for 30 minutes under microwave (pressure: 17.2 bar, equipment power: 150 W). The reaction mixture was diluted with ethyl acetate (50 mL), washed by brine (20 mL×3), dried over anhydrous sodium sulfate and then filtered. The filtrate was concentrated and the residue was purified by column chromatography (silica gel, dichloromethane/methanol=10:1) to afford 4-R-4H-[1,2,4]triazolo[4,3-a][1,5]benzodiazepine, 5,6-dihydro-1,4-dimethyl-8-(2-methyl-2H-1,2,3-triazole-4-yl)-6-(4-chloro-phenyl) as a white solid (80 mg, 44.5%).

Example 41

Synthesis of 4-R-4H-[1,2,4]triazolo[4,3-a][1,5]benzodiazepine, 5,6-dihydro-1,4-dimethyl-8-(5-methyl-1,2,4-oxadiazol-3-yl)-6-(4-chloro-phenyl) (Compound 50)

The title compound was prepared by the following scheme:

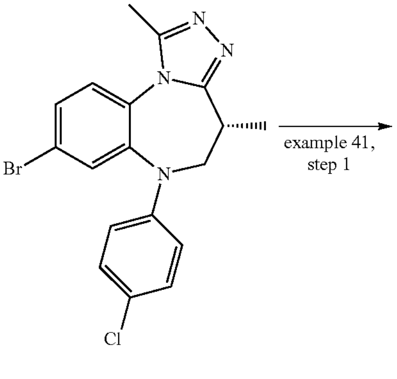

-continued

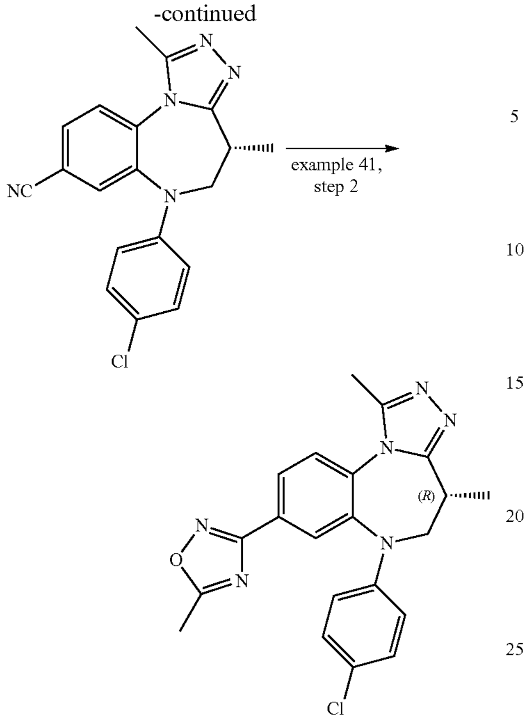

4-R-4H-[1,2,4]triazolo[4,3-a][1,5]benzodiazepine, 5,6-dihydro-1,4-dimethyl-8-cyano-6-(4-chloro-phenyl) (Step 1)

A sealed tube was charged with a mixture of 4-R-4H-[1,2,4]triazolo[4,3-a][1,5]benzodiazepine,5,6-dihydro-1,4-dimethyl-8-bromo-6-(4-chloro-phenyl) (330 mg, 0.82 mmol), zinc cyanide (80 mg, 0.69 mmol), tetrakis(triphenylphosphine)palladium(0) (30 mg) and N,N-dimethylformamide (10 mL). The mixture was heated for 12 hours at 140° C. The resultant mixture was concentrated in vacuo to give a residue. The residue was purified by column chromatography (silica gel, dichloromethane/methanol=30:1) to give 4-R-4H-[1,2,4]triazolo[4,3-a][1,5]benzodiazepine,5,6-dihydro-1,4-dimethyl-8-cyano-6-(4-chloro-phenyl) as a colorless oil (200 mg, 70%). $^1$H NMR (300 MHz, CDC13): δ 8.01 (s, 1H), 7.63 (d, J=8.4 Hz, 1H), 7.58 (d, J=8.4 Hz, 1H), 7.23 (d, J=8.7 Hz, 2H), 6.80 (d, J=8.7 Hz, 2H), 4.00-3.97 (m, 1H), 3.53-3.49 (m, 1H), 2.64-2.60 (m, 1H), 2.65 (s, 3H), 1.58 (d, J=6.9 Hz, 3H).

4-R-4H-[1,2,4]triazolo[4,3-a][1,5]benzodiazepine, 5,6-dihydro-1,4-dimethyl-8-(5-methyl-1,2,4-oxadiazol-3-yl)-6-(4-chloro-phenyl) (Compound 50)

A mixture of hydroxylamine hydrochloride (1 g, 14.4 mmol) and potassium carbonate (2 g, 14.5 mmol) in ethanol (20 mL) was stirred at room temperature for 30 minutes, then 4-R-4H-[1,2,4]triazolo[4,3-a][1,5]benzodiazepine, 6-dihydro-1,4-dimethyl-8-cyano-6-(4-chloro-phenyl) (100 mg, 0.29 mmol) was added and the resultant mixture was stirred at 85° C. for 16 hours. The resultant mixture was filtered and concentrated to give crude 4-R-4H-[1,2,4]triazolo[4,3-a][1,5]benzodiazepine,5,6-dihydro-1,4-dimethyl-8-(N-hydroxycarbamimidoyl)-6-(4-chloro-phenyl) as a colorless oil (80 mg, crude). A mixture of 4-R-4H-[1,2,4]triazolo[4,3-a][1,5]benzodiazepine, 5,6-dihydro-1,4-dimethyl-8-(N-hydroxycarbamimidoyl)-6-(4-chloro-phenyl) (80 mg, 0.21 mmol), p-toluenesulfonic acid (36 mg, 0.21 mmol), zinc chloride (28 mg, 0.21 mmol) in acetonitrile (15 mL) was stirred at 95° C. for 48 hours. The mixture was filtered, and concentrated to give a residue. The residue was purified by column chromatography (silica gel, dichloromethane/methanol=30:1) to give 4-R-4H-[1,2,4]triazolo[4,3-a][1,5]benzodiazepine, 5,6-dihydro-1,4-dimethyl-8-(5-methyl-1,2,4-oxadiazol-3-yl)-6-(4-chloro-phenyl) as a colorless oil (3 mg, 4% for two steps).

Example 42

Synthesis of 4-R-4H-[1,2,4]triazolo[4,3-a][1,5]benzodiazepine,5,6-dihydro-1,4-dimethyl-8-(3-methyl-1,2,4-oxadiazol-5-yl)-6-(4-chloro-phenyl) (Compound 51)

The title compound was prepared by the following scheme:

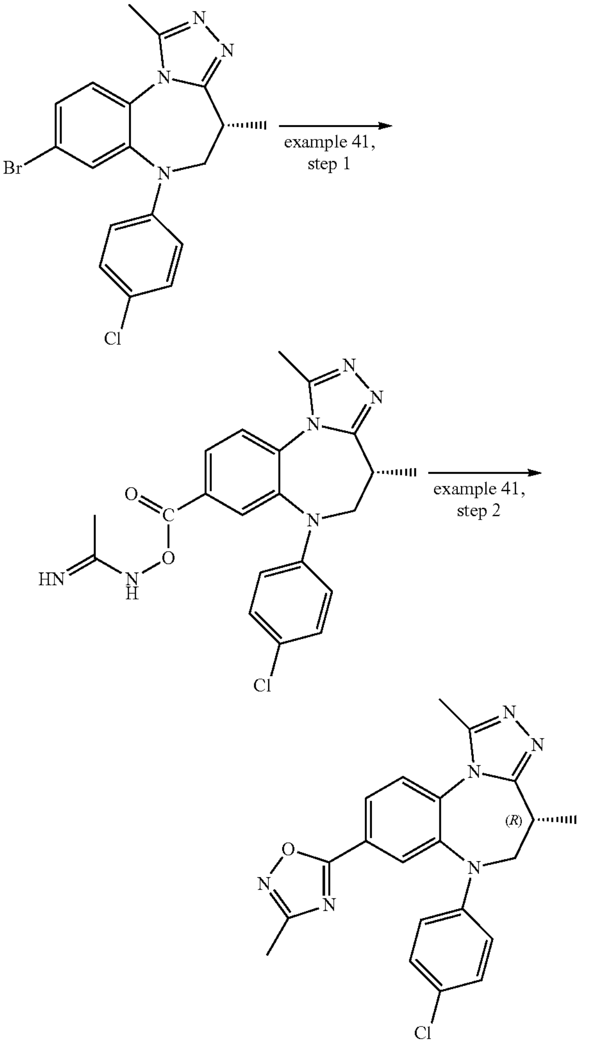

4-R-4H-[1,2,4]triazolo[4,3-a][1,5]benzodiazepine, 6-dihydro-1,4-dimethyl-8-(acetimidamidooxycarbonyl)-6-(4-chloro-phenyl) (Step 1)

A mixture of 4-R-4H-[1,2,4]triazolo[4,3-a][1,5]benzodiazepine, 5,6-dihydro-1,4-dimethyl-8-carboxy-6-(4-chlorophenyl) (100 mg, 0.27 mmol), N-hydroxyacetamidine (40 mg, 0.54 mmol), 1-hydroxybenzotrizole (73 mg, 0.54 mmol), 1-(3-dimethylaminopropyl)-3-ethylcarbodiimide hydrochloride (104 mg, 0.54 mmol), and triethylamine (81 mg, 0.81 mmol) in dichloromethane (15 mL) was stirred at room temperature for 14 hours. The mixture was diluted with dichloromethane (20 mL), washed with water (20 mL*3), dried over anhydrous sodium sulfate, filtered and concentrated in vacuo. The residue was purified by column chromatography (silica gel, dichloromethane/methanol=20:1) to give 4-R-4H-[1,2,4]triazolo[4,3-a][1,5]benzodiazepine, 5,6-dihydro-1,4-dimethyl-8-(acetimidamidooxycarbonyl)-6-(4-chloro-phenyl) as a colorless oil (45 mg, 39%).

4-R-4H-[1,2,4]triazolo[4,3-a][1,5]benzodiazepine,5,6-dihydro-1,4-dimethyl-8-(3-methyl-1,2,4-oxadiazol-5-yl)-6-(4-chloro-phenyl) (Compound 51)

A mixture of 4-R-4H-[1,2,4]triazolo[4,3-a][1,5]benzodiazepine, 5,6-dihydro-1,4-dimethyl-8-(acetimidamidooxycarbonyl)-6-(4-chloro-phenyl) (30 mg, 0.07 mmol), sodium acetate (30 mg, 0.36 mmol) in mixed solution of ethanol (10 mL) and water (3 mL) was stirred at 86° C. for 5 hours. The mixture was filtered, concentrated in vacuo to give a residue. The residue was purified by column chromatography (silica gel, dichloromethane/methanol=30:1) to give 4-R-4H-[1,2,4]triazolo[4,3-a][1,5]benzodiazepine,5,6-dihydro-1,4-dimethyl-8-(3-methyl-1,2,4-oxadiazol-5-yl)-6-(4-chloro-phenyl) as a color less oil (8 mg, 27%).

Example 43

Synthesis of 4H-[1,2,4]triazolo[4,3-a][1,5]benzodiazepine,5,6-dihydro-1,4-dimethyl-8-(1-methyl-1H-pyrazol-4-yl)-6-(5-cyanopyridin-2-yl) (Compound 108) and its (R) and (S) Enantiomers (Compounds 52 and 58)

Compound 108 was prepared by the following scheme:

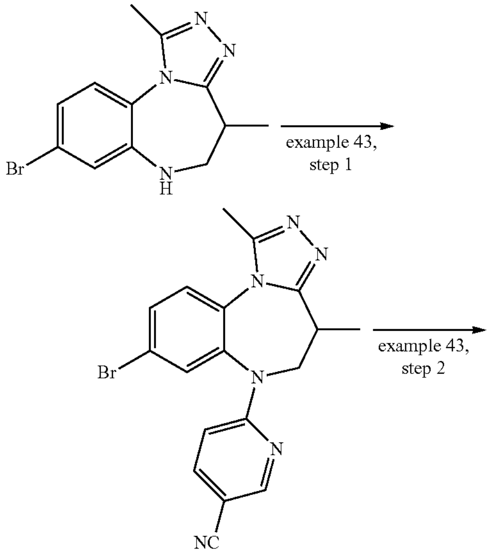

-continued

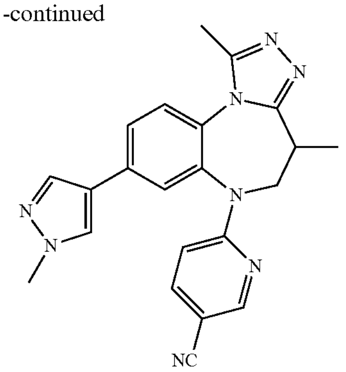

4H-[1,2,4]triazolo[4,3-a][1,5]benzodiazepine,5,6-dihydro-1,4-dimethyl-8-bromo-6-(5-cyanopyridin-2-yl) (Step 1)

A solution of 4H-[1,2,4]triazolo[4,3-a][1,5]benzodiazepine, 5,6-dihydro-1,4-dimethyl-8-bromo (Example 4, step 5; 100 mg, 0.34 mmol), 6-chloronicotinonitrile (95 mg, 0.68 mmol), potassium carbonate (141 mg, 1.02 mmol) in N,N-dimethylformamide (5 mL) was heated at 180° C. for 30 minutes under microwave (pressure: 17.2 bar, equipment power: 150 W). The mixture was concentrated. The residue was dissolved in ethyl acetate (30 mL), washed by brine (20 mL×3), dried over anhydrous sodium sulfate and then filtered. The filtrate was concentrated and the residue was purified by column chromatography (silica gel, dichloromethane/methanol=10:1) to afford 4H-[1,2,4]triazolo[4,3-a][1,5]benzodiazepine,5,6-dihydro-1,4-dimethyl-8-bromo-6-(5-cyanopyridin-2-yl) as a brown solid (44 mg, 32.8%). $^1$H NMR (300 MHz, CDC13): δ 8.44 (s, 1H), 7.72-7.53 (m, 3H), 7.34-7.32 (m, 1H), 6.30 (d, J=9.0 Hz, 1H), 4.50-4.42 (m, 1H), 3.95-3.82 (m, 1H), 3.06-3.04 (m, 1H), 2.55 (s, 3H), 1.61 (d, J=6.3 Hz, 3H).

4H-[1,2,4]triazolo[4,3-a][1,5]benzodiazepine,5,6-dihydro-1,4-dimethyl-8-(1-methyl-1H-pyrazol-4-yl)-6-(5-cyanopyridin-2-yl) (Compound 108)

A solution of 4H-[1,2,4]triazolo[4,3-a][1,5]benzodiazepine, 5,6-dihydro-1,4-dimethyl-8-bromo-6-(5-cyanopyridin-2-yl) (150 mg, 0.38 mmol), 1-methyl-4-(4,4,5,5-tetramethyl-1,3,2-dioxaborolan-2-yl)-1H-pyrazole (160 mg, 0.76 mmol), tetrakis(triphenylphosphine)palladium(0) (44 mg) and potassium carbonate anhydrous (210 mg, 1.52 mmol) in tetrahydrofuran (10 mL) and water (2 mL) was stirred at 100° C. for 30 minutes under microwave (pressure: 17.2 bar, equipment power: 150 W). The reaction mixture was diluted with ethyl acetate (50 mL), washed with brine (20 mL×3), dried over anhydrous sodium sulfate and then filtered. The filtrate was concentrated and the residue was purified by column chromatography (silica gel, dichloromethane/methanol=10:1) to afford 4H-[1,2,4]triazolo[4,3-a][1,5]benzodiazepine, 5,6-dihydro-1,4-dimethyl-8-(1-methyl-1H-pyrazol-4-yl)-6-(5-cyanopyridin-2-yl) as a white solid (120 mg, 80%).

(R)-4H-[1,2,4]triazolo[4,3-a][1,5]benzodiazepine,5,6-dihydro-1,4-dimethyl-8-(1-methyl-1H-pyrazol-4-yl)-6-(5-cyanopyridin-2-yl) (Compound 52) and (S)-4H-[1,2,4]triazolo[4,3-a][1,5]benzodiazepine, 5,6-dihydro-1,4-dimethyl-8-(1-methyl-1H-pyrazol-4-yl)-6-(5-cyanopyridin-2-yl) (Compound 58)

4H-[1,2,4]triazolo[4,3-a][1,5]benzodiazepine,5,6-dihydro-1,4-dimethyl-8-(1-methyl-1H-pyrazol-4-yl)-6-(5-cyanopyridin-2-yl) (120 mg, 0.3 mmol) was separated by chiral prep-HPLC (Daicel AD-H (250 mm×20 mm×5 μm), hexane/ethanol (0.2 diethylamine)=20:80, flow rate: 13 mL/min), then (R)-4H-[1,2,4]triazolo[4,3-a][1,5]benzodiazepine,5,6-dihydro-1,4-dimethyl-8-(1-methyl-1H-pyrazol-4-yl)-6-(5-cyanopyridin-2-yl) (35 mg, 58%) and (S)-4H-[1,2,4]triazolo[4,3-a][1,5]benzodiazepine,5,6-dihydro-1,4-dimethyl-8-(1-methyl-1H-pyrazol-4-yl)-6-(5-cyanopyridin-2-yl) (40 mg, 67%) were obtained. The retention times were 9.478 minute and 13.509 minute respectively in chiral prep-HPLC chromatography.

Example 44

Synthesis of 4-R-4H-[1,2,4]triazolo[4,3-a][1,5]benzodiazepine,5,6-dihydro-1,4-dimethyl-8-(pyrrolidine-1-carbonyl)-6-(4-chloro-phenyl) (Compound 53)

A mixture of 4-R-4H-[1,2,4]triazolo[4,3-a][1,5]benzodiazepine,5,6-dihydro-1,4-dimethyl-8-bromo-6-(4-chloro-phenyl) (200 mg, 0.50 mmol), 1,3-bis-(diphenylphosphino) propane (125 mg, 0.3 mmol), palladium acetate (35 mg), and pyrrolidine (355 mg, 5 mmol) in triethylamine (20 mL) was heated at 90° C. for 12 hours under carbon monoxide atmosphere. The mixture was filtered and the filtrate was concentrated in vacuo and the residue was purified by column chromatography (silica gel, dichloromethane/methanol=10:1) to afford 4-R-4H-[1,2,4]triazolo[4,3-a][1,5]benzodiazepine,5,6-dihydro-1,4-dimethyl-8-(pyrrolidine-1-carbonyl)-6-(4-chloro-phenyl) as a white solid (35 mg, 17%).

Example 45

Synthesis of (R)-6-(4-chlorophenyl)-1,4-dimethyl-8-(1H-1,2,4-triazol-1-yl)-5,6-dihydro-4H-benzo[b][1,2,4]triazolo[4,3-d][1,4]diazepine (Compound 54)

A mixture of (R)-8-bromo-6-(4-chlorophenyl)-1,4-dimethyl-5,6-dihydro-4H-benzo[b][1,2,4]triazolo[4,3-d][1,4]diazepine (40.2 mg, 0.1 mmol), 1H-1,2,4-triazole (13.8 mg, 0.2 mmol), copper(I) iodide (3.8 mg, 0.02 mmol), and cesium carbonate (59 mg, 0.18 mmol) in N-methyl-2-pyrrolidone (3 mL) was stirred at 150° C. for 16 hours. The mixture was diluted with water (10 mL), extracted with ethyl acetate (3*20 mL). The combined organic layer was washed with water (3*20 mL) and brine (3*20 mL) in turns, dried over anhydrous sodium sulfate, filtered and concentrated to give a residue. The residue was purified by prep-TLC (silica-gel, dichloromethane/methanol=15:1) to give (R)-6-(4-chlorophenyl)-1,4-dimethyl-8-(1H-1,2,4-triazol-1-yl)-5,6-dihydro-4H-benzo[b][1,2,4]triazolo[4,3-d][1,4]diazepine as a white solid (10 mg, 25.7%).

Example 46

Synthesis of 4-R-4H-[1,2,4]triazolo[4,3-a][1,5]benzodiazepine,5,6-dihydro-1,4-dimethyl-8-(morpholine-4-carbonyl)-6-(4-chloro-phenyl) (Compound 56)

A mixture of 4-R-4H-[1,2,4]triazolo[4,3-a][1,5]benzodiazepine, 5,6-dihydro-1,4-dimethyl-8-bromo-6-(4-chloro-phenyl) (100 mg, 0.25 mmol), 1,3-bis-(diphenylphosphino) propane (62 mg, 0.15 mmol), palladium acetate (20 mg), and morpholine (108 mg, 1.25 mmol) in triethylamine (20 mL) was heated for 12 hours at 90° C. under carbon monoxide atmosphere. The mixture was filtered and the filtrate was concentrated in vacuo. The residue was purified by column chromatography (silica gel, dichloromethane/methanol=10:1) to yield 4H-[1,2,4]triazolo[4,3-a][1,5]benzodiazepine,5,6-dihydro-1,4-dimethyl-8-(morpholine-4-carbonyl)-6-(4-chloro-phenyl) as a white solid (15 mg, 13.8%).

Example 47

Synthesis of 4-R-4H-[1,2,4]triazolo[4,3-a][1,5]benzodiazepine,5,6-dihydro-1,4-dimethyl-8-(5-aminopyrazin-2-yl)-6-(4-chloro-phenyl) (Compound 55)

A solution of 4-R-4H-[1,2,4]Triazolo[4,3-a][1,5]benzodiazepine,5,6-dihydro-1,4-dimethyl-8-(4,4,5,5-tetramethyl-1,3,2-dioxaborolan-2-yl)-6-(4-chloro-phenyl) (60 mg, 0.13 mmol), 5-bromopyrazin-2-amine (22 mg, 0.13 mmol), Tetrakis(triphenylphosphine)palladium(0)(10 mg) and potassium carbonate (58 mg, 0.42 mmol) in mixed solution of tetrahydrofuran (2 mL) and water (0.22 mL) was degassed by nitrogen three times, and then the mixture was heated at 100° C. under microwave (pressure: 17.2 bar, equipment power: 150 W) for 20 minutes. After cooling to room temperature, dichloromethane (50 mL) was added. The organic layer was separated, dried over anhydrous sodium sulfate, filtered and concentrated in vacuo. The residue was purified by column chromatography (silica gel, dichloromethane/methanol=10:1) to afford 4-R-4H-[1,2,4]Triazolo[4,3-a][1,5]benzodiazepine, 5,6-dihydro-1,4-dimethyl-8-(5-aminopyrazin-2-yl)-6-(4-chloro-phenyl) as a white solid (10 mg, 18%).

Example 48

Synthesis of 4H-[1,2,4]Triazolo[4,3-a][1,5]benzodiazepine, 5,6-dihydro-1,4-dimethyl-8-(1-methyl-2H-1,2,3-triazole-4-yl)-6-(4-chloro-phenyl) (Compound 64)

A solution of 4H-[1,2,4]Triazolo[4,3-a][1,5]benzodiazepine, 5,6-dihydro-1,4-dimethyl-8-(4,4,5,5-tetramethyl-1,3,2-dioxaborolan-2-yl)-6-(4-chloro-phenyl) (230 mg, 0.651 mmol), 4-bromo-1-methyl-2H-1,2,3-triazole (91 mg, 0.56 mmol), tetrakis(triphenylphosphine)palladium(0) (59 mg) and potassium carbonate anhydrous (282 mg, 2.04 mmol) in tetrahydrofuran (10 mL) and water (2 mL) was reacted at 100° C. for 30 minutes with microwave (pressure: 17.2 bar, equipment power: 150 W). The reaction mixture was diluted with ethyl acetate (50 mL), washed by brine (20 mL×3), dried over anhydrous sodium sulfate and then filtered. The filtrate was concentrated and the residue was purified by CombiFlsh (silica gel, dichloromethane/methanol=10:1) to afford 4H-[1,2,4]Triazolo[4,3-a][1,5]benzodiazepine, 5,6-dihydro-1,4-dimethyl-8-(1-methyl-2H-1,2,3-triazole-4-yl)-6-(4-chloro-phenyl) as a white solid (60 mg, 29%).

Example 49

Synthesis of (R)-6-(4-chlorophenyl)-8-(1,5-dimethyl-1H-pyrazol-4-yl)-1,4-dimethyl-5,6-dihydro-4H-benzo[b][1,2,4]triazolo[4,3-d][1,4]diazepine (Compound 59)

A mixture of (R)-8-bromo-6-(4-chlorophenyl)-1,4-dimethyl-5,6-dihydro-4H-benzo[b][1,2,4]triazolo[4,3-d][1,4]diazepine (41 mg, 0.1 mmol), 1,5-dimethyl-4-(4,4,5,5-tetramethyl-1,3,2-dioxaborolan-2-yl)-1H-pyrazole (34 mg, 0.15 mmol), tetrakis(triphenylphosphine)palladium(0) (12 mg)

and cesium carbonate (65 mg, 0.2 mmol) in toluene, ethanol and water (5 mL, 4:2:1) was stirred at 100° C. for 0.5 hour under microwave (pressure: 3.2 bar, equipment power: 150 W). The reaction mixture was evaporated, water (10 mL) was added and the mixture was extracted with ethyl acetate (20 mL). The combined organic layers were dried over anhydrous sodium sulfate, filtered and concentrated to give a residue which was purified by column chromatography (silica gel, petroleum ether/ethyl acetate=2:1), to give (R)-6-(4-chlorophenyl)-8-(1,5-dimethyl-1H-pyrazol-4-yl)-1,4-dimethyl-5,6-dihydro-4H-benzo[b][1,2,4]triazolo[4,3-d][1,4]diazepine as a yellow solid (10 mg, 23%).

Example 50

Synthesis of compound (R)-6-(4-chlorophenyl)-1,4-dimethyl-8-(5-methyl-1H-1,2,4-triazol-1-yl)-5,6-dihydro-4H-benzo[b][1,2,4]triazolo[4,3-d][1,4]diazepine (Compound 65) and (R)-6-(4-chlorophenyl)-1,4-dimethyl-8-(3-methyl-1H-1,2,4-triazol-1-yl)-5,6-dihydro-4H-benzo[b][1,2,4]triazolo[4,3-d][1,4]diazepine (Compound 66)

A mixture of (R)-8-bromo-6-(4-chlorophenyl)-1,4-dimethyl-5,6-dihydro-4H-benzo[b][1,2,4]triazolo[4,3-d][1,4]diazepine (60 mg, 0.15 mmol), 3-methyl-1H-1,2,4-triazole (14 mg, 0.16 mmol), copper (I) iodide (6 mg, 0.03 mmol), 1,10-phenanthroline (11 mg, 0.06 mmol) and cesium carbonate (98 mg, 0.3 mmol) in dimethyl sulfoxide (3 mL) was heated at 130° C. for 30 minutes under microwave (pressure: 1.0 bar, equipment power: 150 W). The reaction mixture was diluted with ethyl acetate (20 mL) and washed with brine (10 mL×3). The organic phase was dried over anhydrous sodium sulfate and then filtered. The filtrate was concentrated to give a crude product which was purified by column chromatography (silica gel, dichloromethane/methanol=20:1) to afford (R)-6-(4-chlorophenyl)-1,4-dimethyl-8-(5-methyl-1H-1,2,4-triazol-1-yl)-5,6-dihydro-4H-benzo[b][1,2,4]triazolo[4,3-d][1,4]diazepine (15 mg, 25%) and (R)-6-(4-chlorophenyl)-1,4-dimethyl-8-(3-methyl-1H-1,2,4-triazol-1-yl)-5,6-dihydro-4H-benzo[b][1,2,4]triazolo[4,3-d][1,4]diazepine (8 mg, 13%) as a light yellow solid.

Example 51

Synthesis of 4H-[1,2,4]Triazolo[4,3-a][1,5]benzodiazepine,5,6-dihydro-(4R)-1,4-dimethyl-8-methylsulfonyl-6-(4-chloro-phenyl) (Compound 60)

A stirred mixture of 4H-[1,2,4]Triazolo[4,3-a][1,5]benzodiazepine,5,6-dihydro-(4R)-1,4-dimethyl-8-bromo-6-(4-chloro-phenyl) (50 mg, 0.124 mmol), sodium methanesulfinate (15.2 mg, 0.149 mmol), (trifluoromethylsulfonyloxy) copper(I) (6.24 mg, 0.0124 mmol) and (1S,2S)-cyclohexane-1,2-diamine (2.8 mg, 0.025 mmol) in dimethyl sulfoxide (5 mL) was degassed by nitrogen three times, and then the mixture was heated at 90° C. for 12 hours. After cooled to room temperature, the reaction mixture was quenched with water (10 mL) and extracted with ethyl acetate (20 mL*2). The combined organic layers were washed with brine (50 mL*2) and dried over anhydrous sodium sulfate, then concentrated in vacuum, the residue was purified by column chromatography (silica gel, petroleum ether/ethyl acetate=1:1) to give 4H-[1,2,4]Triazolo[4,3-a][1,5]benzodiazepine,5,6-dihydro-(4R)-1,4-dimethyl-8-methylsulfonyl-6-(4-chlorophenyl) as a white solid (25 mg, 50%).

Example 52

Synthesis of (R)-5-(6-(4-chlorophenyl)-1,4-dimethyl-5,6-dihydro-4H-benzo[b][1,2,4]triazolo[4,3-d][1,4]diazepin-8-yl)-1-methylpyridin-2(1H)-one (Compound 62)

To a mixture of (R)-8-bromo-6-(4-chlorophenyl)-1,4-dimethyl-5,6-dihydro-4H-benzo[b][1,2,4]triazolo[4,3-d][1,4]diazepine (40.2 mg, 0.1 mmol), 1-methyl-5-(4,4,5,5-tetramethyl-1,3,2-dioxaborolan-2-yl)pyridin-2(1H)-one (44.2 mg, 0.2 mmol), tetrakis(triphenylphosphine)palladium(0) (12 mg, 0.01 mmol), cesium carbonate (98 mg, 0.3 mmol), toluene (2 mL), ethanol (1 mL) and water (3 drops) was stirred at 100° C. for 16 hours. The mixture was diluted with water (10 mL) and extracted with ethyl acetate (3*20 mL). The combined organic layers were washed with water (3*20 mL), brine (3*20 mL), dried over anhydrous sodium sulfate and filtered. The solvent was evaporated in vacuum, and then the residue was purified by column chromatography (silica gel, dichloromethane/methanol=15:1) to give (R)-5-(6-(4-chlorophenyl)-1,4-dimethyl-5,6-dihydro-4H-benzo[b][1,2,4]triazolo[4,3-d][1,4]diazepin-8-yl)-1-methylpyridin-2(1H)-one as a white solid (15 mg, 34.9%).

Example 53

Synthesis of (R)-5-(6-(4-chlorophenyl)-1,4-dimethyl-5,6-dihydro-4H-benzo[b][1,2,4]triazolo[4,3-d][1,4]diazepin-8-yl)pyridin-2(1H)-one (Compound 61)

A mixture of (R)-8-bromo-6-(4-chlorophenyl)-1,4-dimethyl-5,6-dihydro-4H-benzo[b][1,2,4]triazolo[4,3-d][1,4]diazepine (40.2 mg, 0.1 mmol), 5-(4,4,5,5-tetramethyl-1,3,2-dioxaborolan-2-yl)pyridin-2(1H)-one (44.2 mg, 0.2 mmol), tetrakis(triphenylphosphine)palladium(0) (12 mg, 0.01 mmol), cesium carbonate (98 mg, 0.3 mmol), toluene (2 mL), ethanol (1 mL) and water (3 drops) was stirred at 100° C. for 16 hours. The mixture was diluted with water (10 mL) and extracted with ethyl acetate (3*20 mL). The combined organic layers were washed with water (3*20 mL), brine (3*20 mL), dried over anhydrous sodium sulfate and filtered. The solvent was evaporated in vacuum, and then the residue was purified by column chromatography (silica gel, dichloromethane/methanol=15:1) to give (R)-5-(6-(4-chlorophenyl)-1,4-dimethyl-5,6-dihydro-4H-benzo[b][1,2,4]triazolo[4,3-d][1,4]diazepin-8-yl)pyridin-2(1H)-one as a white solid (20 mg, 48%).

Example 54

Synthesis of 4H-[1,2,4]Triazolo[4,3-a][1,5]benzodiazepine, 5,6-dihydro-1,4-dimethyl-8-(2-methyl-2H-1,2,3-triazole-4-yl)-6-(4-cyano-phenyl) (Compound 109 and its (R) and (S) Enantiomers (Compounds 74 and 75)

Compound 109 was synthesized by the following scheme:

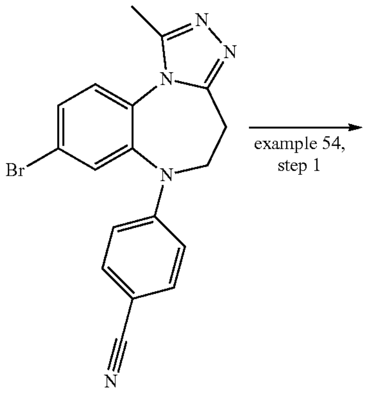

-continued

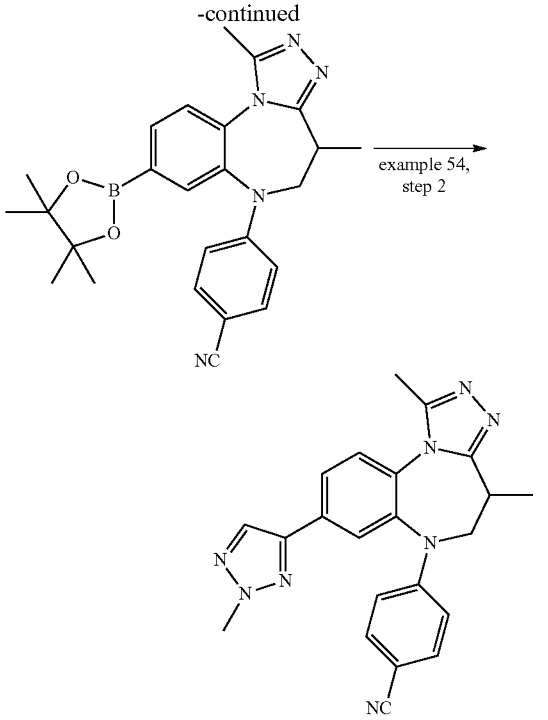

4H-[1,2,4]Triazolo[4,3-a][1,5]benzodiazepine, 5,6-dihydro-1,4-dimethyl-8-(4,4,5,5-tetramethyl-1,3,2-dioxaborolan-2-yl)-6-(4-cyano-phenyl) (Step 1)

A mixture of 4H-[1,2,4]triazolo[4,3-a][1,5]benzodiazepine, 5,6-dihydro-1-methyl-8-bromo-6-(4-cyano-phenyl) (300 mg, 0.76 mmol), 4,4,4',4',5,5,5',5'-octamethyl-2,2'-bi(1,3,2-dioxaborolane) (289 mg, 1.14 mmol), [1,1'-bis(diphenylphosphino)ferrocene]dichloropalladium(II) (32 mg), potassium acetate (224 mg, 2.29 mmol) and N,N-dimethylformamide (10 mL) was heated at 110° C. for 20 minutes with microwave (pressure: 17.2 bar, equipment power: 150 W). The reaction mixture was concentrated and ethyl acetate (100 mL) was added. The mixture was washed with brine (20 mL×3), dried over sodium sulfate anhydrous and filtered. The filtrate was concentrated t and the residue was purified by CombiFlash (silica gel, dichloromethane/methanol=15:1) to give 4H-[1,2,4]Triazolo[4,3-a][1,5]benzodiazepine, 5,6-dihydro-1,4-dimethyl-8-(4,4,5,5-tetramethyl-1,3,2-dioxaborolan-2-yl)-6-(4-cyano-phenyl) as a light yellow solid (270 mg, 80%).

4H-[1,2,4]Triazolo[4,3-a][1,5]benzodiazepine, 5,6-dihydro-1,4-dimethyl-8-(2-methyl-2H-1,2,3-triazole-4-yl)-6-(4-cyano-phenyl) (Compound 109)

A solution of 4H-[1,2,4]Triazolo[4,3-a][1,5]benzodiazepine, 5,6-dihydro-1,4-dimethyl-8-(4,4,5,5-tetramethyl-1,3,2-dioxaborolan-2-yl)-6-(4-cyano-phenyl) (270 mg, 0.61 mmol), 4-bromo-2-methyl-2H-1,2,3-triazole (109 mg, 0.67 mmol), tetrakis(triphenylphosphine)palladium(0) (70 mg) and potassium carbonate anhydrous (337 mg, 2.44 mmol) in tetrahydrofuran (10 mL) and water (2 mL) was reacted at 100° C. for 30 minutes with microwave (pressure: 17.2 bar, equipment power: 150 W). The reaction mixture was diluted with ethyl acetate (50 mL), washed by brine (20 mL×3), dried over anhydrous sodium sulfate and then filtered. The filtrate was concentrated and the residue was purified by CombiFlash (silica gel, dichloromethane/methanol=10:1) to afford 4H-[1,2,4]triazolo[4,3-a][1,5]benzodiazepine, 5,6-dihydro-1,4-dimethyl-8-(2-methyl-2H-1,2,3-triazole-4-yl)-6-(4-cyano-phenyl) as a white solid (65 mg, 27%).

(R)-4H-[1,2,4]Triazolo[4,3-a][1,5]benzodiazepine, 5,6-dihydro-1,4-dimethyl-8-(2-methyl-2H-1,2,3-triazole-4-yl)-6-(4-cyano-phenyl) (Compound 74) and (S)-4H-[1,2,4]Triazolo[4,3-a][1,5]benzodiazepine, 5,6-dihydro-1,4-dimethyl-8-(2-methyl-2H-1,2,3-triazole-4-yl)-6-(4-cyano-phenyl) (Compound 75)

4H-[1,2,4]Triazolo[4,3-a][1,5]benzodiazepine, 5,6-dihydro-1,4-dimethyl-8-(2-methyl-2H-1,2,3-triazole-4-yl)-6-(4-cyano-phenyl) (65 mg, 0.16 mmol) was separated by chiral prep-HPLC (AD-H(AD50) (250 mm×20 mm×5 μm), hexane:ethanol (0.2 DEA)=30:70, flow rate: 13 ml/min), then (R)-4H-[1,2,4]Triazolo[4,3-a][1,5]benzodiazepine, 5,6-dihydro-1,4-dimethyl-8-(2-methyl-2H-1,2,3-triazole-4-yl)-6-(4-cyano-phenyl) (15 mg, 46%) and (S)-4H-[1,2,4]Triazolo[4,3-a][1,5]benzodiazepine, 5,6-dihydro-1,4-dimethyl-8-(2-methyl-2H-1,2,3-triazole-4-yl)-6-(4-cyano-phenyl) (20 mg, 62%) were obtained. The retention times were 10.066 minutes and 11.561 minutes respectively in chiral prep-HPLC chromatography.

Example 55

Synthesis of 4H-[1,2,4]triazolo[4,3-a][1,5]benzodiazepine, 5,6-dihydro-1,4-dimethyl-8-(5-aminopyrazin-2-yl)-6-(4-chlorophenyl) (Compound 110) and its (R) and (S) Enantiomers (Compounds 67 and 63)

A mixture of 4H-[1,2,4]triazolo[4,3-a][1,5]benzodiazepine, 5,6-dihydro-1,4-dimethyl-8-(4,4,5,5-tetramethyl-1,3,2-dioxaborolan-2-yl)-6-(4-chloro-phenyl) (130 mg, 0.295 mmol), 5-bromopyrazin-2-amine (56 mg, 0.324 mmol), potassium carbonate (81 mg, 0.59 mmol), tetrakis(triphenylphosphine)palladium(0) (20 mg) in dioxane (20 mL) under nitrogen was stirred at 100° C. for 16 hours. After cooling to room temperature, the mixture was concentrated in vacuo to give crude product. The residue was purified by column chromatography (silica gel, dichloromethane/methanol=20:1) to give 4H-[1,2,4]triazolo[4,3-a][1,5]benzodiazepine, 5,6-dihydro-1,4-dimethyl-8-(5-aminopyrazin-2-yl)-6-(4-chloro-phenyl) as a brown oil (20 mg, 17%).

(S)-4H-[1,2,4]triazolo[4,3-a][1,5]benzodiazepine, 5,6-dihydro-1,4-dimethyl-8-(5-aminopyrazin-2-yl)-6-(4-chloro-phenyl) (Compound 63) and (R)-4H-[1,2,4]triazolo[4,3-a][1,5]benzodiazepine,5,6-dihydro-1,4-dimethyl-8-(5-aminopyrazin-2-yl)-6-(4-chloro-phenyl) (Compound 67)

4H-[1,2,4]Triazolo[4,3-a][1,5]benzodiazepine,5,6-dihydro-1,4-dimethyl-8-(5-aminopyrazin-2-yl)-6-(4-chloro-phenyl) (20 mg, 0.05 mmol) was separated by chiral prep-HPLC (Daicel OJ-H (250 mm×20 mm×5 um), carbon dioxide:ethanol (0.2% diethylamine)=70:30, flow rate: 40 g/min), then (S)-4H-[1,2,4]triazolo[4,3-a][1,5]benzodiazepine,5,6-dihydro-1,4-dimethyl-8-(5-amino-pyrazin-2-yl)-6-(4-chloro-phenyl) (8 mg, 40%) and (R)-4H-[1,2,4]Triazolo[4,3-a][1,5]benzodiazepine, 5,6-dihydro-1,4-dimethyl-8-(5-aminopyrazin-2-yl)-6-(4-chloro-phenyl) (8 mg, 40%) was obtained. The retention times were 5.77 minutes and 3.68 minutes respectively in chiral HPLC chromatography.

Example 56

Synthesis of 4H-[1,2,4]Triazolo[4,3-a][1,5]benzodiazepine, 5,6-dihydro-1,4-dimethyl-8-(2-methyl-2H-1,2,3-triazole-4-yl)-6-(4-methylsulfonyl-phenyl) (Compound 111) and its (R) and (S) Enantiomers (Compounds 72 and 73)

Compound 111 was synthesized by the following scheme:

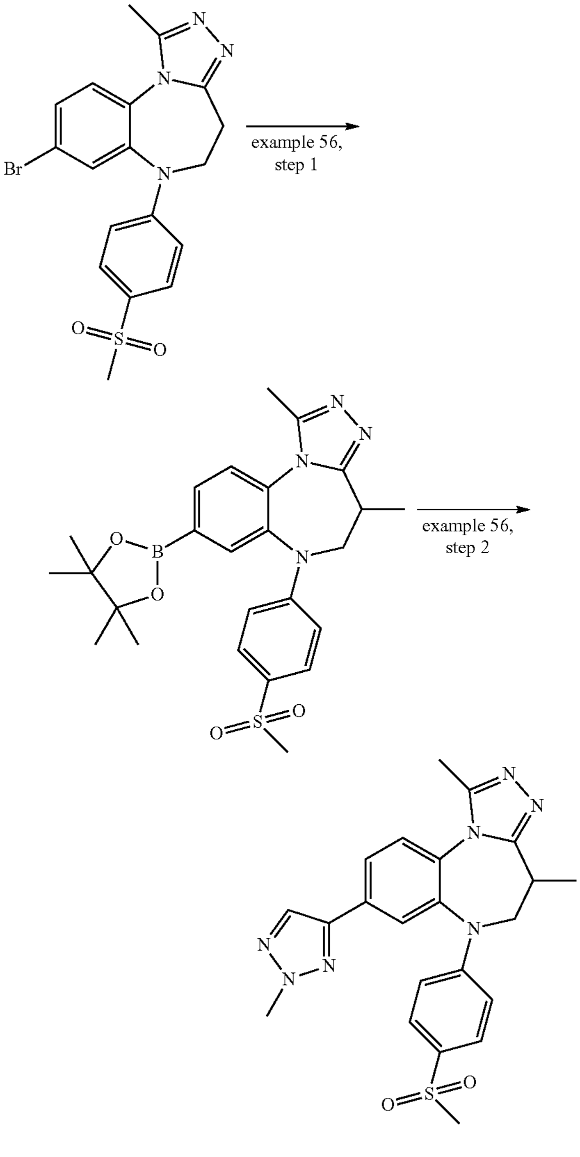

4H-[1,2,4]Triazolo[4,3-a][1,5]benzodiazepine, 5,6-dihydro-1,4-dimethyl-8-(4,4,5,5-tetramethyl-1,3,2-dioxaborolan-2-yl)-6-(4-methylsulfonyl-phenyl) (Step 1)

A mixture of 4H-[1,2,4]triazolo[4,3-a][1,5]benzodiazepine, 5,6-dihydro-1-methyl-8-bromo-6-(4-methylsulfonyl-phenyl) (446 mg, 1 mmol), 4,4,4',4',5,5,5',5'-octamethyl-2,2'- bi(1,3,2-dioxaborolane) (381 mg, 1.5 mmol), [1,1'-bis (diphenylphosphino)ferrocene]dichloropalladium(II) (30 mg), potassium acetate (224 mg, 2.29 mmol) and N,N-dimethylformamide (10 mL) was heated at 110° C. for 20 minutes with microwave (pressure: 17.2 bar, equipment power: 150 W). The reaction mixture was concentrated, the residue was dissolved in ethyl acetate (100 mL), washed by brine (20 mL×3), dried over sodium sulfate anhydrous and filtered. The filtrate was concentrated and the residue was purified by CombiFlash (silica gel, dichloromethane/methanol=15:1) to give 4H-[1,2,4]Triazolo[4,3-a][1,5]benzodiazepine, 5,6-dihydro-1,4-dimethyl-8-(4,4,5,5-tetramethyl-1,3,2-dioxaborolan-2-yl)-6-(4-methylsulfonyl-phenyl) as a light yellow solid (197 mg, 40%).

4H-[1,2,4]Triazolo[4,3-a][1,5]benzodiazepine, 5,6-dihydro-1,4-dimethyl-8-(2-methyl-2H-1,2,3-triazole-4-yl)-6-(4-methylsulfonyl-phenyl) (Compound 111)

A solution of 4H-[1,2,4]Triazolo[4,3-a][1,5]benzodiazepine, 5,6-dihydro-1,4-dimethyl-8-(4,4,5,5-tetramethyl-1,3,2-dioxaborolan-2-yl)-6-(4-methylsulfonyl-phenyl) (197 mg, 0.4 mmol), 4-bromo-2-methyl-2H-1,2,3-triazole (109 mg, 0.67 mmol), tetrakis(triphenylphosphine)palladium(0) (70 mg) and potassium carbonate anhydrous (337 mg, 2.44 mmol) in tetrahydrofuran (10 mL) and water (2 mL) was reacted at 100° C. for 30 minutes with microwave (pressure: 17.2 bar, equipment power: 150 W). The reaction mixture was diluted with ethyl acetate (50 mL), washed by brine (20 mL×3), dried over anhydrous sodium sulfate and filtered. The filtrate was concentrated and the residue was purified by CombiFlash (silica gel, dichloromethane/methanol=10:1) to afford 4H-[1,2,4]Triazolo[4,3-a][1,5]benzodiazepine, 5,6-dihydro-1,4-dimethyl-8-(2-methyl-2H-1,2,3-triazole-4-yl)-6-(4-methylsulfonyl-phenyl) as a white solid (40 mg, 23%).

(R)-4H-[1,2,4]Triazolo[4,3-a][1,5]benzodiazepine, 5,6-dihydro-1,4-dimethyl-8-(2-methyl-2H-1,2,3-triazole-4-yl)-6-(4-cyano-phenyl) (Compound 72) and (S)-4H-[1,2,4]Triazolo[4,3-a][1,5]benzodiazepine, 5,6-dihydro-1,4-dimethyl-8-(2-methyl-2H-1,2,3-triazole-4-yl)-6-(4-methylsulfonyl-phenyl) (Compound 73)

4H-[1,2,4]Triazolo[4,3-a][1,5]benzodiazepine, 5,6-dihydro-1,4-dimethyl-8-(2-methyl-2H-1,2,3-triazole-4-yl)-6-(4-methylsulfonyl-phenyl) (40 mg, 0.09 mmol) was separated by chiral prep-HPLC (AD-H(AD50) (250 mm×20 mm×5 μm), hexane:ethanol (0.2 DEA)=30:70, flow rate: 13 ml/min), then (R)-4H-[1,2,4]Triazolo[4,3-a][1,5]benzodiazepine, 5,6-dihydro-1,4-dimethyl-8-(2-methyl-2H-1,2,3-triazole-4-yl)-6-(4-methylsulfonyl-phenyl) (15 mg, 75%) and (S)-4H-[1,2,4]Triazolo[4,3-a][1,5]benzodiazepine, 5,6-dihydro-1,4-dimethyl-8-(2-methyl-2H-1,2,3-triazole-4-yl)-6-(4-cyano-phenyl) (10 mg, 50%) were obtained. The retention times were 10.066 minutes and 11.561 minutes respectively in chiral prep-HPLC chromatography.

Example 57

Synthesis of 4-(8-(6-aminopyridin-3-yl)-1,4-dimethyl-4H-benzo[b][1,2,4]triazolo[4,3-d][1,4]diazepin-6(5H)-yl)benzamide (Compound 112) and its (R) and (S) Enantiomers (Compounds 69 and 70)

Compound 112 was synthesized by the following scheme:

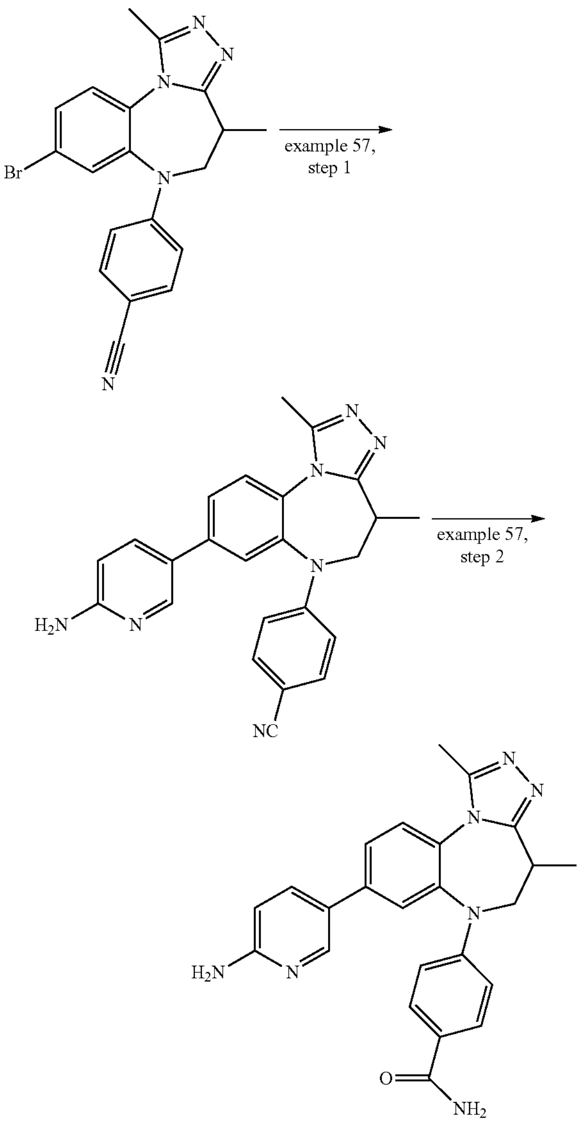

4-(8-(6-aminopyridin-3-yl)-1,4-dimethyl-4H-benzo[b][1,2,4]triazolo[4,3-d][1,4]diazepin-6(5H)-yl)benzonitrile (Step 1)

A mixture of 4-(8-bromo-1,4-dimethyl-4H-benzo[b][1,2,4]triazolo[4,3-d][1,4]diazepin-6(5H)-yl)benzonitrile (244 mg, 0.62 mmol), 5-(4,4,5,5-tetramethyl-1,3,2-dioxaborolan-2-yl)pyridin-2-amine (274 mg, 1.24 mmol), tetrakis(triphenylphosphine)palladium(0) (50 mg) and potassium carbonate (350 mg, 2.53 mmol) in a mixed solution of tetrahydrofuran (10 mL) and water (1 mL) was heated at 100° C. for 30 minutes under microwave (pressure: 17.2 bar, equipment power: 150 W). The reaction mixture was diluted with ethyl acetate (20 mL) and washed with brine (10 mL*3). The organic phase was separated, dried over anhydrous sodium sulfate and then filtered. The filtrate was concentrated to give a crude product, which was purified by column chromatography (silica gel, dichloromethane/methanol=12:1) to afford 4-(8-(6-aminopyridin-3-yl)-1,4-dimethyl-4H-benzo[b][1,2,4]triazolo[4,3-d][1,4]diazepin-6(5H)-yl)benzonitrile as a light yellow solid (150 mg, 59.4%). LRMS $(M+H)^+$: calcd 407.19. found 407.

4-(8-(6-aminopyridin-3-yl)-1,4-dimethyl-4H-benzo[b][1,2,4]triazolo[4,3-d][1,4]diazepin-6(5H)-yl)benzamide (Compound 112)

A mixture of 4-(8-(6-aminopyridin-3-yl)-1,4-dimethyl-4H-benzo[b][1,2,4]triazolo[4,3-d][1,4]diazepin-6(5H)-yl)benzonitrile (150 mg, 0.37 mmol), triphenylphosphine (194 mg, 0.74 mmol) and diacetoxypalladium (8.3 mg, 0.037 mmol) in mixed solution of ethanol (6 mL) and water (2 mL) was heated at 60° C. for 30 minutes under nitrogen atmosphere. The reaction mixture was diluted with ethyl acetate (20 mL) and washed with brine (10 mL*3). The organic phase was separated, dried over anhydrous sodium sulfate and filtered. The filtrate was concentrated to give a crude product, which was purified by column chromatography (silica gel, dichloromethane/methanol=15:1) to afford 4-(8-(6-aminopyridin-3-yl)-1,4-dimethyl-4H-benzo[b][1,2,4]triazolo[4,3-d][1,4]diazepin-6(5H)-yl)benzamide as a white solid (80 mg, 50.8%).

(R)-4-(8-(6-aminopyridin-3-yl)-1,4-dimethyl-4H-benzo[b][1,2,4]triazolo[4,3-d][1,4]diazepin-6(5H)-yl)benzamide (Compound 69) and (S)-4-(8-(6-aminopyridin-3-yl)-1,4-dimethyl-4H-benzo[b][1,2,4]triazolo[4,3-d][1,4]diazepin-6(5H)-yl)benzamide (Compound 70)

4-(8-(6-aminopyridin-3-yl)-1,4-dimethyl-4H-benzo[b][1,2,4]triazolo[4,3-d][1,4]diazepin-6(5H)-yl)benzamide (80 mg, 0.19 mmol) was separated by chiral HPLC (Daicel AD-H (250 mm×20 mm×5 μm), hexane/ethanol (0.2 diethylamine)= 30:70, flow rate: 13 mL/min), then (R)-4-(8-(6-aminopyridin-3-yl)-1,4-dimethyl-4H-benzo[b][1,2,4]triazolo[4,3-d][1,4]diazepin-6(5H)-yl)benzamide (27 mg, 67.5%) and (S)-4-(8-(6-aminopyridin-3-yl)-1,4-dimethyl-4H-benzo[b][1,2,4]triazolo[4,3-d][1,4]diazepin-6(5H)-yl)benzamide (19 mg, 47.5%) were obtained. The retention times were 14.265 minute and 18.705 minute respectively in chiral prep-HPLC chromatography.

Example 58

Synthesis of (R)-5-(1,4-dimethyl-6-(1-methyl-1H-pyrazol-4-yl)-5,6-dihydro-4H-benzo[b][1,2,4]triazolo[4,3-d][1,4]diazepin-8-yl)pyridin-2-amine (Compound 76)

The title compound was synthesized by the following scheme:

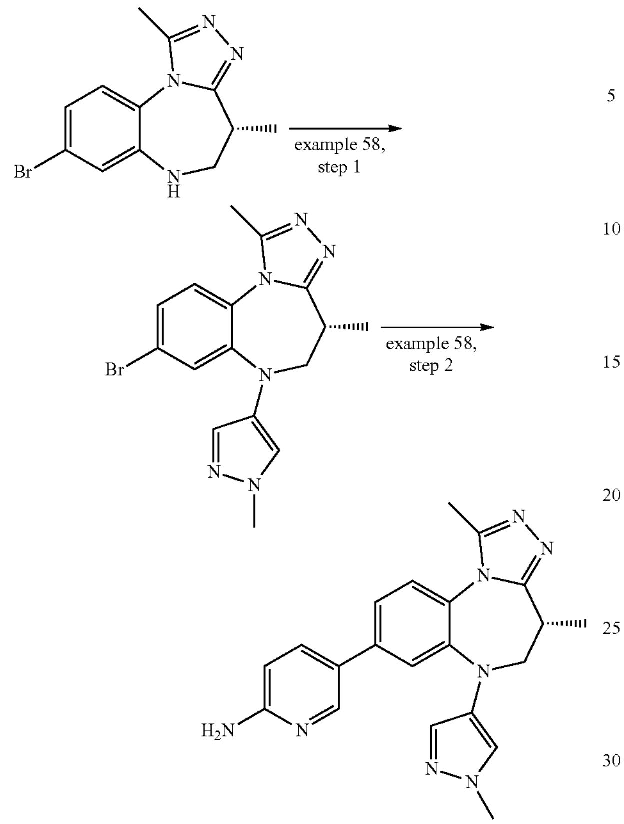

(R)-8-bromo-1,4-dimethyl-6-(1-methyl-1H-pyrazol-4-yl)-5,6-dihydro-4H-benzo[b][1,2,4]triazolo[4,3-d][1,4]diazepine (Step 1)

A mixture of (R)-8-bromo-1,4-dimethyl-5,6-dihydro-4H-benzo[b][1,2,4]triazolo[4,3-d][1,4]diazepine (292 mg, 1 mmol), 4-iodo-1-methyl-1H-pyrazole (312 mg, 1.5 mmol), copper (I) iodide (58 mg, 0.3 mmol), 1,10-phenanthroline (54 mg, 0.3 mmol) and potassium phosphate (424 mg, 2 mmol) in dimethyl sulfoxide (10 mL) was heated at 150° C. for 14 hours under nitrogen. The reaction mixture was diluted with ethyl acetate (20 mL) and washed with brine (20 mL×3). The organic phase was dried over anhydrous sodium sulfate and then filtered. The filtrate was concentrated to give (R)-8-bromo-1,4-dimethyl-6-(1-methyl-1H-pyrazol-4-yl)-5,6-dihydro-4H-benzo[b][1,2,4]triazolo[4,3-d][1,4]diazepine which was used in the next step without further purification. LRMS (M+H)+: calcd 372.07. found 372.

(R)-5-(1,4-dimethyl-6-(1-methyl-1H-pyrazol-4-yl)-5,6-dihydro-4H-benzo[b][1,2,4]triazolo[4,3-d][1,4]diazepin-8-yl)pyridin-2-amine (Compound 76)

A mixture of (R)-8-bromo-1,4-dimethyl-6-(1-methyl-1H-pyrazol-4-yl)-5,6-dihydro-4H-benzo[b][1,2,4]triazolo[4,3-d][1,4]diazepine (38 mg, 0.1 mmol), 5-(4,4,5,5-tetramethyl-1,3,2-dioxaborolan-2-yl)pyridin-2-amine (44 mg, 0.2 mmol), tetrakis(triphenylphosphine)palladium($_0$) (12 mg, 0.02 mmol), potassium fluoride (5.8 mg, 0.1 mmol) and potassium carbonate (49 mg, 0.15 mmol) in a mixed solution of toluene (2 mL), ethanol (1 mL) and water (0.2 mL) was heated at 115° C. for 1.5 hours under microwave (pressure: 2.0 bar, equipment power: 150 W). The reaction mixture was diluted with ethyl acetate (20 mL) and washed with brine (10 mL×3). The organic phase was dried over anhydrous sodium sulfate and filtered. The filtrate was concentrated to give a residue which was purified by column chromatography (silica gel, dichloromethane/methanol=8:1) to afford (R)-5-(1,4-dimethyl-6-(1-methyl-1H-pyrazol-4-yl)-5,6-dihydro-4H-benzo[b][1,2,4]triazolo[4,3-d][1,4]diazepin-8-yl)pyridin-2-amine as a white solid (10 mg, 26%).

Example 59

Synthesis of (R)-5,5'-(1,4-dimethyl-4H-benzo[b][1,2,4]triazolo[4,3-d][1,4]diazepine-6,8(5H)-diyl)dipyridin-2-amine (Compound 71)

The title compound was synthesized by the following scheme:

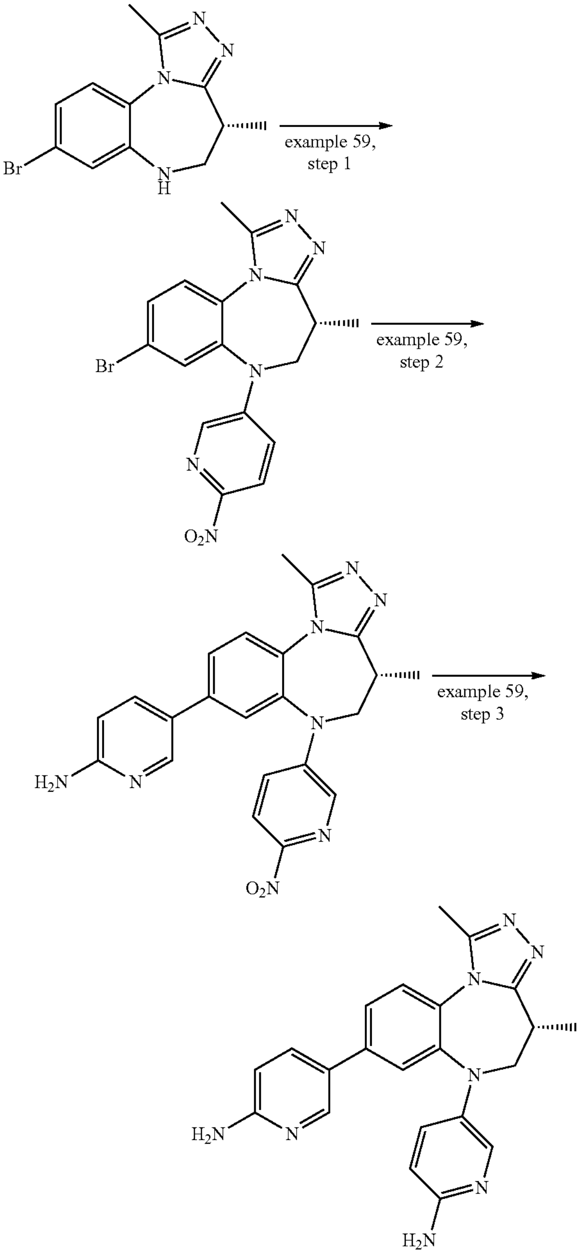

(R)-8-bromo-1,4-dimethyl-6-(6-nitropyridin-3-yl)-5,6-dihydro-4H-benzo[b][1,2,4]triazolo[4,3-d][1,4]diazepine (Step 1)

To a solution of 5-fluoro-2-nitropyridine (284 mg, 2 mmol) and (R)-8-bromo-1,4-dimethyl-5,6-dihydro-4H-benzo[b][1,2,4]triazolo[4,3-d][1,4]diazepine (292 mg, 1 mmol) in dimethyl sulfoxide (5 mL) was added potassium tert-butanolate (223 mg, 2 mmol). The reaction mixture was heated at 120° C. for 1 hour under microwave (pressure: 3.2 bar, equipment power: 150 W). The mixture was diluted with water (50 mL), extracted with ethyl acetate (20 mL×3). The combined organic layers were dried over anhydrous sodium sulfate, filtered and concentrated to give a residue which was purified by column chromatography (silica gel, petroleum ether/ethyl acetate=2:1) to give (R)-8-bromo-1,4-dimethyl-6-(6-nitropyridin-3-yl)-5,6-dihydro-4H-benzo[b][1,2,4]triazolo[4,3-d][1,4]diazepine (320 mg, 77%) as a light yellow solid.

(R)-5-(1,4-dimethyl-6-(6-nitropyridin-3-yl)-5,6-dihydro-4H-benzo[b][1,2,4]triazolo[4,3-d][1,4]diazepin-8-yl)pyridin-2-amine (Step 2)

A mixture of (R)-8-bromo-1,4-dimethyl-6-(6-nitropyridin-3-yl)-5,6-dihydro-4H-benzo[b][1,2,4]triazolo[4,3-d][1,4]diazepine (42 mg, 0.1 mmol), 5-(4,4,5,5-tetramethyl-1,3,2-dioxaborolan-2-yl)pyridin-2-amine (27 mg, 0.12 mmol), tetrakis(triphenylphosphine)palladium(0) (12 mg, 0.01 mmol), potassium fluoride (5.8 mg, 0.1 mmol) and cesium carbonate (49 mg, 0.15 mmol) in a mixed solution of toluene (2 mL), ethanol (1 mL) and water (0.2 mL) was heated at 110° C. for 1.5 hours under microwave (pressure: 3.0 bar, equipment power: 150 W). The reaction mixture was diluted with ethyl acetate (20 mL) and washed with brine (10 mL×3). The organic phase was dried over anhydrous sodium sulfate and filtered. The filtrate was concentrated to give a crude product (R)-5-(1,4-dimethyl-6-(6-nitropyridin-3-yl)-5,6-dihydro-4H-benzo[b][1,2,4]triazolo[4,3-d][1,4]diazepin-8-yl)pyridin-2-amine (22 mg, 51%) which was used in the next step without further purification.

(R)-5,5'-(1,4-dimethyl-4H-benzo[b][1,2,4]triazolo[4,3-d][1,4]diazepine-6,8(5H)-diyl)dipyridin-2-amine (Compound 71)

Iron powder (56 mg, 1 mmol) was added to a mixture of (R)-5-(1,4-dimethyl-6-(6-nitropyridin-3-yl)-5,6-dihydro-4H-benzo[b][1,2,4]triazolo[4,3-d][1,4]diazepin-8-yl)pyridin-2-amine (86 mg, 0.2 mmol) in a mixed solvents of ammonium chloride aqueous (2 mL) and ethanol (10 mL). Once addition was complete, the mixture was heated to 60° C. for 2 hours. The mixture was filtered. The filtrate was concentrated, diluted with water (10 mL), extracted with ethyl acetate (20 mL×2). The combined organic layers were dried over anhydrous sodium sulfate, filtered and concentrated to give a residue which was purified by column chromatography (silica gel, dichloromethane/methanol=8:1) to afford (R)-5,5'-(1,4-dimethyl-4H-benzo[b][1,2,4]triazolo[4,3-d][1,4]diazepine-6,8(5H)-diyl)dipyridin-2-amine (8 mg, 20%).

Example 60

Synthesis of (R)-4-(1,4-dimethyl-8-(6-oxo-1,6-dihydropyridin-3-yl)-4H-benzo[b][1,2,4]triazolo[4,3-d][1,4]diazepin-6(5H)-yl)benzonitrile (Compound 60)

A mixture of (R)-4-(8-bromo-1,4-dimethyl-4H-benzo[b][1,2,4]triazolo[4,3-d][1,4]diazepin-6(5H)-yl)benzonitrile (39.3 mg, 0.1 mmol), (4,5,5-trimethyl-2-(6-oxo-1,6-dihydropyridin-3-yl)-1,3,2-dioxaborolan-4-yl) methylium (66 mg, 0.3 mmol, tetrakis(triphenylphosphine)palladium(0) (12 mg, 0.01 mmol), cesium carbonate (65.2 mg, 0.2 mmol), toluene (2 mL), ethanol (1 mL) and water (3 drops) was stirred at 100° C. for 16 hours. The mixture was diluted with water (5 mL) and extracted with ethyl acetate (3*20 mL). The combined organic layers were washed with water (3*20 mL), brine (3*20 mL), dried over anhydrous sodium sulfate and filtered. The solvent was evaporated in vacuo, and the residue was purified by column chromatography (silica gel, dichloromethane/methanol=15:1) to give (R)-4-(1,4-dimethyl-8-(6-oxo-1,6-dihydropyridin-3-yl)-4H-benzo[b][1,2,4]triazolo[4,3-d][1,4]diazepin-6(5H)-yl)benzonitrile as a white solid (20 mg, 49.0%).

Example 61

Synthesis of (R)-8-bromo-1,4-dimethyl-6-(4-(methylsulfonyl)phenyl)-5,6-dihydro-4H-benzo[b][1,2,4]triazolo[4,3-d][1,4]diazepine (Compound 77)

To a solution of (R)-8-bromo-1,4-dimethyl-5,6-dihydro-4H-benzo[b][1,2,4]triazolo[4,3-d][1,4]diazepine (100 mg, 0.34 mmol) in Methylbenzene (5 mL), were added 1-iodo-4-(methylsulfonyl)benzene (115.2 mg, 0.40 mmol) and 1-iodo-4-(methylsulfonyl)benzene (115.2 mg, 0.40 mmol). $Cs_2CO_3$ (222.3 mg, 0.68 mmol), tris(dibenzylideneacetone)dipalladium(0) (31.4 mg, 0.03 mmol) and 2-dicyclohexylphosphino-2',6'-dimethoxybiphenyl (39.22 mg, 0.07 mmol) were added. The mixture was via vacuo/$N_2$ and stirred at 90° C. for 18 h under $N_2$ atmosphere. After concentration, the mixture was poured into water (10 mL) and extracted with dichloromethane (20 mL×3). The organic layer was dried over sodium sulfate and filtered. The filtrate was concentrated and purified by prep-TLC (elute: DCM:$CH_3OH$=10:1) to give (R)-8-bromo-1,4-dimethyl-6-(4-(methylsulfonyl)phenyl)-5,6-dihydro-4H-benzo[b][1,2,4]triazolo[4,3-d][1,4]diazepine (60 mg, 39%).

Example 62

Synthesis of (R)-5-(1,4-dimethyl-6-(4-(methylsulfonyl)phenyl)-5,6-dihydro-4H-benzo[b][1,2,4]triazolo[4,3-d][1,4]diazepin-8-yl)pyridin-2(1H)-one (Compound 78)

To a solution of (R)-8-bromo-1,4-dimethyl-6-(4-(methylsulfonyl)phenyl)-5,6-dihydro-4H-benzo[b][1,2,4]triazolo[4,3-d][1,4]diazepine (150 mg, 0.34 mmol) in 1,4-dioxane and $H_2O$ (10:1, 5 mL) were added 5-(4,4,5,5-tetramethyl-1,3,2-dioxaborolan-2-yl)pyridin-2(1H)-one (218.50 mg, 88.95 mmol), $Cs_2CO_3$ (218.5 mg, 0.67 mmol) and Tetrakis(triphenylphosphine)palladium(0) (24.5 mg, 0.03 mmol). The mixture was purged with $N_2$ and stirred in the microwave at 130° C. for 20 min. The reaction solution was concentrated and purified by prep-TLC (elute: DCM:$CH_3OH$=15:1) to give (R)-5-(1,4-dimethyl-6-(4-(methylsulfonyl)phenyl)-5,6-dihydro-4H-benzo[b][1,2,4]triazolo[4,3-d][1,4]diazepin-8-yl)pyridin-2(1H)-one (70 mg, 45%).

Example 63

Synthesis of (R)-5-(1,4-dimethyl-6-(4-(methylsulfonyl)phenyl)-5,6-dihydro-4H-benzo[b][1,2,4]triazolo[4,3-d][1,4]diazepin-8-yl)pyrazin-2-amine (Compound 79)

To a solution of (R)-1,4-dimethyl-6-(4-(methylsulfonyl)phenyl)-8-(4,4,5,5-tetramethyl-1,3,2-dioxaborolan-2-yl)-5, 6-dihydro-4H-benzo[b][1,2,4]triazolo[4,3-d][1,4]diazepine (0.34 mmol) in 1,4-dioxane and $H_2O$ (10:1, 5 mL) was added 5-bromopyrazin-2-amine (63.2 mg, 0.36 mmol), $Cs_2CO_3$ (197.3 mg, 0.61 mmol) and Tetrakis(triphenylphosphine)palladium(0) (21.9 mg, 0.03 mmol). The mixture was purged with $N_2$ and stirred in the microwave at 130° C. for 20 min. The reaction solution was concentrated and purified by prep-TLC (elute: DCM:$CH_3OH$=15:1) to give (R)-5-(1,4-dimethyl-6-(4-(methylsulfonyl)phenyl)-5,6-dihydro-4H-benzo[b][1,2,4]triazolo[4,3-d][1,4]diazepin-8-yl)pyrazin-2-amine (39 mg, 28%).

Example 64

Synthesis of (R)-4-(1,4-dimethyl-8-(1H-pyrazol-4-yl)-4H-benzo[b][1,2,4]triazolo[4,3-d][1,4]diazepin-6(5H)-yl)benzonitrile (Compound 80)

To a solution of (R)-4-(8-bromo-1,4-dimethyl-4H-benzo[b][1,2,4]triazolo[4,3-d][1,4]diazepin-6(5H)-yl)benzonitrile (100 mg, 0.26 mmol) in DME/$H_2O$ (3:1, 2 mL) was added 4-(4,4,5,5-tetramethyl-1,3,2-dioxaborolan-2-yl)-1H-pyrazole (70 mg, 0.36 mmol), cesium carbonate (164 mg, 0.50 mmol) and Tetrakis(triphenylphosphine)palladium(0)(22 mg, 0.02 mmol). The mixture was stirred in the microwave at 130° C. for 20 min. The reaction mixture was concentrated and purified by prep-TLC (elute: DCM:MeOH=15:1) to give (R)-4-(1,4-dimethyl-8-(1H-pyrazol-4-yl)-4H-benzo[b][1,2,4]triazolo[4,3-d][1,4]diazepin-6(5H)-yl)benzonitrile (15 mg, 15%).

Example 65

Synthesis of (R)-2-(4-(6-(4-cyanophenyl)-1,4-dimethyl-5,6-dihydro-4H-benzo[b][1,2,4]triazolo[4,3-d][1,4]diazepin-8-yl)-1H-pyrazol-1-yl)acetamide (Compound 81)

The title compound was synthesized by the following scheme:

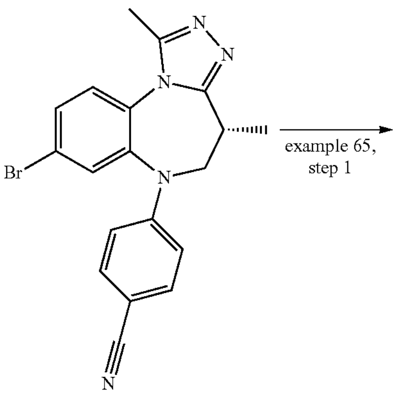

-continued

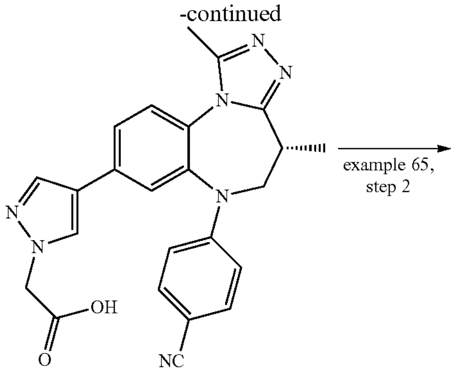

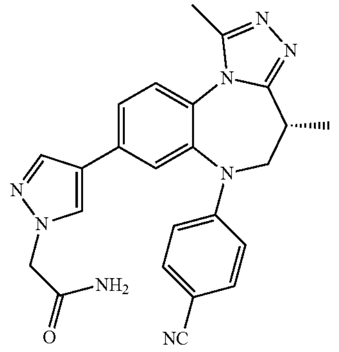

2(R)-2-(4-(6-(4-cyanophenyl)-1,4-dimethyl-5,6-dihydro-4H-benzo[b][1,2,4]triazolo[4,3-d][1,4]diazepin-8-yl)-1H-pyrazol-1-yl)acetic acid (Step 1)

To a solution of (R)-4-(8-bromo-1,4-dimethyl-4H-benzo[b][1,2,4]triazolo[4,3-d][1,4]diazepin-6(5H)-yl)benzonitrile (100 mg, 0.25 mmol) in 1,4-dioxane/$H_2O$ (10:1, 2 mL) was added ethyl 2-(4-(4,4,5,5-tetramethyl-1,3,2-dioxaborolan-2-yl)-1H-pyrazol-1-yl)acetate (84 mg, 0.3 mmol), Cesium carbonate (163 mg, 0.5 mmol) and Tetrakis(triphenylphosphine)palladium(0) (18.4 mg, 0.025 mmol). The mixture was purged with $N_2$ and stirred in the microwave at 130° C. for 0.5 hr. The mixture was partitioned between ethyl acetate and water. The aqueous layer was washed with ethyl acetate and concentrated in vacuum to give 2(R)-2-(4-(6-(4-cyanophenyl)-1,4-dimethyl-5,6-dihydro-4H-benzo[b][1,2,4]triazolo[4,3-d][1,4]diazepin-8-yl)-1H-pyrazol-1-yl)acetic acid (30 mg, 27%).

(R)-2-(4-(6-(4-cyanophenyl)-1,4-dimethyl-5,6-dihydro-4H-benzo[b][1,2,4]triazolo[4,3-d][1,4]diazepin-8-yl)-1H-pyrazol-1-yl)acetamide (Compound 81)

To a solution of 2(R)-2-(4-(6-(4-cyanophenyl)-1,4-dimethyl-5,6-dihydro-4H-benzo[b][1,2,4]triazolo[4,3-d][1,4]diazepin-8-yl)-1H-pyrazol-1-yl)acetic acid (30 mg, 0.068 mmol) in DMF (1 mL) was added DIPEA (74 mg, 0.58 mmol), $NH_4Cl$ (15 mg, 0.28 mmol) and HATU (0.13 mmol, 50 mg). The mixture was stirred at room temperature for 12 hrs. The mixture was partitioned between ethyl acetate and water. The organic layer was washed with brine and dried over sodium sulfate. Concentration and purification by prep-TLC (elute: DCM:MeOH=15:1) to give (R)-2-(4-(6-(4-cyanophenyl)-1,4-dimethyl-5,6-dihydro-4H-benzo[b][1,2,4]triazolo[4,3-d][1,4]diazepin-8-yl)-1H-pyrazol-1-yl)acetamide (7 mg, 23%).

Example 66

Synthesis of (R)-5-(6-(5-chloropyridin-2-yl)-1,4-dimethyl-5,6-dihydro-4H-benzo[b][1,2,4]triazolo[4,3-d][1,4]diazepin-8-yl)pyridin-2(1H)-one (Compound 82)

The title compound was synthesized by the following scheme:

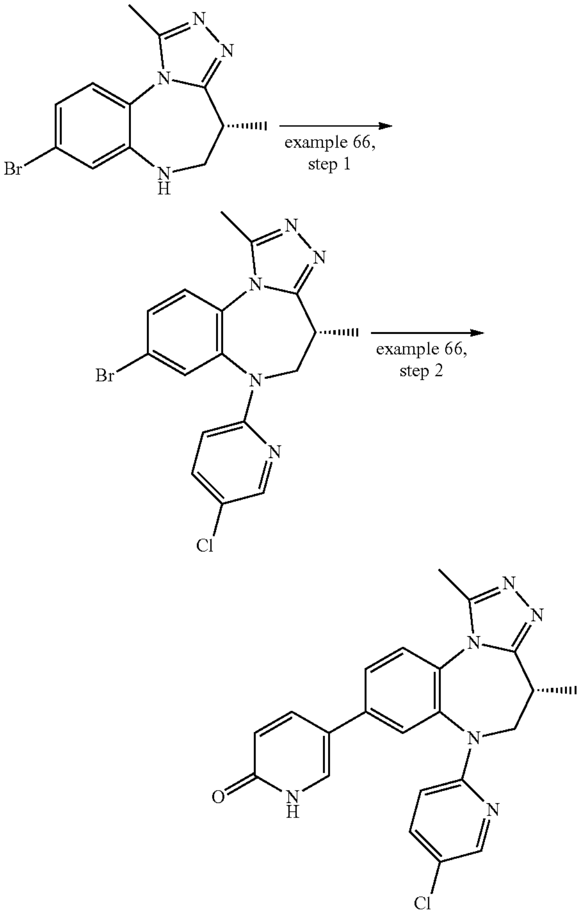

(R)-8-bromo-6-(5-chloropyridin-2-yl)-1,4-dimethyl-5,6-dihydro-4H-benzo[b][1,2,4]triazolo[4,3-d][1,4]diazepine (Step 1)

To a solution of (R)-8-bromo-1,4-dimethyl-5,6-dihydro-4H-benzo[b][1,2,4]triazolo[4,3-d][1,4]diazepine (1.0 g, 3.4 mmol) in DMF (5 mL) was added NaH (280 mg, 6.8 mmol) at 0° C. After 0.5 h, 5-chloro-2-fluoropyridine (540 mg, 4.08 mmol) was added. The mixture was stirred at room temperature overnight. After quenching with $H_2O$ (30 mL), the reaction mixture was extracted with ethyl acetate (10 mL*3). The organic layer was washed with brine and dried over sodium sulfate. Concentrated in vacuo gave (R)-8-bromo-6-(5-chloropyridin-2-yl)-1,4-dimethyl-5,6-dihydro-4H-benzo[b][1,2,4]triazolo[4,3-d][1,4]diazepine (1.0 g, crude) for the next step directly. LRMS $(M+H+)^+$: calcd 403.02. found 404.01.

(R)-5-(6-(5-chloropyridin-2-yl)-1,4-dimethyl-5,6-dihydro-4H-benzo[b][1,2,4]triazolo[4,3-d][1,4]diazepin-8-yl)pyridin-2(1H)-one (Compound 82)

To a solution of (R)-8-bromo-6-(5-chloropyridin-2-yl)-1,4-dimethyl-5,6-dihydro-4H-benzo[b][1,2,4]triazolo[4,3-d][1,4]diazepine (100 mg, 0.24 mmol) in 1,4-dioxane/$H_2O$ (10:1, 2 mL) was added 5-(4,4,5,5-tetramethyl-1,3,2-dioxaborolan-2-yl)pyridin-2(1H)-one (65 mg, 0.29 mmol), Cesium carbonate (156 mg, 0.48 mmol) and Tetrakis(triphenylphosphine)palladium(0) (18.4 mg, 0.025 mmol). The mixture was purged with $N_2$ and stirred in the microwave at 130° C. for 0.5 hr. After filtration, concentrated in vacuo and purification by prep-TLC (elute: DCM:MeOH=15:1) gave (R)-5-(6-(5-chloropyridin-2-yl)-1,4-dimethyl-5,6-dihydro-4H-benzo[b][1,2,4]triazolo[4,3-d][1,4]diazepin-8-yl)pyridin-2(1H)-one (30 mg, 30%).

Example 67

Synthesis of (R)-5-(6-(5-chloropyridin-2-yl)-1,4-dimethyl-5,6-dihydro-4H-benzo[b][1,2,4]triazolo[4,3-d][1,4]diazepin-8-yl)pyrazin-2-amine (Compound 83)

The title compound was synthesized by the following scheme:

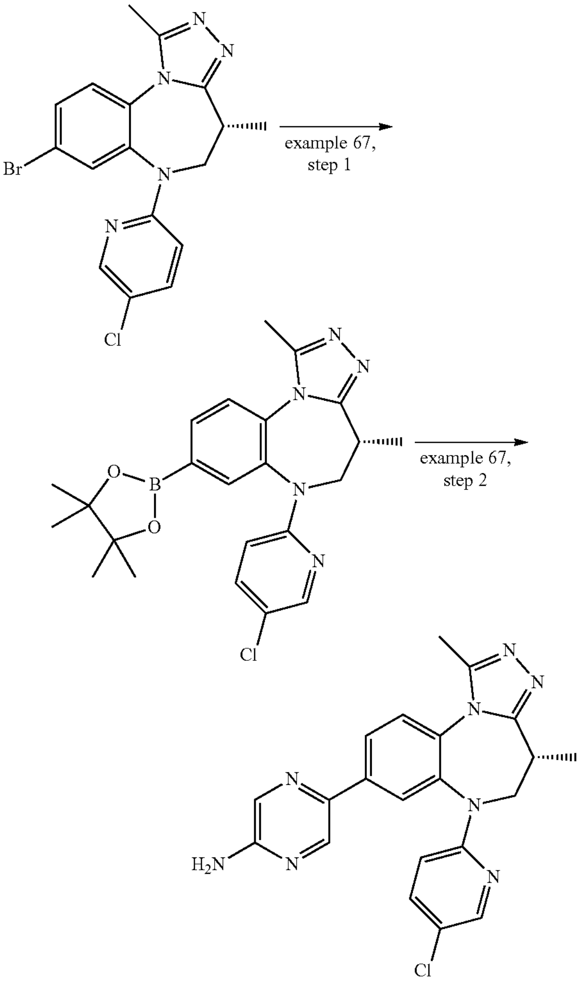

(R)-6-(5-chloropyridin-2-yl)-1,4-dimethyl-8-(4,4,5,5-tetramethyl-1,3,2-dioxaborolan-2-yl)-5,6-dihydro-4H-benzo[b][1,2,4]triazolo[4,3-d][1,4]diazepine (Step 1)

To a solution of (R)-8-bromo-6-(5-chloropyridin-2-yl)-1,4-dimethyl-5,6-dihydro-4H-benzo[b][1,2,4]triazolo[4,3-d][1,4]diazepine (150 mg, 0.37 mmol) in 1,4-dioxane (5 mL) were added 4,4,4',4',5,5,5',5'-octamethyl-2,2'-bi(1,3,2-dioxaborolane) (112.95 mg, 0.46 mmol), KOAc (72.75 mg, 0.74 mmol) and Tetrakis(triphenylphosphine)palladium(0) (27.1 mg, 0.037 mmol). The mixture was via $N_2$/vacuo and stirred at 90° C. for 18 h under $N_2$ atmosphere. The mixture was filtered and the crude (R)-6-(5-chloropyridin-2-yl)-1,4-dimethyl-8-(4,4,5,5-tetramethyl-1,3,2-dioxaborolan-2-yl)-5,6-dihydro-4H-benzo[b][1,2,4]triazolo[4,3-d][1,4]diazepine was used for the next step.

(R)-5-(6-(5-chloropyridin-2-yl)-1,4-dimethyl-5,6-dihydro-4H-benzo[b][1,2,4]triazolo[4,3-d][1,4]diazepin-8-yl)pyrazin-2-amine (Compound 83)

To a solution of (R)-6-(5-chloropyridin-2-yl)-1,4-dimethyl-8-(4,4,5,5-tetramethyl-1,3,2-dioxaborolan-2-yl)-5,6-dihydro-4H-benzo[b][1,2,4]triazolo[4,3-d][1,4]diazepine in 1,4-dioxane/$H_2O$ (10:1, 5 mL) were added 5-bromopyrazin-2-amine (69.33 mg, 0.40 mmol), $Cs_2CO_3$ (197.3 mg, 0.61 mmol) and Tetrakis(triphenylphosphine)palladium(0) (24.1 mg, 0.033 mmol). The mixture was purged with $N_2$ and stirred in the microwave at 130° C. for 20 min. The reaction solution was concentrated and purified by prep-TLC (elute: DCM: $CH_3OH$=15:1) to give (R)-5-(6-(5-chloropyridin-2-yl)-1,4-dimethyl-5,6-dihydro-4H-benzo[b][1,2,4]triazolo[4,3-d][1,4]diazepin-8-yl)pyrazin-2-amine (110 mg, 59%).

Example 68

Synthesis of 4-(8-methoxy-1,4-dimethyl-4H-pyrido[2,3-b][1,2,4]triazolo[4,3-d][1,4]diazepin-6(5H)-yl)benzonitrile (Compound 84)

The title compound was synthesized by the following scheme:

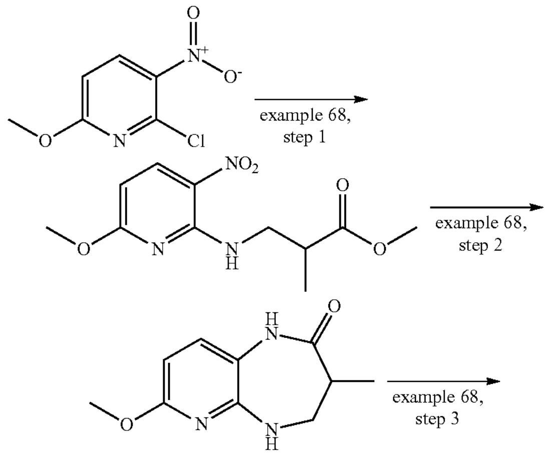

-continued

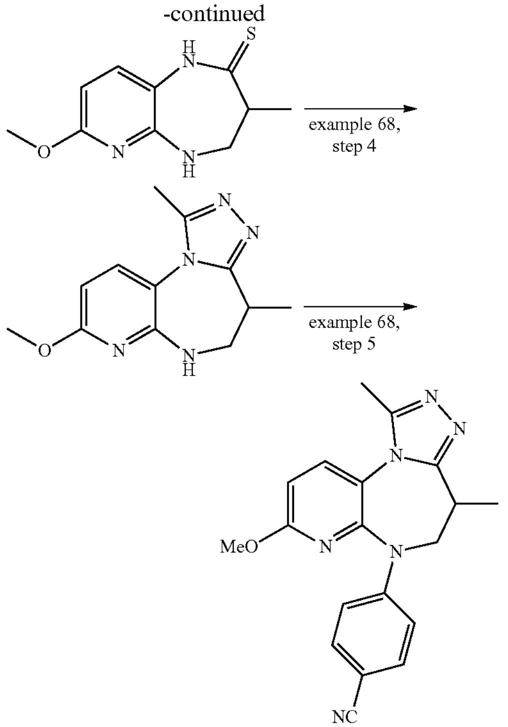

Methyl-3-((6-methoxy-3-nitropyridin-2-yl)amino)-2-methylpropanoate (Step 1)

To a solution of 2-chloro-6-methoxy-3-nitropyridine (3 g, 15.91 mmol) in tetrahydrofuran (20 mL) was added methyl-3-amino-2-methylpropanoate (2.05 g, 17.50 mmol) and potassium carbonate (4.40 g, 31.82 mmol). The mixture was stirred at 50° C. for 12 hours. The reaction mixture was concentrated in vacuo and washed with water (20 mL), extracted with acetic ester (20 mL×3). The combined organic phase was dried by anhydrous sodium sulphate, and then filtered. The filtrate was concentrated and purified by column chromatograph silica gel (elute: dichloromethane/Methanol: 100:1→80:1) to give methyl-3-((6-methoxy-3-nitropyridin-2-yl)amino)-2-methylpropanoate (4.2 g, 97%) as a yellow oil.

7-methoxy-3-methyl-4,5-dihydro-1H-pyrido[2,3-b][1,4]diazepin-2(3H)-one (Step 2)

To a solution of methyl-3-((6-methoxy-3-nitropyridin-2-yl)amino)-2-methylpropanoate (4.0 g, 14.86 mmol) in anhydrous ethanol (50 mL) was added iron powder reduced (8.30 g, 148.56 mmol) and acetic acid (17.84 g, 297.12 mmol). The mixture was stirred at 90° C. for 12 hours. The reaction mixture was neutralized to pH 8 with solid sodium hydrogencarbonate, concentrated in vacuo and washed with water (20 mL), filtered. The filtrate was extracted with acetic ester (200 mL×3). The combined organic phase was dried by anhydrous sodium sulphate, and then filtered. The filtrate was concentrated and purified by column chromatograph silica gel (elute: dichloromethane/Methanol: 80:1→50:1) to give 7-methoxy-3-methyl-4,5-dihydro-1H-pyrido[2,3-b][1,4]diazepin-2(3H)-one (3 g, 96%) as a yellow solid.

7-methoxy-3-methyl-4,5-dihydro-1H-pyrido[2,3-b][1,4]diazepine-2(3H)-thione (Step 3)

To a solution of 7-methoxy-3-methyl-4,5-dihydro-1H-pyrido[2,3-b][1,4]diazepin-2(3H)-one (2.7 g, 13.03 mmol) in anhydrous tetrahydrofuran (30 mL) was added Lawesson's Reagent (8.32 g, 20.60 mmol). The mixture was stirred at 80° C. for 12 hours. The reaction mixture was concentrated in vacuo and washed with brine (20 mL), and then the mixture was filtered through a celite pad. The filtrate was extracted with acetic ester (20 mL×3). The combined organic phase was dried by anhydrous sodium sulphate, and then filtered. The filtrate was concentrated and purified by column chromatograph silica gel (elute: dichloromethane/Methanol: 80:1→50:1→30:1) to give 7-methoxy-3-methyl-4,5-dihydro-1H-pyrido[2,3-b][1,4]diazepine-2(3H)-thione (1.8 g, 62%) as a yellow solid.

8-methoxy-1,4-dimethyl-5,6-dihydro-4H-pyrido[2,3-b][1,2,4]triazolo[4,3-d][1,4]diazepine (Step 4)

To a solution of 7-methoxy-3-methyl-4,5-dihydro-1H-pyrido[2,3-b][1,4]diazepine-2(3H)-thione (1.8 g, 8.06 mmol) in n-butanol (25 mL) was added acetohydrazide (5.97 g, 80.61 mmol). The mixture was stirred at 130° C. for 3 hours. The reaction mixture was concentrated in vacuo and washed with brine (20 mL), and then the mixture was filtered through a celite pad. The filtrate was extracted with acetic ester (20 mL×3). The combined organic phase was dried by anhydrous sodium sulphate, and then filtered. The filtrate was concentrated and purified by column chromatograph silica gel (elute: dichloro methane/Methanol: 80:1→35:1→20:1) to give 8-methoxy-1,4-dimethyl-5,6-dihydro-4H-pyrido[2,3-b][1,2,4]triazolo[4,3-d][1,4]diazepine (1.2 g, 61%) as a yellow solid.

4-(8-methoxy-1,4-dimethyl-4H-pyrido[2,3-b][1,2,4]triazolo[4,3-d][1,4]diazepin-6(5H)-yl)benzonitrile (Compound 84)

To a solution of 8-methoxy-1,4-dimethyl-5,6-dihydro-4H-pyrido[2,3-b][1,2,4]triazolo[4,3-d][1,4]diazepine (50 mg, 0.203 mmol) in toluene (2 mL) was added 4-iodobenzonitrile (94 mg, 0.406 mmol), Bis(dibenzylideneacetone) Palladium (28 mg, 0.03 mmol), 2-dicyclohexylphosphin-2',6'-dimethoxybiphenyl (25 mg, 0.06 mmol) and cesium carbonate (132 mg, 0.406 mmol). The mixture was purged with $N_2$ and stirred at 110° C. for 12 hours. The reaction mixture was washed with brine (5 mL), and then the mixture was filtered. The filtrate was extracted with acetic ester (10 mL×3), the combined organic phase was dried by anhydrous sodium sulphate, and then filtered. The filtrate was concentrated and purified by preparative HPLC (Mobile phase A: water with 0.05% ammonia solution; Mobile phase B: MeCN; column temperature: 30° C., Gradient: 30-60% B 10 min) to give 4-(8-methoxy-1,4-dimethyl-4H-pyrido[2,3-b][1,2,4]triazolo[4,3-d][1,4]diazepin-6(5H)-yl)benzonitrile (2.7 mg, 31%) as a colorless solid.

Example 69

Synthesis of (R)-5-(6-(4-chlorophenyl)-1,4-dimethyl-5,6-dihydro-4H-benzo[b][1,2,4]triazolo[4,3-d][1,4]diazepin-8-yl)-6-methylpyridin-2(1H)-one (Compound 85)

To a solution of (R)-6-(4-chlorophenyl)-1,4-dimethyl-8-(4,4,5,5-tetramethyl-1,3,2-dioxaborolan-2-yl)-5,6-dihydro-4H-benzo[b][1,2,4]triazolo[4,3-d][1,4]diazepine (100 mg, 0.22 mmol) in dioxane/water (11 mL, dioxane/water=10:1) was added 5-Bromo-6-methyl-1H-pyridin-2-one (51 mg, 0.27 mmol), cesium carbonate (145 mg, 0.44 mmol) and [1,1'-bis(diphenylphosphino)ferrocene]dichloropalladium (II) (17 mg, 0.022 mmol) under nitrogen atmosphere. The mixture was stirred and heated to reflux overnight. The mixture was cooled down and poured into water (30 mL) and extracted with ethyl acetate (20 ml×3). The combined organic phase was concentrated, and the residue was purified by HPLC (Mobile phase A: water with 0.05% ammonia solution; Mobile phase B: MeCN; column temperature: 30° C., Gradient: 25-55% B, 15 min) to give (R)-5-(6-(4-chlorophenyl)-1,4-dimethyl-5,6-dihydro-4H-benzo[b][1,2,4]triazolo[4,3-d][1,4]diazepin-8-yl)-6-methylpyridin-2(1H)-one as a white solid (16 mg, 17%).

Example 70

Synthesis of 6-(4-chlorophenyl)-10-fluoro-1-methyl-5,6-dihydro-4H-benzo[b][1,2,4]triazolo[4,3-d][1,4]diazepine (Compound 17)

The title compound was synthesized by the following scheme:

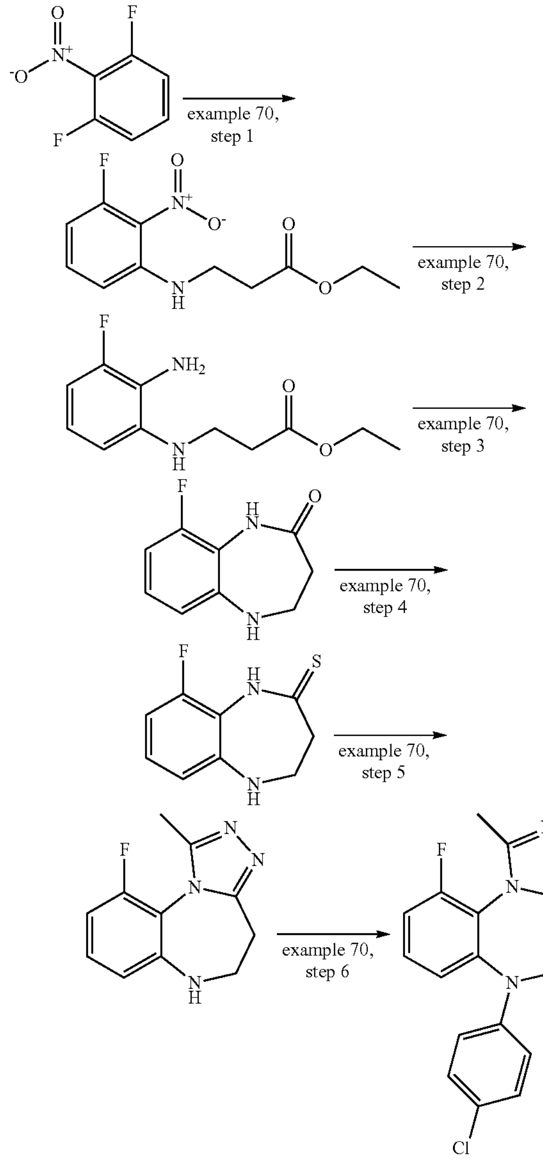

Ethyl 3-(3-fluoro-2-nitrophenylamino)propionate (Step 1)

A round bottomed flask was charged with ethyl 3-aminopropanoate hydrochloride (1 g, 6.51 mmol), 1,3-difluoro-2-nitrobenzene (1.036 g, 6.51 mmol), potassium carbonate (2.70 g, 19.53 mmol), and a stirbar. THF (35 mL, 0.2 M) was added, and the mixture was stirred at 100° C. overnight. The mixture was concentrated with celite and purified by silica gel chromatography (eluting with hexanes/ethyl acetate) to yield ethyl 3-(3-fluoro-2-nitrophenylamino)propionate as a yellow amorphous solid (1.473 g, 5.75 mmol, 88%).

Ethyl 3-(2-amino-3-fluorophenylamino)propanoate (Step 2)

A round bottomed flask was charged with palladium on carbon (0.306 g, 0.287 mmol) and a stirbar. Ethyl 3-(3-fluoro-2-nitrophenylamino)propionate (1.473 g, 5.75 mmol) in 1:1 EtOH:EtOAc (40 mL) was added, and the flask was evacuated and purged with hydrogen three times before being stirred at room temperature overnight. The mixture was filtered, concentrated with celite, and purified by silica gel chromatography (eluting with hexanes/ethyl acetate) to yield ethyl 3-(2-amino-3-fluorophenylamino)propanoate as a brown oil (1.074 g, 4.75 mmol, 83%).

9-fluoro-4,5-dihydro-1H-benzo[b][1,4]diazepin-2(3H)-one (Step 3)

A disposable tube was charged with ethyl 3-(2-amino-3-fluorophenylamino)propanoate (800 mg, 3.54 mmol) and a stirbar. Toluene (10 mL) was added, followed by tetraisopropoxytitanium (523 μl, 1.768 mmol), and the solution was stirred at 80° C. 0.5 h. The solution was diluted with ethyl acetate, concentrated with celite, and purified by silica gel chromatography (eluting with hexanes/ethyl acetate) to yield 9-fluoro-4,5-dihydro-1H-benzo[b][1,4]diazepin-2(3H)-one as a white amorphous solid (0.618 g, 3.43 mmol, 97%).

9-fluoro-4,5-dihydro-1H-benzo[b][1,4]diazepine-2(3H)-thione (Step 4)

A disposable tube was charged with 9-fluoro-4,5-dihydro-1H-benzo[b][1,4]diazepin-2(3H)-one (0.037 g, 0.205 mmol) and THF. Lawesson's Reagent (45.7 mg, 0.113 mmol) was added, and the solution was stirred at 80° C. 1 h. The mixture was concentrated, partitioned between water and ethyl acetate, separated, dried with sodium sulfate, concentrated with celite, and purified by silica gel chromatography (eluting with hexanes/ethyl acetate) to yield 9-fluoro-4,5-dihydro-1H-benzo[b][1,4]diazepine-2(3H)-thione as an off-white amorphous solid (0.040 g, 0.204 mmol, 99%).

10-fluoro-1-methyl-5,6-dihydro-4H-benzo[b][1,2,4]triazolo[4,3-d][1,4]diazepine (Step 5)

A disposable tube was charged with 9-fluoro-4,5-dihydro-1H-benzo[b][1,4]diazepine-2(3H)-thione (40 mg, 0.204 mmol) and a stirbar. nBuOH (5 mL) was added, followed by acetohydrazide (30.2 mg, 0.408 mmol), and the solution was stirred at 130° C. overnight. The solution was concentrated with celite and purified by silica gel chromatography (eluting with methylene chloride/methanol/1% ammonium hydroxide) to yield 10-fluoro-1-methyl-5,6-dihydro-4H-benzo[b][1,2,4]triazolo[4,3-d][1,4]diazepine as an off-white amorphous solid (0.022 g, 0.101 mmol, 50%).

6-(4-chlorophenyl)-10-fluoro-1-methyl-5,6-dihydro-4H-benzo[b][1,2,4]triazolo[4,3-d][1,4]diazepine (Compound 17)

A disposable tube was charged with 10-fluoro-1-methyl-5,6-dihydro-4H-benzo[b][1,2,4]triazolo[4,3-d][1,4]diazepine (22 mg, 0.101 mmol), 1-chloro-4-iodobenzene (31.3 mg, 0.131 mmol), RuPhos precat. (3.67 mg, 5.04 μmol), dicyclohexyl(2',6'-diisopropoxybiphenyl-2-yl)phosphine (2.352 mg, 5.04 μmol), sodium 2-methylpropan-2-olate (19.38 mg, 0.202 mmol), and a stirbar before being evacuated and purged with nitrogen three times. Toluene (1 mL, 0.4 M) was added, and the mixture was stirred at 90° C. 6 h. The mixture was cooled, diluted with ethyl acetate, filtered, and concentrated before being purified by silica gel chromatography (eluting with methylene chloride/methanol/1% ammonium hydroxide) and reverse phase HPLC to yield the title compound as a white amorphous solid (0.012 g, 0.036 mmol, 36%).

Example 71

Synthesis of 6-(4-chlorophenyl)-1,5-dimethyl-5,6-dihydro-4H-benzo[b][1,2,4]triazolo[4,3-d][1,4]diazepine (Compound 18)

The title compound was synthesized by the following scheme:

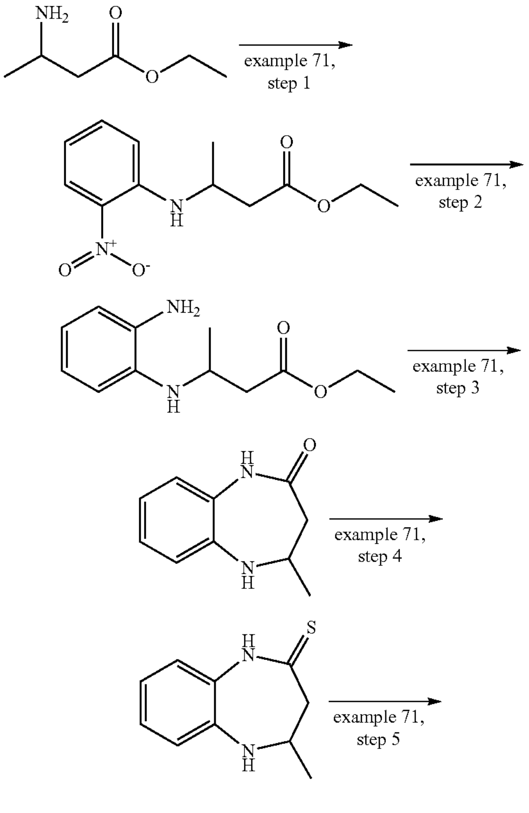

-continued

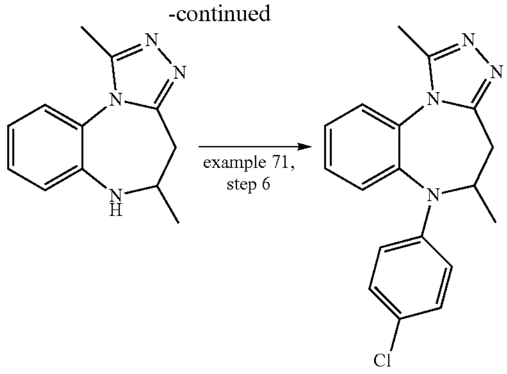

Ethyl 3-(2-nitrophenylamino)butanoate (Step 1)

A round bottomed flask was charged with ethyl 3-aminobutanoate (1 ml, 6.82 mmol), 1-fluoro-2-nitrobenzene (0.720 ml, 6.82 mmol), potassium carbonate (1884 mg, 13.63 mmol), and a stirbar. THF (35 mL, 0.2 M) was added, and the mixture was stirred at 100° C. for 36 h. The mixture was concentrated with celite and purified by silica gel chromatography to yield ethyl 3-(2-nitrophenylamino)butanoate as a yellow amorphous solid (0.776 mg, 3.08 mmol, 45%).

Ethyl 3-(2-aminophenylamino)butanoate (Step 2)

A round bottomed flask was charged with palladium on carbon (327 mg, 0.308 mmol) and a stirbar. Ethyl 3-(2-nitrophenylamino)butanoate (776 mg, 3.08 mmol) in 1:1 EtOH: EtOAc (40 mL) was added, and the flask was evacuated and purged with hydrogen three times. Stirred at room temperature for 3 h. The mixture was filtered and concentrated to yield ethyl 3-(2-aminophenylamino)butanoate as an oil.

4-methyl-4,5-dihydro-1H-benzo[b][1,4]diazepin-2(3H)-one (Step 3)

An round bottomed flask was charged with ethyl 3-(2-aminophenylamino)butanoate (684 mg, 3.08 mmol) and a stirbar. MeOH (15 mL, 0.1 M) was added, followed by sodium methoxide (249 mg, 4.62 mmol), and the solution was stirred at reflux for 48 h. The mixture was concentrated with celite and purified by silica gel chromatography (eluting with hexanes/ethyl acetate) to yield 4-methyl-4,5-dihydro-1H-benzo[b][1,4]diazepin-2(3H)-one as an off-white amorphous solid (0.22 g, 1.25 mmol, 41%).

4-methyl-4,5-dihydro-1H-benzo[b][1,4]diazepine-2(3H)-thione (Step 4)

A disposable tube was charged with 4-methyl-4,5-dihydro-1H-benzo[b][1,4]diazepin-2(3H)-one (220 mg, 1.248 mmol) in THF (12 mL). Lawesson's Reagent (278 mg, 0.687 mmol) was added, and the solution was stirred at 80° C. 1 h. The solution was concentrated with celite and purified by silica gel chromatography to yield 4-methyl-4,5-dihydro-1H-benzo[b][1,4]diazepine-2(3H)-thione as a yellow foam (0.163 g, 0.848 mmol, 68%).

1,5-dimethyl-5,6-dihydro-4H-benzo[b][1,2,4]triazolo[4,3-d][1,4]diazepine (Step 5)

A disposable tube was charged with 4-methyl-4,5-dihydro-1H-benzo[b][1,4]diazepine-2(3H)-thione (163 mg, 0.848 mmol) and a stirbar. nBuOH (5 mL) was added, followed by acetohydrazide (126 mg, 1.695 mmol), and the solution was stirred at 130° C. overnight. The solution was concentrated and purified by silica gel chromatography (eluting with methylene chloride/methanol/1% ammonium hydroxide) to yield 1,5-dimethyl-5,6-dihydro-4H-benzo[b][1,2,4]triazolo[4,3-d][1,4]diazepine as an off-white amorphous solid (0.126 g, 0.588 mmol, 69%).

6-(4-chlorophenyl)-1,5-dimethyl-5,6-dihydro-4H-benzo[b][1,2,4]triazolo[4,3-d][1,4]diazepine (Compound 18)

A disposable tube was charged with 1,5-dimethyl-5,6-dihydro-4H-benzo[b][1,2,4]triazolo[4,3-d][1,4]diazepine (69 mg, 0.322 mmol), 1-chloro-4-iodobenzene (100 mg, 0.419 mmol), RuPhos precat. (11.73 mg, 0.016 mmol), dicyclohexyl(2',6'-diisopropoxybiphenyl-2-yl)phosphine (7.51 mg, 0.016 mmol), sodium 2-methylpropan-2-olate (61.9 mg, 0.644 mmol), and a stirbar before being evacuated and purged with nitrogen three times. Toluene (1 mL, 0.4 M) was added, and the mixture was stirred at 90° C. 36 h. The mixture was cooled, diluted with ethyl acetate, filtered, and concentrated before being purified by silica gel chromatography (eluting with methylene chloride/methanol/1% ammonium hydroxide) and reverse phase HPLC to yield the title compound as a white amorphous solid (0.011 g, 0.034 mmol, 11%).

Example 72

Synthesis of 6-(4-chlorophenyl)-1,5,5-trimethyl-5,6-dihydro-4H-benzo[b][1,2,4]triazolo[4,3-d][1,4]diazepine (Compound 22)

The title compound was synthesized by the following scheme:

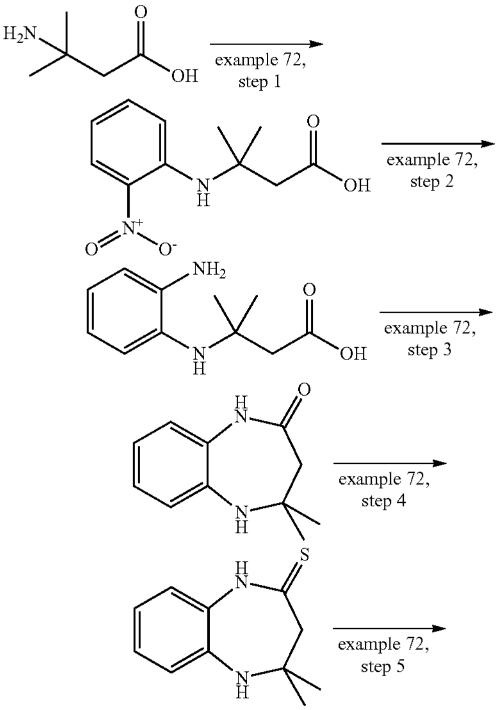

-continued

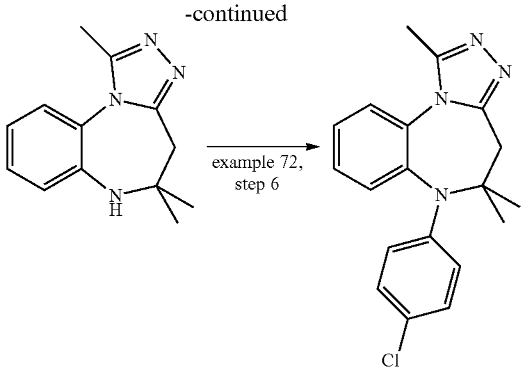

3-methyl-3-(2-nitrophenylamino)butanoic acid (Step 1)

A round bottomed flask was charged with 3-amino-3-methylbutanoic acid (1.452 g, 12.39 mmol), potassium carbonate (2.57 g, 18.59 mmol), and a stirbar. EtOH (20 mL, 0.5 M) was added, followed by 1-fluoro-2-nitrobenzene (2.84 ml, 15.49 mmol), and the solution was stirred at reflux overnight. The mixture was cooled, concentrated with celite, and purified by silica gel chromatography (eluting with methylene chloride/methanol/ammonium hydroxide) to yield 3-methyl-3-(2-nitrophenylamino)butanoic acid as a red solid (2.32 g, 9.73 mmol, 79%).

3-(2-aminophenylamino)-3-methylbutanoic acid (Step 2)

A round bottomed flask was charged with 3-methyl-3-(2-nitrophenylamino)butanoic acid (2.319 g, 9.73 mmol), palladium on carbon (0.518 g, 0.487 mmol), and a stirbar. 1:1 EtOH:EtOAc (100 mL) was added, and the flask was evacuated and purged with hydrogen three times before being stirred at room temperature 2 h. The mixture was filtered to give a residue containing 3-(2-aminophenylamino)-3-methylbutanoic acid.

4,4-dimethyl-4,5-dihydro-1H-benzo[b][1,4]diazepin-2(3H)-one (Step 3)

An round bottomed flask was charged with crude 3-(2-aminophenylamino)-3-methylbutanoic acid (2.19 g, 10.52 mmol), HOBT (1.932 g, 12.62 mmol), EDC (2.419 g, 12.62 mmol), and a stirbar. DMF (20 mL, 0.5 M) was added, and the solution was stirred at rt overnight. The solution was diluted with water, extracted three times with methylene chloride, dried with sodium sulfate, concentrated with celite, and purified by silica gel chromatography (eluting with hexanes/ethyl acetate/1% isopropanol) to yield 4,4-dimethyl-4,5-dihydro-1H-benzo[b][1,4]diazepin-2(3H)-one as a yellow amorphous solid (0.697 g, 3.66 mmol, 35%).

4,4-dimethyl-4,5-dihydro-1H-benzo[b][1,4]diazepine-2(3H)-thione (Step 4)

A disposable tube was charged with 4,4-dimethyl-4,5-dihydro-1H-benzo[b][1,4]diazepin-2(3H)-one (697 mg, 3.66 mmol) in THF (20 mL). Lawesson's Reagent (815 mg, 2.015 mmol) was added, and the solution was stirred at 80° C. for 3 h. The solution was concentrated, partitioned between water and ethyl acetate, separated, dried with sodium sulfate, concentrated with celite, and purified by silica gel chromatography to yield 4,4-dimethyl-4,5-dihydro-1H-benzo[b][1,4]diazepine-2(3H)-thione as a yellow oily solid (0.60 g, 2.91 mmol, 79%).

1,5,5-trimethyl-5,6-dihydro-4H-benzo[b][1,2,4]triazolo[4,3-d][1,4]diazepine (Step 5)

A disposable tube was charged with 4,4-dimethyl-4,5-dihydro-1H-benzo[b][1,4]diazepine-2(3H)-thione (600 mg, 2.91 mmol) and a stirbar. nBuOH (30 mL) was added, followed by acetohydrazide (431 mg, 5.82 mmol), and the solution was stirred at 130° C. overnight. The solution was concentrated with celite and purified by silica gel chromatography (eluting with methylene chloride/methanol/ammonium hydroxide) to yield 1,5,5-trimethyl-5,6-dihydro-4H-benzo[b][1,2,4]triazolo[4,3-d][1,4]diazepine as an off-white amorphous solid (0.153 g, 0.67 mmol, 23%).

6-(4-chlorophenyl)-1,5,5-trimethyl-5,6-dihydro-4H-benzo[b][1,2,4]triazolo[4,3-d][1,4]diazepine (Compound 22)

A disposable tube was charged with 1,5,5-trimethyl-5,6-dihydro-4H-benzo[b][1,2,4]triazolo[4,3-d][1,4]diazepine (150 mg, 0.657 mmol), 1-chloro-4-iodobenzene (204 mg, 0.854 mmol), RuPhos precat. (23.94 mg, 0.033 mmol), sodium 2-methylpropan-2-olate (126 mg, 1.314 mmol), and a stirbar before being evacuated and purged with nitrogen three times. Toluene (3 mL, 0.5 M) was added, and the mixture was stirred at 90° C. 48 h. The mixture was cooled, diluted with ethyl acetate, filtered, and purified by reverse phase HPLC to yield the title compound as an off-white amorphous solid.

Biological Assays

A. IC50 Measurements for Inhibitors Using BRD4 AlphaLisa Binding Assay.

His/Flag epitope tagged BRD4 $BD1_{142-168}$ was cloned, expressed and purified to homogeneity. BRD4 binding and inhibition was assessed by monitoring the engagement of biotinylated H4-tetraacetyl peptide (Millipore #12-379) with the target using the AlphaLisa technology (Perkin-Elmer). Specifically, in a 384 well ProxiPlate BRD4 (BD1) (30 nM final) was combined with peptide (200 nM final) in 40 mM HEPES (pH 7.0), 40 mM NaCl, 1 mM DTT, 0.01% (w/v) BSA, and 0.008% (w/v) Brij-35 either in the presence of DMSO (final 1.2% DMSO) or compound dilution series in DMSO. After 20 minute incubation at room temperature Alpha streptavidin donor beads and AlphaLisa anti-Flag acceptor beads were added to a final concentration of 10 ug/mL each. After three hours equilibration plates were read on an Envision instrument and $IC_{50}$s calculated using a four parameter non-linear curve fit.

B. cMyc RNA Quantification Assay (QuantiGene® Assay):

MV4:11 (AML) cells were seeded in a 96-well plate and incubated in the presence of various concentrations of compounds for 4 h. Relative mRNA levels were quantitated by using QuantiGene 2.0 assay (Affymetrix) according to the manufacturer's recommendation. Signals were detected by using an Envision plate reader (Perkin-Elmer). Biological duplicates were averaged and normalized to vehicle (DMSO) control to calculate percent MYC mRNA levels.

C. Cell-Based IL-6 Quantification Assay (ELISA, Mesoscale Assay):

100,000 THP-1 cells were seeded in RPMI1640-10% FBS in 96-well plates. LPS (*E. Coli* Invitrogen) in RPMI-10% FBS at a final concentration of 4 μg/mL was added to the wells and the cells are then incubated in the presence of various concentrations of compounds for 16 h. Plates are spun (2 rpm, 5 min), an aliquot of 25 uL supernatant is transferred in to an ELISA plate (Mesoscale technology, MSD) and the detection of IL-6 is performed using manufacturer's instructions. The amount of cells in each well is assessed using CellTiter-Glo® (Promega). The ratio of ELISA value/CellTiter-Glo value is used to calculate the percent of inhibition of IL-6 secretion.

The results of these assays are set forth in Table 2, below.

TABLE 2

Activity of Exemplary Compounds of the Invention

| Compound No. | BRD4 AlphaLisa | IL-6 | cMyc mRNA |
|---|---|---|---|
| 1 | B | B | B |
| 2 | B | C | C |
| 3 | B | B | C |
| 4 | D | D | NT |
| 5 | C | C | NT |
| 6 | C | D | NT |
| 7 | D | * | NT |
| 8 | C | C | NT |
| 9 | C | C | NT |
| 10 | C | C | NT |
| 11 | C | C | NT |
| 12 | D | D | NT |
| 13 | B | B | NT |
| 14 | B | C | NT |
| 15 | A | A | B |
| 16 | B | B | B |
| 17 | C | * | C |
| 18 | B | * | C |
| 19 | A | A | B |
| 20 | A | B | B |
| 21 | B | B | C |
| 22 | D | C | B |
| 23 | A | A | A |
| 24 | A | * | C |
| 25 | A | B | A |
| 26 | A | A | A |
| 27 | B | B | C |
| 28 | C | C | C |
| 29 | A | A | A |
| 30 | A | NT | NT |
| 31 | B | NT | NT |
| 32 | C | NT | NT |
| 33 | B | NT | NT |
| 34 | B | NT | NT |
| 35 | B | NT | NT |
| 36 | B | NT | NT |
| 37 | C | * | C |
| 38 | B | B | B |
| 39 | A | A | A |
| 40 | C | * | NT |
| 41 | A | B | A |
| 42 | B | * | C |
| 43 | A | A | A |
| 44 | A | A | A |
| 45 | B | * | NT |
| 46 | A | B | B |
| 47 | B | B | B |
| 48 | A | A | A |
| 49 | A | A | A |
| 50 | B | A | A |
| 51 | B | A | A |
| 52 | A | A | B |
| 53 | B | B | C |
| 54 | A | A | A |
| 55 | A | A | A |
| 56 | B | * | NT |
| 58 | C | C | C |
| 59 | A | A | A |
| 60 | B | B | C |
| 61 | A | A | A |
| 62 | A | A | A |
| 63 | B | * | C |

TABLE 2-continued

Activity of Exemplary Compounds of the Invention

| Compound No. | BRD4 AlphaLisa | IL-6 | cMyc mRNA |
|---|---|---|---|
| 64 | A | A | A |
| 65 | B | B | C |
| 66 | A | A | A |
| 67 | A | A | A |
| 68 | A | C | C |
| 69 | B | C | C |
| 70 | A | C | C |
| 71 | A | C | C |
| 72 | B | * | C |
| 73 | A | B | B |
| 74 | B | * | NT |
| 75 | A | A | A |
| 76 | NT | B | B |
| 77 | C | * | C |
| 78 | B | NT | C |
| 79 | A | NT | B |
| 80 | A | A | A |
| 81 | A | * | C |
| 82 | B | * | B |
| 83 | A | A | A |
| 84 | ** | * | C |
| 85 | B | * | B |

In Table 2,
"A" represents a value under 100 nM;
"B" a value between 100 nM and 1 μM;
"C" a value greater than 1 μM and less than or equal to 10 μM,
"D" a value greater than 10 μM;
"*" a value greater than 1 μM, which was the highest concentration of the particular compound tested in that assay; and
"**" a value greater than 0.5 μM, which was the highest concentration of the particular compound tested in that assay.
"NT" represents that the compound was not tested in a particular assay.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

We claim:

1. A compound of Formula (II):

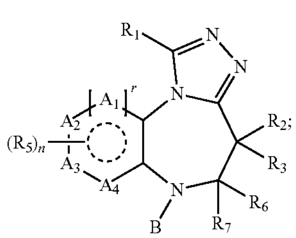

II or a pharmaceutically acceptable salt thereof, wherein:

$R_1$ is alkyl, alkenyl, alkynyl, aralkyl, aryl, cycloalkyl, heteroaryl, heterocycloalkyl, or halo, each of which is optionally substituted; or CN, $OR_A$, $NR_AR_B$, $N(R_C)S(O)_qR_AR_B$, $N(R_A)C(O)R_B$, $N(R_C)C(O)NR_AR_B$, $N(R_A)C(O)OR_A$, $N(R_C)C(S)NR_AR_B$, $S(O)_qR_A$, $C(O)R_A$, $C(O)OR_A$, $OC(O)R_A$, or $C(O)NR_AR_B$;

each $R_A$ is independently optionally substituted alkyl; optionally substituted aryl; optionally substituted heteroaryl; optionally substituted heterocyclic; optionally substituted carbocyclic; or hydrogen;

each $R_B$ is independently optionally substituted alkyl; optionally substituted aryl; optionally substituted heteroaryl; optionally substituted heterocyclic; optionally substituted carbocyclic; or hydrogen;

each $R_C$ is independently optionally substituted alkyl, optionally substituted alkenyl or optionally substituted alkynyl; optionally substituted aryl; optionally substituted heteroaryl; optionally substituted heterocyclic; optionally substituted carbocyclic; or hydrogen;

each of $A_1$, $A_2$, $A_3$, and $A_4$ is independently CR, N, NR, O, or S;

B is phenyl optionally substituted with 1 to 5 independently selected $R_4$ groups;

$R_2$ and $R_3$ are each independently H, halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —$CO_2$R, C(O)N(R')(R"), —C(O)SR, or —$(CH_2)_pR_x$; or $R_2$ and $R_3$ together with the atoms to which each is attached, forms an optionally substituted 3-7 membered saturated or partially unsaturated spiro-fused ring having 0-3 heteroatoms independently selected from nitrogen, oxygen, or sulfur;

$R_6$ is H, halogen, optionally substituted alkyl, optionally substituted aryl, optionally substituted aralkyl, optionally substituted heteroaryl —OR, —SR, —N(R')(R"), —C(O)R, —$CO_2$R, —C(O)N(R')(R"), or —$(CH_2)_pR_x$;

$R_7$ is H, halogen, optionally substituted alkyl, optionally substituted aryl, optionally substituted aralkyl, optionally substituted heteroaryl, —OR, —SR, —N(R')(R"), —C(O)R, —$CO_2$R, —C(O)N(R')(R"), or —$(CH_2)_pR_x$;

or $R_6$ and $R_7$ together with the atoms to which each is attached, forms an optionally substituted 3-7 membered saturated or unsaturated spiro-fused ring having 0-3 heteroatoms independently selected from nitrogen, oxygen, or sulfur;

or any one of $R_2$ and $R_3$, together with any one of $R_6$ and $R_7$, together with the atoms to which each is attached, may form an optionally substituted aryl, optionally substituted cycloalkyl, optionally substituted heteroaryl, or optionally substituted heterocycloalkyl;

each $R_x$ is independently halogen, optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, —OR, —SR, —CN, —N(R')(R"), —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, —OC(O)N(R')(R");

each R is independently hydrogen, $C_{1-6}$ aliphatic, a 5-6 membered aryl ring, a 3-7 membered saturated, partially unsaturated, or completely unsaturated carbocyclic ring, a 7-12 membered bicyclic saturated, partially unsaturated, or completely unsaturated carbocyclic ring, a 3-7 membered monocyclic heteroaryl ring having 1-3 heteroatoms independently selected from nitrogen, oxygen, and sulfur, a 3-7 membered saturated, partially unsaturated, or completely unsaturated heterocyclic ring having 1-2 heteroatoms independently selected from nitrogen, oxygen, and sulfur, a 7-12 membered bicyclic saturated, partially unsaturated, or completely unsaturated heterocyclic ring having 1-4 heteroatoms independently selected from nitrogen, oxygen, and sulfur, or a 7-12 membered bicyclic heteroaryl ring having 1-4 heteroatoms independently selected from nitrogen, oxygen, and sulfur; each of which is optionally substituted;

each R' is independently —R, —C(O)R, —C(S)R, —$CO_2$R, —C(O)$N(R)_2$, —C(S)$N(R)_2$, —S(O)R, —$SO_2$R, —$SO_2N(R)_2$, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;

each R" is independently —R, —C(O)R, —C(S)R, —$CO_2$R, —C(O)$N(R)_2$, —C(S)$N(R)_2$, —S(O)R, —$SO_2$R, —$SO_2N(R)_2$, or two R on the same nitrogen are taken together with their intervening atoms to form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted; or R' and R", together with the atoms to which each is attached, can form a 3-7 membered monocyclic saturated, partially unsaturated, or completely unsaturated heterocyclic ring having 1-2 heteroatoms independently selected from nitrogen, oxygen, and sulfur; a 7-12 membered bicyclic saturated, partially unsaturated, or completely unsaturated fused heterocyclic ring having 1-3 heteroatoms independently selected from nitrogen, oxygen, and sulfur; a 3-7 membered monocyclic heteroaryl ring; or a 7-12 membered bicyclic heteroaryl; each of which is optionally substituted;

each $R_4$ is independently optionally substituted alkyl, optionally substituted alkenyl, optionally substituted alkynyl, optionally substituted aryl, optionally substituted aralkyl, optionally substituted cycloalkyl, optionally substituted heteroaryl, optionally substituted heterocycloalkyl, halogen, —OR, —SR, —N(R')(R"), —CN, —$NO_2$, —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, or —OC(O)N($R^1$)(R");

each $R_5$ is independently —R, halogen, —OR, —SR, —N(R')(R"), —CN, —$NO_2$, —C(O)R, —C(S)R, —$CO_2$R, —C(O)N(R')(R"), —C(O)SR, —C(O)C(O)R, —C(O)$CH_2$C(O)R, —C(S)N(R')(R"), —C(S)OR, —S(O)R, —$SO_2$R, —$SO_2$N(R')(R"), —N(R')C(O)R, —N(R')C(O)N(R')(R"), —N(R')C(S)N(R')(R"), —N(R')$SO_2$R, —N(R')$SO_2$N(R')(R"), —N(R')N(R')(R"), —N(R')C(═N(R'))N(R')(R"), —C═NN(R')(R"), —C═NOR, —C(═N(R'))N(R')(R"), —OC(O)R, or —OC(O)N($R^1$)(R");

r is 0 or 1;

n is 0-5;

each q is independently 0, 1, or 2; and each p is independently an integer selected from 1-6.

2. The compound of claim 1, wherein the ring formed by $A_1$, $A_2$, $A_3$, $A_4$, and the atoms to which each is attached, is phenyl, pyridino, pyrimidino, pyrazino, or pyridazino.

3. The compound of claim 1, wherein $R_1$ is halo, alkyl, aralkyl, aryl, or heteroaryl.

4. The compound of claim 3, wherein $R_1$ is methyl, ethyl, propyl, i-propyl, butyl, s-butyl, t-butyl, pentyl, hexyl, or heptyl.

5. The compound of claim 1, wherein $R_2$ and $R_3$ are each independently H, methyl, ethyl, propyl, i-propyl, butyl, s-butyl, pentyl, hexyl, —OR, —SR, —CN, —N(R')(R"), —C(O)R, —C(S)R, —$CO_2$R, —C(O)N(R')(R"), —C(O)SR, or —$(CH_2)_pR_x$.

6. The compound of claim 5, wherein $R_2$ and $R_3$ are each independently H, methyl, or —$(CH_2)_pR_x$.

7. The compound of claim 1, wherein $R_2$ and $R_3$ together with the atoms to which each is attached, forms an optionally substituted 3-7 membered saturated or partially unsaturated spiro-fused ring having 0-3 heteroatoms independently selected from nitrogen, oxygen, or sulfur.

8. The compound of claim 1, wherein $R_6$ and $R_7$ are each independently H, methyl, ethyl, propyl, i-propyl, butyl, s-butyl, pentyl, hexyl, —OR, —SR, —N(R')(R"), —C(O)R, —$CO_2$R, —C(O)N(R')(R"), or —$(CH_2)_pR_x$.

9. The compound of claim 1, wherein $R_x$ is —N(R')(R"), —C(O)R, —C(S)R, —$CO_2$R, —C(O)N(R')(R"), —C(S)N(R')(R"), —S(O)R, —$SO_2$R, —$SO_2$N(R')(R"), —N(R')C(O)R, —N(R')$SO_2$R, —OC(O)R, —OC(O)N(R')(R"), methyl, ethyl, propyl, i-propyl, butyl, s-butyl, pentyl or hexyl.

10. A compound of Formula III:

(III)

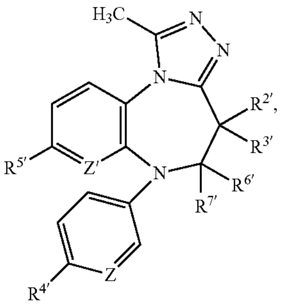

or a pharmaceutically acceptable salt thereof, wherein:

each of Z and Z' is independently selected from N or CH;

$R^{2'}$ and $R^{3'}$ are independently selected from hydrogen and methyl; or $R^{2'}$ and $R^{3'}$ are taken together with the carbon atom to which they are bound to form cyclopropyl optionally substituted with an optionally substituted alkyl;

$R^{4'}$ is selected from chloro, —$NH_2$, —CN, —C(O)$NH_2$, —S(O)$_2CH_3$, and $CF_3$;

$R^{5'}$ is selected from phenyl, pyrazolyl, pyridinyl, triazolyl, pyrazinyl, pyridinonyl, pyrimidinyl, oxadiazolyl, —$OCH_3$, —C(O)$NH_2$, —C(O)NH—$CH_2CH_2$OH, —C≡C—C$(CH_3)_2$OH, —C≡C—C$(CH_3)_2NH_2$, and bromo, wherein the phenyl, pyrazolyl, pyridinyl, triazolyl, pyrazinyl, pyridinonyl, pyrimidinyl, or oxadiazolyl is optionally substituted with one or more substituents independently selected from optionally substituted alkyl, —$NH_2$, COOH, C(O)$NH_2$, and $CH_2CONH_2$; and each of $R^{6'}$ and $R^{7'}$ is independently selected from methyl and hydrogen.

11. The compound of claim 10, wherein:

each of Z and Z' is CH;

$R^{4'}$ is selected from chloro, —CN, —C(O)$NH_2$, —S(O)$_2$ $CH_3$, $CF_3$; and $R^{5'}$ is selected from phenyl, pyrazolyl, pyridinyl, triazolyl, pyrazinyl, pyridinonyl, pyrimidinyl, oxadiazolyl, —C(O)$NH_2$, wherein the phenyl, pyrazolyl, pyridinyl, triazolyl, pyrazinyl, pyridinonyl, pyrimidinyl, or oxadiazolyl is optionally substituted with one or more of —$CH_3$, —$NH_2$, COOH, C(O)$NH_2$, $CH_2CONH_2$, $CH_2CH_2$OH.

12. The compound of claim 11, wherein:

$R^{2'}$ is (R)-methyl, $R^{3'}$ is hydrogen;

$R^{4'}$ is chloro;

$R^{5'}$ is selected from pyridinyl, triazolyl, pyrimidinyl or pyrazinyl, wherein $R^{5'}$ is substituted with methyl or $NH_2$; and each of $R^{6'}$ and $R^{7'}$ is hydrogen.

13. A compound selected from

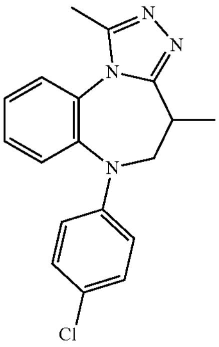

;

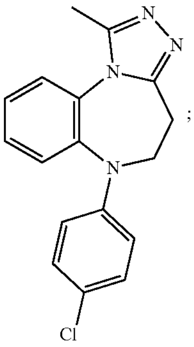

;

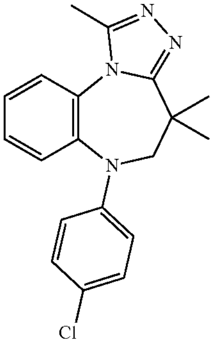

;

-continued
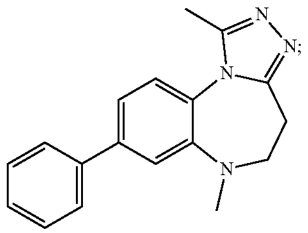
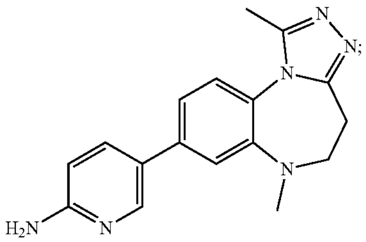
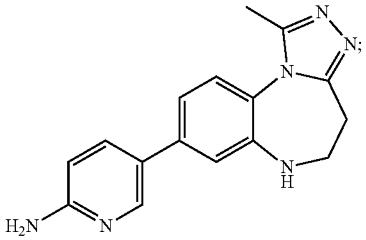
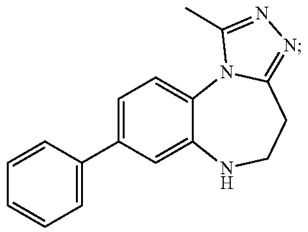
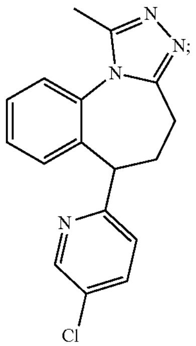
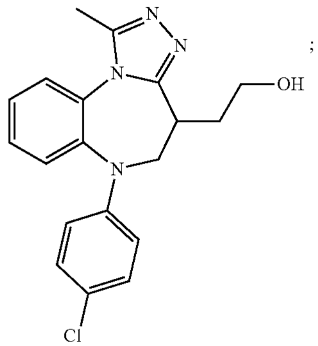
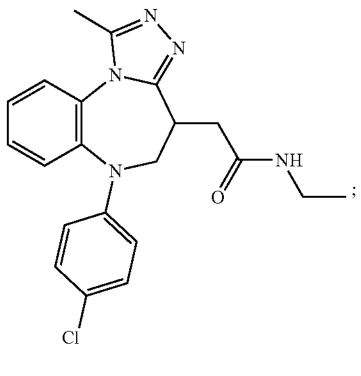
-continued
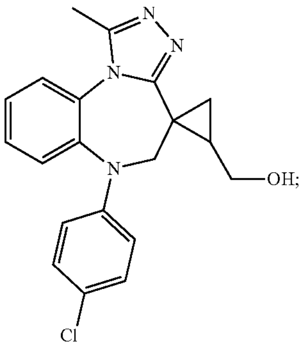
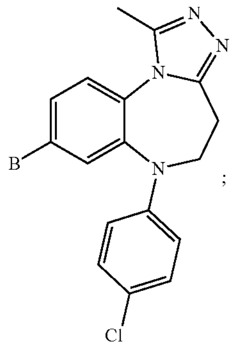
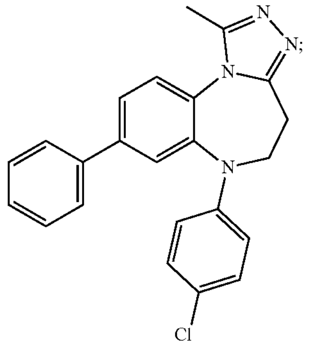
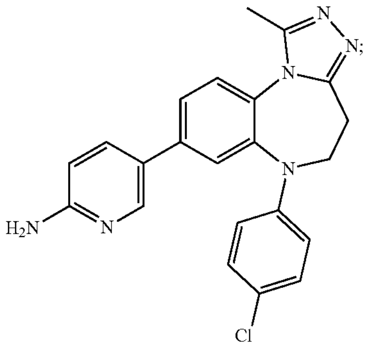
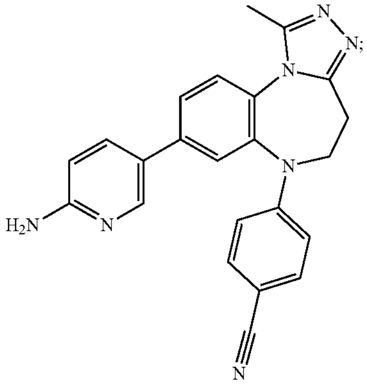

-continued
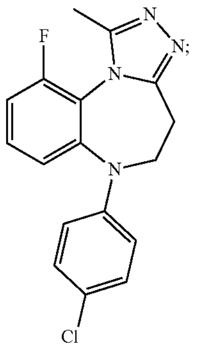
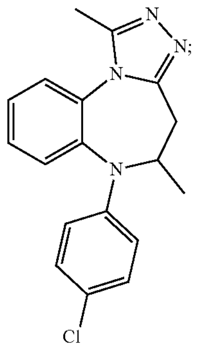
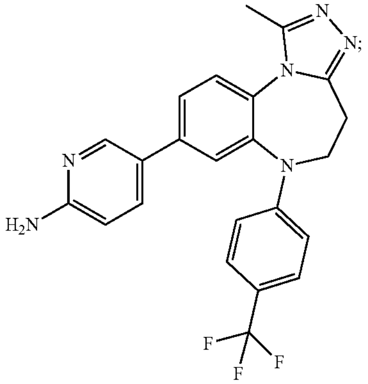
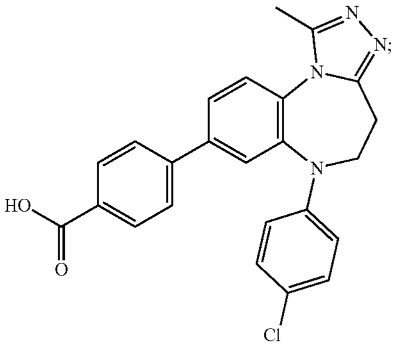
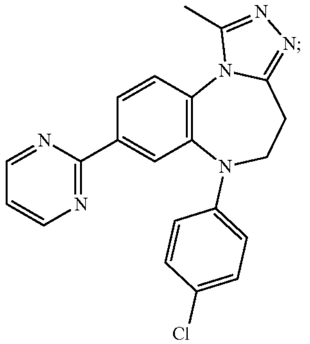
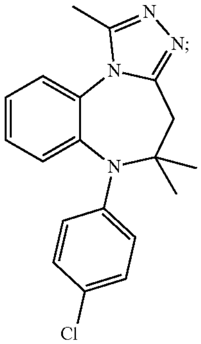
-continued
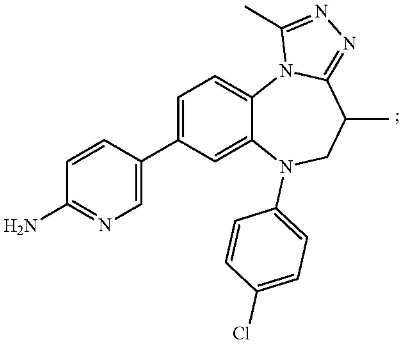
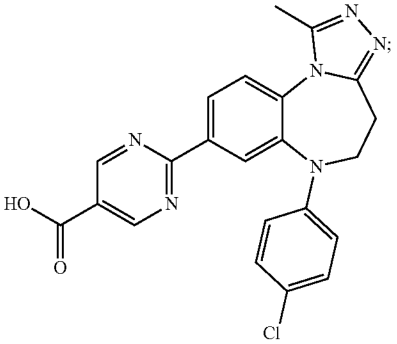
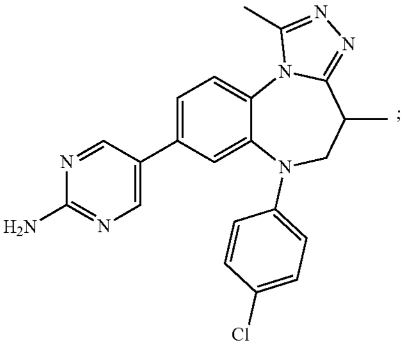
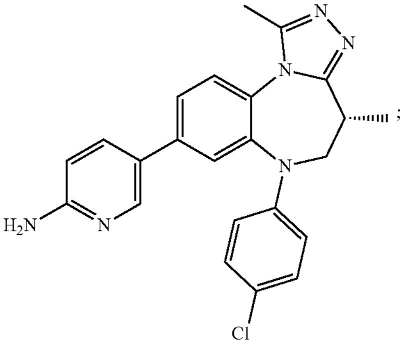
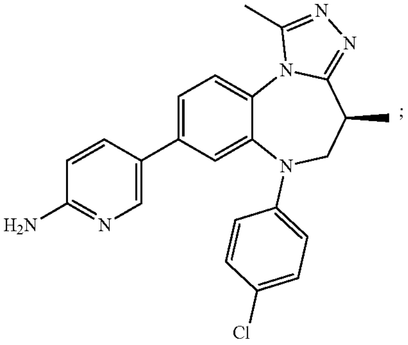

-continued
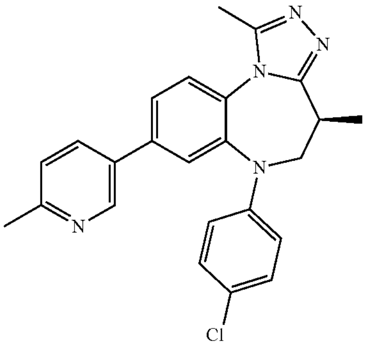
;
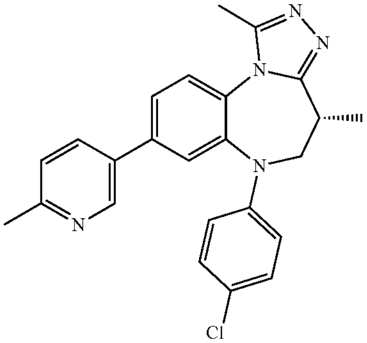
;
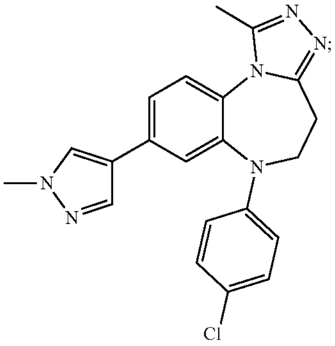
;
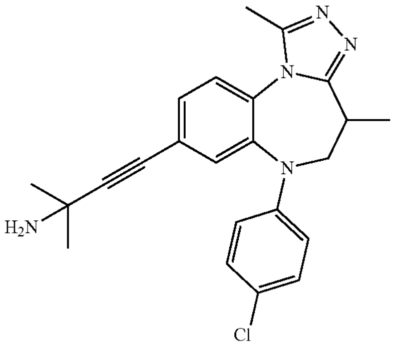
;
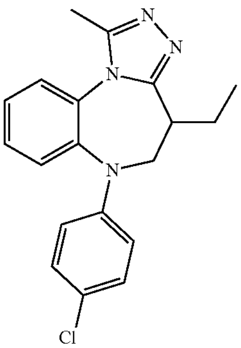
;
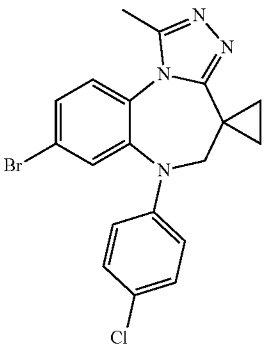
;
-continued
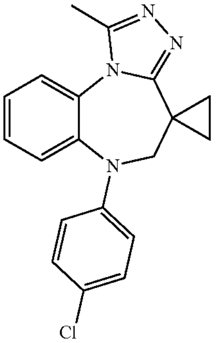
;
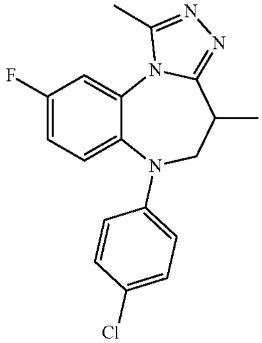
;
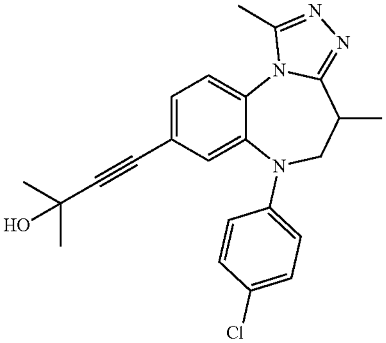
;
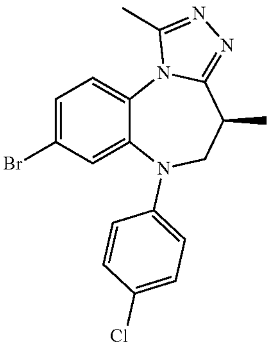
;
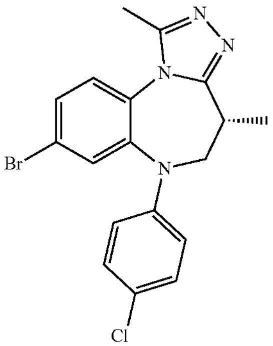
;
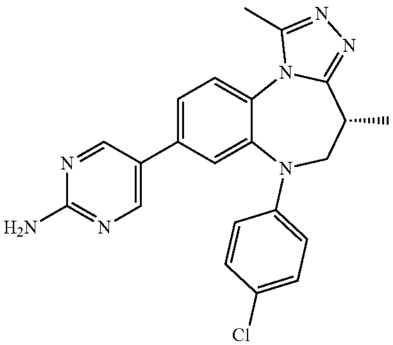
;
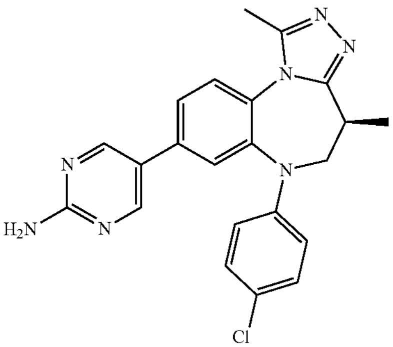
;

-continued
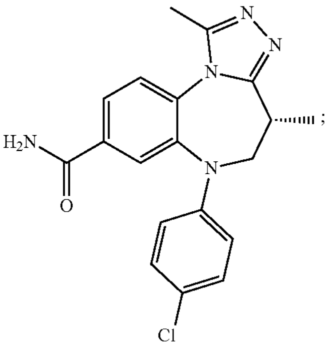
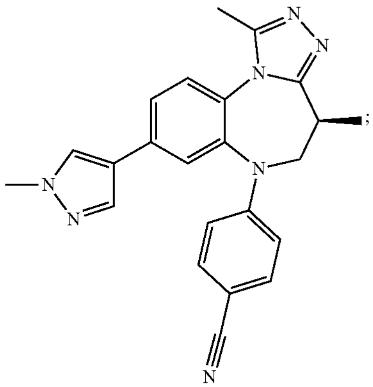
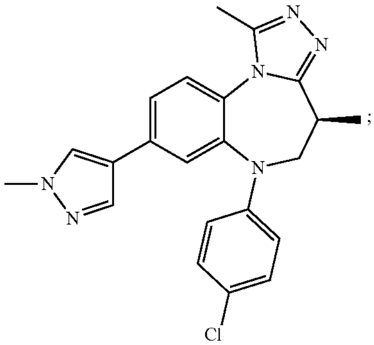
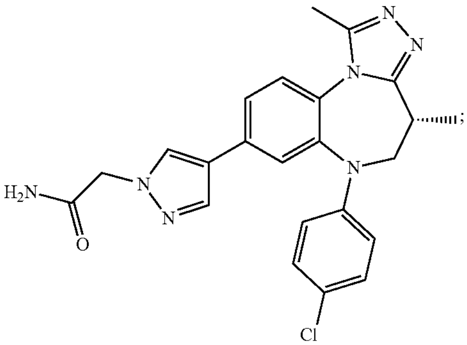
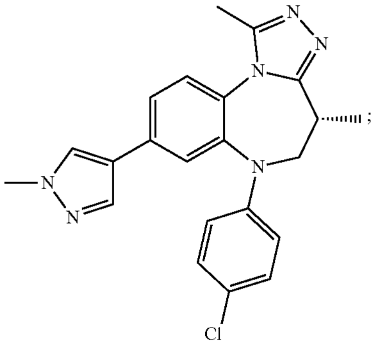
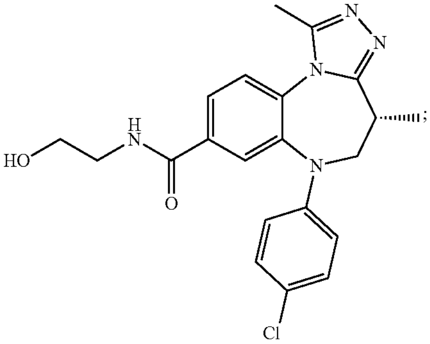
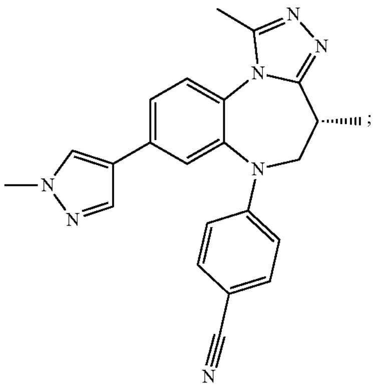
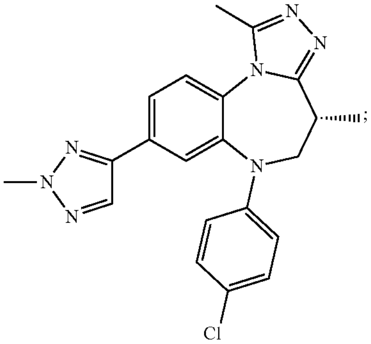

-continued
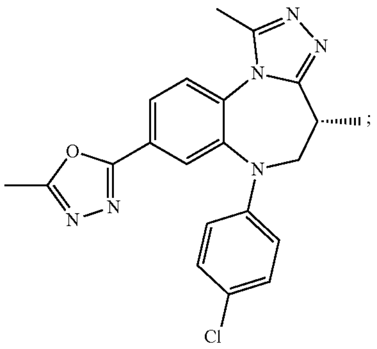
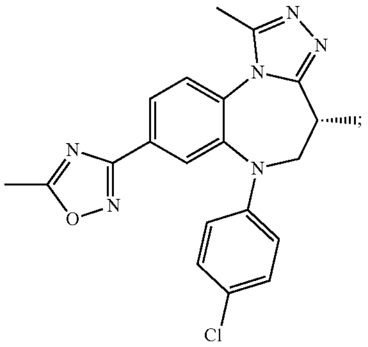
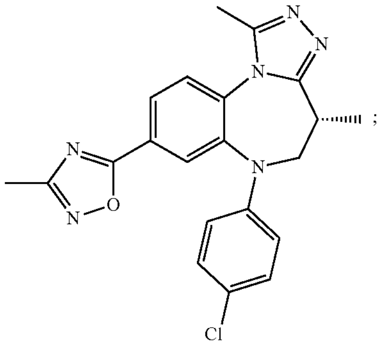
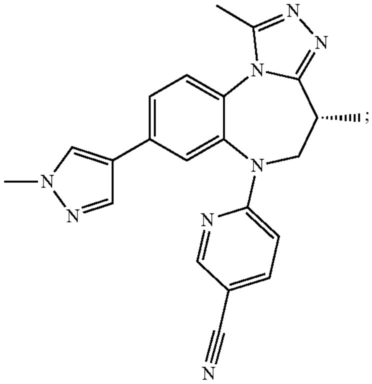
-continued
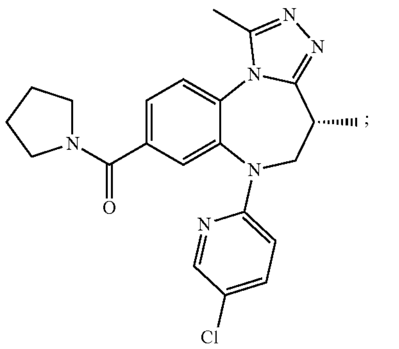
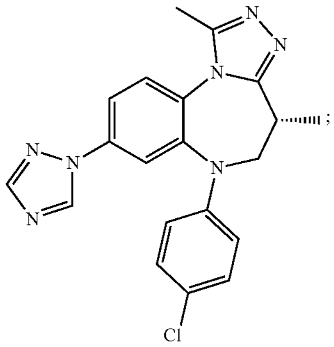
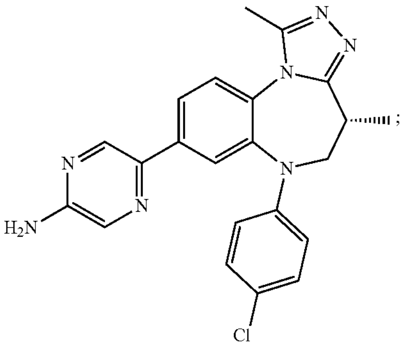
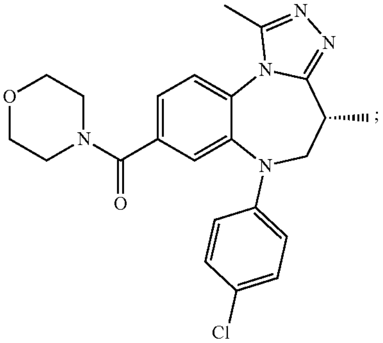

-continued
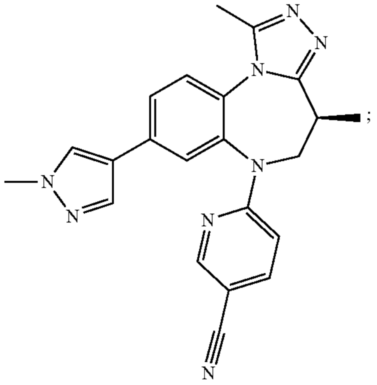
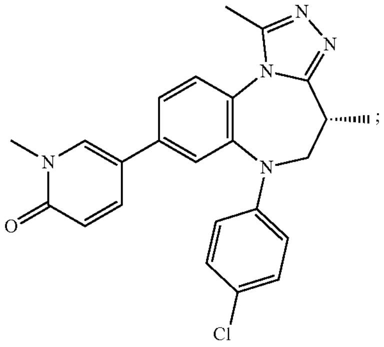
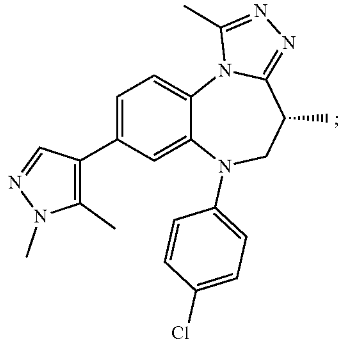
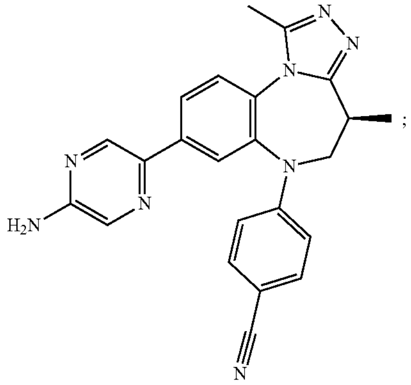
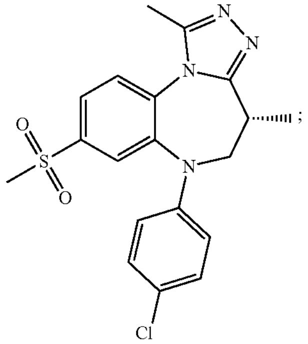
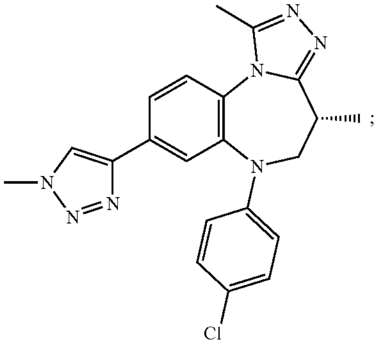
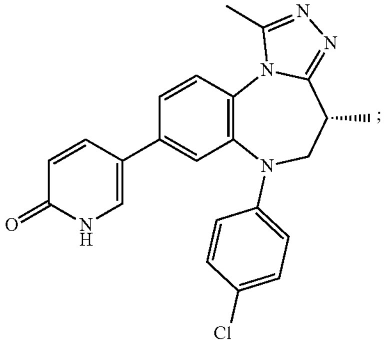
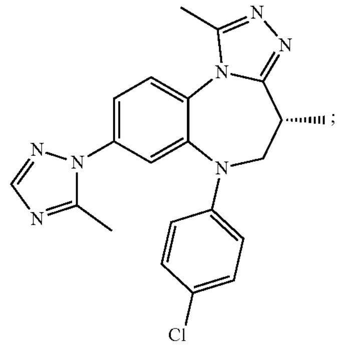

-continued
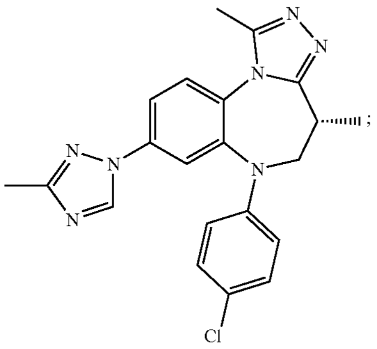
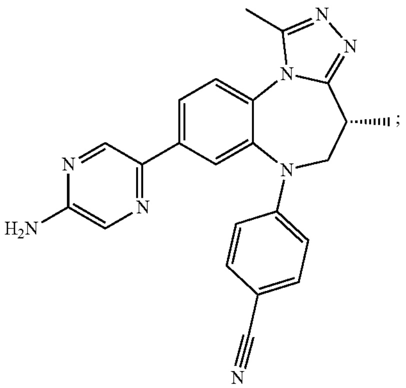
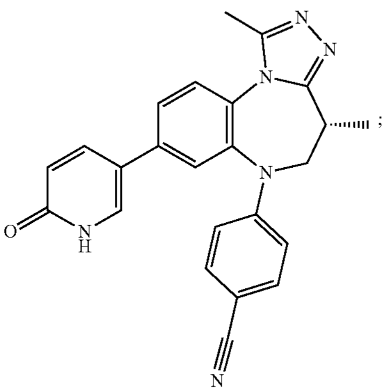
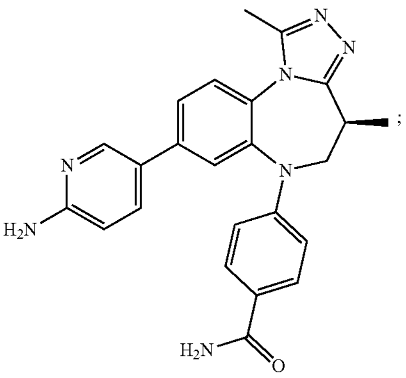
-continued
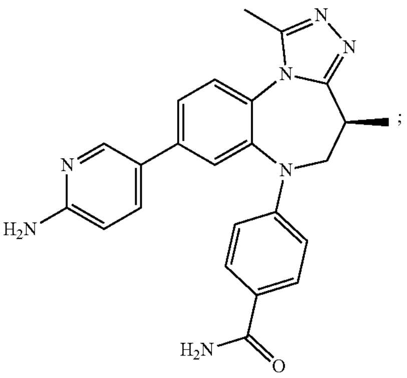
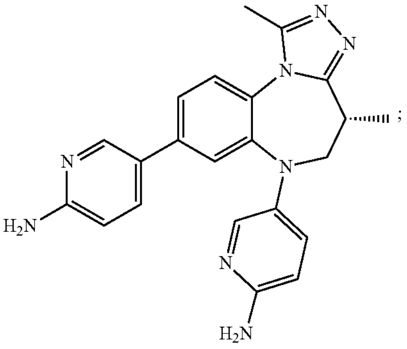
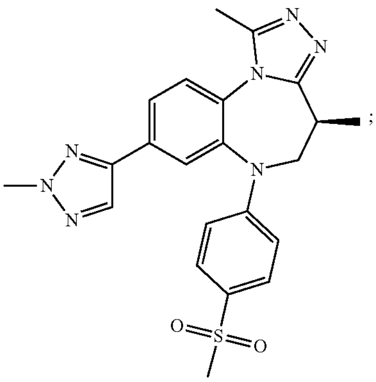
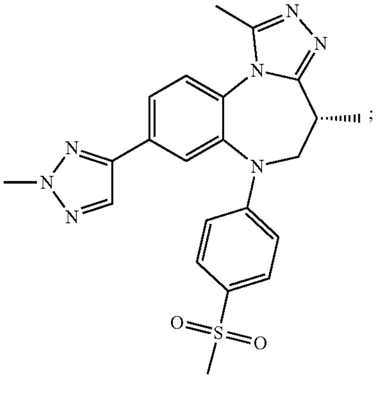

-continued
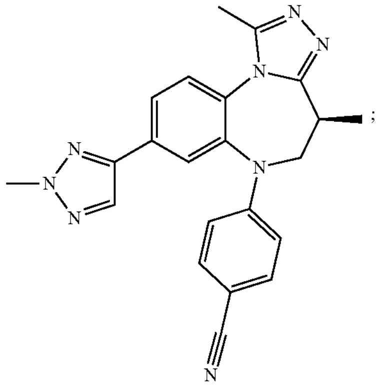
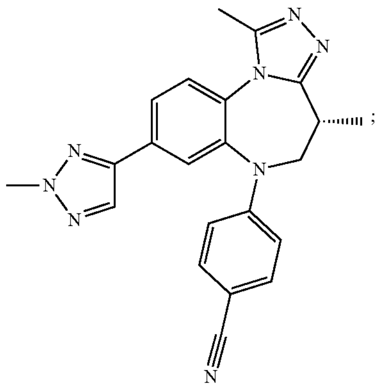
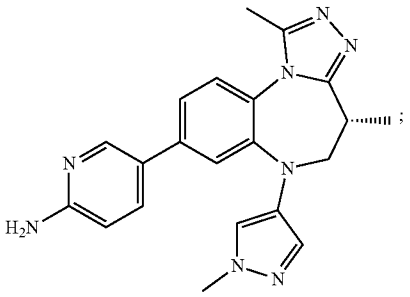
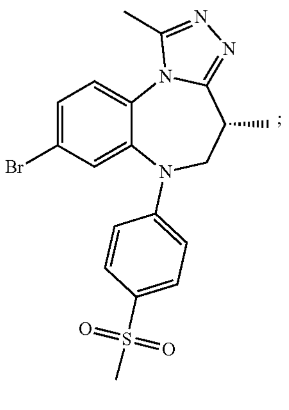
-continued
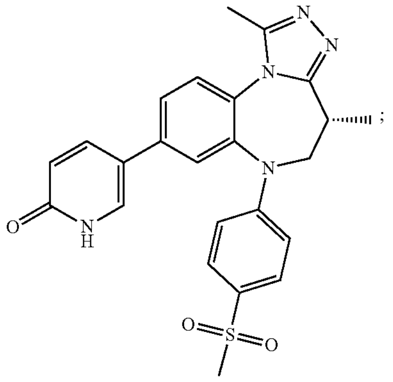
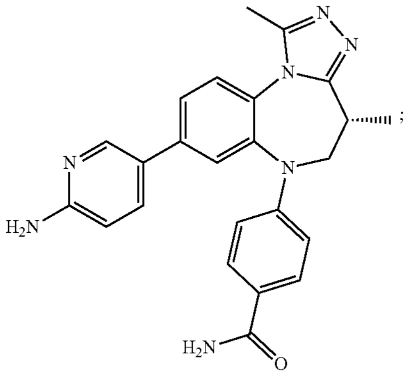
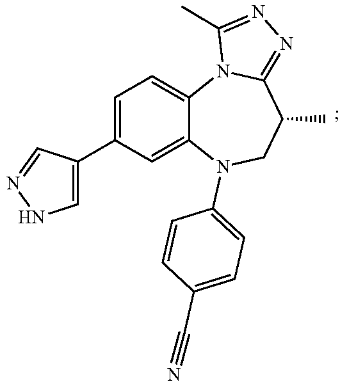
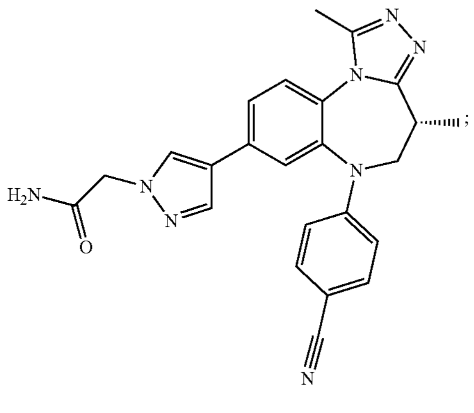

-continued
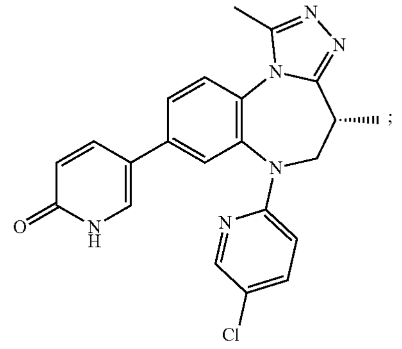
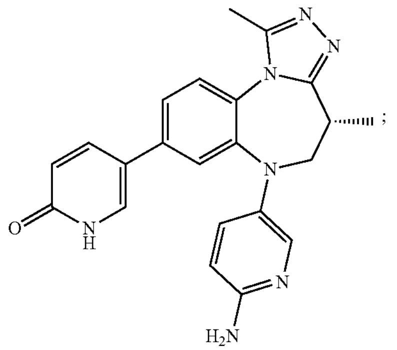
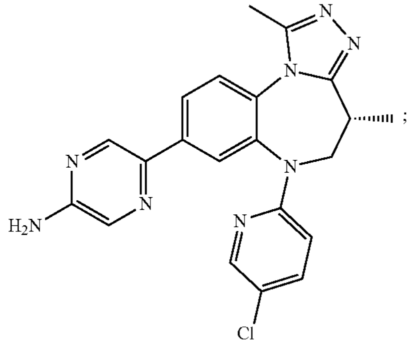
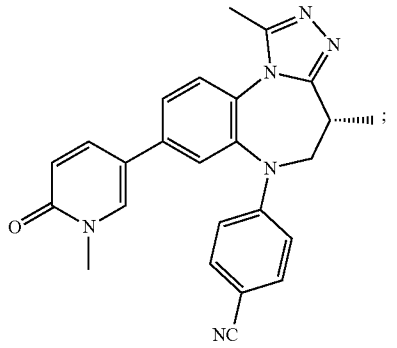
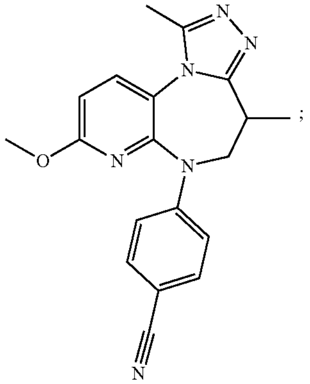
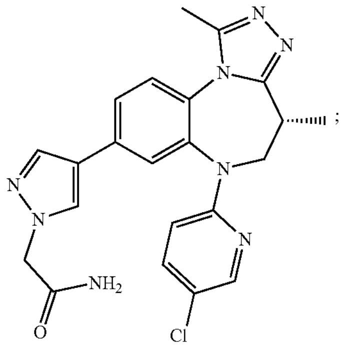
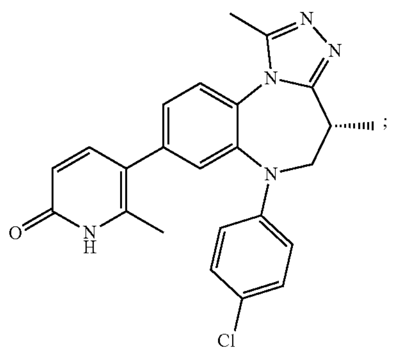
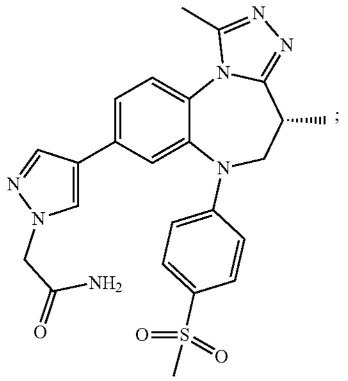

-continued
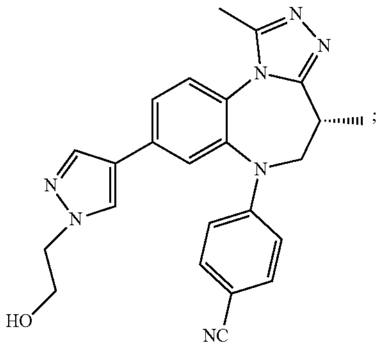
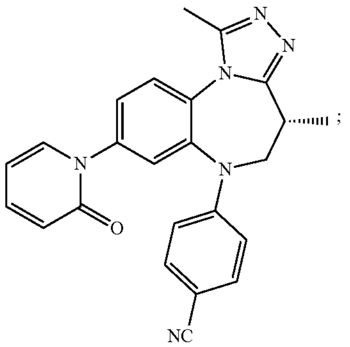
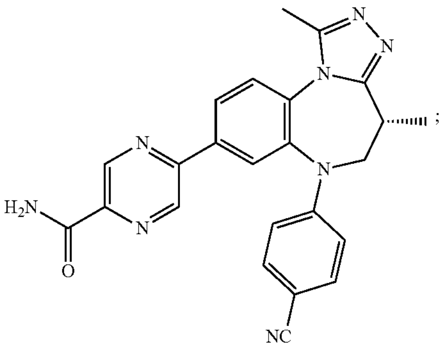
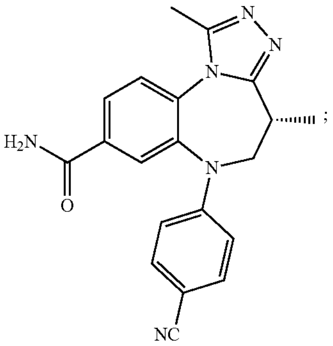
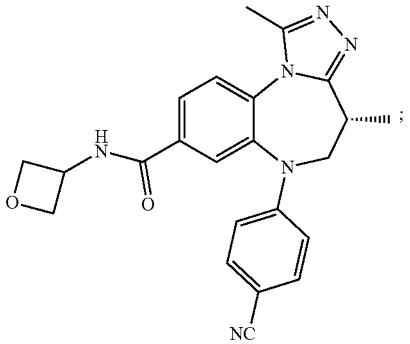
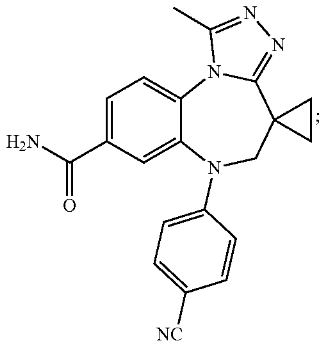
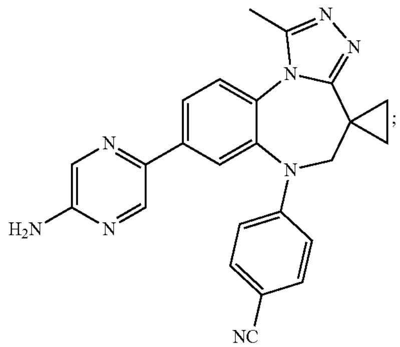
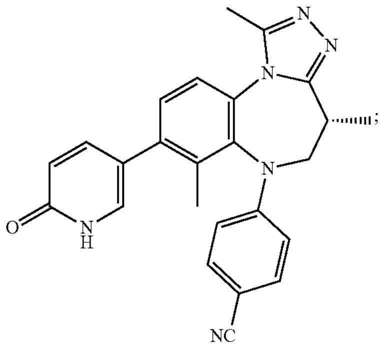
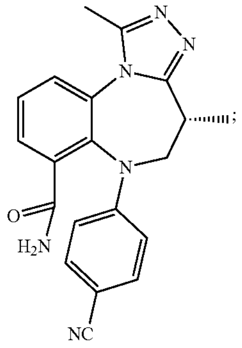
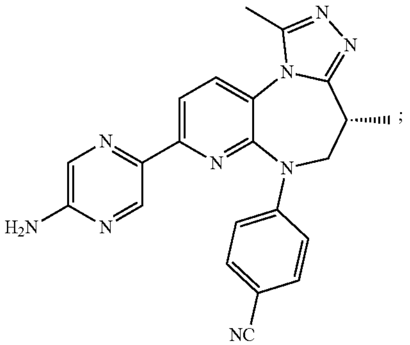

-continued
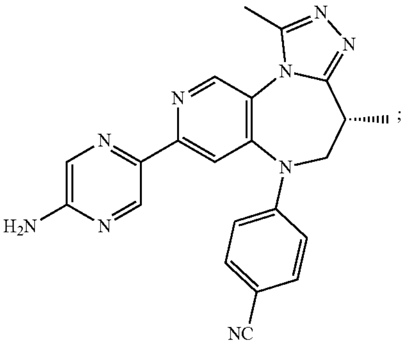
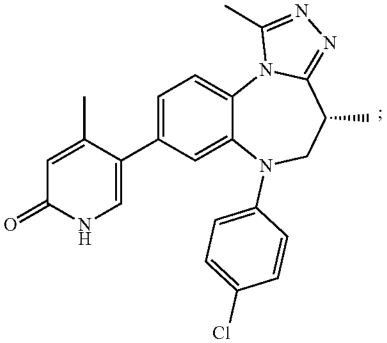
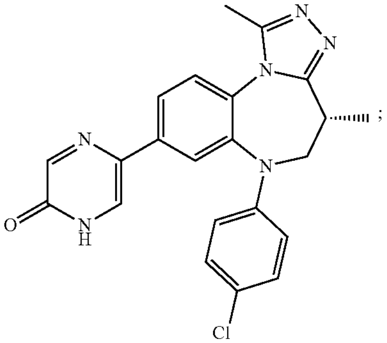
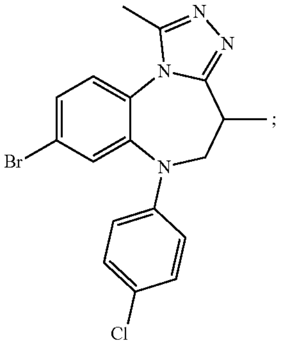
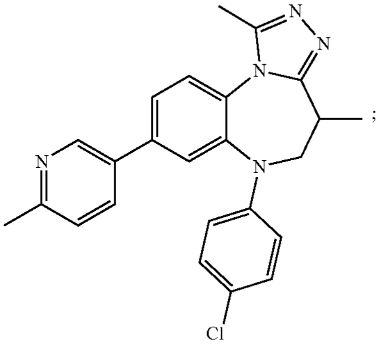
-continued
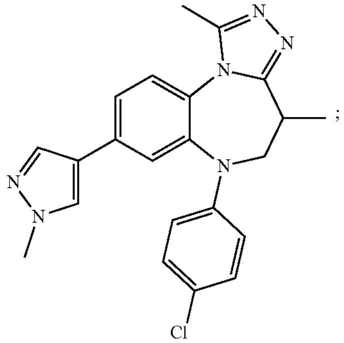
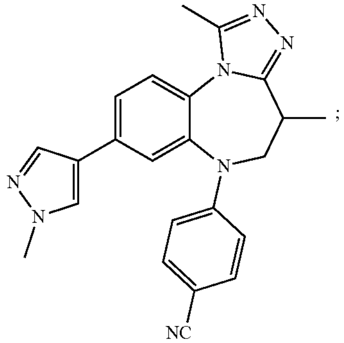
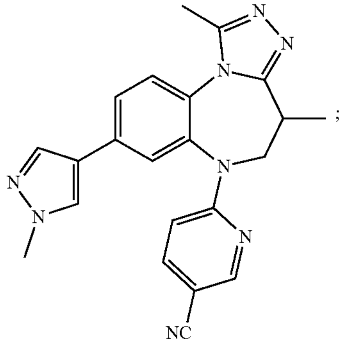
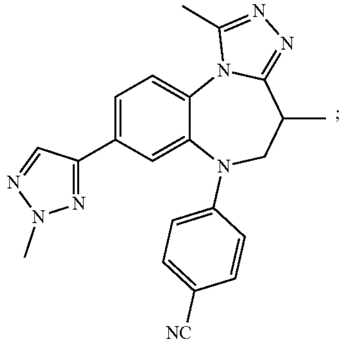
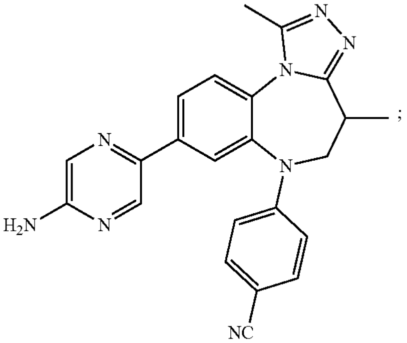

-continued

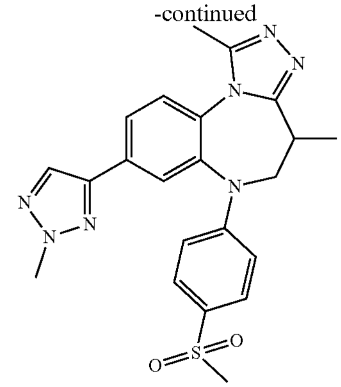

; and

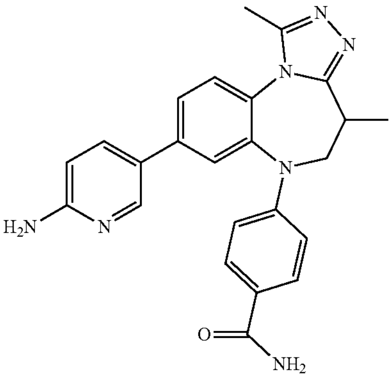

;

or a pharmaceutically acceptable salt thereof.

14. A composition comprising a compound according to claim 1 and a pharmaceutically acceptable adjuvant, carrier, or vehicle.

15. A method of treating a cancer selected from diffuse large B-cell lymphoma, Hodgkin's lymphoma, non-Hodgkin's lymphoma, T-cell lymphoma, primary central nervous system lymphoma, and multiple myeloma, in a patient in need thereof, comprising the step of administering to said patient a compound according to claim 1.

16. A composition comprising a compound according to claim 10 and a pharmaceutically acceptable adjuvant, carrier, or vehicle.

17. A method of treating a cancer selected from diffuse large B-cell lymphoma, Hodgkin's lymphoma, non-Hodgkin's lymphoma, T-cell lymphoma, primary central nervous system lymphoma, and multiple myeloma, in a patient in need thereof, comprising the step of administering to said patient a compound according to claim 10.

* * * * *